United States Patent
Liang et al.

(10) Patent No.: US 8,501,763 B2
(45) Date of Patent: Aug. 6, 2013

(54) INHIBITORS OF FOCAL ADHESION KINASE

(75) Inventors: Congxin Liang, Palm Beach Gardens, FL (US); Marcel Koenig, Palm Beach Gardens, FL (US); Yuanjun He, Palm Beach Gardens, FL (US); Par Holmberg, Bodafors (SE)

(73) Assignee: The Scripps Research Institute, La Jolla, CA (US)

( * ) Notice: Subject to any disclaimer, the term of this patent is extended or adjusted under 35 U.S.C. 154(b) by 602 days.

(21) Appl. No.: 12/531,010

(22) PCT Filed: Mar. 10, 2008

(86) PCT No.: PCT/US2008/003205
§ 371 (c)(1),
(2), (4) Date: May 7, 2010

(87) PCT Pub. No.: WO2008/115369
PCT Pub. Date: Sep. 25, 2008

(65) Prior Publication Data
US 2011/0046121 A1 Feb. 24, 2011

Related U.S. Application Data

(60) Provisional application No. 60/895,379, filed on Mar. 16, 2007, provisional application No. 60/946,637, filed on Jun. 27, 2007, provisional application No. 61/030,025, filed on Feb. 20, 2008.

(51) Int. Cl.
| | | |
|---|---|---|
| A01N 43/42 | (2006.01) | |
| A61K 31/44 | (2006.01) | |
| A61K 31/4965 | (2006.01) | |
| A61K 31/535 | (2006.01) | |
| C07D 295/00 | (2006.01) | |
| C07D 265/30 | (2006.01) | |

(52) U.S. Cl.
USPC .......... 514/287; 514/255.03; 514/239.5; 544/106; 544/392

(58) Field of Classification Search
USPC .......... 514/287, 255.03, 239.5; 544/106, 544/392
See application file for complete search history.

(56) References Cited

U.S. PATENT DOCUMENTS

| 8,039,479 B2 * | 10/2011 | Michellys et al. ............ 514/275 |
| 2005/0090515 A1 | 4/2005 | Pease et al. |
| 2010/0317663 A1 | 12/2010 | Adams et al. |

FOREIGN PATENT DOCUMENTS

| JP | 2010-507665 A | 3/2010 |
| JP | 2010-512329 A | 4/2010 |
| WO | WO-2004/002410 A2 | 1/2004 |
| WO | WO-2004/002410 A3 | 1/2004 |
| WO | WO-2008/051547 A1 | 5/2008 |
| WO | WO-2008/115369 A2 | 9/2008 |
| WO | WO-2008/115369 A3 | 9/2008 |

OTHER PUBLICATIONS

Morissette et al. "High-throughput crystallization: polymorphs, salts, co-crystals and solvates of pharmaceutical solids" Advanced Drug Delivery Reviews, 2004, vol. 56, pp. 275-300.*
"Chinese Application Serial No. 200880015910.X, Response filed Jan. 13, 2012 to Office Action mailed Aug. 30, 2011", 84 pgs.
"Chinese Application Serial No. 200880015910.X, Office Action mailed Feb. 3, 2012", (w/ English Translation), 10 pgs.
"Chinese Application Serial No. 200880015910.X, First Office Action mailed Aug. 30, 2011", (English Translation), 6 pgs.
"European Patent Application No. 08726698.7, Office Action mailed Oct. 13, 2011", 3 pgs.
"Chinese Application Serial No. 200880015910.x, Office Action mailed Jul. 23, 2012", (w/ English Translation), 10 pgs.
"Application Serial No. PCT/US2008/003205, International Search Report and the Written Opinion mailed Sep. 9. 2008".
Ahmed, G., et al., "Preparation of fused bicycle derivatives of 2,4-Diaminopyrimidine as ALK and c-Met kinase inhibitors", Chemical Abstract Service, Columbus, Ohio, (2008).
"Chinese Application Serial No. 200880015910.X, Response filed Nov. 7, 2012 to Office Action mailed Jul. 23, 2012", 61 pgs.
"Taiwanese Application Serial No. 97109125, Office Action mailed Jan. 23, 2013", (w/ English Translation of Search Report), 6 pgs.
"European Application Serial No. 08726698.7, Communication pursuant to Article 94(3) EPC mailed Mar. 12, 2013", 4 pgs.
"Japanese Application Serial No. 2009-553600, Office Action mailed May 14, 2013", (w/ English Translation), 8 pgs.

* cited by examiner

Primary Examiner — Kendra D Carter
(74) Attorney, Agent, or Firm — Schwegman Lundberg & Woessner, P.A.

(57) ABSTRACT

The invention provides inhibitors of focal adhesion kinase, an enzyme involved in the attachment of the cytoskeleton of a cell to an extracellular matrix, which has been implicated in processes such as cell migration, cell proliferation, and cell survival. The inhibitors are derivatives of a 5-substituted 2,4-diaminopyridine wherein the substituents are as defined herein. The invention also provides a method of using the inhibitors in treatment of cancer, and methods of preparation of the inhibitors by use of coupling reactions.

16 Claims, No Drawings

INHIBITORS OF FOCAL ADHESION KINASE

CROSS-REFERENCE TO RELATED APPLICATIONS

This application is a national stage application under 35 U.S.C. §371 of PCT/US2008/003205, filed Mar. 10, 2008, and published as WO 2008/115369A2 on Sep. 25, 2008, which claims the priority of U.S. Provisional Application Ser. No. 60/895,379, filed Mar. 16, 2007; of U.S. Provisional Application Ser. No. 60/946,637, filed Jun. 27, 2007, and of U.S. Provisional Application Ser. No. 61/030,025, filed Feb. 20, 2008, all of which applications and publication are incorporated herein by reference in their entireties.

BACKGROUND

Integrins are the major cell surface receptors for extracellular matrix molecules, which play critical roles in a variety of biological processes. Focal adhesion kinase (FAK) has recently been established as a key component of the signal transduction pathways triggered by integrins. Aggregation of FAK with integrins and cytoskeletal proteins in focal contacts has been proposed to be responsible for FAK activation. Recent results from a number of different approaches have shown that integrin signaling through FAK leads to increased cell migration on fibronectin as well as potentially regulating cell proliferation and survival. J L Guan (1997 August-September), *Int J Biochem Cell Biol.*, 29(8-9):1085-96. Interaction with integrin and focal adhesion kinase (FAK) regulates the cancer cell adhesion and invasion into extracellular matrix (ECM). In addition, phosphorylation of FAK correlates with the increase of cell motility and invasion. Adhesion and spreading of cancer cells on a variety of ECM proteins, including collagen type IV, leads to an increase in tyrosine phosphorylation and activation of FAK. H Sawai, et al. (2005), *Molecular Cancer*, 4:37.

SUMMARY

An embodiment of the present invention provides a compound of formula (I):

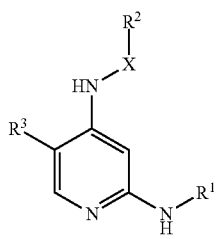

(I)

wherein:

$R^1$ and $R^2$ are each independently a 5-12 membered monocyclic, bicyclic or polycyclic, aromatic or partially aromatic ring system wherein each ring system independently comprises 0-3 heteroatoms selected from the group consisting of N, O, S, S(O), and $S(O)_2$, and each ring system is substituted with 0-5 substituents independently selected from Y;

wherein Y comprises halo, hydroxyl, cyano, thio, nitro, trifluoromethyl, oxo, $(C_1-C_6)$alkyl, $(C_2-C_6)$alkenyl, $(C_2-C_6)$alkynyl, alkoxy, methylenedioxy, ethylenedioxy, NH(R), $N(R)_2$, SR, C(O)NH(R), C(O)N(R)$_2$, RC(O)N(R), C(O)C(O)NR$_2$, C(O)C(O)OR, RC(O)O, ROC(O), ROC(O)O, RC(O), $RSO_2$, $RSO_2(C_1-C_3)$alkyl, $SO_2N(R)_2$, $N(R)SO_2R$, urea bearing 0-3 R, $(C_5-C_{10})$aryl, $(C_2-C_{10})$heteroaryl, $(C_2-C_{10})$dihydroheteroaryl, $(C_2-C_{10})$tetrahydroheteroaryl, $(C_2-C_{10})$hexahydroheteroaryl, $(C_3-C_{10})$mono- or bicyclic cycloalkyl, or $(C_2-C_{10})$mono- or bicyclo-heterocyclyl, wherein each R independently comprises hydrogen or substituted or unsubstituted aryl or substituted or unsubstituted $(C_1-C_6)$alkyl, or where two R groups taken together with a nitrogen atom to which they are attached form together with the nitrogen atom a heterocyclic ring comprising 0-2 additional heteroatoms selected from the group consisting of N, O, S, S(O), and $S(O)_2$, and substituted with 0-3 $(C_1-C_3)$alkyl, hydroxyl, $(C_1-C_3)$hydroxyalkyl or $(C_1-C_3)$alkoxy$(C_1-C_3)$alkyl groups;

wherein any alkyl, alkenyl, alkynyl, alkoxy, aryl, heteroaryl, dihydroheteroaryl, tetrahydroheteroaryl, hexahydroheteroaryl, cycloalkyl or heterocyclyl of Y or R, or both, can be further substituted by 1-3 substituents selected from halo, hydroxyl, cyano, thio, nitro, trifluoromethyl, oxo, $(C_1-C_6)$alkyl, $(C_2-C_6)$alkenyl, $(C_2-C_6)$alkynyl, alkoxy, methylenedioxy, ethylenedioxy, NH(R), $N(R)_2$, SR, C(O)NH(R), C(O)N(R)$_2$, RC(O)N(R), C(O)C(O)NR$_2$, C(O)C(O)OR, RC(O)O, ROC(O), ROC(O)O, RC(O), $RSO_2$, $RSO_2(C_1-C_3)$alkyl, $SO_2N(R)_2$, $N(R)SO_2R$, urea bearing 0-3 R, or with a substituted or unsubstituted $(C_5-C_{10})$aryl, $(C_2-C_{10})$heteroaryl, $(C_2-C_{10})$dihydroheteroaryl, $(C_2-C_{10})$tetrahydroheteroaryl, $(C_2-C_{10})$hexahydroheteroaryl, $(C_3-C_{10})$mono- or bicyclic cycloalkyl, or $(C_2-C_{10})$mono- or bicyclo-heterocyclyl;

X is a bond or $(C_1-C_3)$alkyl comprising 0-1 heteroatom selected from the group consisting of NR, O, S, S(O), and $S(O)_2$, wherein the $(C_1-C_3)$alkyl is substituted with 0-1 hydroxy, halo, $(C_1-C_3)$alkoxy, $(C_1-C_3)$alkylamino, or $(C_1-C_3)_2$dialkylamino groups;

$R^3$ is trifluoromethyl, halo, nitro, or cyano;

or a salt, tautomer, solvate, hydrate, or a prodrug thereof.

An embodiment of a compound of the invention is a derivative of 2,4-diamino-pyridine bearing a halo, nitro, trifluoromethyl or cyano group on the pyridine 5-position, wherein the substituents are as specified above. Specific examples are provided below. An embodiment of an inventive compound can be used to inhibit the activity of a protein kinase, such as focal adhesion kinase (FAK). Most of the compounds 1-123 as shown in Table 1 were tested in a cell-free or a cellular FAK assay, or both, and of the compounds that were tested, all showed 50% inhibitory concentrations ($IC_{50}$) of less than 10 µM against focal adhesion kinase in the above cell-free assay, except for compounds 3 and 5 shown above in Table 1 which possess $IC_{50}$ values of greater than 10 µM; or showed greater than about 50% inhibition of FAK in the cellular assay at concentrations of 1 µM; or both. Certain of the compounds have not yet been evaluated for biological activity.

An embodiment of the present invention provides a method of inhibiting a protein kinase, in vitro or in vivo, comprising contacting a compound of the invention at an effective concentration, and the protein kinase. The protein kinase can be inhibited in vitro, such as when carrying out an assay to determine the bioactivity of a specific compound of the invention. The protein kinase can also be inhibited in vivo, that is, within the body tissues of a living mammal, such as a human patient.

An embodiment of the present invention provides a method of treating a malcondition in a mammal that is mediated by abnormal protein kinase activities, comprising administration of a compound of the invention in a dosage, at a frequency, and for a duration to produce a beneficial effect on the mammal. The malcondition can be cancer and the mammal can be a human patient.

An embodiment of the invention provides a method of preparing a compound of formula (I) comprising contacting a compound of formula (II):

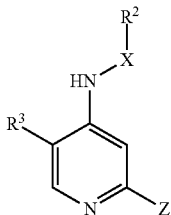

(II)

and a compound of formula (III):

R$^1$—NH$_2$ (III)

in the presence of a zero-valent transition metal complex, for sufficient time and at a sufficient temperature to provide a product of formula (I):

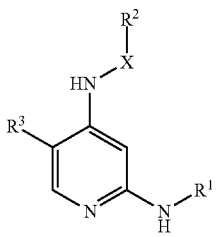

(I)

wherein Z comprises a leaving group and R$^1$, R$^2$, and R$^3$ are defined herein. The zero-valent transition metal complex can be a zero-valent palladium complex. The zero-valent palladium complex can comprise Pd$_2$(dba)$_3$, and can further comprises a phosphine ligand. The phosphine ligand can comprise xantphos. The leaving group can be a halo group, such as a chloro group.

Another embodiment of the invention provides a method of preparing a compound of formula (I) comprising contacting a compound of formula (II):

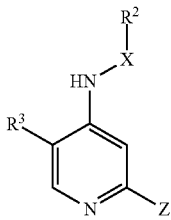

(II)

and a compound of formula (III):

R$^1$—NH$_2$ (III)

in the presence of an acid, for sufficient time and at a sufficient temperature to provide a product of formula (I):

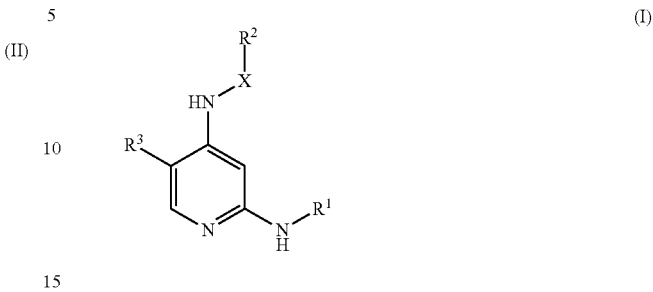

wherein Z comprises a leaving group and R$^1$, R$^2$, and R$^3$ are defined herein. Z can be a halo, such as chloro. The acid can be aqueous hydrochloric acid, and the reaction can be carried out in n-butanol.

DETAILED DESCRIPTION OF THE INVENTION

Definitions

"Treating" or "treatment" within the meaning herein refers to an alleviation of symptoms associated with a disorder or disease, or inhibition of further progression or worsening of those symptoms, or prevention or prophylaxis of the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by inhibition of focal adhesion kinase (FAK) activity. A therapeutically effective amount is also one in which any toxic or detrimental effects of compounds of the invention are outweighed by the therapeutically beneficial effects. For example, in the context of treating cancer, a therapeutically effective amount of a FAK inhibitor of the invention is an amount sufficient to control the cancer, mitigate the progress of the cancer, or relieve the symptoms of the cancer.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH3), —CH=C(CH3)2, —C(CH3)=CH2, —C(CH3)=CH(CH3), —C(CH2CH3)=CH2, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl groups include aromatic and non-aromatic ring compounds containing 3 or more ring members, of which one or more is a heteroatom such as, but not limited to, N, O, S, or P. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms.
The phrase "heterocyclyl group" includes fused ring species including those having fused aromatic and non-aromatic groups. The phrase also includes polycyclic ring systems containing a heteroatom such as, but not limited to, quinuclidyl and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups.

Heteroaryl groups are aromatic ring compounds containing 5 or more ring members, of which, one or more is a heteroatom such as, but not limited to, N, O, and S. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl moiety, or both.

Heteroarylalkyl groups are alkyl groups as defined above in which a hydrogen or carbon bond of an alkyl group is replaced with a bond to a heteroaryl group as defined above. Heteroarylalkyl groups can be substituted on the heteroaryl moiety, the alkyl moiety, or both.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or Spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The term "amine" (or "amino"), where referring to a compound, includes primary, secondary, tertiary amines and quaternary ammonium salts, and to molecules containing one or more amino groups. When referring to a substituent group, the terms include functional groups having a basic nitrogen in free, salt, or quaternarized form, e.g., the formula —$NR_2$ or —$NR_3^+$ wherein each R can independently be hydrogen, alkyl, aryl, heterocyclyl, and the like. Amino groups include, but are not limited to, —$NH_2$, alkylamino, dialkylamino, arylamino, alkylarylamino, diarylamino, aralkylamino, and heterocyclylamino groups and the like. Quarternary ammonium salts are amine or amino groups within the meaning herein, for example a trimethylammonium group bonded to a carbon moiety is an amino group. Thus, trimethylammonium hydrochloride and tetramethylammonium chloride are both ammonium ions, and amines, within the meaning herein.

The term "amide" (or "amino") includes C- and N-amide groups, i.e., —$C(O)NR_2$, and —$NRC(O)R$ groups, respectively. Amide groups therefore include but are not limited to carbamoyl groups (—$C(O)NH_2$) and formamide groups (—$NHC(O)H$).

The term "urethane" (or "carbamyl") includes N- and O-urethane groups, i.e., —$NRC(O)OR$ and —$OC(O)NR_2$ groups, respectively.

The term "sulfonamide" (or "sulfonamido") includes S- and N-sulfonamide groups, i.e., —$SO_2NR_2$ and —$NRSO_2R$ groups, respectively. Sulfonamide groups therefore include but are not limited to sulfamoyl groups (—$SO_2NH_2$).

The term "amidine" or "amidino" includes groups of the formula —$C(NR)NR_2$. Typically, an amidino group is —$C(NH)NH_2$.

The term "guanidine" or "guanidino" includes groups of the formula —$NRC(NR)NR_2$. Typically, a guanidino group is —$NHC(NH)NH_2$.

"Halo," "halogen," and "halide" include fluorine, chlorine, bromine and iodine.

The terms "comprising," "including," "composed of," are open-ended terms as used herein, and do not preclude the existence of additional elements or components. In a claim element, use of the forms "comprising," "having," or "including" means that whatever element is comprised, had, or included, is not necessarily the only element encompassed by the subject of the clause that contains that word.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

COMPOUNDS OF THE INVENTION

An embodiment of the present invention provides a compound of formula (I):

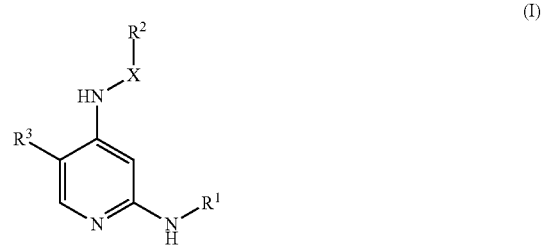

wherein:

$R^1$ and $R^2$ are each independently a 5-12 membered monocyclic, bicyclic or polycyclic, aromatic or partially aromatic ring system wherein each ring system independently comprises 0-3 heteroatoms selected from the group consisting of N, O, S, S(O), and $S(O)_2$, and each ring system is substituted with 0-5 substituents independently selected from Y;

wherein Y comprises halo, hydroxyl, cyano, thio, nitro, trifluoromethyl, oxo, $(C_1$-$C_6)$alkyl, $(C_2$-$C_6)$alkenyl, $(C_2$-$C_6)$ alkynyl, alkoxy, methylenedioxy, ethylenedioxy, NH(R), N(R)$_2$, SR, C(O)NH(R), C(O)N(R)$_2$, RC(O)N(R), C(O)C(O)NR$_2$, C(O)C(O)OR, RC(O)O, ROC(O), RC(O), RSO$_2$, RSO$_2$($C_1$-$C_3$)alkyl, SO$_2$N(R)$_2$, N(R)SO$_2$R, urea bearing 0-3 R, $(C_5$-$C_{10})$aryl, $(C_2$-$C_{10})$heteroaryl, $(C_2$-$C_{10})$dihydroheteroaryl, $(C_2$-$C_{10})$tetrahydroheteroaryl, $(C_2$-$C_{10})$hexahydroheteroaryl, $(C_3$-$C_{10})$mono- or bicyclic cycloalkyl, or $(C_2$-$C_{10})$mono- or bicyclo-heterocyclyl, wherein each wherein each R independently comprises hydrogen or substituted or unsubstituted aryl or substituted or unsubstituted $(C_1$-$C_6)$ alkyl, or where two R groups taken together with a nitrogen atom to which they are attached form together with the nitrogen atom a heterocyclic ring comprising 0-2 additional heteroatoms selected from the group consisting of N, O, S, S(O), and S(O)$_2$, and substituted with 0-3 $(C_1$-$C_3)$alkyl, hydroxyl, $(C_1$-$C_3)$hydroxyalkyl or $(C_1$-$C_3)$alkoxy$(C_1$-$C_3)$alkyl groups;

wherein any alkyl, alkenyl, alkynyl, alkoxy, aryl, heteroaryl, dihydroheteroaryl, tetrahydroheteroaryl, hexahydroheteroaryl, cycloalkyl or heterocyclyl of Y or R, or both, can be further substituted by 1-3 substituents selected from halo, hydroxyl, cyano, thio, nitro, trifluoromethyl, oxo, $(C_1$-$C_6)$ alkyl, $(C_2$-$C_6)$alkenyl, $(C_2$-$C_6)$alkynyl, alkoxy, methylenedioxy, ethylenedioxy, NH(R), N(R)$_2$, SR, C(O)NH(R), C(O)N(R)$_2$, RC(O)N(R), C(O)C(O)NR$_2$, C(O)C(O)OR, RC(O)O, ROC(O), RC(O), RSO$_2$, RSO$_2$($C_1$-$C_3$)alkyl, SO$_2$N(R)$_2$, N(R)SO$_2$R, urea bearing 0-3 R, or with a substituted or unsubstituted $(C_5$-$C_{10})$aryl, $(C_2$-$C_{10})$heteroaryl, $(C_2$-$C_{10})$dihydroheteroaryl, $(C_2$-$C_{10})$tetrahydroheteroaryl, $(C_2$-$C_{10})$hexahydroheteroaryl, $(C_3$-$C_{10})$mono- or bicyclic cycloalkyl, or $(C_2$-$C_{10})$mono- or bicyclo-heterocyclyl;

X is a bond or $(C_1$-$C_3)$alkyl comprising 0-1 heteroatom selected from the group consisting of NR, O, S, S(O), and S(O)$_2$, wherein the $(C_1$-$C_3)$alkyl is substituted with 0-1 hydroxy, halo, $(C_1$-$C_3)$alkoxy, $(C_1$-$C_3)$alkylamino, or $(C_1$-$C_3)_2$dialkylamino groups; the alkyl group X can be bonded to the pyridine 4-amino group and to $R^2$ at any combination of atoms of the alkyl group, including on the same atom so, for example, an n-propyl group can be bonded both to the pyridine 4-amino group and to $R^2$ on the same carbon atom of the n-propyl group, such as the 2-carbon; alternatively the pyridine 4-amino group and $R^2$ can be bonded to different carbon atoms of the alkyl group X, such as in the case of a 1,3-disubstituted propyl group.

$R^3$ is trifluoromethyl, halo, nitro, or cyano;

or a salt, tautomer, solvate, hydrate, or a prodrug thereof.

Various embodiments of the inventive compounds are derivatives of 2,4-diaminopyridine bearing a halo, nitro, trifluoromethyl or cyano group on the pyridine 5-position, wherein the 2-amino and 4-amino groups both bear ring structures, optionally via a 1-3 carbon linker X for the 4-amino group substituent. The pyridine 2-amino and 4-amino substituents can be monocyclic or bicyclic, aromatic or partly aromatic, carbocyclic or heterocyclic ring systems, containing 5-10 constituent atoms each, which can be further substituted as described herein.

$R^1$ is bonded directly to the pyridine 2-amino group, but $R^2$ can be bonded to the pyridine 4-amino group directly or can be linked through a linking group X, wherein X comprises a bond or $(C_1$-$C_3)$alkyl wherein the $(C_1$-$C_3)$alkyl can include 0-1 heteroatom selected from the groups consisting of O, S, NH, or NR, and can be substituted with 0-1 hydroxy, halo, $(C_1$-$C_3)$alkoxy, $(C_1$-$C_3)$alkylamino, or $(C_1$-$C_3)_2$dialkylamino groups. In one embodiment, X is a bond. In another embodiment, X is a methylene group. In another embodiment, X is an ethyl group (which can be 1, 1 or 1,2 bonded) or an n-propyl group (which can be bonded in any chemically feasible manner to the pyridine 4-amino group and to $R^2$). Examples are provided in Table 1.

For example, $R^1$ can be selected from phenyl, pyridine, pyrimidine, thiazole, oxazole, pyrazole, triazole, imidazole, pyrazine, pyridazine, triazine, indole, 2,3-dihydro-isoindole-1-one, or 3,4-dihydro-1H-quinolin-2-one groups substituted with 0-3 Y groups as defined above.

In another embodiment, $R^2$ can be selected from phenyl, pyridine, pyrimidine, oxazole, pyrazole, triazole, imidazole, pyrazine, pyridazine, triazine, indole, 2,3-dihydro-isoindole-1-one, or 3,4-dihydro-1H-quinolin-2-one substituted with 0-3 Y groups.

More specifically, $R^1$ or $R^2$ can be a phenyl, such as a substituted phenyl.

Further compounds of the invention can include heterocyclic groups bonded to the pyridyl amino groups. For example $R^1$ or $R^2$ can be pyridinyl, thiazolyl, isoindolyl, quinolyl, pyrimidyl and the like.

The phenyl or heteroaryl or partially reduced heteroaryl groups can bear substituents as defined above, for example, it can bear any of the substituents shown on the respective phenyl group substituents as shown for selected compounds in Table 1 below including methoxy, oxo, methylsulfonyl, N-methylaminosulfonyl, morpholinyl, N-methylcarboxamide, or N,N-dimethylcarboxyamido. Other substituents can be provided, for example through the simple expedient of selecting the appropriate reagents for use in the inventive method of preparation.

In various embodiments, the compound or set of compounds, either per se or as are used in practice of embodiments of the inventive methods, can be any one of any of the combinations and/or sub-combinations of the above-listed embodiments.

Specific examples of inventive compounds are provided in Table 1 and in the Examples section herein.

Methods of Preparation

An embodiment of the present invention provides a method of preparation of the inventive FAK-inhibitory compounds, involving the coupling of a pyridine group bearing a leaving group at the 2-position with an aryl or heteroaryl amino group in the presence of a zero-valent palladium complex, which serves as a catalyst. By "zero-valent" is meant that the palladium metal of the complex is in the 0 oxidation state; that is, the complex is formed between ligands and palladium existing as a neutral metal atom. The palladium catalyst can be Pd$_2$(dba)$_3$, a complex of palladium metal and dibenzylideneacetone. Addition of a phosphine-bearing ligand, for example xantphos, 9,9-dimethyl-4,5-bis(diphenylphosphino)xanthene, can result in formation of complex between the palladium and the phosphorus-containing ligand, which is also effective in bringing about a coupling reaction between the pyridine derivative bearing a leaving group and the aryl or heteroaryl amine.

The coupling reaction between the pyridine bearing a leaving group on the 2-position, and the aryl or heteroarylamine, in the presence of the zero-valent palladium catalyst can be carried out in any suitable organic solvent, for example in dioxane. An acid scavenger such as cesium carbonate can be added. The reaction can be conducted at any suitable temperature, and for any suitable duration. For example, the reaction temperature can be about 100-140° C., and the reaction can be carried out for a duration of about 20 minutes to about 12 hours.

Another embodiment of the present invention provides a method of preparation of the inventive FAK-inhibitory compounds, involving the coupling of a pyridine group bearing a leaving group at the 2-position with an aryl or heteroaryl amino group in the presence of an acid. The acid can be hydrochloric acid, such as aqueous hydrochloric acid, and the reaction can be carried out in n-butanol solution, for example at about 140° C. for about 12 hours.

Compositions and Combination Treatments

Another aspect of an embodiment of the invention provides compositions of the compounds of the invention, alone or in combination with another FAK inhibitor or another type of kinase inhibitor or another type of therapeutic agent, or all of the above. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy,* 19th Ed., 1995, incorporated by reference herein. The compositions can appear in conventional forms, for example capsules, tablets, aerosols, solutions, suspensions or topical applications.

Typical compositions include a compound of the invention which inhibits the enzymatic activity of the focal adhesion kinase, and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention which inhibits the enzymatic activity of the focal adhesion kinase to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly (anhydrides).

For nasal administration, the preparation can contain a compound of the invention which inhibits the enzymatic activity of the focal adhesion kinase, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |

-continued

| Coating: | |
|---|---|
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such treatment, prevention, elimination, alleviation or amelioration of a malcondition that is mediated through the action of FAK, for example, cancer. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge. FAK inhibitor activity of the compounds of the invention can be determined by use of an in vitro assay system which measures the inhibition of FAK. Inhibition constants (i.e., $K_i$ or $IC_{50}$ values as known in the art) for the kinase inhibitors of the invention can be determined by the method described in the Examples.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g, specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

The compounds of the invention can be used therapeutically in combination with i) one or more other FAK inhibitors and/or ii) one or more other types of protein kinase inhibitors and/or one or more other types of therapeutic agents which can be administered orally in the same dosage form, in a separate oral dosage form (e.g., sequentially or non-sequentially) or by injection together or separately (e.g., sequentially or non-sequentially).

Accordingly, in another embodiment the invention provides combinations, comprising:
a) a compound of the invention as described herein; and
b) one or more compounds comprising:
   i) other compounds of the present invention,
   ii) other protein kinase inhibitors, such as inhibitors of PYK2 or src, or
   iii) other anti-cancer agents.

Combinations of the invention include mixtures of compounds from (a) and (b) in a single formulation and compounds from (a) and (b) as separate formulations. Some combinations of the invention can be packaged as separate formulations in a kit. In some embodiments, two or more compounds from (b) are formulated together while a compound of the invention is formulated separately.

The dosages and formulations for the other agents to be employed, where applicable, will be as set out in the latest edition of the *Physicians' Desk Reference*, incorporated herein by reference.

Methods of Treatment

An embodiment of the present invention provides a method for inhibiting a protein kinase, such as FAK, with a compound of the invention. The method involves contacting the protein kinase with a suitable concentration of an inventive compound. The contacting can take place in vitro, for example in carrying out an assay to determine the kinase inhibitory activity of an inventive compound undergoing experimentation related to a submission for regulatory approval. For example, an assay can include a control compound, an experimental inventive compound, the kinase enzyme under study such as FAK, a suitable substrate for the enzyme, and optionally a reporter group of some kind such as a fluorescent or a radiolabeled reporter group, along with suitable solutions and buffers for carrying out the assay. The components of the assay can be provided as a kit, including the components as listed above plus informational material, such as a brochure or a computer-readable disc.

The method for inhibiting a protein kinase, such as FAK, can also be carried out in vivo, that is, within the living body of a mammal, such as a human patient or a test animal. The inventive compound can be supplied to the living organism via one of the routes as described above, e.g., orally, or can be provided locally within the body tissues, for example by injection of a tumor within the organism. In the presence of the inventive compound, inhibition of the kinase takes place, and the effect thereof can be studied.

An embodiment of the present invention provides a method of treatment of a malcondition in a patient that is mediated by abnormal protein kinase activities, wherein the patient is administered the inventive compound in a dosage, at a frequency, and for a duration to produce a beneficial effect on the patient. The inventive compound can be administered by any suitable means, examples of which are described above. As discussed above, it is believed that cancer can be one such malcondition that is mediated by abnormal protein kinase activities, specifically by abnormal FAK activities, such as in malignant cells undergoing metastasis. It is believed that inhibition of such abnormal activities can serve to either kill metastasizing cells, inactivate them, reduce their mobility within the body, or reverse their metastatic transformation.

It is believed that there are at least two mechanisms by which inhibition of FAK can act to effectively treat cancer. In the first mechanism, certain tumors are believed to be activated or driven by FAK, such that inhibition of FAK will serve to kill the tumor cells. In the second mechanism, FAK is believed to be involved in the adhesion of metastasizing cancer cells in circulation in the lymph system to sites wherein they bring about metastatic transformation of new cell populations. In these cases, blocking adhesion serves not only to prevent the induction of new sites of the cancer, but the circulating metastasized cells are caused to undergo apoptosis, resulting in their death.

EXAMPLES

TABLE 1

Exemplary Compounds of the Invention

| Compound # | Structure (as TFA salt) | Synthetic Example | MW (MS, m/z, as TFA salt) |
|---|---|---|---|
| 1 | | Ex. 1 | 673.5 |
| 2 | | Ex. 3 | 537.6 |
| 3 | | Ex. 9 | 581.5 |
| 4 | | Ex. 8 | 627.6 |

TABLE 1-continued

Exemplary Compounds of the Invention

| Compound # | Structure (as TFA salt) | Synthetic Example | MW (MS, m/z, as TFA salt) |
|---|---|---|---|
| 5 | | — | 629.6 |
| 6 | | Ex. 10 | 501.5 |
| 7 | | Ex. 2 | 446.2 |
| 8 | | Ex. 4 | 492.1 |
| 9 | | Ex. 5 | 506.15 |
| 10 | | Ex. 6 | 516.2 |

TABLE 1-continued

Exemplary Compounds of the Invention

| Compound # | Structure (as TFA salt) | Synthetic Example | MW (MS, m/z, as TFA salt) |
|---|---|---|---|
| 11 | | Ex. 7 | 484.15 |
| 12 | | Ex. 11 | 470.2 |
| 13 | | Ex. 12 | 515.2 |
| 14 | | Ex. 13 | 673.5 |
| 15 | | Ex. 15 | 604.5 |
| 16 | | Ex. 14 | 650.6 |

TABLE 1-continued

Exemplary Compounds of the Invention

| Compound # | Structure (as TFA salt) | Synthetic Example | MW (MS, m/z, as TFA salt) |
|---|---|---|---|
| 17 | | Ex. 16 | 565.2 |
| 18 | | Ex. 17 | 505.2 |
| 19 | | Ex. 18 | 459.3 |
| 20 | | Ex. 19 | 537.2 |
| 21 | | Ex. 20 | 460.3 |
| 22 | | — | 588.5 |

TABLE 1-continued

Exemplary Compounds of the Invention

| Compound # | Structure (as TFA salt) | Synthetic Example | MW (MS, m/z, as TFA salt) |
|---|---|---|---|
| 23 | | — | 562.9 |
| 24 | | Ex. 22 | 643.6 |
| 25 | | — | 654.6 |
| 26 | | — | 614.5 |
| 27 | | — | 554.5 |
| 28 | | — | 567.5 |

TABLE 1-continued

Exemplary Compounds of the Invention

| Compound # | Structure (as TFA salt) | Synthetic Example | MW (MS, m/z, as TFA salt) |
|---|---|---|---|
| 29 | | — | 680.6 |
| 30 | | — | 568.5 |
| 31 | | — | 472.5 |
| 32 | | Ex. 21 | 509.1 |

TABLE 1-continued

Exemplary Compounds of the Invention

| Compound # | Structure (as TFA salt) | Synthetic Example | MW (MS, m/z, as TFA salt) |
|---|---|---|---|
| 33 | | Ex. 23 | 537.1 |
| 34 | | Ex. 24 | 556.1 |
| 35 | | Ex. 26 | 388.1 |
| 36 | | Ex. 27 | 389.1 |
| 37 | | Ex. 28 | 388.1 |

TABLE 1-continued

Exemplary Compounds of the Invention

| Compound # | Structure (as TFA salt) | Synthetic Example | MW (MS, m/z, as TFA salt) |
|---|---|---|---|
| 38 | | Ex. 29 | 465.1 |
| 39 | | Ex. 30 | 495.1 |
| 40 | | Ex. 31 | 458.1 |
| 41 | | Ex. 32 | 444.1 |

TABLE 1-continued

Exemplary Compounds of the Invention

| Compound # | Structure (as TFA salt) | Synthetic Example | MW (MS, m/z, as TFA salt) |
|---|---|---|---|
| 42 | | Ex. 33 | 530.2 |
| 43 | | Ex. 34 | 559.1 |
| 44 | | Ex. 35 | 530.1 |
| 45 | | Ex. 36 | 575.11 |

TABLE 1-continued

Exemplary Compounds of the Invention

| Compound # | Structure (as TFA salt) | Synthetic Example | MW (MS, m/z, as TFA salt) |
|---|---|---|---|
| 46 | | Ex. 37 | 435.1 |
| 47 | | Ex. 38 | 530.25 |
| 48 | | Ex. 39 | 532.2 |
| 49 | | Ex. 40 | 488.2 |

TABLE 1-continued

Exemplary Compounds of the Invention

| Compound # | Structure (as TFA salt) | Synthetic Example | MW (MS, m/z, as TFA salt) |
|---|---|---|---|
| 50 | | Ex. 41 | 472.1 |
| 51 | | Ex. 42 | 459.15 |
| 52 | | Ex. 43 | 543.2 |
| 53 | | Ex. 44 | 486.2 |

TABLE 1-continued

Exemplary Compounds of the Invention

| Compound # | Structure (as TFA salt) | Synthetic Example | MW (MS, m/z, as TFA salt) |
|---|---|---|---|
| 54 | | Ex. 45 | 402.2 |
| 55 | | Ex. 46 | 402.2 |
| 56 | | Ex. 47 | 442.1 |
| 57 | | Ex. 48 | 458.2 |

TABLE 1-continued

Exemplary Compounds of the Invention

| Compound # | Structure (as TFA salt) | Synthetic Example | MW (MS, m/z, as TFA salt) |
|---|---|---|---|
| 58 | | Ex. 49 | 472.2 |
| 59 | | Ex. 50 | 473.2 |
| 60 | | Ex. 51 | 490.2 |
| 61 | | Ex. 52 | 502.2 |

TABLE 1-continued

Exemplary Compounds of the Invention

| Compound # | Structure (as TFA salt) | Synthetic Example | MW (MS, m/z, as TFA salt) |
|---|---|---|---|
| 62 | | Ex. 53 | 523.25 |
| 63 | | Ex. 54 | 536.2 |
| 64 | | Ex. 55 | 512.2 |
| 65 | | Ex. 56 | 511.25 |

TABLE 1-continued

Exemplary Compounds of the Invention

| Compound # | Structure (as TFA salt) | Synthetic Example | MW (MS, m/z, as TFA salt) |
|---|---|---|---|
| 66 | | Ex. 57 | 507.15 |
| 67 | | Ex. 58 | 459.2 |
| 68 | | Ex. 59 | 486.2 |
| 69 | | Ex. 60 | 515.2 |

TABLE 1-continued

Exemplary Compounds of the Invention

| Compound # | Structure (as TFA salt) | Synthetic Example | MW (MS, m/z, as TFA salt) |
|---|---|---|---|
| 70 | | Ex. 61 | 475.2 |
| 71 | | Ex. 62 | 491.5 |
| 72 | | Ex. 63 | 507.2 |
| 73 | | Ex. 64 | 468.2 |

TABLE 1-continued

Exemplary Compounds of the Invention

| Compound # | Structure (as TFA salt) | Synthetic Example | MW (MS, m/z, as TFA salt) |
|---|---|---|---|
| 74 | | Ex. 65 | 512.1 |
| 75 | | Ex. 66 | 452.2 |
| 76 | | Ex. 67 | 520.2 |
| 77 | | Ex. 68 | 460.1 |

TABLE 1-continued
Exemplary Compounds of the Invention
| Compound # | Structure (as TFA salt) | Synthetic Example | MW (MS, m/z, as TFA salt) |
|---|---|---|---|
| 78 | 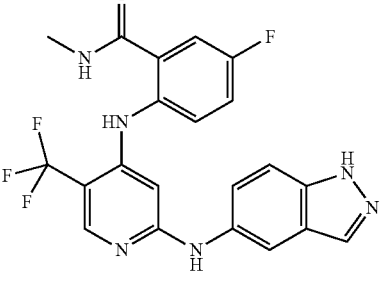 | Ex. 69 | 445.1 |
| 79 | 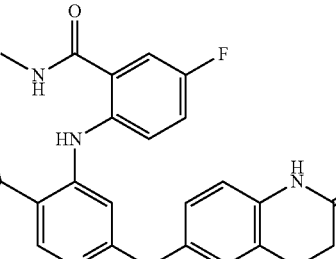 | Ex. 70 | 474.15 |
| 80 | 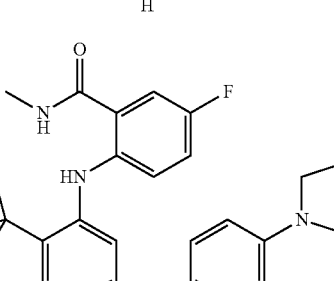 | Ex. 71 | 488.2 |
| 81 | 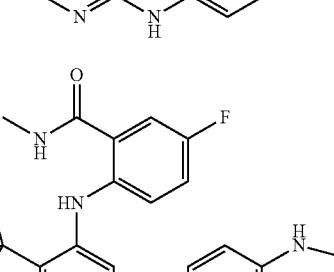 | Ex. 72 | 462.1 |
| 82 | 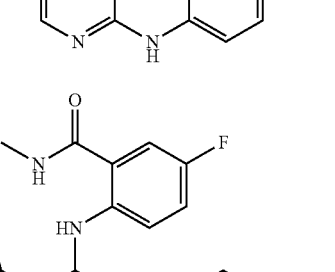 | Ex. 73 | 460.2 |

TABLE 1-continued

Exemplary Compounds of the Invention

| Compound # | Structure (as TFA salt) | Synthetic Example | MW (MS, m/z, as TFA salt) |
|---|---|---|---|
| 83 | | Ex. 74 | 499.2 |
| 84 | | Ex. 75 | 463.2 |
| 85 | | Ex. 76 | 435.1 |
| 86 | | Ex. 77 | — |

TABLE 1-continued

Exemplary Compounds of the Invention

| Compound # | Structure (as TFA salt) | Synthetic Example | MW (MS, m/z, as TFA salt) |
|---|---|---|---|
| 87 | | Ex. 78 | — |
| 88 | | Ex. 79 | 460.2 |
| 89 | | Ex. 80 | 428.15 |
| 90 | | Ex. 81 | 457.2 |

TABLE 1-continued

Exemplary Compounds of the Invention

| Compound # | Structure (as TFA salt) | Synthetic Example | MW (MS, m/z, as TFA salt) |
|---|---|---|---|
| 91 | | Ex. 82 | 443.15 |
| 92 | | Ex. 83 | 489.2 |
| 93 | | Ex. 84 | 457.15 |
| 94 | | Ex. 85 | 538.2 |

TABLE 1-continued

Exemplary Compounds of the Invention

| Compound # | Structure (as TFA salt) | Synthetic Example | MW (MS, m/z, as TFA salt) |
|---|---|---|---|
| 95 | | Ex. 86 | 478.1 |
| 96 | | Ex. 87 | 443.2 |
| 97 | | Ex. 88 | 443.2 |
| 98 | | Ex. 89 | 443.1 |
| 99 | | Ex. 90 | 444.15 |

TABLE 1-continued

Exemplary Compounds of the Invention

| Compound # | Structure (as TFA salt) | Synthetic Example | MW (MS, m/z, as TFA salt) |
|---|---|---|---|
| 100 | | Ex. 91 | 444.2 |
| 101 | | Ex. 92 | 442.2 |
| 102 | | Ex. 93 | 463.2 |
| 103 | | Ex. 94 | 386.2 |
| 104 | | Ex. 95 | 451.0 |

TABLE 1-continued

Exemplary Compounds of the Invention

| Compound # | Structure (as TFA salt) | Synthetic Example | MW (MS, m/z, as TFA salt) |
|---|---|---|---|
| 105 | | Ex. 96 | 469.2 |
| 106 | | Ex. 97 | 517.15 |
| 107 | | Ex. 98 | — |
| 108 | | Ex. 99 | 545.2 |

TABLE 1-continued

Exemplary Compounds of the Invention

| Compound # | Structure (as TFA salt) | Synthetic Example | MW (MS, m/z, as TFA salt) |
|---|---|---|---|
| 109 | | Ex. 100 | 527.2 |
| 110 | | Ex. 101 | 501.2 |
| 111 | | Ex. 102 | 445.1 |
| 112 | | Ex. 103 | 445.1 |

TABLE 1-continued

Exemplary Compounds of the Invention

| Compound # | Structure (as TFA salt) | Synthetic Example | MW (MS, m/z, as TFA salt) |
|---|---|---|---|
| 113 | | Ex. 104 | 431.1 |
| 114 | | Ex. 105 | 456.1 |
| 115 | | Ex. 106 | 506.98 |
| 116 | | Ex. 107 | — |

TABLE 1-continued

Exemplary Compounds of the Invention

| Compound # | Structure (as TFA salt) | Synthetic Example | MW (MS, m/z, as TFA salt) |
|---|---|---|---|
| 117 | | Ex. 108 | 525.1 |
| 118 | | Ex. 109 | 444.2 |
| 119 | | Ex. 110 | 509.1 |
| 120 | | | 615.5 |

TABLE 1-continued

Exemplary Compounds of the Invention

| Compound # | Structure (as TFA salt) | Synthetic Example | MW (MS, m/z, as TFA salt) |
|---|---|---|---|
| 121 | | | 606.5 |
| 122 | | | 600.6 |
| 123 | | | 445.3 |

Abbreviations

| DCM | dichloromethane |
|---|---|
| DMSO | dimethylsulfoxide |
| FAK | focal adhesion kinase |
| HPLC | high pressure liquid chromatography |
| M | molar |
| MeOH | methanol |
| MTBD | 7-methyl-1,5,7-triazabicyclo[4.4.0]dec-5-ene |
| Pd$_2$(dba)$_3$ | Tris(dibenzylideneacetone)dipalladium(0). |
| TFA | trifluoracetic acid |
| Xantphos | 9,9-Dimethyl-4,5-bis(diphenylphosphino)xanthene |

General Procedures

Method A: A mixture of the aryl halide, the aniline or amine (1.5 eq.), Pd$_2$(dba)$_3$ (0.05-0.2 eq), xantphos (0.1-0.3 eq) and cesium carbonate (2 eq.) in dioxane is heated in a Biotage Initiator microwave synthesizer at 140° C. for 2 h. The solvent is removed and following aqueous work-up and/or filtration the residue is purified by preparative HPLC (0.1% TFA in water/acetonitrile gradient) or silica gel chromatography (dichloromethane/methanol or ethyl acetate/hexanes gradient).

Method B: A mixture of the aryl halide, the aniline or amine (1.0 eq.), Pd$_2$(dba)$_3$ (0.05-0.2 eq), xantphos (0.1-0.3 eq.) and cesium carbonate (2 eq.) in dioxane is heated in a Biotage Initiator microwave synthesizer at 120° C. for 20-30 min. The solvent is removed and following aqueous work-up and/or filtration the residue is purified by preparative HPLC (0.1% TFA in water/acetonitrile gradient) or silica gel chromatography (dichloromethane/methanol or ethyl acetate/hexanes gradient).

Method C: A mixture of the aryl halide, the aniline or amine (1.5 eq.), Pd$_2$(dba)$_3$ (0.05-0.2 eq), xantphos (0.1-0.3 eq.) and cesium carbonate (2 eq.) in dioxane is heated in a Biotage Initiator microwave synthesizer at 90-100° C. for 4 h. The solvent is removed and following aqueous work-up and/or filtration the residue is purified by preparative HPLC (0.1% TFA in water/acetonitrile gradient) or silica gel chromatography (dichloromethane/methanol or ethyl acetate/hexanes gradient gradient).

Method D: A mixture of the aryl halide, the aniline or amine (1.5 eq.), Pd$_2$(dba)$_3$ (0.05-0.2 eq), xantphos (0.1-0.3 eq.) and cesium carbonate (2 eq.) in dioxane is heated in an oil bath at 100° C. for 12-15 h. The solvent is removed and following aqueous work-up and/or filtration the residue is purified by preparative HPLC (0.1% TFA in water/acetonitrile gradient) or silica gel chromatography (dichloromethane/methanol or ethyl acetate/hexanes gradient).

Method E: A mixture of the aryl halide, the aniline or amine (1 eq.), $Pd_2(dba)_3$ (0.05-0.2 eq), xantphos (0.1-0.3 eq.) and cesium carbonate (2 eq.) in dioxane is heated in a Biotage Initiator microwave synthesizer at 100° C. for 1 h. The solvent is removed and following aqueous work-up and/or filtration the residue is purified by preparative HPLC (0.1% TFA in water/acetonitrile gradient) or silica gel chromatography (dichloromethane/methanol or ethyl acetate/hexanes gradient).

Method F: The mixture of the aryl halide, the aniline (1 eq.) and aq. HCl (1 eq.) in n-butanol is heated in an oil bath at 140-160° C. for 12-14 h. It is neutralized, the solvent is removed and following aqueous work-up and/or filtration the residue is purified by preparative HPLC (0.1% TFA in water/acetonitrile gradient) or silica gel chromatography (dichloromethane/methanol or ethyl acetate/hexanes gradient).

Method G: To a 25 mL round bottom flask charged with the appropriate iodopyridine (1 equiv), $Pd_2(dba)_3$ (0.05 eq.), xantphos (0.05 equiv) and 2-amino-N-methylbenzamide (1.05 eq.), 1,2-dichlorobenzene is added followed by the addition of MTBD (2 eq.). The round bottom flask is capped with a rubber septum and argon is purged through the solution for 30 min. The reaction is heated at 80° C. for 12 hrs. The volatiles are evaporated and the crude subjected to preparative HPLC affording the desired product.

Method H: To a 25 mL round bottom flask charged with the appropriate pyridine derivative (1 eq.), $Pd_2(dba)_3$ (0.1 eq.), xantphos (0.1 eq.) and the aniline (1.05 eq.), 1,2-dichlorobenzene is added followed by the addition of MTBD (2.5 eq.). The reaction mixture is degassed with argon during 15 min before being heated to 90° C. After 16 h at 90° C. the volatiles are evaporated. The crude is further purified by preparative HPLC affording the desired product.

General procedure for the preparation of 4-iodopyridines: To a solution of diisopropylamine (1.1 equiv) in anhydrous THF at 0° C., under an argon atmosphere, a 2.5 M solution of n-BuLi (1 equiv) in hexane is added dropwise. The reaction mixture is stirred for 30 min, then cooled to −78° C. A solution of the appropriate 2,5-disubstituted pyridine (1 equiv) precooled to −40° C. is added dropwise via a syringe. The resulting suspension is stirred for 15 min, after which a solution of $I_2$ (1.1 equiv) in THF, cooled to 0° C., is added. The reaction is stirred for an additional 10 min, then the reaction mixture is diluted with $H_2O$ and EtOAc. The organic layer is separated, dried over $Na_2SO_4$ and concentrated. The crude material can be further purified by preparative HPLC.

The following compounds were prepared in this way:

6-Chloro-4-iodonicotinonitrile

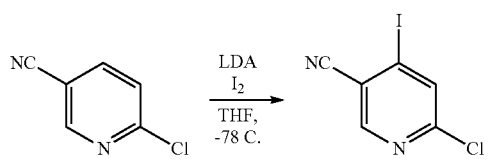 [SMILES: N#Cc1ccc(Cl)nc1 ; N#Cc1cnc(Cl)cc1I]

$^1$H NMR (THF-$d_8$) δ 8.51 (s, 1H), 8.09 (s, 1H).

2,5-Dichloro-4-iodopyridine

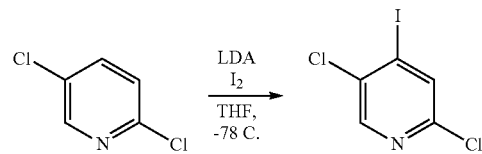 [SMILES: Clc1ccc(Cl)nc1 ; Clc1cc(I)c(Cl)cn1]

$^1$H NMR (CDCl$_3$) δ 8.37 (s, 1H), 7.88 (s, 1H).

2,5-Dibromo-4-iodopyridine

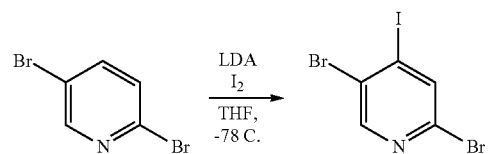

$^1$H NMR (THF-$d_8$) δ 8.37 (s, 1H), 8.06 (s, 1H).

6-Bromo-4-iodonicotinonitrile

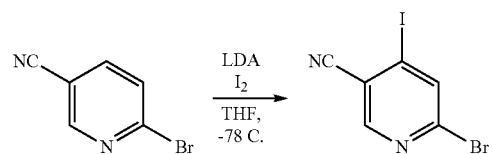 [SMILES: N#Cc1ccc(Br)nc1 ; N#Cc1cnc(Br)cc1I]

$^1$H NMR (THF-$d_8$) δ 8.59 (d, J=0.5 Hz, 1H), 8.35 (d, J=0.5 Hz, 1H).

2-Bromo-5-chloro-4-iodopyridine

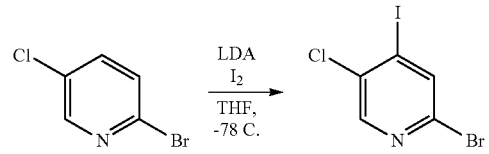 [SMILES: Clc1ccc(Br)nc1 ; Clc1cnc(Br)cc1I]

$^1$H NMR (THF-$d_8$) δ 8.37 (d, J=0.4 Hz, 1H), 8.18 (d, J=0.4 Hz, 1H).

2-Bromo-5-fluoro-4-iodopyridine

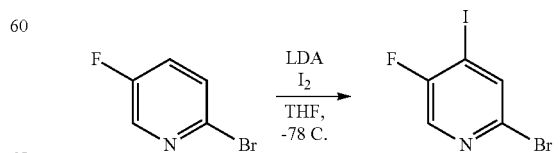

$^1$H NMR (THF-$d_8$) δ 8.37 (s, 1H), 7.84 (d, J=4.4 Hz, 1H).

EXAMPLE 1

N²-(2-methoxy-4-morpholinophenyl)-N⁴-(pyridin-2-yl)-5-(trifluoromethyl)pyridine-2,4-diamine

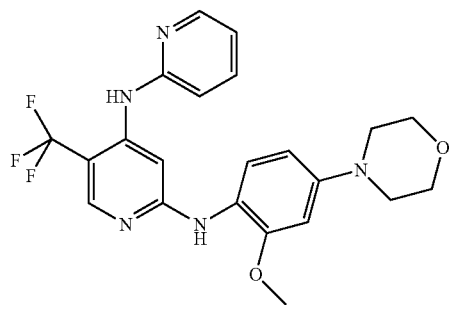

2-chloro-4-iodo-5-(trifluoromethyl)pyridine

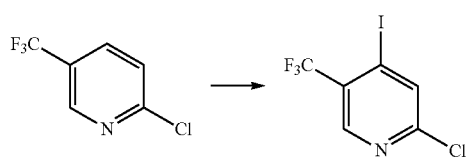 [SMILES: FC(F)(F)c1ccc(Cl)nc1 ; FC(F)(F)c1cnc(Cl)cc1I]

Literature Procedure: *Eur. J. Org. Chem.*, 2003, 1559-1568.
*Eur. J. Org. Chem.*, 2004, 3793-3798.

N-(2-chloro-5-(trifluoromethyl)pyridin-4-yl)pyridin-2-amine

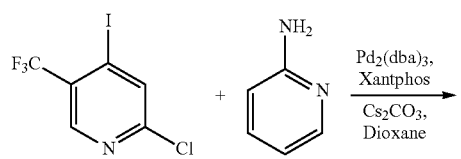

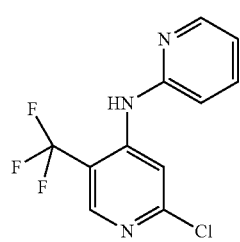

Method A was applied to a mixture of 2-chloro-4-iodo-5-(trifluoromethyl)pyridine (45 mg, 0.15 mmol), 2-aminopyridine (28 mg, 0.30 mmol), Pd₂(dba)₃ (12 mg, 0.013 mmol), xantphos (8 mg, 0.014 mmol) and cesium carbonate (108 mg, 0.33 mmol) in dioxane (2.5 ml).

N²-(2-methoxy-4-morpholinophenyl)-N⁴-(pyridin-2-yl)-5-(trifluoromethyl)pyridine-2,4-diamine

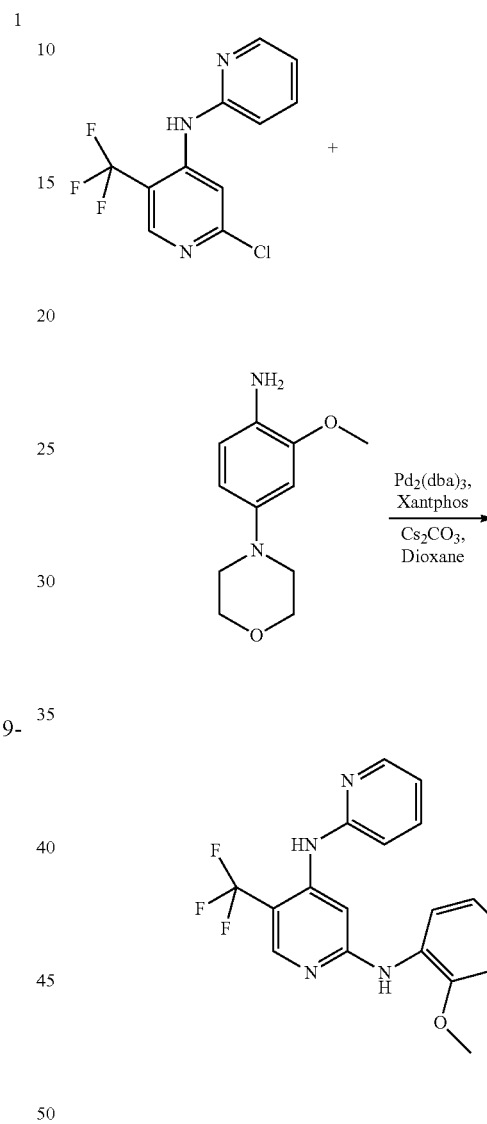

Method A was applied to a mixture of N-(2-chloro-5-(trifluoromethyl)pyridin-4-yl)pyridin-2-amine (16 mg, 0.059 mmol), 2-methoxy-4-morpholinoaniline (17 mg, 0.082 mmol), Pd₂(dba)₃ (6 mg, 0.0066 mmol), xantphos (5.5 mg, 0.0095 mmol) and cesium carbonate (43 mg, 0.13 mmol) in dioxane (3 ml). The bis-TFA salt of the title compound was obtained as a yellow solid.

¹H-NMR (400 MHz, d₆-DMSO) δ 9.15 (vbr s, 1H) 8.52 (br s, 1H), 8.28 (d, J=4.0 Hz, 1H), 8.11 (s, 1H), 7.79 (dt, 1H), 7.50 (s, 1H), 7.34 (d, J=7.6 Hz, 1H), 7.29 (d, J=8.4 Hz, 1H), 7.10 (t, J=5.6 Hz, 1H), 6.68 (d, J=2.4 Hz, 1H), 6.54 (dd, J=2.2, 8.6 Hz, 1H), 3.78 (s, 3H), 3.75 (t, J=4.8 Hz, 4H), 3.15 (t, J=4.6 Hz, 4H); $^{19}$F-NMR (376 MHz, d$_6$-DMSO) δ −58.6 (br s, 3F), −74.0 (s, 6F); MS (m/z): 446.2 [M+1]$^+$.

EXAMPLE 2

N$^2$-(2-methoxy-5-morpholinophenyl)-N$^4$-(pyridin-2-yl)-5-(trifluoromethyl)pyridine-2,4-diamine

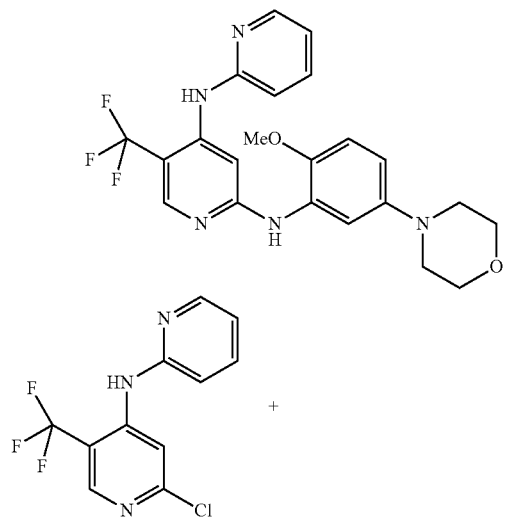

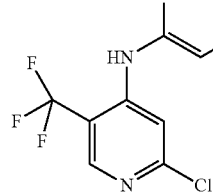

Method A was applied to a mixture of N-(2-chloro-5-(trifluoromethyl)pyridin-4-yl)pyridin-2-amine (40 mg, 0.15 mmol), 2-methoxy-5-morpholinoaniline (44 mg, 0.21 mmol), Pd$_2$(dba)$_3$ (13 mg, 0.014 mmol), xantphos (14 mg, 0.024 mmol) and cesium carbonate (101 mg, 0.31 mmol) in dioxane (3 ml). The TFA salt of the title compound was obtained as a yellow solid.

$^1$H-NMR (400 MHz, d$_6$-DMSO) δ 9.42 (vbr s, 1H), 8.74 (vbr s, 1H), 8.29 (dd, J=1.4, 5.0 Hz, 1H), 8.23 (s, 1H), 7.85-7.81 (m, 1H), 7.64 (s, 1H), 7.38 (d, J=8.0 Hz, 1H), 7.30 (br s, 1H), 7.14 (dt, 1H), 7.05 (d, J=9.2 Hz, 1H), 6.88 (dd, J=2.8, 8.8 Hz, 1H), 3.76-3.73 (s, t, 7H), 3.05 (t, J=4.4 Hz, 4H); MS (m/z): 446.2 [M+1]$^+$.

EXAMPLE 3

2-(2-(2-methoxy-4-morpholinophenylamino)-5-(trifluoromethyl)pyridin-4-ylamino)-N-methylbenzenesulfonamide

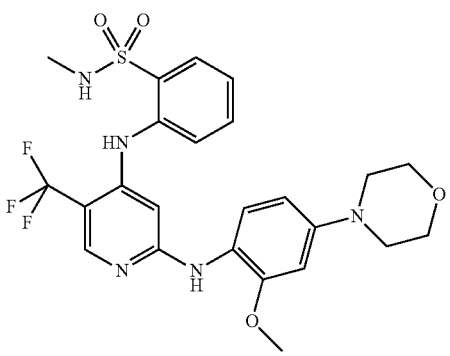

2-(2-chloro-5-(trifluoromethyl)pyridin-4-ylamino)-N-methylbenzenesulfonamide

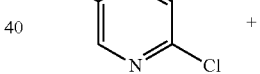

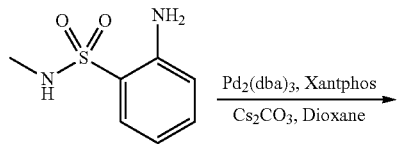

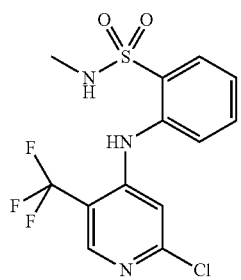

Method B was applied to a mixture of 2-chloro-4-iodo-5-(trifluoromethyl)pyridine (40 mg, 0.13 mmol), 2-amino-N-methylbenzenesulfonamide (22 mg, 0.12 mmol), Pd$_2$(dba)$_3$ (11 mg, 0.012 mmol), xantphos (12 mg, 0.021 mmol) and cesium carbonate (79 mg, 0.24 mmol) in dioxane (3.5 ml).

2-(2-(2-methoxy-4-morpholinophenylamino)-5-(trifluoromethyl)pyridin-4-ylamino)-N-methylbenzenesulfonamide

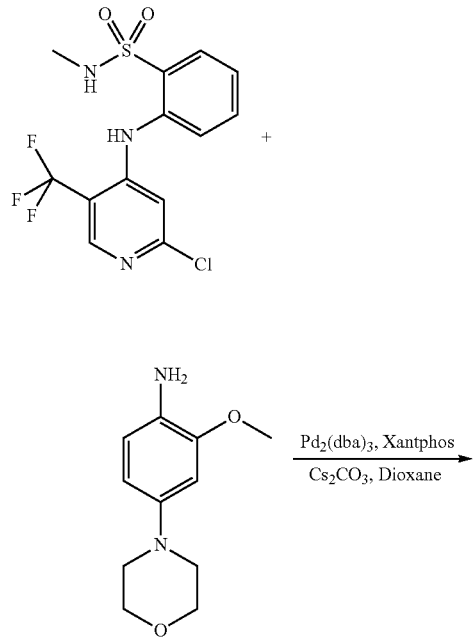

EXAMPLE 4

N-methyl-2-(2-(2-oxo-1,2,3,4-tetrahydroquinolin-6-ylamino)-5-(trifluoromethyl)pyridin-4-ylamino)benzenesulfonamide

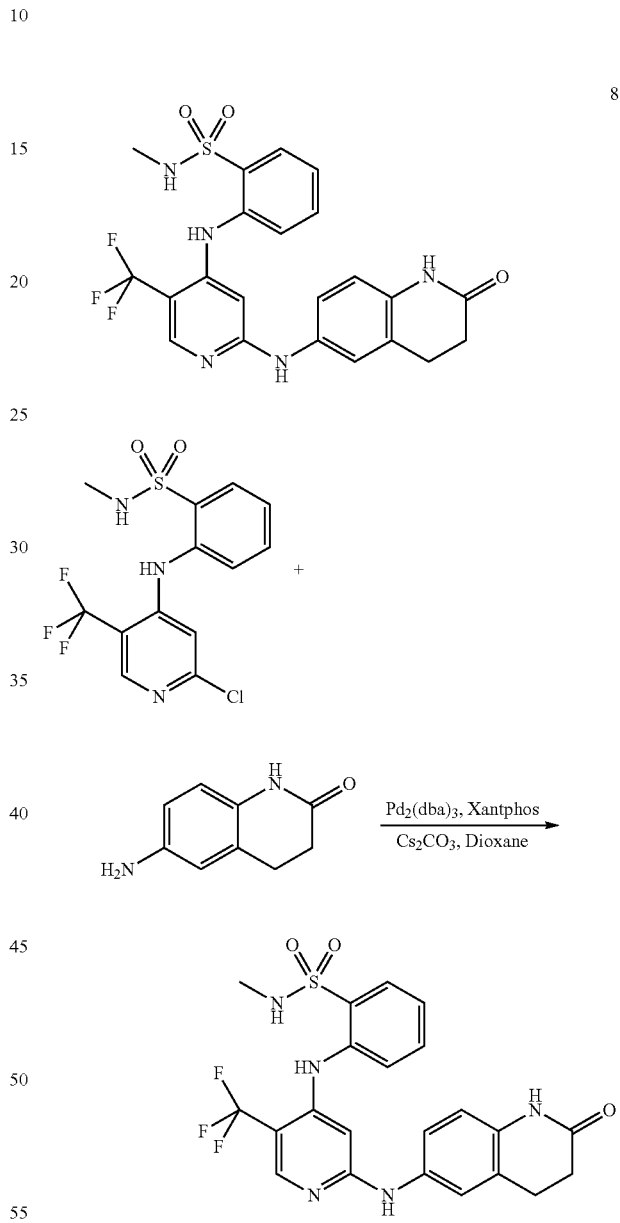

Method A was applied to a mixture of 2-(2-chloro-5-(trifluoromethyl)pyridin-4-ylamino)-N-methylbenzenesulfonamide (25 mg, 0.068 mmol), 2-methoxy-4-morpholinoaniline (25 mg, 0.12 mmol), $Pd_2(dba)_3$ (9 mg, 0.0098 mmol), xantphos (9 mg, 0.016 mmol) and cesium carbonate (48 mg, 0.15 mmol) in dioxane (3 ml). The TFA salt of the title compound was obtained as a pale yellow solid.

$^1$H-NMR (400 MHz, $d_6$-DMSO) δ 8.75 (v br s, 1H), 8.30 (br s, 1H), 8.16 (s, 1H), 7.81 (d, J=7.6 Hz, 1H), 7.69-7.64 (m, 2H), 7.59 (d, J=8.0 Hz, 1H), 7.39-7.32 (m, 2H), 6.63 (d, J=2.0 Hz, 1H), 6.49 (dd, J=2.0, 8.8 Hz, 1H), 6.42 (s, 1H), 3.78 (s, 3H), 3.74 (t, J=4.8 Hz, 4H), 3.11 (t, J=4.4 Hz, 4H), 2.44 (d, J=4.8 Hz, 3H); MS (m/z): 538.2 [M+1]$^+$.

Method A was applied to a mixture of 2-(2-chloro-5-(trifluoromethyl)pyridin-4-ylamino)-N-methylbenzenesulfonamide (31 mg, 0.085 mmol), 6-amino-3,4-dihydroquinolin-2(1H)-one (21 mg, 0.13 mmol), $Pd_2(dba)_3$ (10 mg, 0.011 mmol), xantphos (10 mg, 0.017 mmol) and cesium carbonate (75 mg, 0.23 mmol) in dioxane (3 ml). The TFA salt of the title compound was obtained as a pale yellow solid.

$^1$H-NMR (400 MHz, $d_6$-DMSO) δ 10.01 (s, 1H), 9.32 (br s, 1H), 8.26 (s, d, 2H), 7.83 (d, J=8.4 Hz, 1H), 7.73-7.64 (m, 2H), 7.35-7.31 (m, 2H), 7.22 (dd, J=2.0, 8.4 Hz, 1H), 6.78 (d,

J=8.4 Hz, 1H), 6.51 (s, 1H), 2.83 (t, J=7.6 Hz, 2H), 2.44-2.40 (s, t, 5H); $^{19}$F-NMR (376 MHz, d$_6$-DMSO) δ −58.8 (s), −74.7 (s); MS (m/z): 492.1 [M+1]$^+$.

EXAMPLE 5

N-methyl-2-(2-(4-(2-oxopyrrolidin-1-yl)phenylamino)-5-(trifluoromethyl)pyridin-4-ylamino)benzenesulfonamide

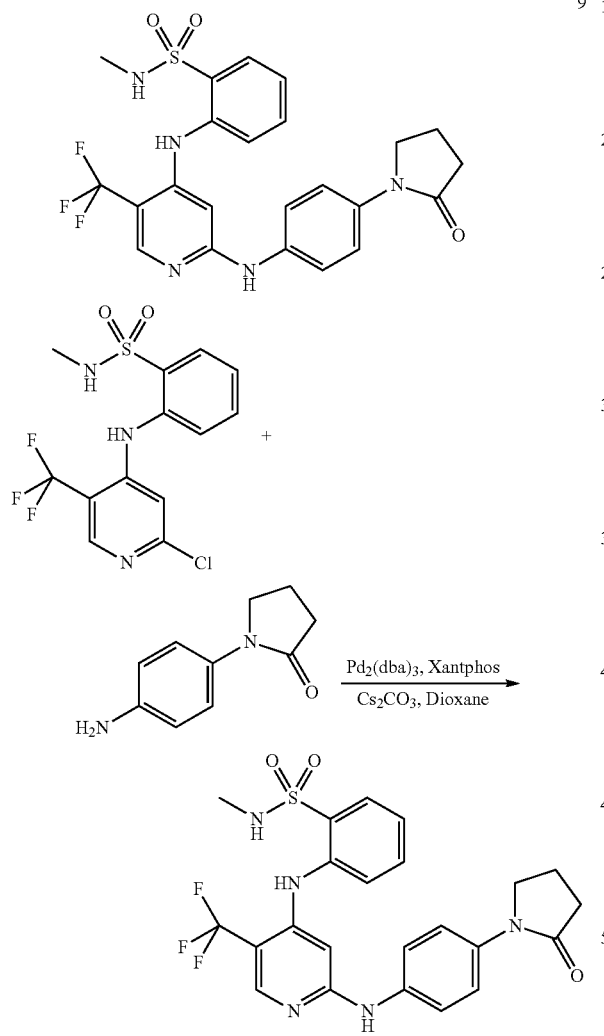

Method D was applied to a mixture of 2-(2-chloro-5-(trifluoromethyl)pyridin-4-ylamino)-N-methylbenzenesulfonamide (34 mg, 0.093 mmol), 1-(4-aminophenyl)pyrrolidin-2-one (25 mg, 0.14 mmol), Pd$_2$(dba)$_3$ (12 mg, 0.013 mmol), xantphos (12 mg, 0.021 mmol) and cesium carbonate (84 mg, 0.27 mmol) in dioxane (3.5 ml). The TFA salt of the title compound was obtained as a pale yellow solid.

$^1$H-NMR (400 MHz, d$_6$-DMSO) δ 9.38 (br s, 1H), 8.31 (s, 1H), 8.19 (br s, 1H), 7.82 (d, J=8.0 Hz, 1H), 7.73 (dd, 1H), 7.68 (dd, J=0.8, 4.0 Hz, 2H), 7.56 (s, 4H), 7.33-7.29 (m, 1H), 6.63 (s, 1H), 3.80 (t, J=7.0 Hz, 2H), 2.47 (s, 3H), 2.44 (d, 2H), 2.07-2.03 (m, 2H); $^{19}$F-NMR (376 MHz, d$_6$-DMSO) δ −58.7 (s, 3F), −74.7 (s, 3F); MS (m/z): 506.15 [M+1]$^+$.

EXAMPLE 6

2-(2-(2-methoxy-4-morpholinophenylamino)-5-(trifluoromethyl)pyridin-4-ylamino)-N,N-dimethylbenzamide

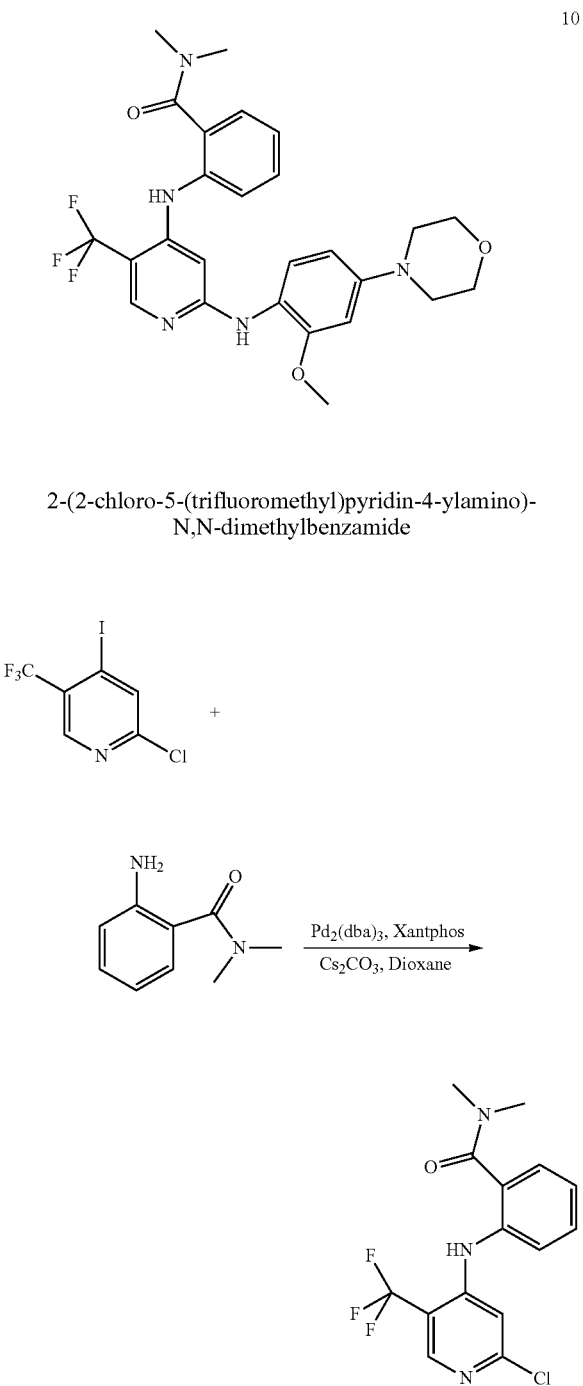

2-(2-chloro-5-(trifluoromethyl)pyridin-4-ylamino)-N,N-dimethylbenzamide

Method B was applied.

2-(2-(2-methoxy-4-morpholinophenylamino)-5-(trifluoromethyl)pyridin-4-ylamino)-N,N-dimethylbenzamide

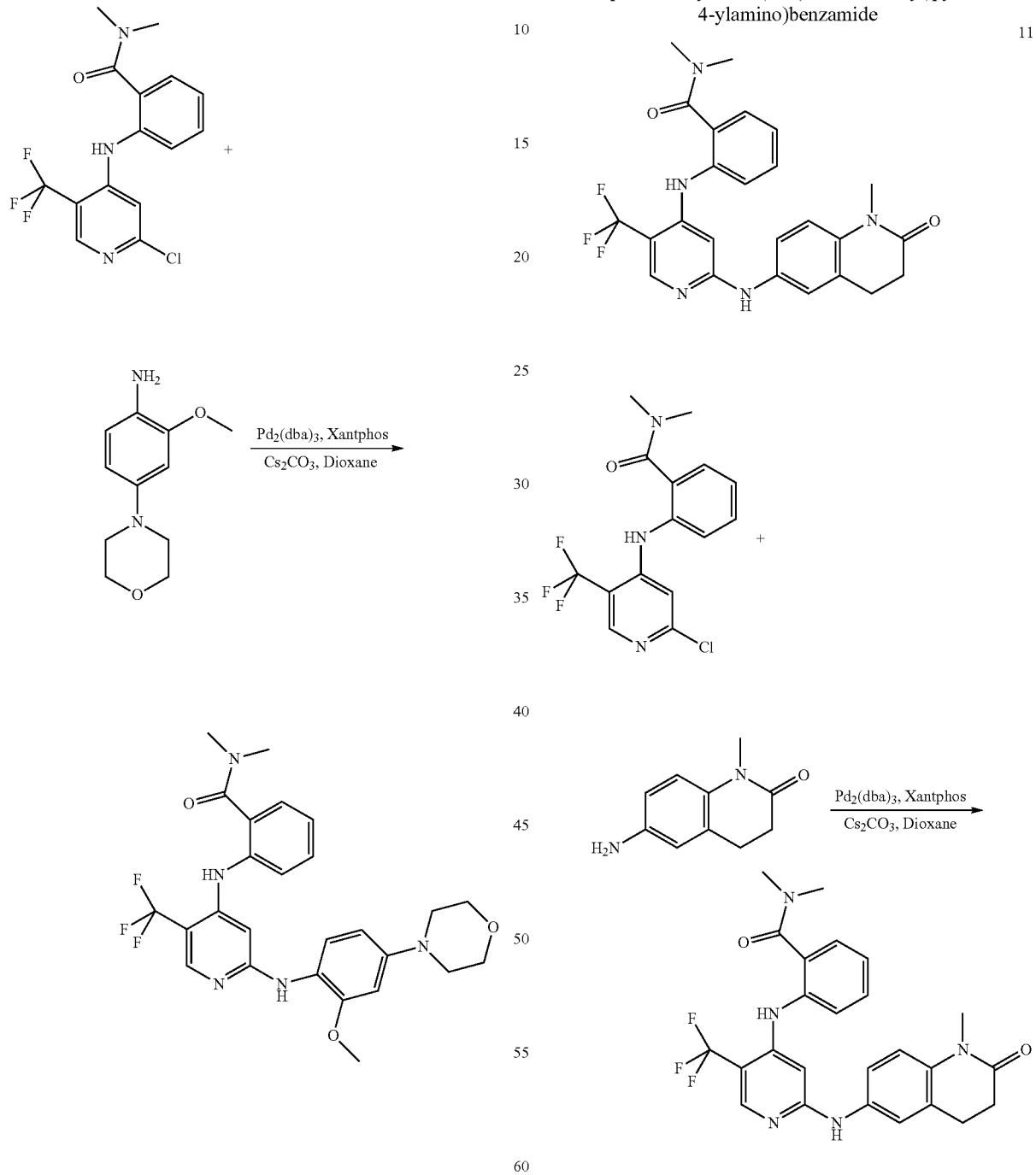

Method C was applied. The title compound was obtained as the TFA salt.

¹H NMR (400 MHz, DMSO-d$_6$) δ 9.37 (broad s, 1H), 8.76 (s, 1H), 7.96 (s, 1H), 7.54 (m, 1H), 7.45 (m, 2H), 7.35 (m, 1H), 7.19 (d, J=8.4 Hz, 1H), 6.64 (d, J=2.4 Hz, 1H), 6.50 (dd, J=8.4 Hz, 2.4 Hz, 1H), 3.76 (s, 3H), 3.73 (m, 4H), 3.15 (m, 4H), 2.92 (s, 3H), 2.86 (s, 3H); MS (m/z): 516.2 [M+1]$^+$.

EXAMPLE 7

N,N-dimethyl-2-(2-(1-methyl-2-oxo-1,2,3,4-tetrahydroquinolin-6-ylamino)-5-(trifluoromethyl)pyridin-4-ylamino)benzamide Method C was applied. The title compound was obtained as the TFA salt.

¹H-NMR (400 MHz, d$_6$-DMSO) δ 9.54 (br s, 1H), 8.46 (br s, 1H), 8.21 (s, 1H), 7.54-7.44 (m, 3H), 7.38 (d, J=2.4 Hz, 1H), 7.35-7.28 (m, 2H), 7.01 (d, J=8.8 Hz, 1H), 6.18 (s, 1H), 3.21 (s, 3H), 2.92 (s, 3H), 2.87 (s, 3H), 2.81 (t, J=7.2 Hz, 2H), 2.50 (t, partially covered by DMSO, 2H); $^{19}$F-NMR (376 MHz, d$_6$-DMSO) δ −59.8 (s, 3F), −74.5 (s, 3F); MS (m/z): 484.15 [M+1]$^+$.

EXAMPLE 8

7(2-(2-methoxy-4-morpholinophenylamino)-5-(trifluoromethyl)pyridin-4-ylamino)-2-methylisoindolin-1-one

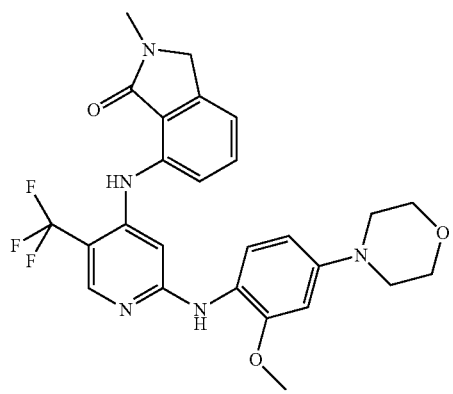

7-(2-chloro-5-(trifluoromethyl)pyridin-4-ylamino)-2-methylisoindolin-1-one

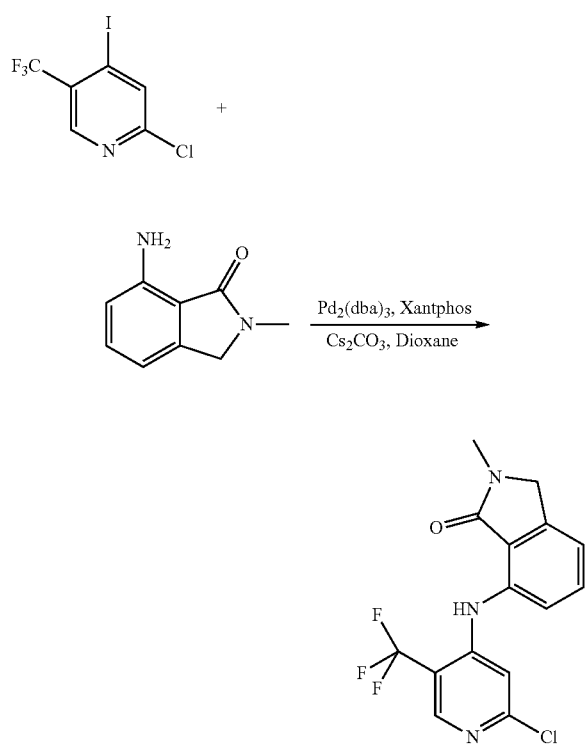

Method B was applied.

7-(2-(2-methoxy-4-morpholinophenylamino)-5-(trifluoromethyl)pyridin-4-ylamino)-2-methylisoindolin-1-one

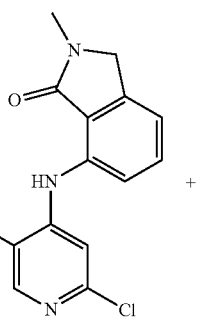

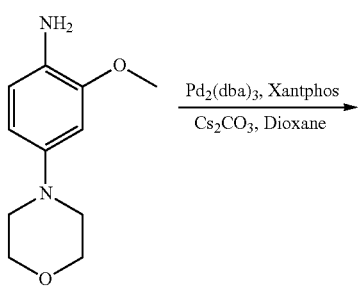

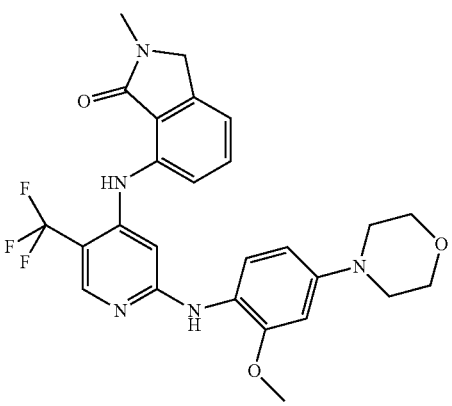

Method C was applied. The title compound was obtained as the TFA salt.

$^1$H NMR (400 MHz, DMSO-d$_6$) δ 9.45 (s, 1H), 8.90 (broad s, 1H), 8.19 (s, 1H), 7.52 (m, 1H), 7.43 (m, 1H), 7.19 (d, J=7.2 Hz, 1H), 6.82 (s, 1H), 6.67 (d, J=2.4 Hz, 1H), 6.51 (dd, J=8.8

Hz, 2.4 Hz, 1H), 4.47 (s, 2H), 3.82 (s, 3H), 3.74 (m, 4H), 3.13 (m, 4H), 3.05 (s, 3H); MS (m/z): 514.2 [M+1]⁺.

EXAMPLE 9

7,7'-(5-(trifluoromethyl)pyridine-2,4-diyl)bis(azanediyl)bis(2-methylisoindolin-1-one)

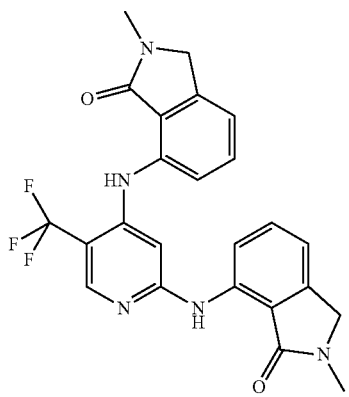

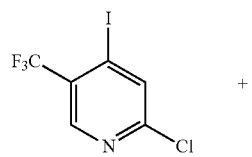

+

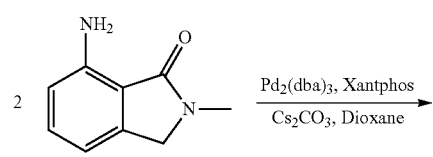

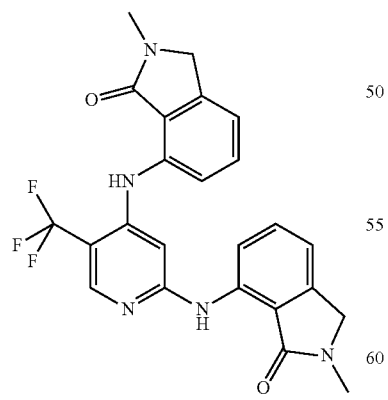

Method A was applied. The title compound was obtained as the TFA salt.

¹H NMR (400 MHz, DMSO-d₆) δ 9.97 (s, 1H), 9.47 (s, 1H), 8.46 (s, 1H), 8.39 (d, J=8.4 Hz, 1H), 7.60 (m, 2H), 7.51 (d, J=8.4 Hz, 1H), 7.21 (m, 1H), 7.12 (d, J=7.2 Hz, 1H), 7.06 (s, 1H), 4.49 (s, 2H), 4.46 (s, 2H), 3.07 (s, 6H); MS (m/z): 468.2 [M+1]⁺.

EXAMPLE 10

2-(2-(2-methoxy-4-morpholinophenylamino)-5-(trifluoromethyl)pyridin-4-ylamino)-N-methylbenzamide

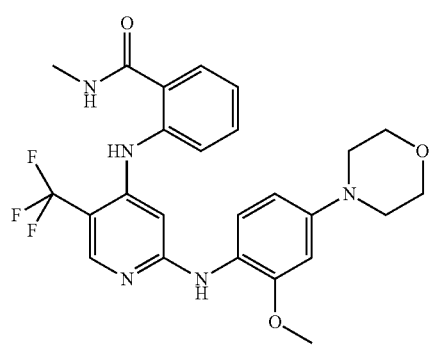

2-(2-chloro-5-(trifluoromethyl)pyridin-4-ylamino)-N-methylbenzamide

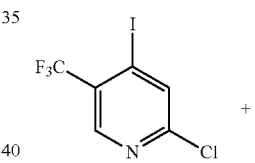

+

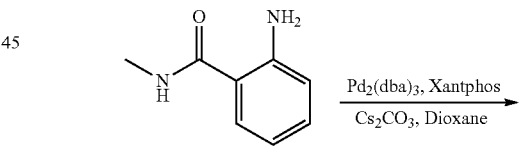

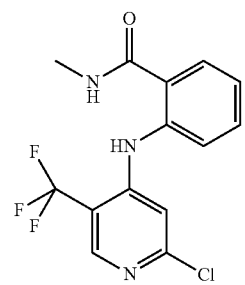

Method B was applied to a mixture of 2-chloro-4-iodo-5-(trifluoromethyl)pyridine (103 mg, 0.34 mmol), 2-amino-N-methylbenzamide (51 mg, 0.34 mmol), Pd₂(dba)₃ (30 mg, 0.033 mmol), xantphos (28 mg, 0.014 mmol) and cesium carbonate (234 mg, 0.72 mmol) in dioxane (4.5 ml).

2-(2-(2-methoxy-4-morpholinophenylamino)-5-(trifluoromethyl)pyridin-4-ylamino)-N-methylbenzamide

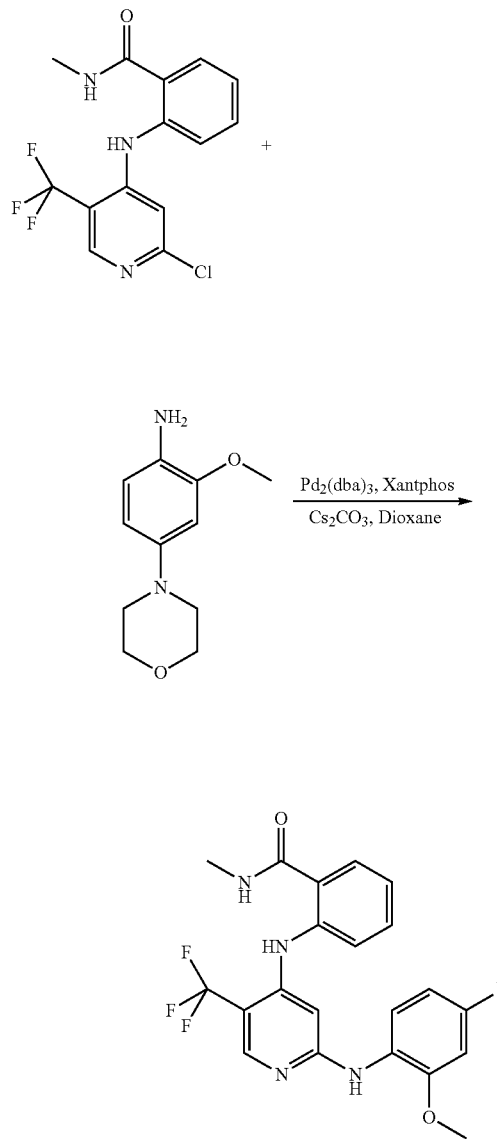

Method C was applied to a mixture of 2-(2-chloro-5-(trifluoromethyl)pyridin-4-ylamino)-N-methylbenzamide (23 mg, 0.070 mmol), 2-methoxy-4-morpholinoaniline (23 mg, 0.11 mmol), Pd$_2$(dba)$_3$ (9 mg, 0.0098 mmol), xantphos (8 mg, 0.014 mmol) and cesium carbonate (34 mg, 0.10 mmol) in dioxane (3 ml). The title compound was obtained as a pale yellow solid.

$^1$H-NMR (400 MHz, d$_6$-DMSO) δ 10.35 (br s, 1H), 9.00 (vbr s, 1H), 8.69 (t, J=4.4 Hz, 1H), 8.10 (s, 1H), 7.72 (d, J=7.6 Hz, 1H), 7.53-7.49 (m, 2H), 7.29 (d, J=8.0 Hz, 1H), 7.18 (br s, 1H), 6.65 (d, J=2.4 Hz, 1H), 6.52 (s, 1H), 6.52 (dd, 1H), 3.79 (s, 1H), 3.74 (t, J=4.6 Hz, 4H), 3.13 (t, J=4.6 Hz, 4H), 2.76 (d, J=4.4 Hz, 3H); MS (m/z): 502.2 [M+1]$^+$.

EXAMPLE 11

N-methyl-2-(2-(1-methyl-2-oxo-1,2,3,4-tetrahydroquinolin-6-ylamino)-5-(trifluoromethyl)pyridin-4-ylamino)benzamide

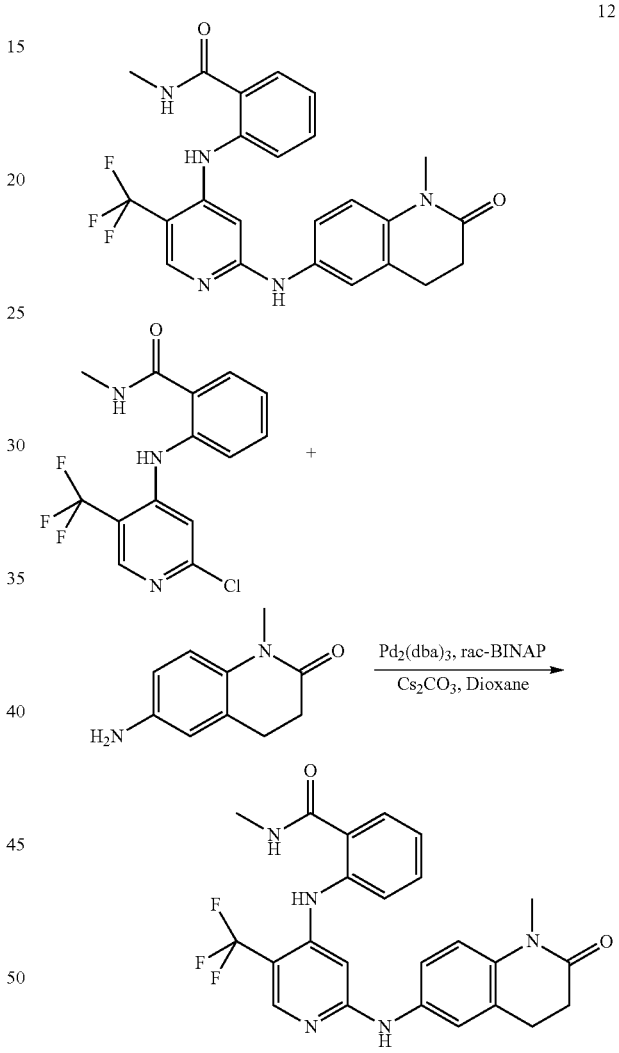

Method C was applied to a mixture of 2-(2-chloro-5-(trifluoromethyl)pyridin-4-ylamino)-N-methylbenzamide (32 mg, 0.097 mmol), 6-amino-1-methyl-3,4-dihydroquinolin-2(1H)-one (19 mg, 0.11 mmol), Pd$_2$(dba)$_3$ (9 mg, 0.0098 mmol), rac-BINAP (10 mg, 0.016 mmol) and cesium carbonate (62 mg, 0.19 mmol) in dioxane (3 ml). The TFA salt of the title compound was obtained as a pale yellow solid.

$^1$H-NMR (400 MHz, d$_6$-DMSO) δ 10.26 (s, 1H), 9.37 (br s, 1H), 9.69 (q, J=4.4 Hz, 1H), 8.26 (s, 1H), 7.72 (dd, J=1.2; 8.0 Hz, 1H), 7.60 (dd, J=1.0, 7.6 Hz, 1H), 7.52 (dt, 1H), 7.42-7.36 (m, 2H), 7.15 (dt, 1H), 7.03 (d, J=8.8 Hz, 1H), 6.69 (s, 1H), 3.22 (s, 3H), 2.84 (t, J=7.2 Hz, 2H), 2.76 (d, J=4.4 Hz, 3H), 2.50 (t, partially covered by DMSO, 2H); $^{19}$F-NMR (376 MHz, d$_6$-DMSO) δ −59.4 (s, 3F), −74.6 (s, 3F); MS (m/z): 470.2 [M+1]$^+$.

EXAMPLE 12

2-(2-(2-methoxy-4-(4-methylpiperazin-1-yl)phenylamino)-5-(trifluoromethyl)pyridin-4-ylamino)-N-methylbenzamide

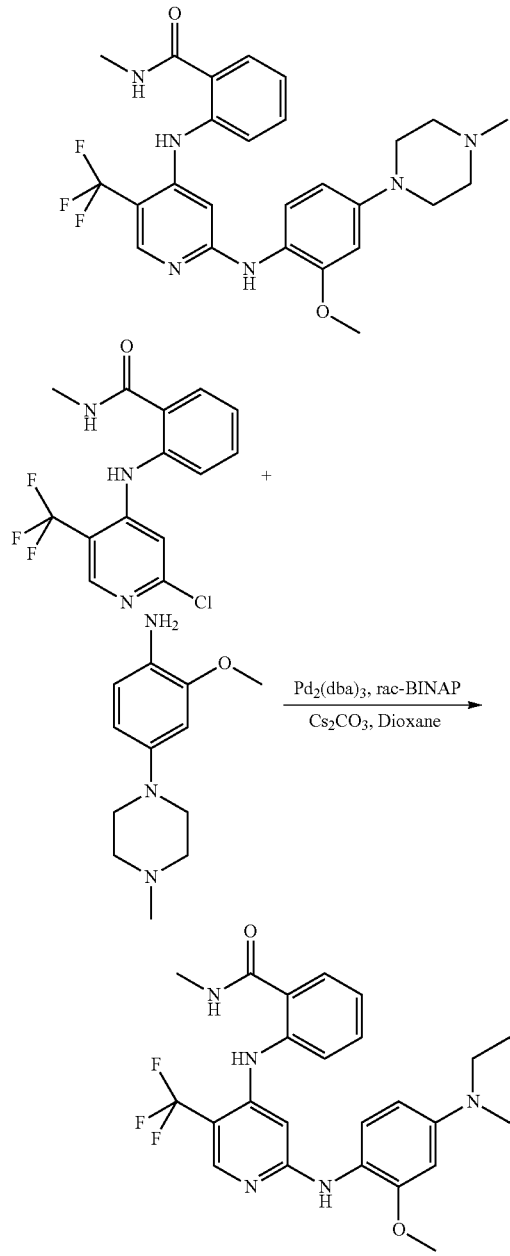

Method C was applied to a mixture of 2-(2-chloro-5-(trifluoromethyl)pyridin-4-ylamino)-N-methylbenzamide (30 mg, 0.091 mmol), 2-methoxy-4-(4-methylpiperazin-1-yl)aniline (40 mg, 0.18 mmol), Pd$_2$(dba)$_3$ (11 mg, 0.012 mmol), rac-BINAP (12 mg, 0.019 mmol) and cesium carbonate (75 mg, 0.23 mmol) in dioxane (3 ml). The bis-TFA salt of the title compound was obtained as a pale yellow solid.

$^1$H-NMR (400 MHz, d$_6$-DMSO) δ 10.35 (s, 1H), 9.80 (br s, 1H), 9.05 (vbr s, 1H), 8.69 (q, J=4.5 Hz, 1H), 8.14 (s, 1H), 7.72 (d, J=8.0 Hz, 1H), 7.54-7.49 (m, 2H), 7.40 (d, J=8.8 Hz, 1H), 7.18-7.15 (m, 1H), 6.70 (d, J=2.4 Hz, 1H), 6.57 (s, 1H), 6.54 (d, J=2.4 Hz, 1H), 3.86 (br d, 2H), 3.80 (s, 3H), 3.52 (br d, 2H), 3.15 (br q, 2H), 2.94 (br t, 2H), 2.87 (s, 3H), 2.76 (d, J=4.8 Hz, 3H); MS (m/z): 515.2 [M+1]$^+$.

EXAMPLE 13

N$^2$-(2-methoxy-4-morpholinophenyl)-N$^4$-(pyridin-3-yl)-5-(trifluoromethyl)pyridine-2,4-diamine

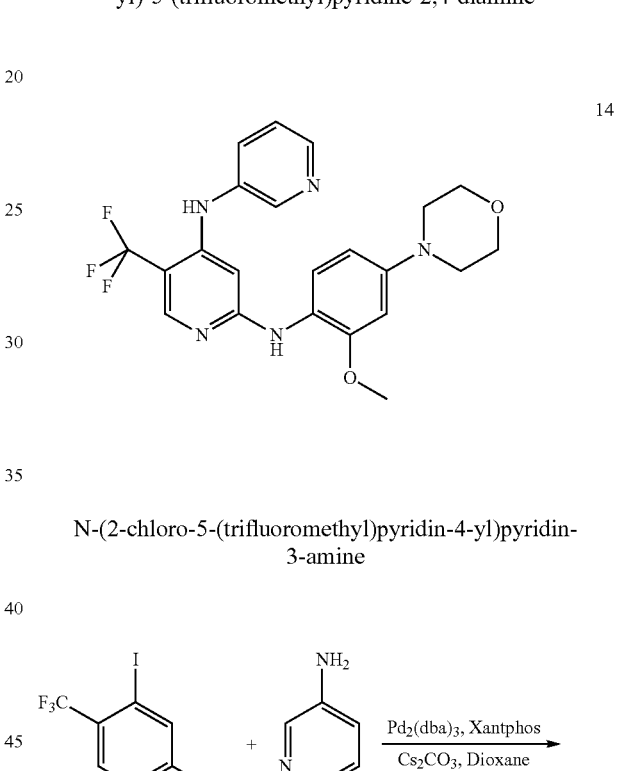

N-(2-chloro-5-(trifluoromethyl)pyridin-4-yl)pyridin-3-amine

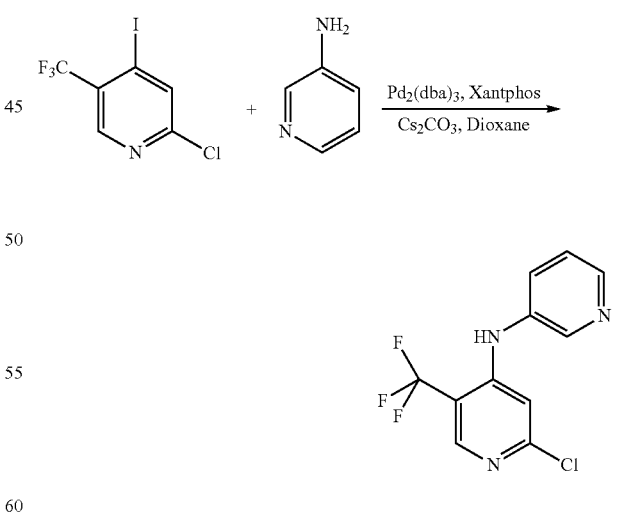

Method B was applied to a mixture of 2-chloro-4-iodo-5-(trifluoromethyl)pyridine (105 mg, 0.34 mmol), 3-aminopyridine (34 mg, 0.36 mmol), Pd$_2$(dba)$_3$ (20 mg, 0.022 mmol), xantphos (20 mg, 0.035 mmol) and cesium carbonate (225 mg, 0.69 mmol) in dioxane (4.5 ml).

$N^2$-(2-methoxy-4-morpholinophenyl)-$N^4$-(pyridin-3-yl)-5-(trifluoromethyl)pyridine-2,4-diamine Method C was applied to a mixture of N-(2-chloro-5-(trifluoromethyl)pyridin-4-yl)pyridin-3-amine (48 mg, 0.17 mmol), 2-methoxy-4-morpholinoaniline (55 mg, 0.27 mmol), Pd$_2$(dba)$_3$ (22 mg, 0.024 mmol), xantphos (24 mg, 0.041 mmol) and cesium carbonate (121 mg, 0.37 mmol) in dioxane (3 ml). The bis-TFA salt of the title compound was obtained as a pale yellow solid.

$^1$H-NMR (400 MHz, d$_6$-DMSO) δ 9.42 (vbr s, 1H), 8.95 (br s, 1H), 8.57 (d, J=2.0 Hz, 1H), 8.53 (d, J=4.4 Hz, 1H), 8.05 (s, 1H), 7.84 (dd, J=2.0, 6.8 Hz, 1H), 7.58 (dd, J=4.8, 8.0 Hz, 1H), 7.17 (d, J=8.4 Hz, 1H), 6.64 (d, J=2.4 Hz, 1H), 6.52 (dd, J=2.4, 8.8 Hz, 1H), 6.01 (s, 1H), 3.77 (s, 3H), 3.74 (t, J=4.8 Hz, 4H), 3.15 (t, J=4.8 Hz, 4H); $^{19}$F-NMR (376 MHz, d$_6$-DMSO) δ −59.6 (s, 3F), −73.4 (s, 6F); MS (m/z): 446.2 [M+1]$^+$.

EXAMPLE 14

$N^2$-(2-methoxy-4-morpholinophenyl)-$N^4$-(3-(methylsulfonyl)benzyl)-5-(trifluoromethyl)pyridine-2,4-diamine

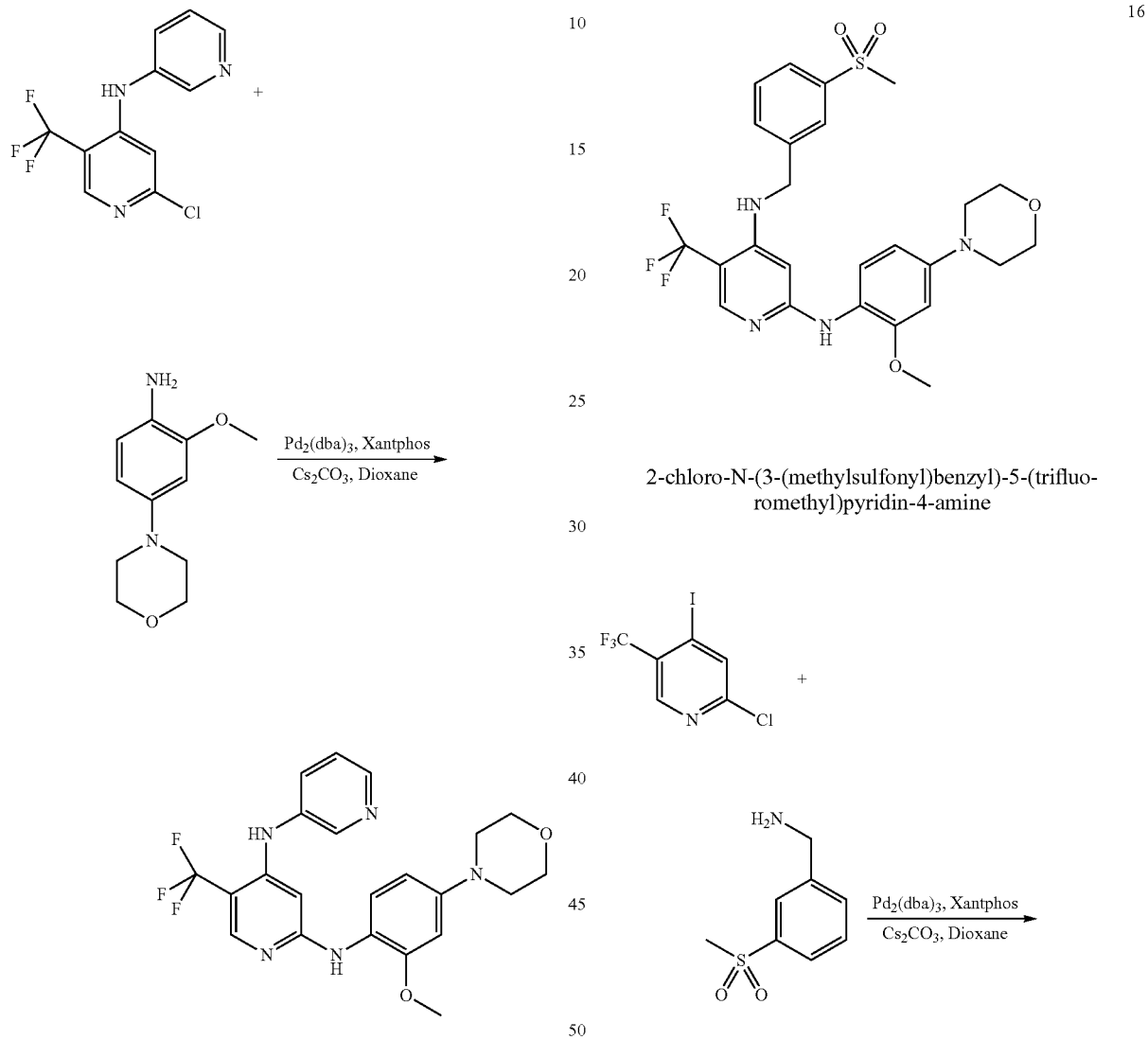

2-chloro-N-(3-(methylsulfonyl)benzyl)-5-(trifluoromethyl)pyridin-4-amine

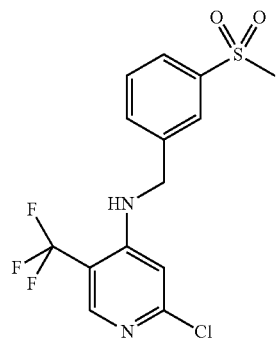

Method E was applied.

N²-(2-methoxy-4-morpholinophenyl)-N⁴-(3-(methylsulfonyl)benzyl)-5-(trifluoromethyl)pyridine-2,4-diamine

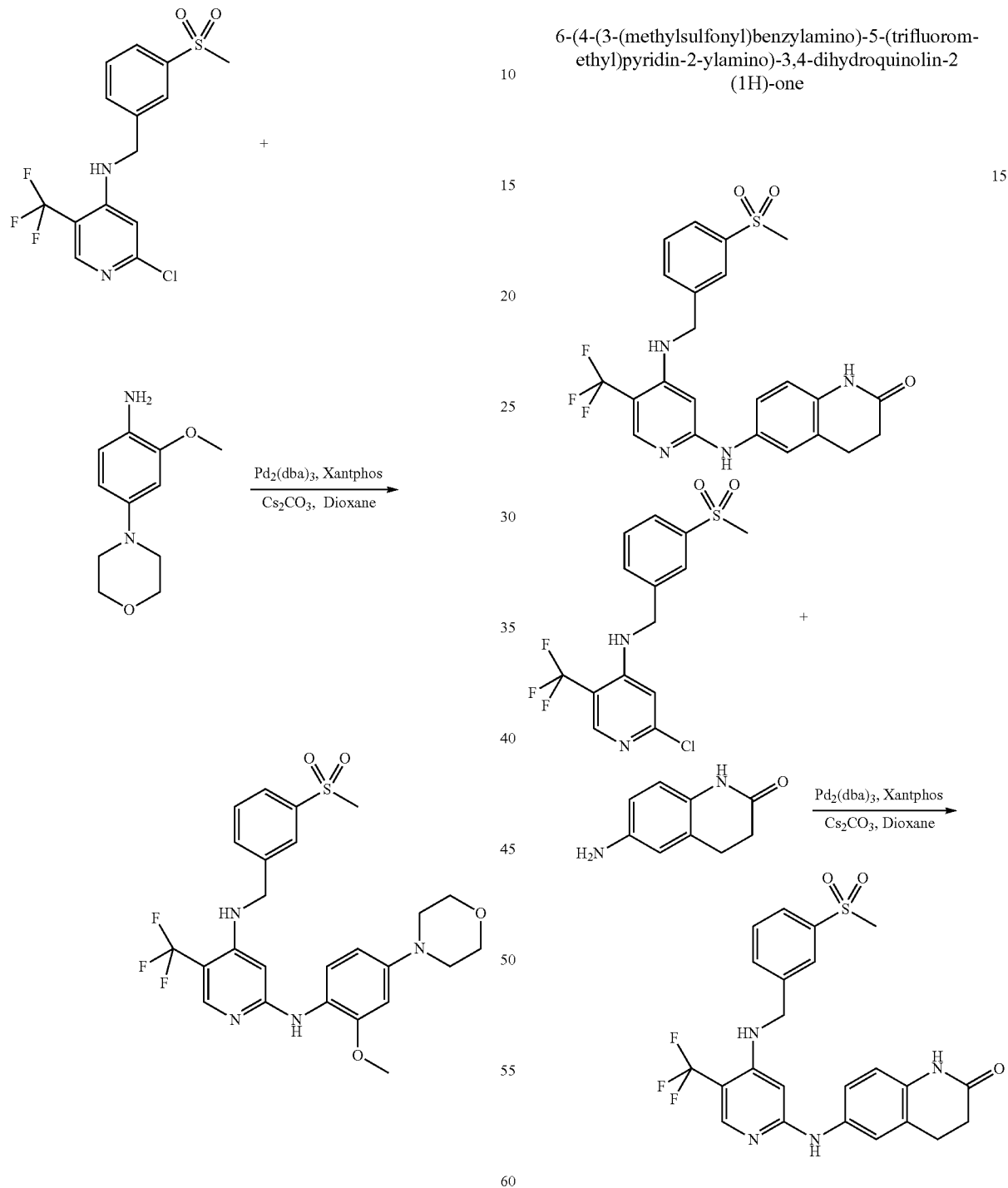

Method C was applied. The title compound was obtained as the TFA salt.

¹H NMR (400 MHz, DMSO-d$_6$) δ 7.92 (s, 1H), 7.86 (d, J=9.2 Hz, 1H), 7.85 (s, 1H), 7.66 (t, J=7.6 Hz, 1H), 7.54 (d, J=7.6 Hz, 1H), 6.98 (d, J=9.2 Hz, 1H), 6.63 (s, 1H), 6.48 (d, J=8.4 Hz, 1H), 5.73 (s, 1H), 4.55 (d, J=6 Hz, 2H), 3.75 (m, 4H), 3.68 (s, 3H), 3.21 (s, 3H), 3.17 (m, 4H); MS (m/z): 537.25 [M+1]⁺.

EXAMPLE 15

6-(4-(3-(methylsulfonyl)benzylamino)-5-(trifluoromethyl)pyridin-2-ylamino)-3,4-dihydroquinolin-2(1H)-one Method C was applied. The title compound was obtained as the TFA salt.

¹H NMR (400 MHz, DMSO-d$_6$) δ 10.01 (s, 1H), 8.02 (s, 1H), 7.86 (s, 1H), 7.84 (d, J=8.4 Hz, 1H), 7.67 (m, 1H), 7.59 (d, J=7.6 Hz, 1H), 7.16 (s, 1H), 7.04 (d, J=6.8 Hz, 1H), 6.74 (d, J=8.4 Hz, 1H), 5.80 (s, 1H), 4.46 (d, J=6 Hz, 2H), 3.19 (s,

3H), 2.77 (t, J=7.4 Hz, 2H), 2.39 (t, J=7.4 Hz, 2H); MS (m/z): 491.25 [M+1]⁺; MS (m/z): 491.2 [M+1]⁺.

EXAMPLE 16

(3-methoxy-4-(4-(3-(methylsulfonyl)benzylamino)-5-(trifluoromethyl)pyridin-2-ylamino)phenyl)(morpholino)methanone

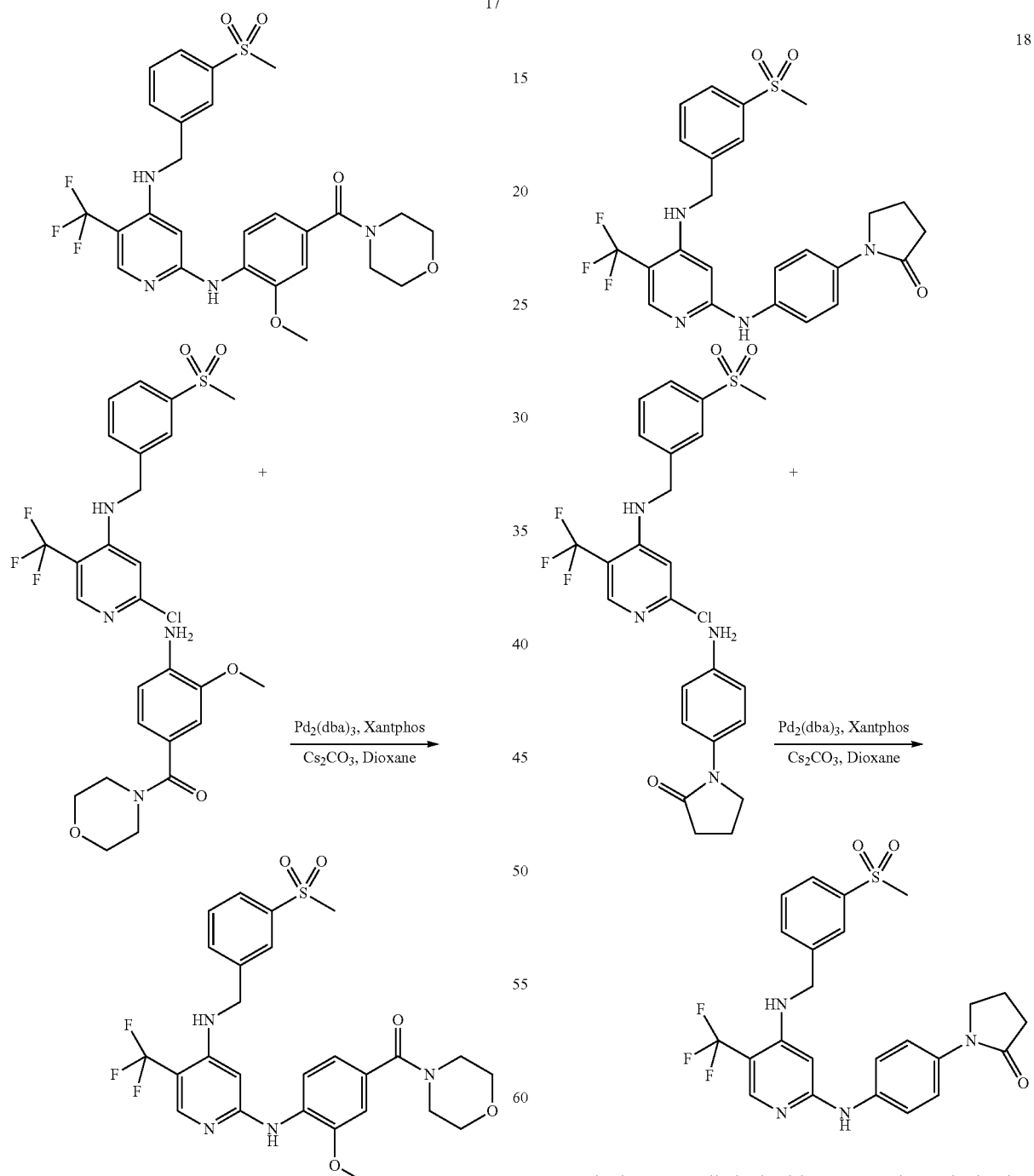

Method C was applied. The title compound was obtained as the TFA salt.

¹H NMR (400 MHz, DMSO-d₆) δ 8.06 (s, 1H), 7.93 (s, 1H), 7.84 (m, 2H), 7.64 (m, 2H), 7.04 (s, 1H), 6.93 (d, J=8.4 Hz, 1H), 6.20 (s, 1H), 4.55 (d, J=6.0 Hz, 2H), 3.80 (s, 3H), 3.50 (m, 8H), 3.21 (s, 3H); MS (m/z): 565.2 [M+1]⁺.

EXAMPLE 17

1-(4-(4-(3-(methylsulfonyl)benzylamino)-5-(trifluoromethyl)pyridin-2-ylamino)phenyl)pyrrolidin-2-one

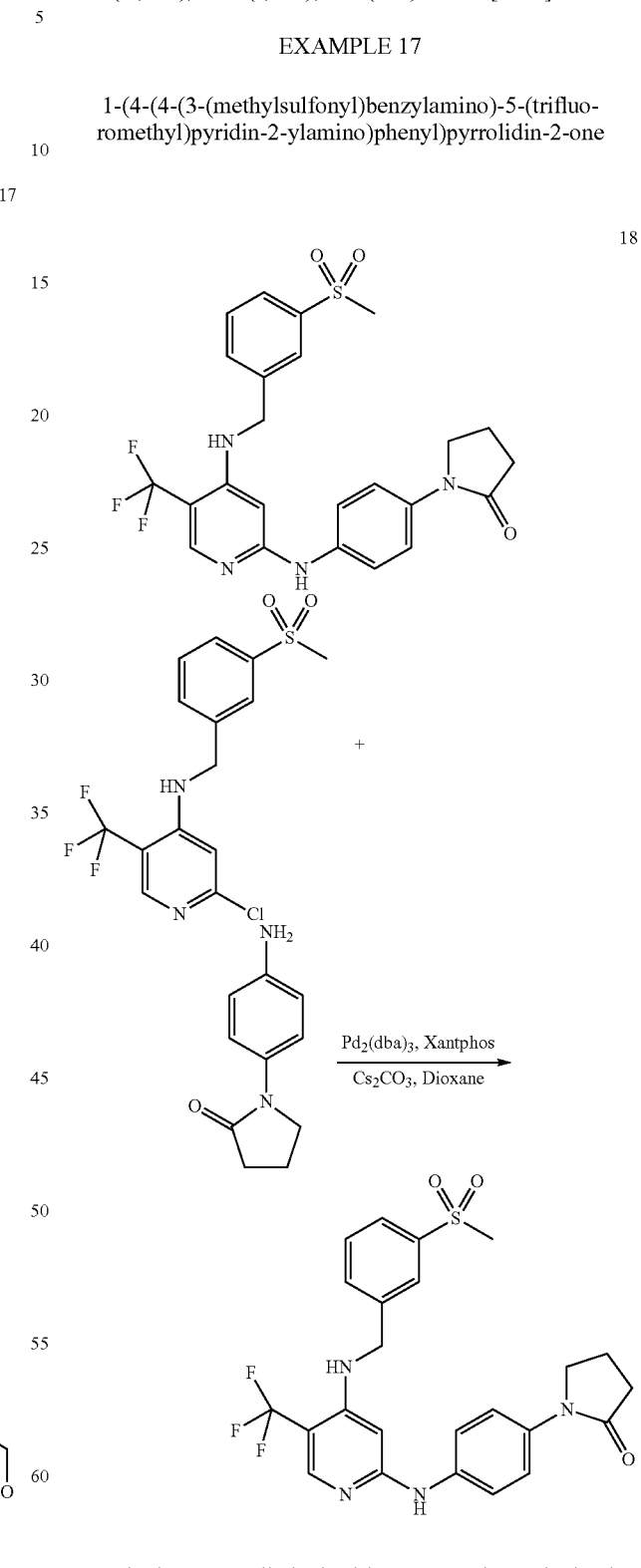

Method C was applied. The title compound was obtained as the TFA salt.

¹H NMR (400 MHz, DMSO-d₆) δ 8.06 (s, 1H), 7.86 (m, 2H), 7.66 (m, 1H), 7.58 (m, 1H), 7.53 (m, 2H), 5.82 (s, 1H), 4.54 (d, J=6.0 Hz, 2H), 3.80 (t, J=7.6 Hz, 2H), 3.19 (s, 3H), 2.67 (m, 1H), 2.32 (m, 1H), 2.02 (m, 2H); MS (m/z): 505.2 [M+1]+.

EXAMPLE 18

N4-benzyl-N2-(2-methoxy-4-morpholinophenyl)-5-(trifluoromethyl)pyridine-2,4-diamine

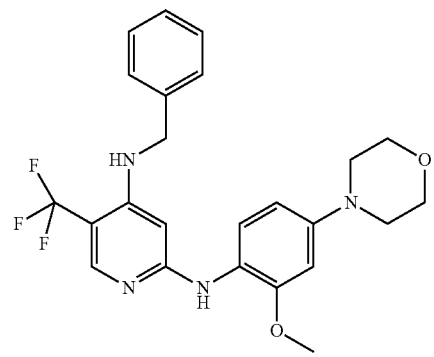

+

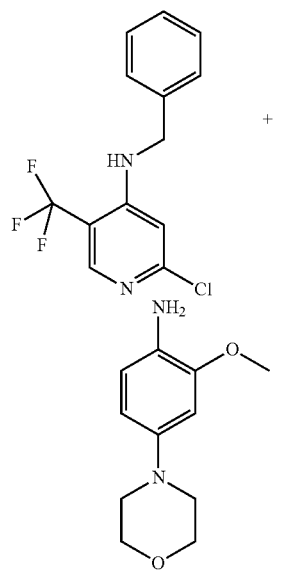

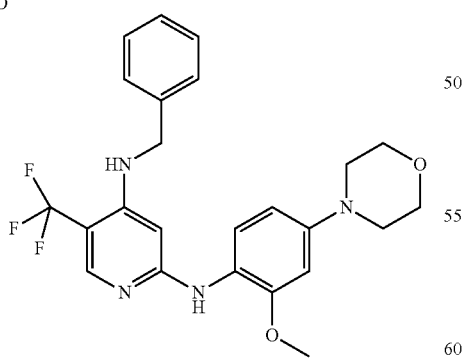

Method C was applied. The title compound was obtained as the TFA salt.

1H NMR (400 MHz, DMSO-d6) δ 9.44 (broad s, 1H), 8.15 (broad s, 1H), 7.92 (s, 1H), 7.36 (m, 2H), 7.28 (m, 1H), 7.19 (m, 2H), 6.94 (d, J=8.4 Hz, 1H), 6.65 (s, 1H), 6.51 (dd, J=8.4 Hz, 2.4 Hz, 1H), 5.69 (s, 1H), 4.41 (d, J=6.0 Hz, 2H), 3.76 (m, 4H), 3.67 (s, 3H), 3.19 (m, 4H); MS (m/z): 459.3 [M+1]+.

EXAMPLE 19

N2-(2-methoxy-4-morpholinophenyl)-N4-(2-(methylsulfonyl)benzyl)-5-(trifluoromethyl)pyridine-2,4-diamine

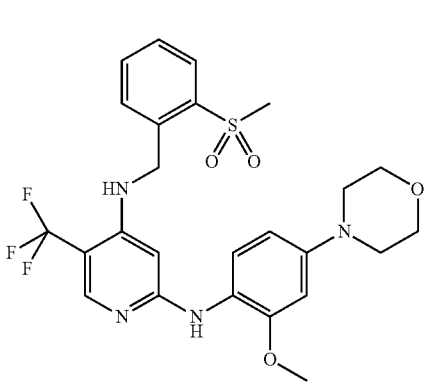

2-chloro-N-(2-(methylsulfonyl)benzyl)-5-(trifluoromethyl)pyridin-4-amine

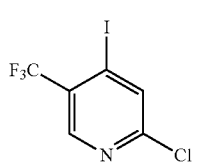

+

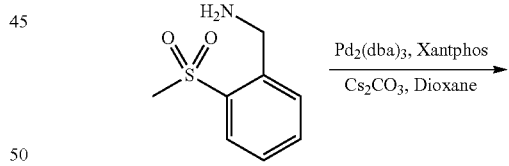

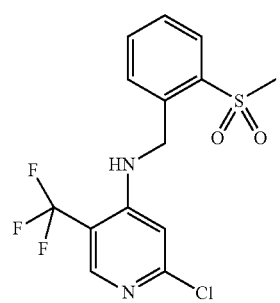

Method E was applied.

101

N²-(2-methoxy-4-morpholinophenyl)-N⁴-(2-(methylsulfonyl)benzyl)-5-(trifluoromethyl)pyridine-2,4-diamine

102

2-chloro-N-(pyridin-2-ylmethyl)-5-(trifluoromethyl)pyridin-4-amine

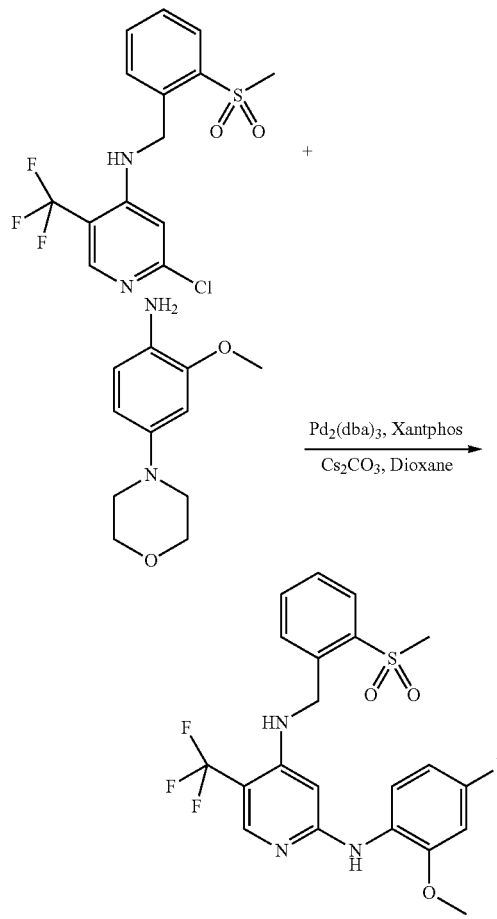

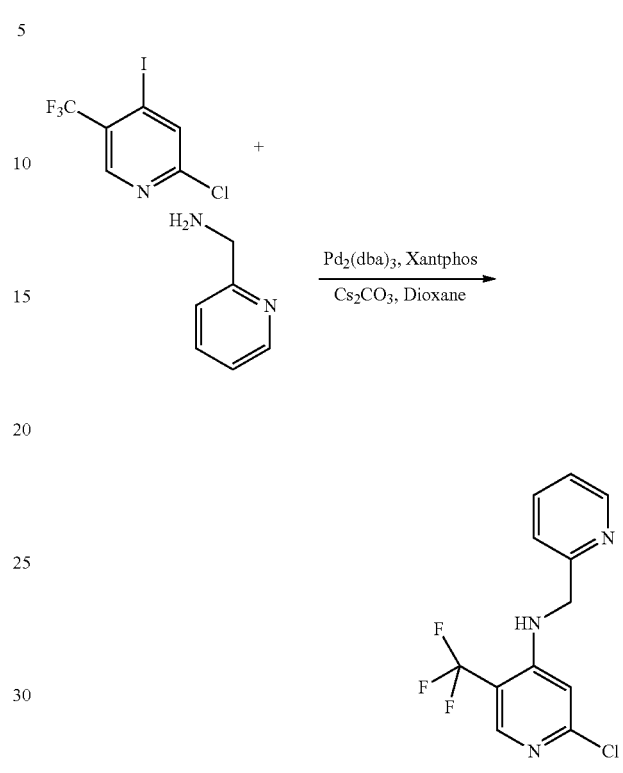

Method C was applied. The title compound was obtained as the TFA salt.

¹H NMR (400 MHz, DMSO-d₆) δ 7.99 (m, 2H), 7.74 (m, 1H), 7.61 (m, 1H), 7.34 (d, J=7.6 Hz, 1H), 6.90 (d, J=8.4 Hz, 1H), 6.55 (s, 1H), 6.40 (d, J=8.0 Hz, 1H), 5.51 (s, 1H), 4.86 (d, J=5.6 Hz, 2H), 3.75 (m, 4H), 3.60 (s, 3H), 3.18 (s, 3H), 3.15 (m, 4H); MS (m/z): 537.2 [M+1]⁺.

EXAMPLE 20

N²-(2-methoxy-4-morpholinophenyl)-N⁴-(pyridin-2-ylmethyl)-5-(trifluoromethyl)pyridine-2,4-diamine Method E was applied.

N²-(2-methoxy-4-morpholinophenyl)-N⁴-(pyridin-2-ylmethyl)-5-(trifluoromethyl)pyridine-2,4-diamine

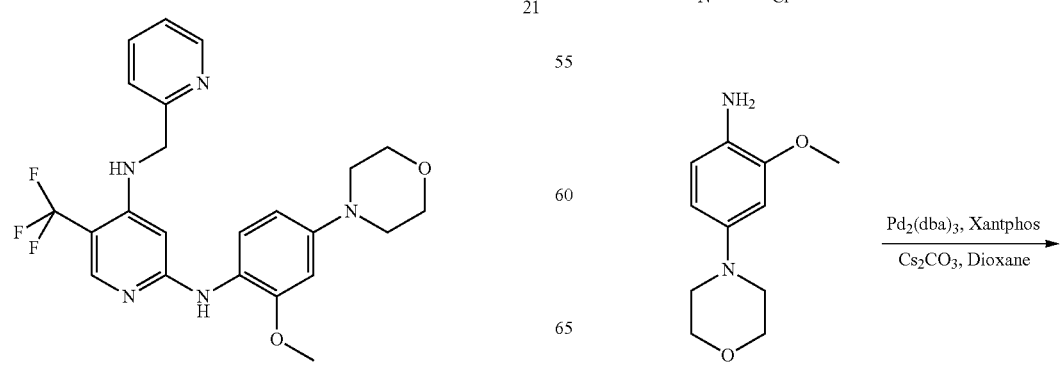

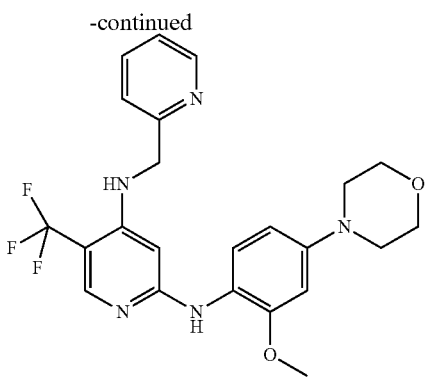

Method C was applied. The title compound was obtained as the bis-TFA salt.

MS (m/z): 460.3 [M+1]$^+$.

EXAMPLE 21

5-(2-(2-methoxy-4-morpholinophenylamino)-5-(trifluoromethyl)pyridin-4-ylamino)-N-methylthiazole-4-carboxamide

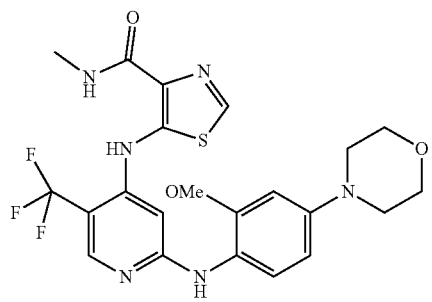

2-chloro-5-(trifluoromethyl)pyridin-4-amine

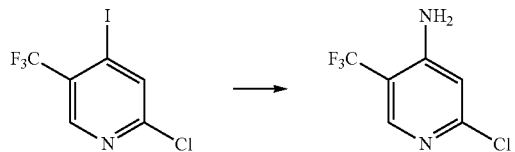 [SMILES: FC(F)(F)c1cnc(Cl)cc1I ; Nc1cc(Cl)ncc1C(F)(F)F]

2-chloro-4-iodo-5-(trifluoromethyl)pyridine was dissolved in 7 M Ammonia/Methanol. It was heated in a Biotage Initiator microwave synthesizer at 130° C. for 1 h. A mixture of the 2- and 4-substituted products was obtained. The solvent was removed and the residue was purified by silica gel chromatography (DCM/MeOH) gradient. The pure title compound was isolated.

5-(2-chloro-5-(trifluoromethyl)pyridin-4-ylamino)-N-methylthiazole-4-carboxamide

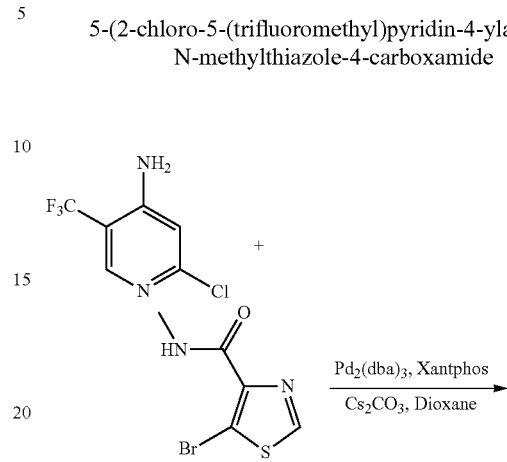

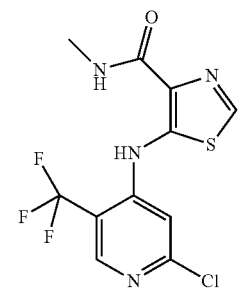

A mixture of 2-chloro-5-(trifluoromethyl)pyridin-4-amine (41 mg, 0.21 mmol) and 5-bromo-N-methylthiazole-4-carboxamide (54 mg, 0.24 mmol; synthesized from the corresponding ethyl-ester), Pd$_2$(dba)$_3$ (19 mg, 0.021 mmol), xantphos (37 mg, 0.064 mmol) and cesium carbonate (138 mg, 0.42 mmol) in dioxane (3.5 ml) were heated in a Biotage Initiator microwave synthesizer at 140° C. for 2 h. The solvent was removed and the residue was purified by silica gel chromatography (DCM/MeOH gradient) to give the title compound as a pale yellow solid in 27% isolated yield.

5-(2-(2-methoxy-4-morpholinophenylamino)-5-(trifluoromethyl)pyridin-4-ylamino)-N-methylthiazole-4-carboxamide

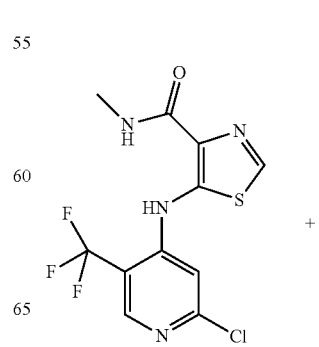

-continued

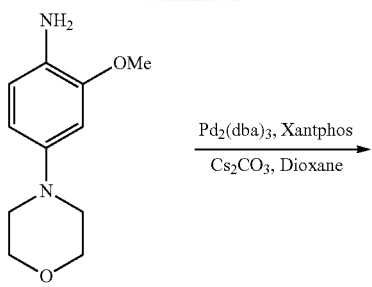

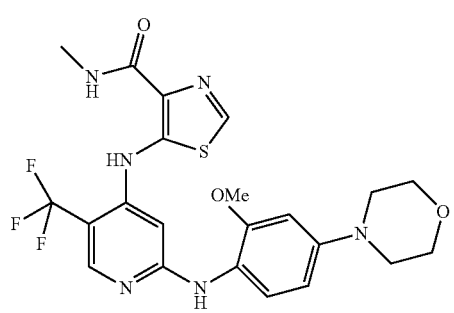

Method C was applied. The TFA salt of the title compound was obtained.

¹H-NMR (400 MHz, 10% DMSO/d₆-DMSO) δ 11.33 (s, 1H), 8.90 (s, 1H), 8.63 (s, 1H), 8.45 (d, J=4.4 Hz, 1H), 8.19 (s, 1H), 7.52-7.48 (m, 1H), 7.40 (d, J=8.8 Hz, 1H), 6.66 (d, J=2.4 Hz, 1H), 6.53 (dd, J=2.4, 7.6 Hz, 1H), 3.79 (s, 3H), 3.75 (br t, 4H), 3.12 (br t, 4H), 2.78 (d, 3H); MS (m/z): 509.1 [M+1]⁺.

EXAMPLE 22

N²-(2-methoxy-4-morpholinophenyl)-N⁴-(5-(pyrimidin-2-yl)thiazol-4-yl)-5-(trifluoromethyl)pyridine-2,4-diamine

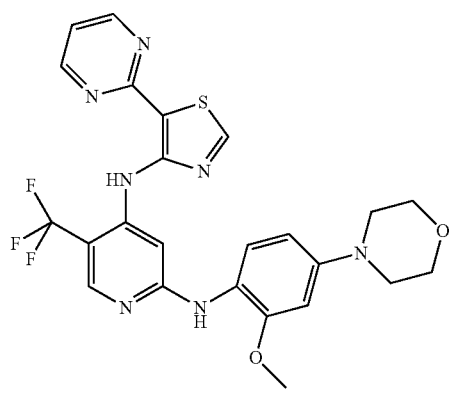

N-(2-chloro-5-(trifluoromethyl)pyridin-4-yl)-5-(pyrimidin-2-yl)thiazol-4-amine

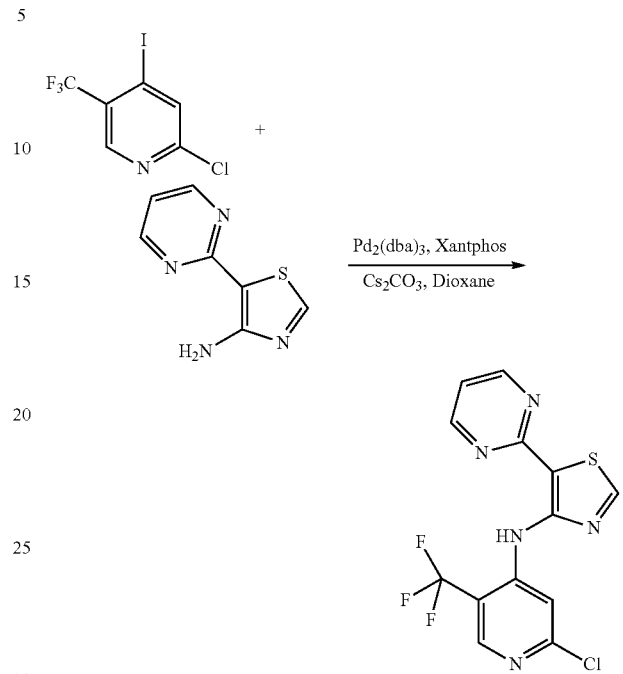

Method A was applied to a mixture of 2-chloro-4-iodo-5-(trifluoromethyl)pyridine (69 mg, 0.22 mmol), 5-(pyrimidin-2-yl)thiazol-4-amine (26 mg, 0.15 mmol), Pd₂(dba)₃ (17 mg, 0.019 mmol), xantphos (14 mg, 0.029 mmol) and cesium carbonate (97 mg, 0.30 mmol) in dioxane (3.5 ml).

N²-(2-methoxy-4-morpholinophenyl)-N⁴-(5-(pyrimidin-2-yl)thiazol-4-yl)-5-(trifluoromethyl)pyridine-2,4-diamine

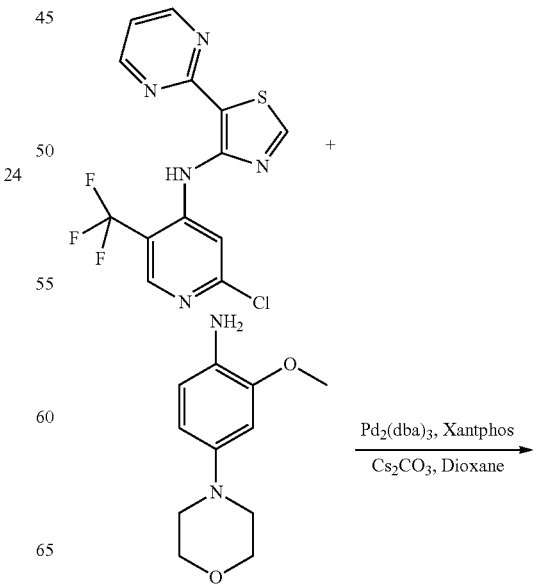

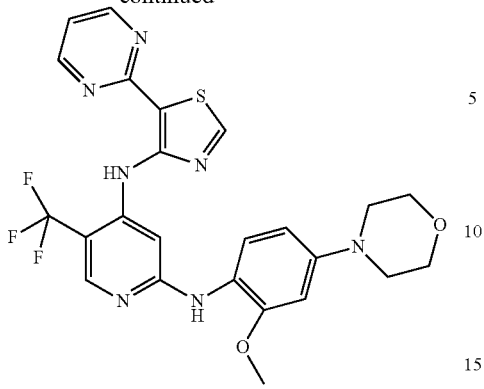

Method A was applied to a mixture of N-(2-chloro-5-(trifluoromethyl)pyridin-4-yl)-5-(pyrimidin-2-yl)thiazol-4-amine (11 mg, 0.03 mmol), 2-methoxy-4-morpholinoaniline (15 mg, 0.07 mmol), $Pd_2(dba)_3$ (8 mg, 0.0088 mmol), xantphos (7 mg, 0.061 mmol) and cesium carbonate (97 mg, 0.30 mmol) in dioxane (3.5 ml). The title compound was obtained as the TFA salt.

$^1$H-NMR (400 MHz, 10% DMSO/$d_6$-DMSO) δ 11.00 (s, 1H), 9.08 (s, 1H), 8.75 (d, J=4.8 Hz, 2H), 8.11 (s, 1H), 7.87 (s, 1H), 7.70 (s, 1H), 7.31-7.29 (m, 2H), 6.58 (s, 1H), 6.45 (d, J=8.4 Hz, 1H), 3.7-2.7 (s, 2 t, 11H, covered by DMSO and water); MS (m/z): 530.2 $[M+1]^+$.

EXAMPLE 23

$N^2$-(5-(ethylsulfonyl)-2-methoxyphenyl-$N^4$-(5-(pyrimidin-2-yl)thiazol-4-yl)-5-(trifluoromethyl)pyridine-2,4-diamine

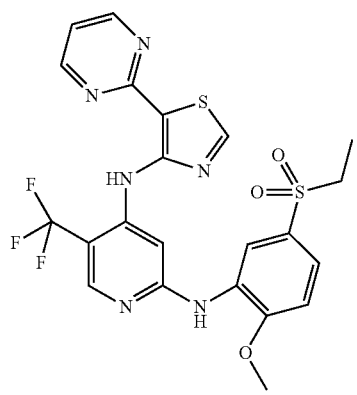

+

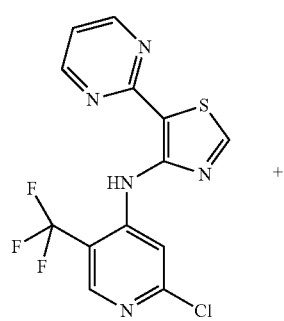

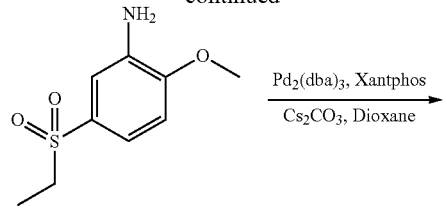

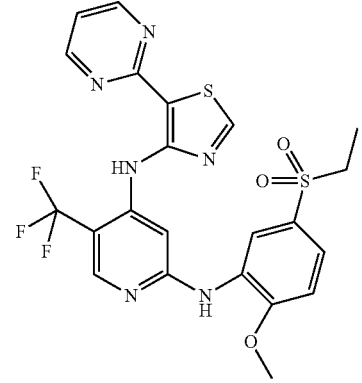

Method A was applied to a mixture of N-(2-chloro-5-(trifluoromethyl)pyridin-4-yl)-5-(pyrimidin-2-yl)thiazol-4-amine (7 mg, 0.019 mmol), 5-(ethylsulfonyl)-2-methoxyaniline (8 mg, 0.037 mmol), $Pd_2(dba)_3$ (7 mg, 0.0076 mmol), xantphos (7 mg, 0.012 mmol) and cesium carbonate (31 mg, 0.095 mmol) in dioxane (2 ml). The TFA salt of the title compound was obtained as pale yellow solid.

$^1$H-NMR (400 MHz, $d_6$-DMSO) δ 11.15 (s, 1H), 9.27 (s, 1H), 8.94 (s, 1H), 8.85 (d, J=4.8 Hz, 2H), 8.58 (d, J=2.0 Hz, 1H), 8.34 (s, 1H), 8.10 (s, 1H), 7.53 (dd, J=2.4, 8.8 Hz, 1H), 7.38 (t, J=5.0 Hz, 1H), 7.28 (d, J=7.3 Hz, 1H), 3.96 (s, 3H), 3.21 (q, J=7.2 Hz, 2H), 1.13 (t, J=7.2 Hz, 3H); $^{19}$F-NMR (376 MHz, $d_6$-DMSO) δ −60.0 (s), −74.4 (s); MS (m/z): 537.1 $[M+1]^+$.

EXAMPLE 24

Methyl 4-(2-(2-methoxy-5-morpholinophenylamino)-5-(trifluoromethyl)pyridin-4-ylamino)-2-(methylthio)thiazole-5-carboxylate

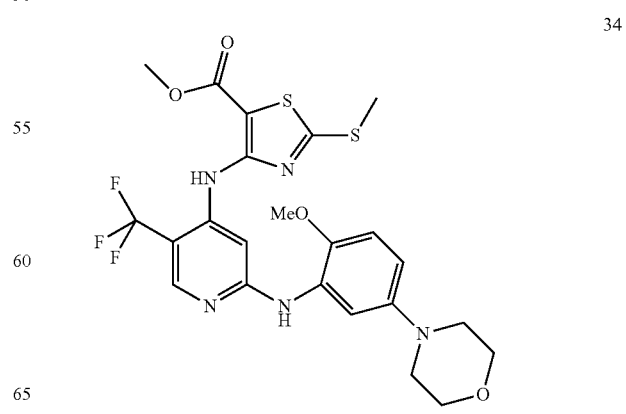

Methyl 4-(2-chloro-5-(trifluoromethyl)pyridin-4-ylamino)-2-(methylthio)thiazole-5-carboxylate

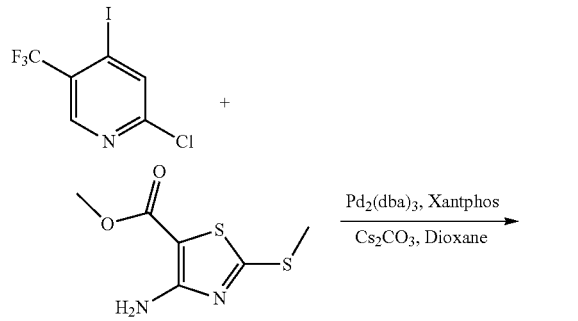

Method A was applied to a mixture of 2-chloro-4-iodo-5-(trifluoromethyl)pyridine (156 mg, 0.51 mmol) and methyl 4-amino-2-(methylthio)thiazole-5-carboxylate (86 mg, 0.42 mmol), Pd₂(dba)₃ (26 mg, 0.028 mmol), xantphos (21 mg, 0.036 mmol) and cesium carbonate (270 mg, 0.83 mmol) in dioxane (4.5 ml).

Methyl 4-(2-(2-methoxy-5-morpholinophenylamino)-5-(trifluoromethyl)pyridin-4-ylamino)-2-(methylthio)thiazole-5-carboxylate

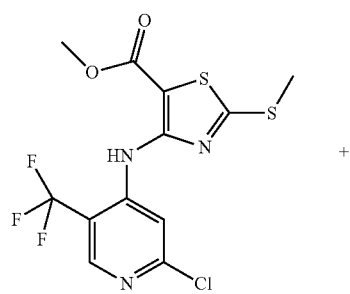

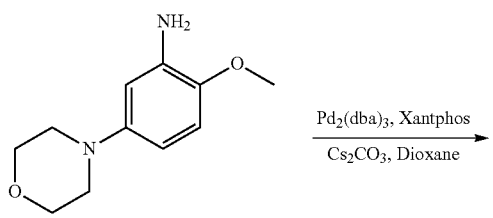

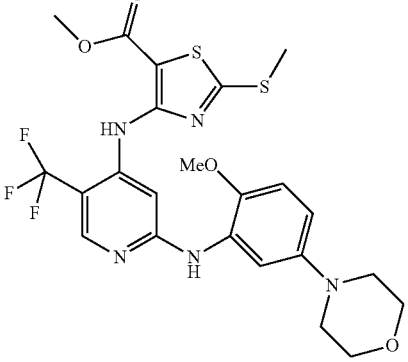

Method A was applied to a mixture of methyl 4-(2-chloro-5-(trifluoromethyl)pyridin-4-ylamino)-2-(methylthio)thiazole-5-carboxylate (33 mg, 0.086 mmol), 2-methoxy-5-morpholinoaniline (38 mg, 0.18 mmol), Pd₂(dba)₃ (9 mg, 0.0098 mmol), xantphos (8 mg, 0.014 mmol) and cesium carbonate (58 mg, 0.18 mmol) in dioxane (3.5 ml). The TFA salt of the title compound was obtained as a yellow solid.

$^1$H-NMR (400 MHz, $d_6$-DMSO) δ 9.66 (s, 1H), 8.92 (br s, 1H), 8.26 (s, 1H), 7.72 (s, 1H), 7.28 (s, 1H), 7.00 (d, J=8.8 Hz, 1H), 6.78 (dd, J=2.8, 8.8 Hz, 1H), 3.83 (s, 3H), 3.74 (s, t, 7H), 3.02 (t, J=4.6 Hz, 4H); $^{19}$F-NMR (376 MHz, $d_6$-DMSO) δ -58.6 (s, 3F), -74.2 (s, 3F); MS (m/z): 556.1 [M+1]$^+$.

EXAMPLE 25

General Procedure for Buchwald Hartwig Amination of Iodopyridines

To a 25 mL round bottom flask charged with the appropriate iodopyridine (1 equiv), Pd₂(dba)₃ (0.05 equiv), Xantphos (0.05 equiv) and 2-amino-N-methylbenzamide (1.05 equiv), 1,2-dichlorobenzene was added followed by the addition of MTBD (2 equivalents). The round bottom flask was capped with a rubber septum and argon was purged through the solution for 30 min. The volatiles were evaporated and the crude subjected to preparative HPLC affording the desired product. The following compounds were prepared by this procedure:

2-(2-chloro-5-cyanopyridin-4-ylamino)-N-methylbenzamide

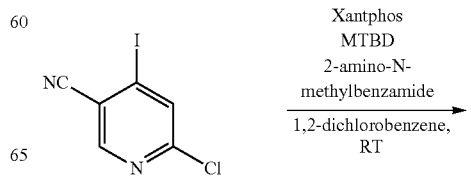

-continued

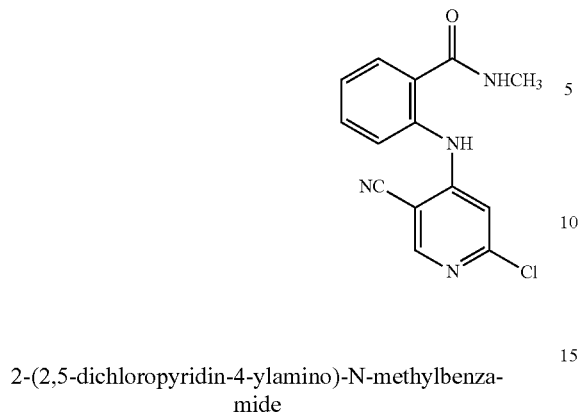

2-(2,5-dichloropyridin-4-ylamino)-N-methylbenza-
mide

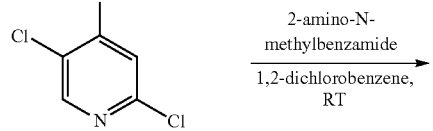

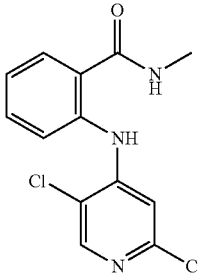

2-(2,5-dibromopyridin-4-ylamino)-N-methylbenzamide

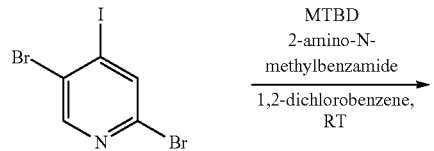

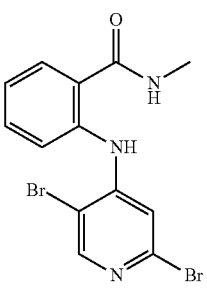

EXAMPLE 26

N-Methyl-2-(2-(pyridin-2-ylamino)-5-(trifluorom-
ethyl)pyridin-4-ylamino)benzamide

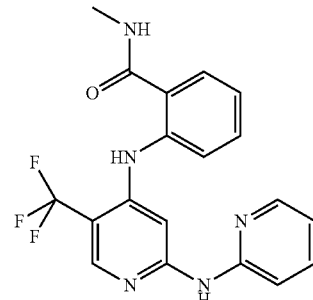

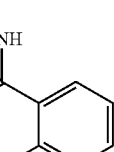

+

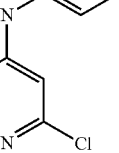

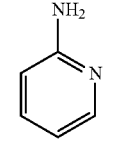
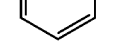

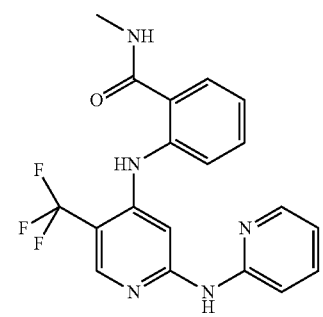

Method C was applied to the mixture of 2-(2-chloro-5-(trifluoromethyl)pyridin-4-ylamino)-N-methylbenzamide (48 mg, 0.15 mmol), 2-aminopyridine (20 mg, 0.21 mmol), $Pd_2(dba)_3$ (11 mg, 0.012 mmol), xantphos (11 mg, 0.019 mmol) and cesium carbonate in dioxane (3 ml). The TFA salt of the title compound was obtained as a yellow solid.

$^1$H-NMR (400 MHz, $d_6$-DMSO) δ 10.97 (br s, 1H), 10.54 (s, 1H), 8.74 (q, J=4.4 Hz, 1H), 8.43 (s, 1H), 8.29 (dd, J=1.1, 5.2 Hz, 1H), 7.92 (t, J=7.3 Hz, 1H), 7.76 (dd, J=1.4, 7.9 Hz, 1H), 7.67 (dd, J=0.9, 8.2 Hz, 1H), 7.59 (dt, J=1.3, 7.3 Hz, 1H), 7.41 (br s, 1H), 7.35 (d, J=8.5 Hz, 1H), 7.26 (dt, J=0.8, 7.5 Hz, 1H), 7.13 (t, J=6.2 Hz, 1H), 2.77 (d, J=4.6 Hz, 3H); MS (m/z): 388.1 [M+1]$^+$.

EXAMPLE 27

N-Methyl-2-(2-(pyrimidin-2-ylamino)-5-(trifluoromethyl)pyridin-4-ylamino)benzamide

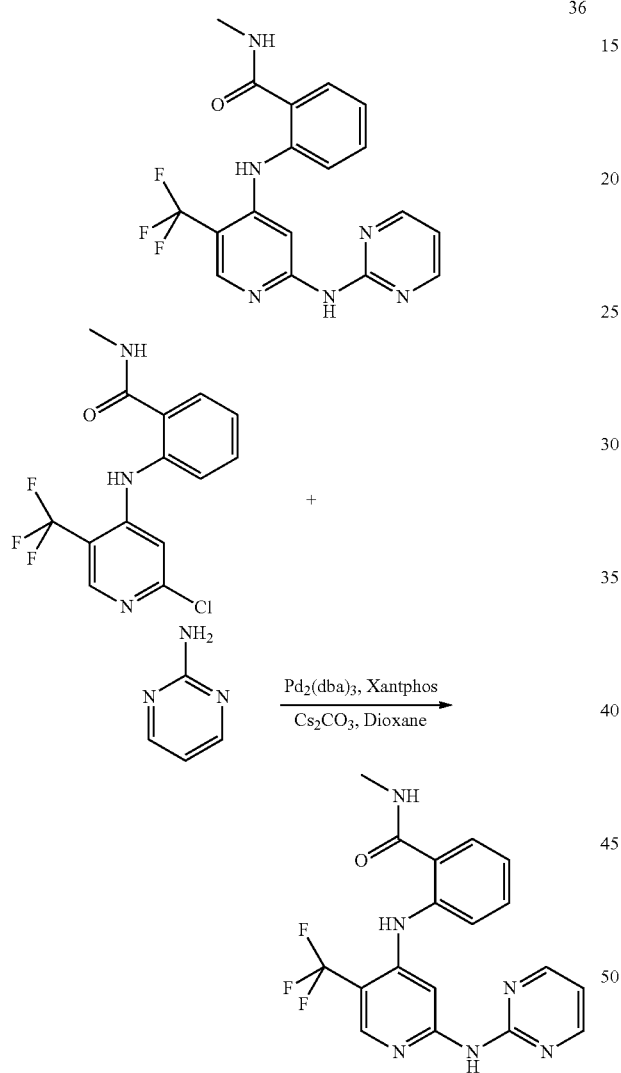

Method C was applied to the mixture of 2-(2-chloro-5-(trifluoromethyl)pyridin-4-ylamino)-N-methylbenzamide (41 mg, 0.12 mmol), 2-aminopyrimidine (20 mg, 0.21 mmol), Pd$_2$(dba)$_3$ (11 mg, 0.012 mmol), xantphos (11 mg, 0.019 mmol) and cesium carbonate (75 mg, 0.23 mmol) in dioxane (3.5 ml). The TFA salt of the title compound was obtained as a yellow solid.

$^1$H-NMR (400 MHz, d$_6$-DMSO) δ 11.09 (br s, 1H), 10.72 (s, 1H), 8.76 (q, J=4.4 Hz, 1H), 8.65 (d, J=4.9 Hz, 2H), 8.47 (s, 1H), 7.85 (s, 1H), 7.77 (dd, J=1.3, 7.9 Hz, 1H), 7.70 (dd, J=0.7, 8.2 Hz, 1H), 7.62 (dt, J=1.4, 7.9 Hz, 1H), 7.31-7.25 (m, 1H), 7.16 (t, J=4.9 Hz, 1H), 2.77 (d, J=4.6 Hz, 3H); $^{19}$F-NMR (376 MHz, d$_6$-DMSO) δ −60.8 (s, 3F), −74.4 (s, 3F); MS (m/z): 389.1 [M+1]$^+$.

EXAMPLE 28

N-Methyl-2-(2-(pyridin-3-ylamino)-5-(trifluoromethyl)pyridin-4-ylamino)benzamide

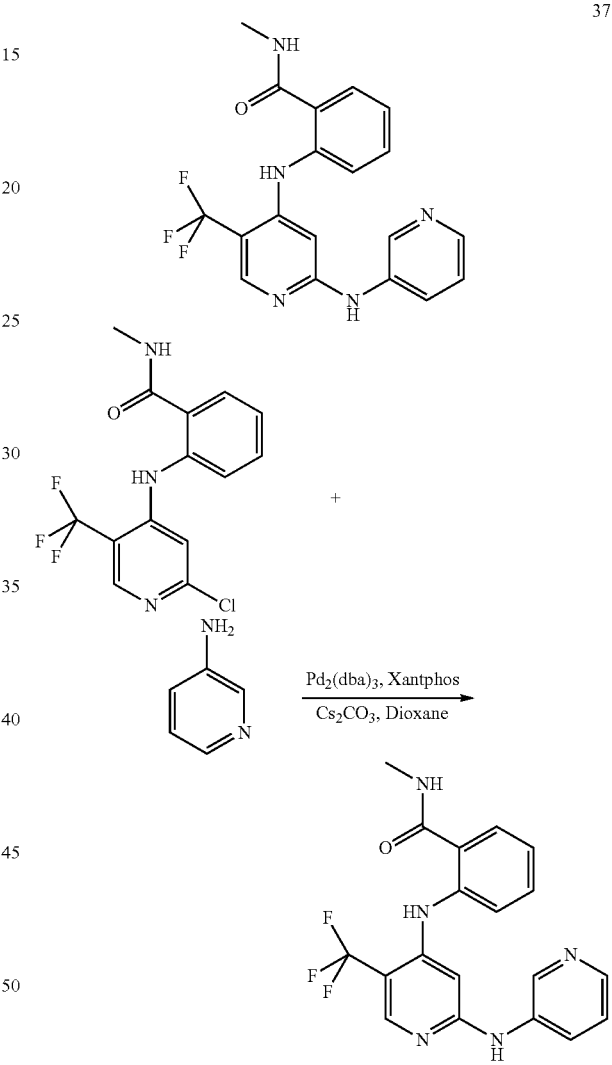

Method C was applied to the mixture of 2-(2-chloro-5-(trifluoromethyl)pyridin-4-ylamino)-N-methylbenzamide (42 mg, 0.13 mmol), 3-aminopyridine (17 mg, 0.18 mmol), Pd$_2$(dba)$_3$ (11 mg, 0.012 mmol), xantphos (11 mg, 0.019 mmol) and cesium carbonate (82 mg, 0.25 mmol) in dioxane (3.0 ml). The TFA salt of the title compound was obtained as a yellow solid.

$^1$H-NMR (400 MHz, d$_6$-DMSO) δ 10.33 (s, 1H), 10.09 (s, 1H), 9.30 (d, J=2.3 Hz, 1H), 8.72 (q, J=4.4 Hz, 1H), 8.40-8.36 (m, 3H), 7.81 (dd, J=5.3, 8.6 Hz, 1H), 7.75 (dd, J=1.4, 7.9 Hz, 1H), 7.62 (dd, J=0.9, 8.2 Hz, 1H), 7.54 (dt, J=1.3, 8.2 Hz, 1H), 7.21-7.17 (m, 1H), 6.88 (s, 1H), 2.77 (d, J=4.5 Hz, 3H);

$^{19}$F-NMR (376 MHz, d$_6$-DMSO) δ −59.8 (s, 3F), −74.5 (s, 4.4F); MS (m/z): 388.1 [M+1]$^+$.

EXAMPLE 29

N-Methyl-2-(2-(4-(pyrimidin-5-yl)phenylamino)-5-(trifluoromethyl)pyridin-4-ylamino)benzamide

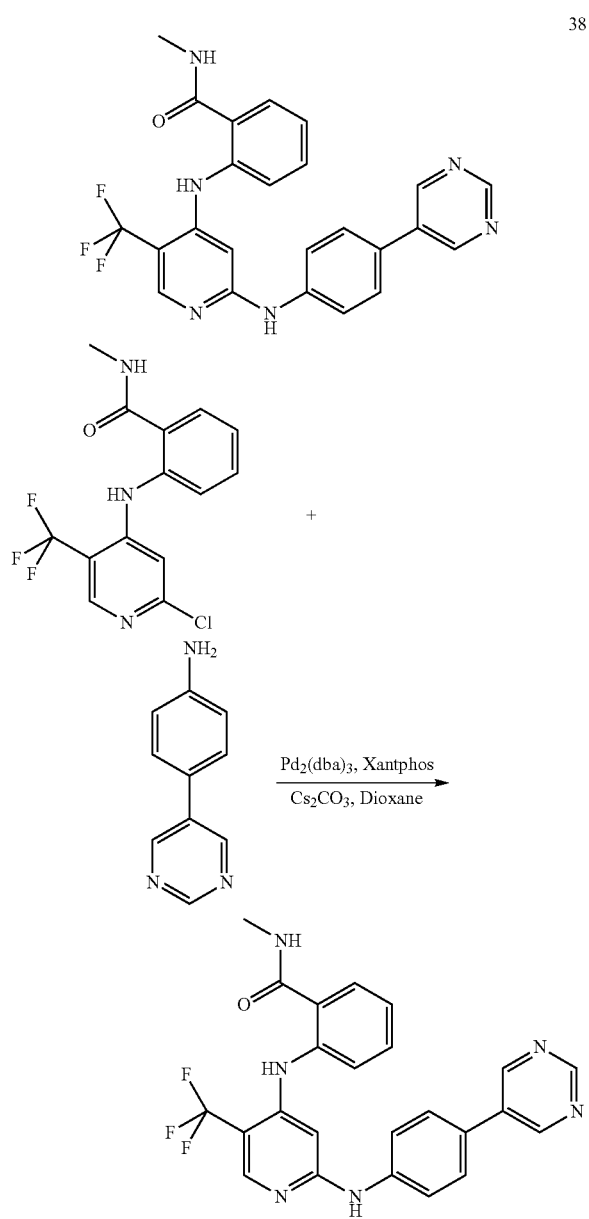

Method C was applied. The TFA salt of the title compound was obtained as a pale yellow solid.

$^1$H-NMR (400 MHz, d$_6$-DMSO) δ 10.26 (s, 1H), 9.54 (s, 1H), 9.12 (s, 1H), 9.12 (s, 2H), 8.70 (q, J=4.5 Hz, 1H), 8.34 (s, 1H), 7.81-7.72 (m, 5H), 6.20 (dd, J=0.9, 8.2 Hz, 1H), 7.55 (dt, J=1.3, 7.7 Hz, 1H), 7.17-7.12 (m, 1H), 6.84 (s, 1H), 2.77 (d, J=4.6 Hz, 3H); $^{19}$F-NMR (376 MHz, d$_6$-DMSO) δ −59.4 (s, 3F), −74.6 (s, 3F); MS (m/z): 465.1 [M+1]$^+$.

EXAMPLE 30

2-(2-(2-Methoxy-4-(pyrimidin-5-yl)phenylamino)-5-(trifluoromethyl)pyridin-4-ylamino)-N-methylbenzamide

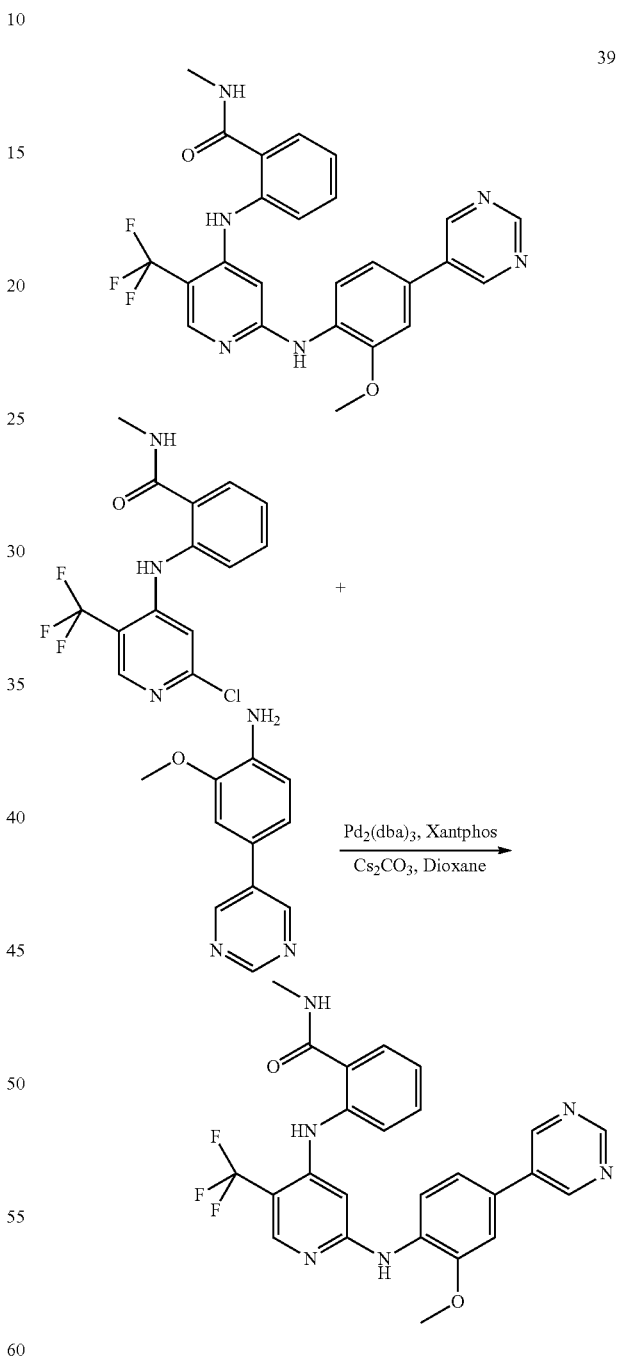

Method C was applied to the mixture of 2-(2-chloro-5-(trifluoromethyl)pyridin-4-ylamino)-N-methylbenzamide (42 mg, 0.13 mmol), 2-methoxy-4-(pyrimidin-5-yl)aniline (33 mg, 0.16 mmol), Pd$_2$(dba)$_3$ (11 mg, 0.012 mmol), xantphos (12 mg, 0.021 mmol) and cesium carbonate (84 mg, 0.26 mmol) in dioxane (3.5 ml). The TFA salt of the title compound was obtained as a pale yellow solid.

¹H-NMR (400 MHz, d₆-DMSO) δ 10.30 (s, 1H), 9.18 (s, 2H), 9.14 (s, 1H), 8.84 (br s, 1H), 8.69 (q, J=4.4 Hz, 1H), 8.29 (s, 1H), 8.25 (d, J=8.4 Hz, 1H), 7.72 (dd, J=1.3, 7.9 Hz, 1H), 7.60-7.51 (m, 2H), 7.46 (d, J=2.0 Hz, 1H), 7.38 (dd, J=2.0, 8.4 Hz, 1H), 7.06 (s, 1H), 2.77 (d, J=4.6 Hz, 1H); MS (m/z): 495.1 [M+1]⁺.

EXAMPLE 31

N-Methyl-2-(2-(3-methyl-2-oxo-2,3-dihydrobenzo[d]oxazol-6-ylamino)-5-(trifluoromethyl)pyridin-4-ylamino)benzamide

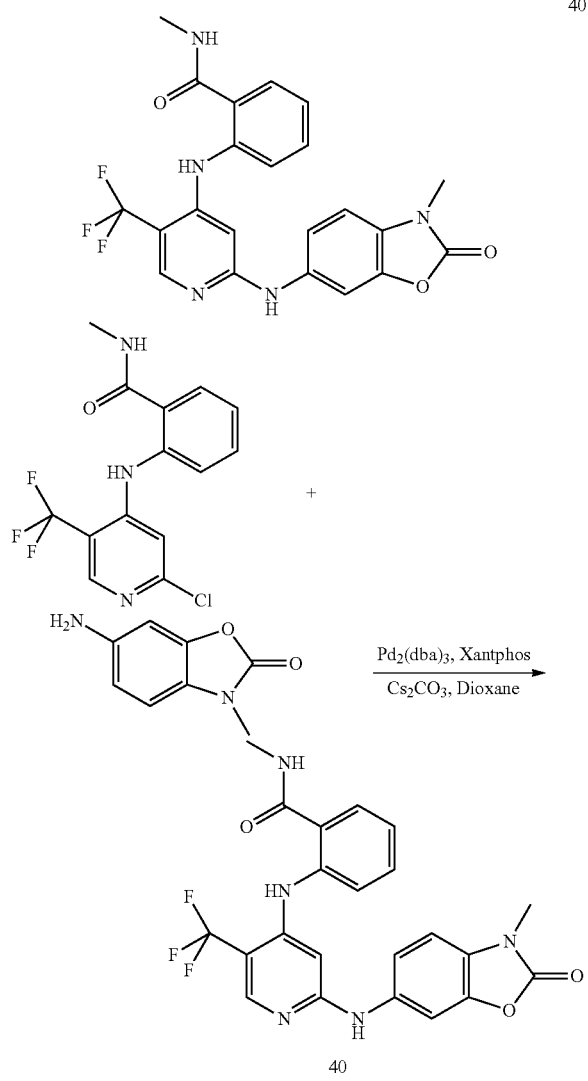

Method C was applied. The TFA salt of the title compound was obtained as a pale yellow solid.

¹H-NMR (400 MHz, d₆-DMSO) δ 10.30 (s, 1H), 9.54 (br s, 1H), 8.70 (q, J=4.4 Hz, 1H), 8.28 (s, 1H), 7.77 (d, J=1.8 Hz, 1H), 7.73 (dd, J=1.3, 7.9 Hz, 1H), 7.60 (dd, J=0.8, 7.8 Hz, 1H), 7.52 (dt, J=1.3, 7.8 Hz, 1H), 7.24 (dd, J=1.9, 8.5 Hz, 1H), 7.19-7.14 (m, 2H), 6.71 (s, 1H), 3.32 (s, 3H), 2.76 (d, J=4.5 Hz, 3H); ¹⁹F-NMR (376 MHz, d₆-DMSO) δ −59.5 (s, 3F), −74.8 (s, 3F); MS (m/z): 458.1 [M+1]⁺.

EXAMPLE 32

N-Methyl-2-(2-(2-oxo-2,3-dihydrobenzo[d]oxazol-6-ylamino)-5-(trifluoromethyl)pyridin-4-ylamino)benzamide

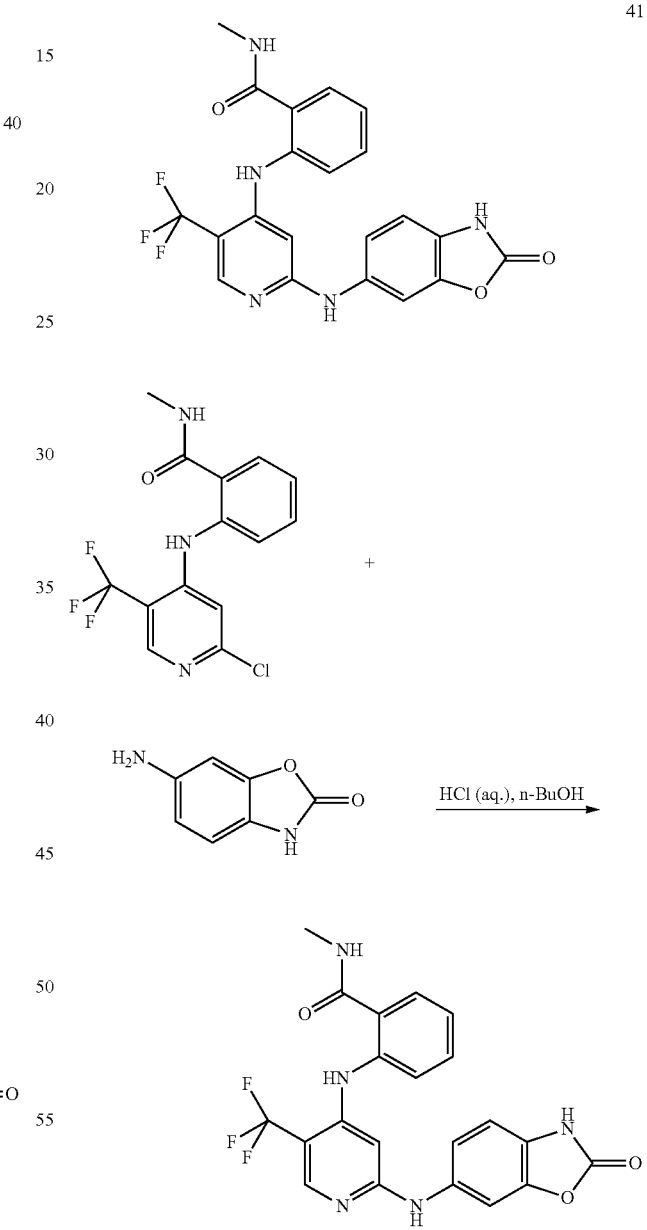

Method F was applied. The TFA salt of the title compound was obtained as a white solid.

¹H-NMR (400 MHz, d₆-DMSO) δ 11.48 (s, 1H), 10.23 (s, 1H), 9.38 (s, 1H), 8.69 (q, J=4.4 Hz, 1H), 8.27 (s, 1H), 7.75 (d, J=1.6 Hz, 1H), 7.72 (dd, J=1.4, 7.9 Hz, 1H), 7.59 (dd, J=0.8, 8.2 Hz, 1H), 7.51 (dt, J=1.3, 7.8 Hz, 1H), 7.18-7.12 (m, 2H), 7.00 (d, J=8.4 Hz, 1H), 2.76 (d, J=4.6 Hz, 1H); $^{19}$F-NMR (376 MHz, d$_6$-DMSO) δ −59.3 (s, 3F), −74.4 (s, 3F); MS (m/z): 444.1 [M+1]$^+$.

EXAMPLE 33

N-(2-(Diethylamino)ethyl)-6-(4-(2-(methylcarbamoyl)phenylamino)-5-(trifluoromethyl)pyridin-2-ylamino)nicotinamide

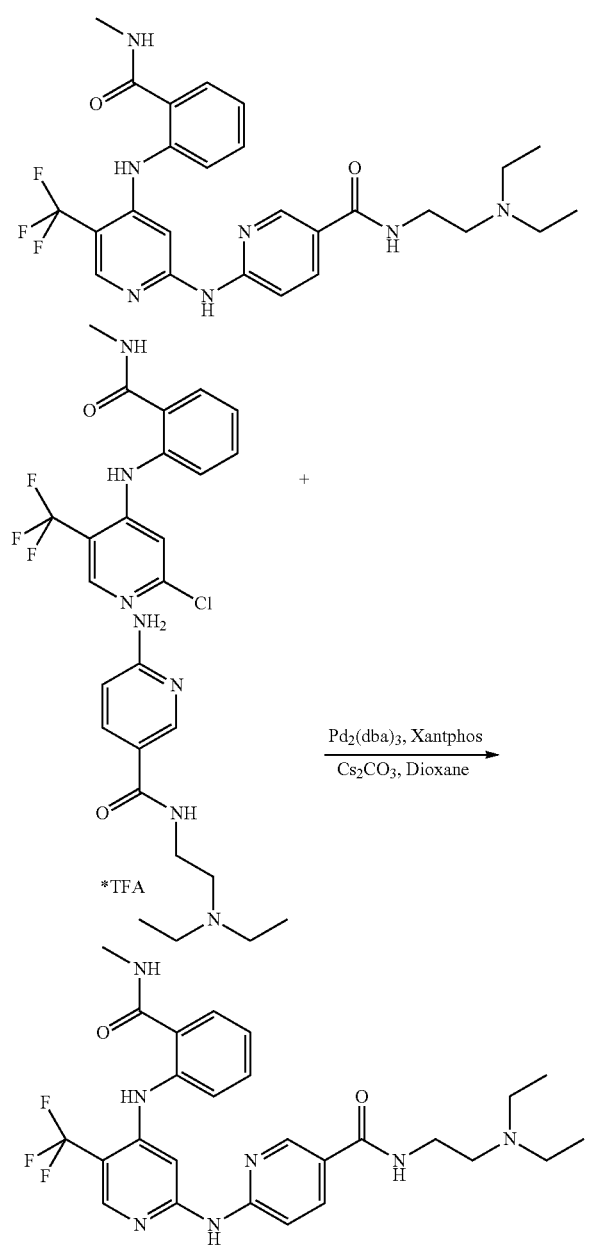

Method C was applied to the mixture of 2-(2-chloro-5-(trifluoromethyl)pyridin-4-ylamino)-N-methylbenzamide (41 mg, 0.12 mmol), 6-amino-N-(2-(diethylamino)ethyl) nicotinamide, TFA salt (63 mg, 0.18 mmol), Pd$_2$(dba)$_3$ (18 mg, 0.020 mmol), xantphos (17 mg, 0.029 mmol) and cesium carbonate (133 mg, 0.41 mmol) in dioxane (4.0 ml). The bis-TFA salt of the title compound was obtained as a pale yellow solid.

$^1$H-NMR (400 MHz, d$_6$-DMSO) δ 10.51 (s, 1H), 10.45 (br s, 1H), 9.19 (br s, 1H), 8.74-8.69 (m, 1H), 8.65 (d, J=2.2 Hz, 1H), 8.40 (s, 1H), 8.10 (dd, J=2.4, 8.8 Hz, 1H), 7.99 (s, 1H), 7.75 (dd, J=1.4, 7.9 Hz, 1H), 7.67 (t, J=8.5 Hz, 2H), 7.58-7.54 (m, 1H), 7.20-7.16 (m, 1H), 3.60 (q, J=6.1 Hz, 2H), 3.26-3.18 (m, 6H), 2.78 (d, J=4.6 Hz, 3H), 1.21 (t, J=7.2 Hz, 6H); $^{19}$F-NMR (376 MHz, d$_6$-DMSO) δ −59.9 (s, 3F), −74.2 (s, 6F); MS (m/z): 530.2 [M+1]$^+$.

EXAMPLE 34

N-(2-(Diethylamino)ethyl)-3-methoxy-4-(4-(2-(methylcarbamoyl)phenylamino)-5-(trifluoromethyl)pyridin-2-ylamino)benzamide

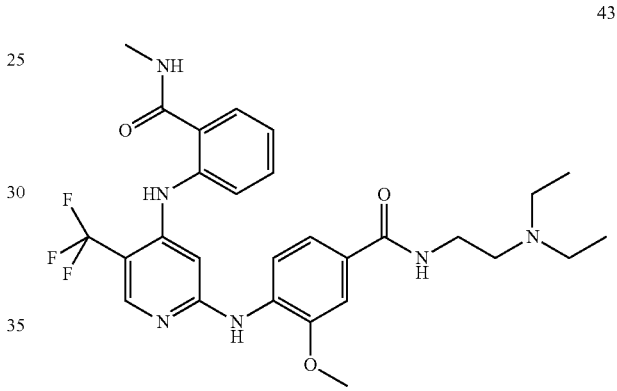

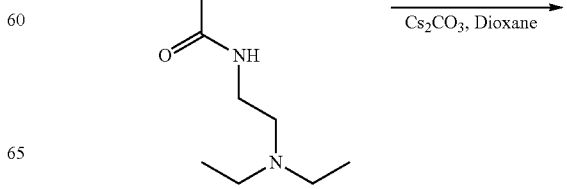

-continued

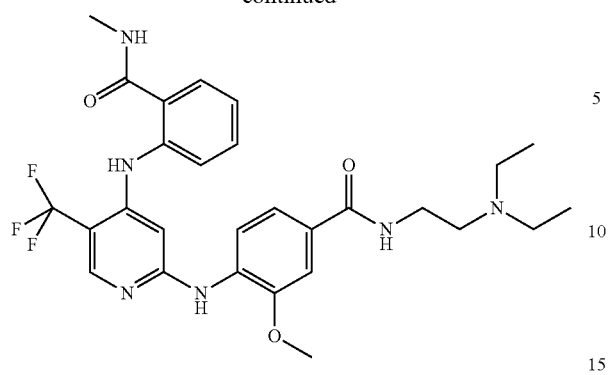

Method D was applied.

$^1$H NMR (400 MHz, CD$_3$CN-d$_3$) δ 10.47 (broad s, 1H), 10.19 (broad s, 1H), 9.94 (broad s, 1H), 8.44 (s, 1H), 8.23 (s, 1H), 7.68 (d, J=8.4 Hz, 1H), 7.60 (d, J=7.6 Hz, 1H), 7.54-7.46 (m, 4H), 7.19-7.15 (m, 2H), 6.51 (s, 1H), 3.92 (s, 3H), 3.70 (q, J=4.8 Hz, 2H), 3.29 (q, J=4.8 Hz, 2H), 3.24-3.17 (m, 4H), 2.82 (d, J=4.8 Hz, 3H), 1.27 (t, J=7.2 Hz, 6H); ESI-MS (m/z): 559.1 (M+1).

EXAMPLE 35

(S)-2-(2-(4-(3-Hydroxypyrrolidine-1-carbonyl)-2-methoxyphenylamino)-5-(trifluoromethyl)pyridin-4-ylamino)-N-methylbenzamide

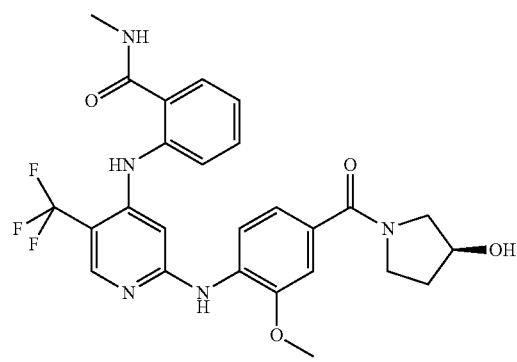

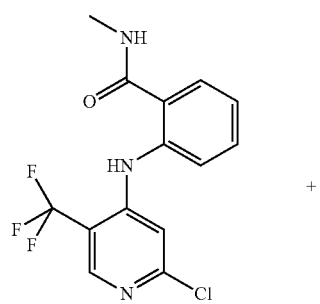

+

-continued

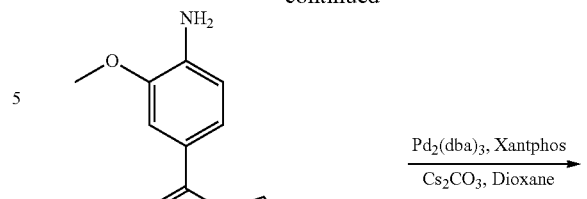

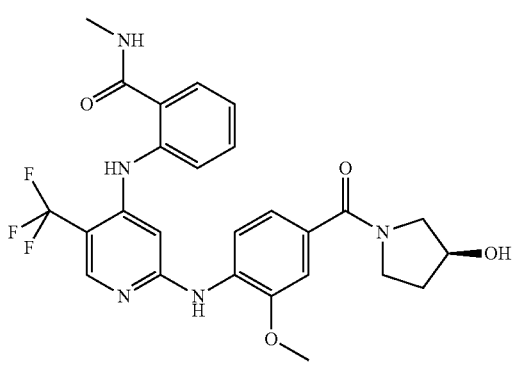

Method D was applied. The TFA salt of the title compound was obtained.

$^1$H NMR (400 MHz, CD$_3$CN-d$_3$) δ 10.48 (s, 1H), 10.11 (broad s, 1H), 8.19 (s, 1H), 7.61 (d, J=8.0 Hz, 1H), 7.54-7.46 (m, 3H), 7.22-7.10 (m, 4H), 6.47 (d, J=4.8 Hz, 1H), 4.44, 4.33 (2s, 1H), 3.88 (s, 3H), 3.67-3.54 (m, 3H), 3.45-3.37 (m, 2H), 3.22 (d, J=11.6 Hz, 1H), 2.83 (d, J=4.8 Hz, 3H); ESI-MS (m/z): 530.1 (M+1).

EXAMPLE 36

(S)-N-(3-(Dimethylamino)-2-hydroxy-3-oxopropyl)-3-methoxy-4-(4-(2-(methylcarbamoyl)phenylamino)-5-(trifluoromethyl)pyridin-2-ylamino)benzamide

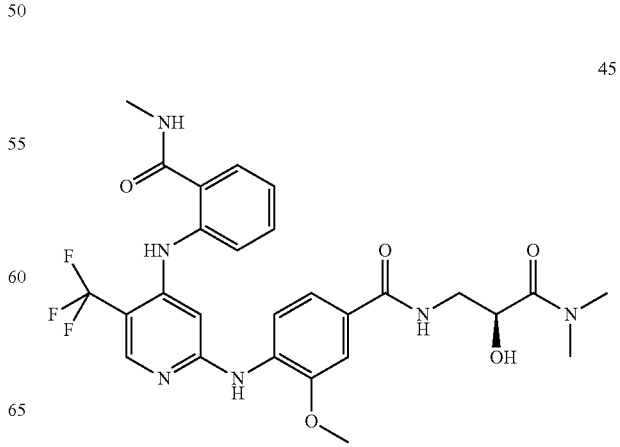

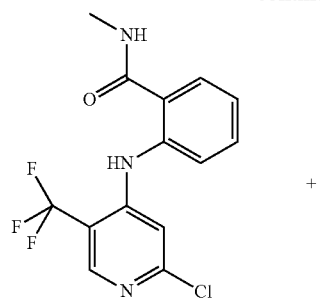

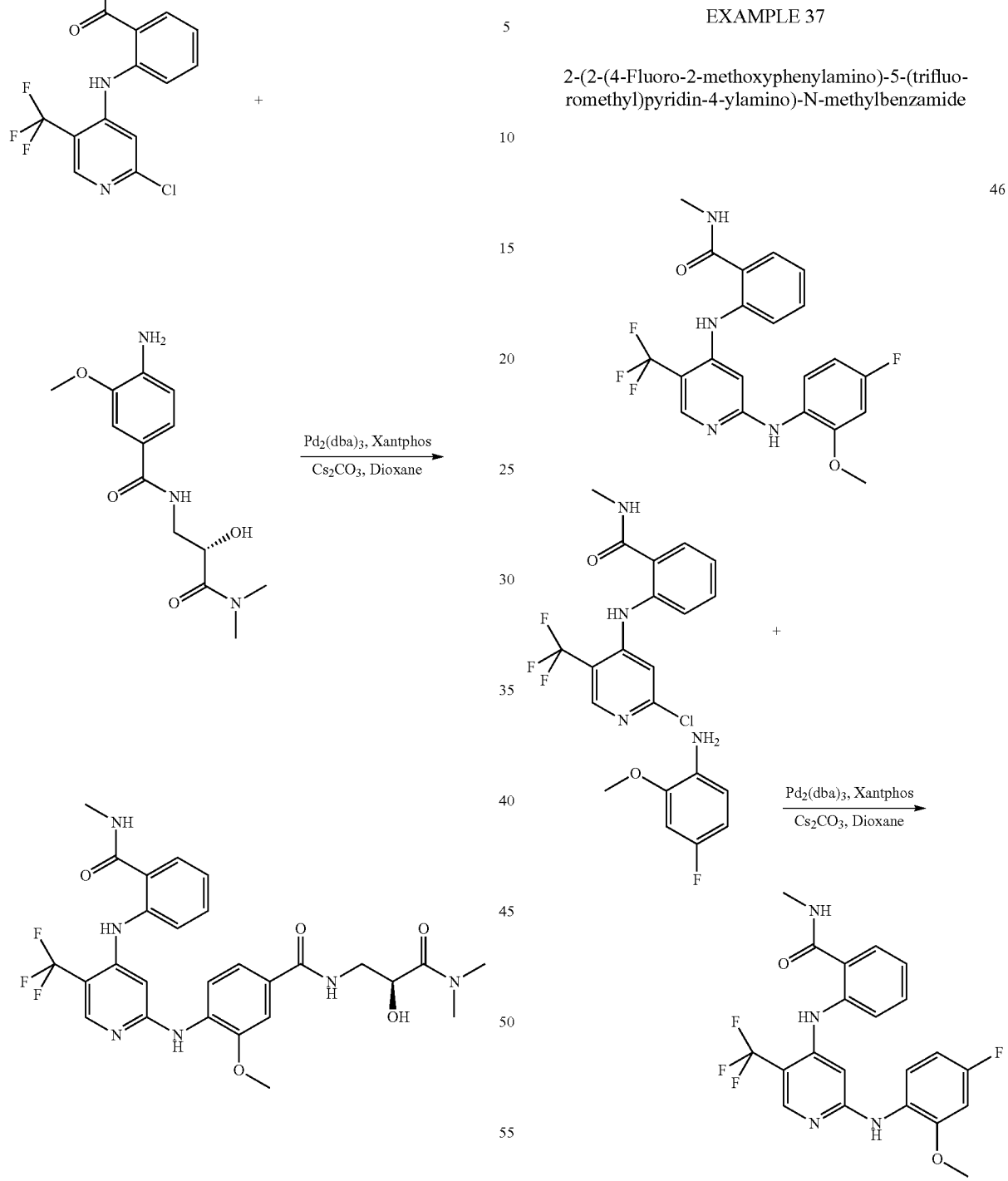

Method D was applied. The TFA salt of the title compound was obtained.

¹H NMR (400 MHz, DMSO-d₆) δ 10.34 (s, 1H), 8.95 (broad s, 1H), 8.71-8.69 (m, 1H), 8.53-8.50 (m, 1H), 8.30 (s, 1H), 8.17 (d, J=8.4 Hz, 1H), 7.72 (dd, J=7.6 Hz, 1.0 Hz, 1H), 7.59-7.46 (m, 3H), 7.15 (t, J=6.8 Hz, 1H), 7.06 (s, 1H), 4.56-4.53 (m, 1H), 3.89 (s, 3H), 3.53-3.47 (m, 1H), 3.27-3.20 (m, 1H), 3.08 (s, 3H), 2.85 (s, 3H), 2.77 (d, J=4.8 Hz, 3H); ESI-MS (m/z): 575.11 (M+1).

EXAMPLE 37

2-(2-(4-Fluoro-2-methoxyphenylamino)-5-(trifluoromethyl)pyridin-4-ylamino)-N-methylbenzamide Method D was applied. The TFA salt of the title compound was obtained.

¹H NMR (400 MHz, DMSO-d₆) δ 10.33 (s, 1H), 9.02 (broad s, 1H), 8.71-8.68 (m, 1H), 8.19 (s, 1H), 7.72 (d, J=7.6 Hz, 1H), 7.68-7.64 (m, 1H), 7.54-7.51 (m, 2H), 7.19-7.15 (m, 1H), 7.01 (dd, J=11.0 Hz, 2.4 Hz, 1H), 6.77 (td, J=8.8 Hz, 2.8 Hz, 1H), 6.66 (s, 1H), 3.82 (s, 3H), 2.76 (d, J=4.4 Hz, 3H); ESI-MS (m/z): 435.1 (M+1).

EXAMPLE 38

2-(2-(2-Methoxy-4-(1-methylpiperidin-4-yloxy)phenylamino)-5-(trifluoromethyl)pyridin-4-ylamino)-N-methylbenzamide

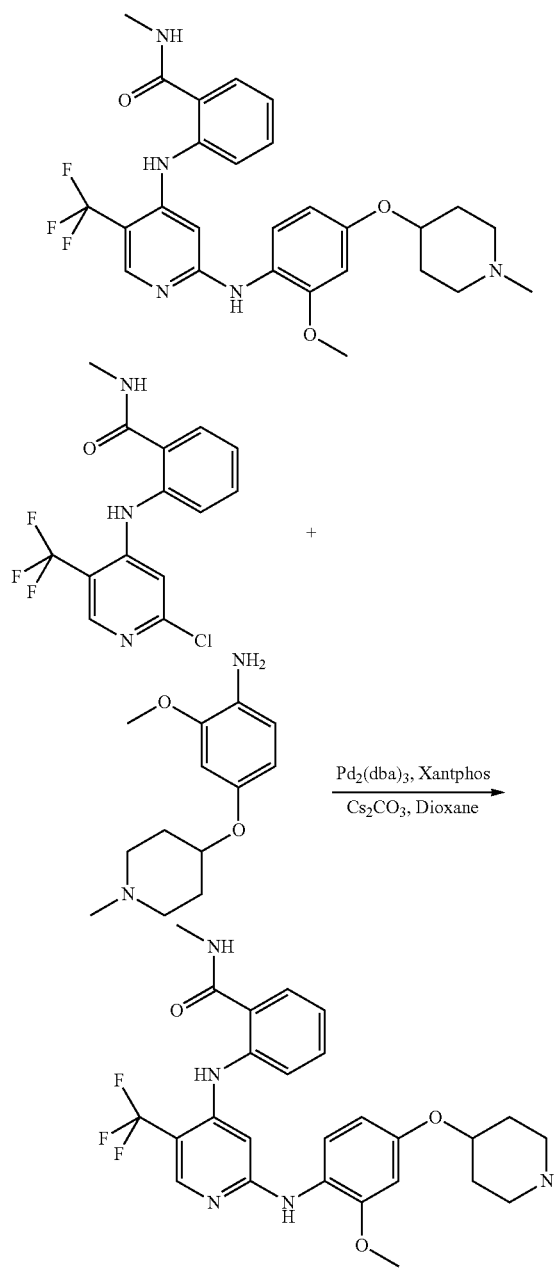

Method D was applied. The bis-TFA salt of the title compound was obtained.

$^1$H NMR (400 MHz, DMSO-d$_6$) δ 10.21 (s, 1H), 9.47 (broad s, 1H), 8.67-8.64 (m, 1H), 8.51 (broad s, 1H), 8.16 (s, 1H), 7.69 (d, J=7.2 Hz, 1H), 7.57 (t, J=9.0 Hz, 1H), 7.50-7.45 (m, 2H), 7.09 (td, J=7.2 Hz, 2.0 Hz, 1H), 6.71 (d, J=2.4 Hz, 1H), 6.63-6.55 (m, 2H), 4.70-4.44 (m, 1H), 3.79 (s, 3H), 3.51 (d, J=12.0 Hz, 1H), 3.33 (d, J=10.8 Hz, 1H), 3.21-3.04 (m, 2H), 2.82 (dd, J=12.8 Hz, 4.8 Hz, 3H), 2.76 (d, J=4.8 Hz, 3H), 2.27-2.32 (m, 1H), 2.07-2.04 (m, 1H), 1.98-1.91 (m, 1H), 1.76-1.65 (m, 1H); ESI-MS (m/z): 530.25 (M+1).

EXAMPLE 39

2-(2-(4-(2-(Diethylamino)ethoxy)-2-methoxyphenylamino)-5-(trifluoromethyl)pyridin-4-ylamino)-N-methylbenzamide

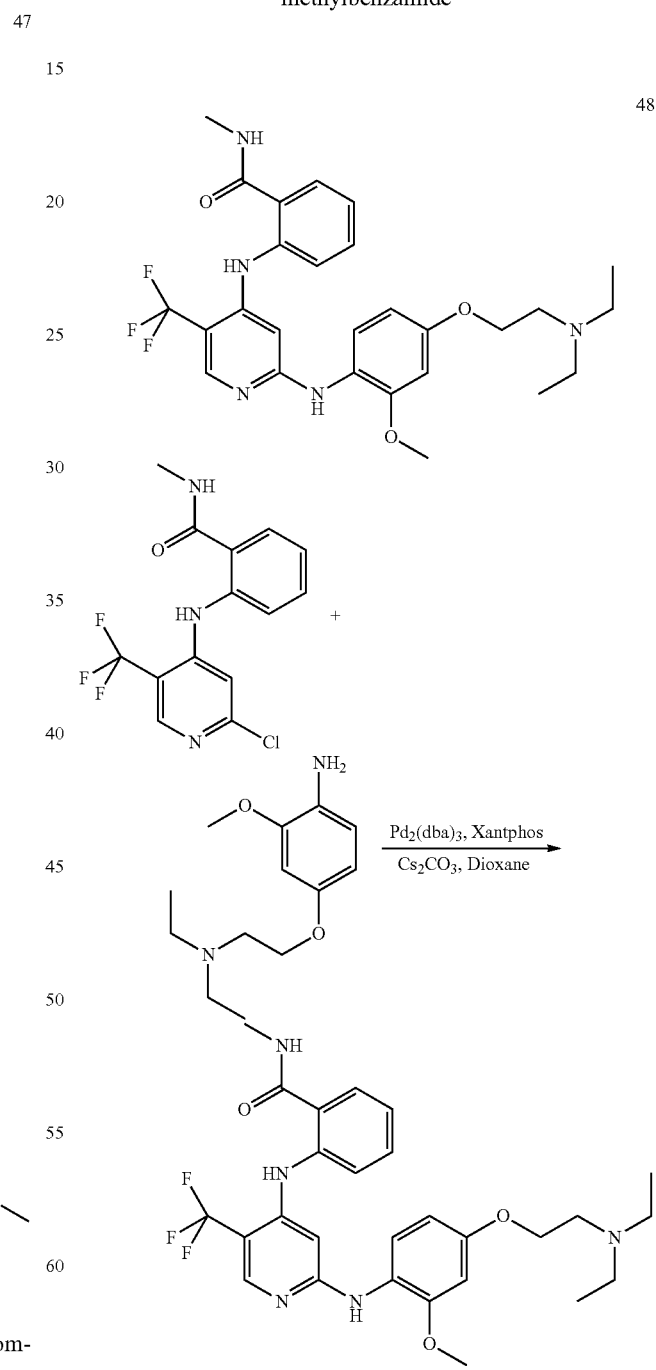

Method D was applied. The bis-TFA salt of the title compound was obtained.

¹H NMR (400 MHz, DMSO-d₆) δ 10.28 (s, 1H), 9.40 (broad s, 1H), 8.72 (broad s, 1H), 8.69-8.65 (m, 1H), 8.17 (s, 1H), 7.71 (d, J=8.0 Hz, 1H), 7.56 (d, J=8.0 Hz, 1H), 7.52-7.46 (m, 2H), 7.12 (td, J=7.0 Hz, 2.0 Hz, 1H), 6.68 (d, J=2.8 Hz, 1H), 6.61 (s, 1H), 6.57 (dd, J=8.0 Hz, 2.4 Hz, 1H), 4.30 (t, J=4.8 Hz, 2H), 3.81 (s, 3H), 3.51 (q, J=4.8 Hz, 2H), 3.29-3.18 (m, 4H), 2.76 (d, J=4.8 Hz, 3H), 1.24 (t, J=7.2 Hz, 6H); ESI-MS (m/z): 532.2 (M+1).

EXAMPLE 40

3-Methoxy-N,N-dimethyl-4-(4-(2-(methylcarbamoyl)phenylamino)-5-(trifluoromethyl)pyridin-2-ylamino)benzamide

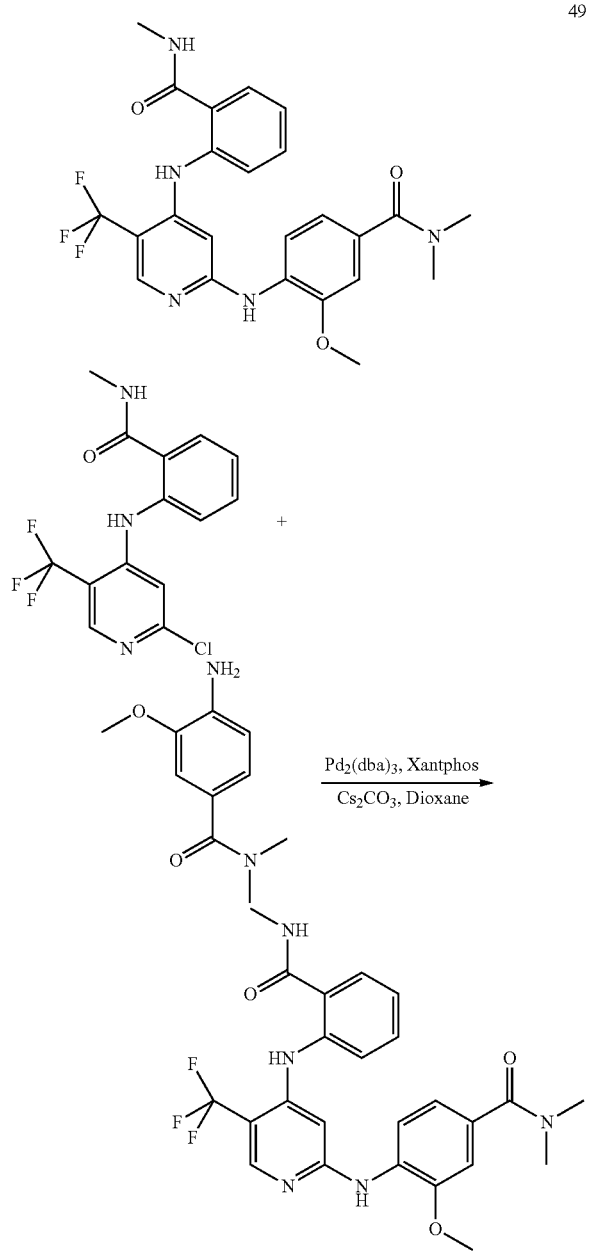

Method D was applied. The TFA salt of the title compound was obtained.

¹H NMR (400 MHz, DMSO-d₆) δ 10.32 (s, 1H), 8.96 (broad s, 1H), 8.69 (q, J=4.8 Hz, 1H), 8.26 (s, 1H), 8.02 (d, J=8.4 Hz, 1H), 7.71 (dd, J=8.0 Hz, 1.2 Hz, 1H), 7.52-7.50 (m, 2H), 7.15 (t, J=7.6 Hz, 1H), 7.06 (d, J=2.0 Hz, 1H), 6.97 (dd, J=7.6 Hz, 2.4 Hz, 1H), 6.95 (s, 1H), 3.85 (s, 3H), 2.96 (s, 6H), 2.76 (d, J=4.8 Hz, 3H); ESI-MS (m/z): 488.2 (M+1).

EXAMPLE 41

N,N,3-Trimethyl-4-(4-(2-(methylcarbamoyl)phenylamino)-5-(trifluoromethyl)pyridin-2-ylamino)benzamide

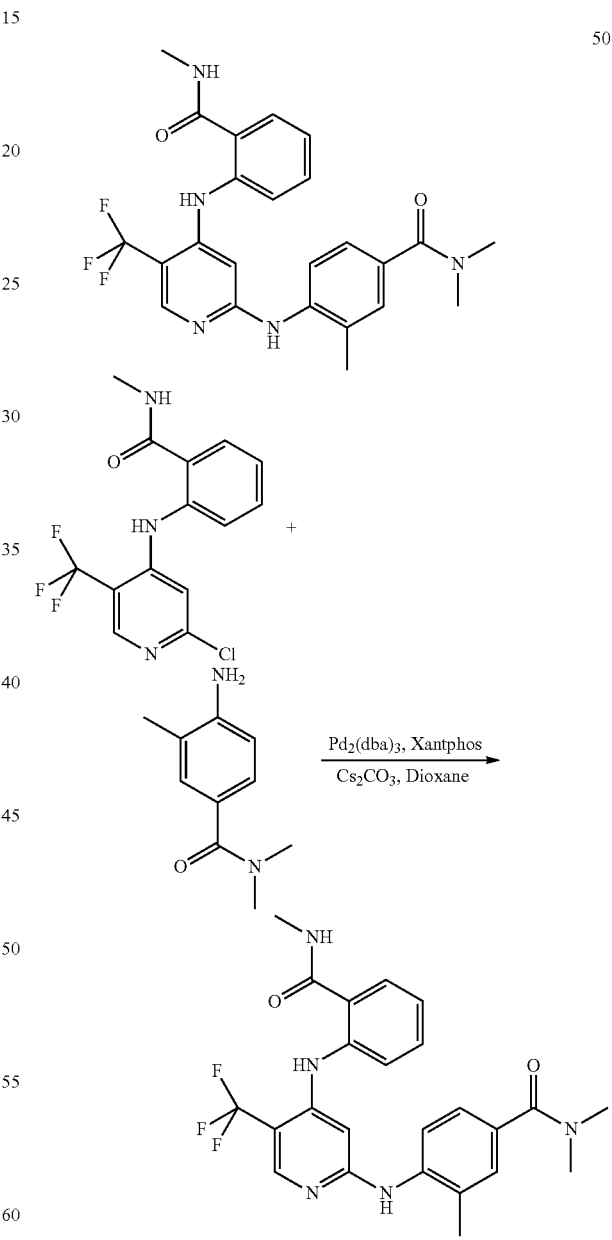

Method D was applied. The TFA salt of the title compound was obtained.

¹H NMR (400 MHz, DMSO-d₆) δ 10.29 (s, 1H), 9.00 (broad s, 1H), 8.69 (q, J=4.0 Hz, 1H), 8.22 (s, 1H), 7.70 (dd, J=8.0 Hz, 1.2 Hz, 1H), 7.56 (s, 1H), 7.54 (s, 1H), 7.50 (td, J=7.2 Hz, 1.2 Hz, 1H), 7.27 (d, J=1.2 Hz, 1H), 7.22 (dd, J=8.0 Hz, 2.0 Hz, 1H), 7.15 (td, J=7.4 Hz, 1.2 Hz, 1H), 6.66 (s, 1H), 2.94 (s, 6H), 2.76 (d, J=4.8 Hz, 3H), 2.22 (s, 3H); ESI-MS (m/z): 472.1 (M+1).

EXAMPLE 42

N,N-Dimethyl-6-(4-(2-(methylcarbamoyl)phenylamino)-5-(trifluoromethyl)pyridin-2-ylamino)nicotinamide

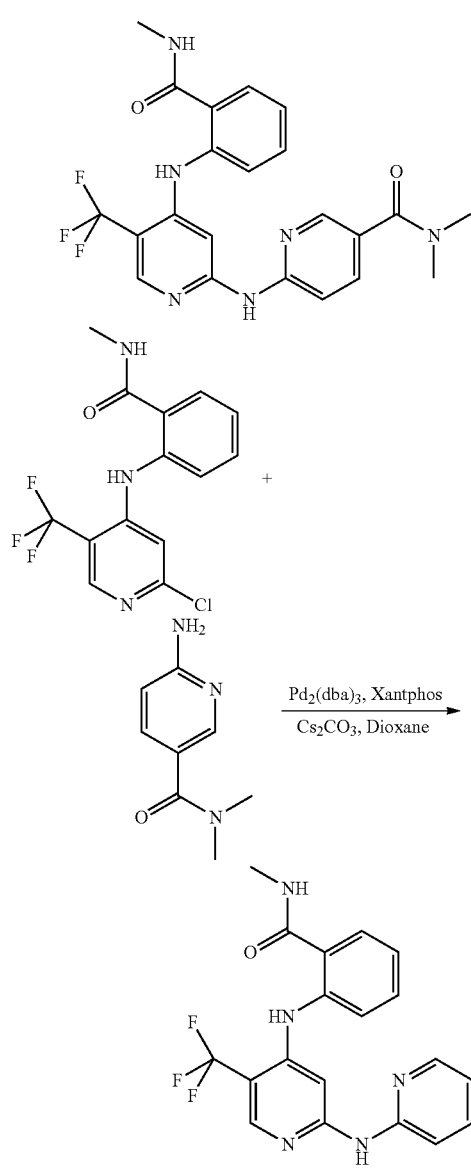

Method D was applied. The TFA salt of the title compound was obtained.

¹H NMR (400 MHz, DMSO-d₆) δ 10.63 (broad s, 1H), 10.52 (s, 1H), 8.73 (q, J=4.8 Hz, 1H), 8.41 (s, 1H), 8.28 (d, J=2.0 Hz, 1H), 7.83 (dd, J=8.8 Hz, 2.4 Hz, 1H), 7.75 (dd, J=7.6 Hz, 1.2 Hz, 1H), 7.68 (d, J=8.0 Hz, 1H), 7.59 (td, J=7.8 Hz, 1.2 Hz, 1H), 7.50 (d, J=8.8 Hz, 1H), 7.22 (t, J=7.6 Hz, 1H), 2.98 (s, 6H), 2.76 (d, J=4.8 Hz, 3H); ESI-MS (m/z): 459.15 (M+1).

EXAMPLE 43

N-(2-(Diethylamino)ethyl)-3-methyl-4-(4-(2-(methylcarbamoyl)phenylamino)-5-(trifluoromethyl)pyridin-2-ylamino)benzamide

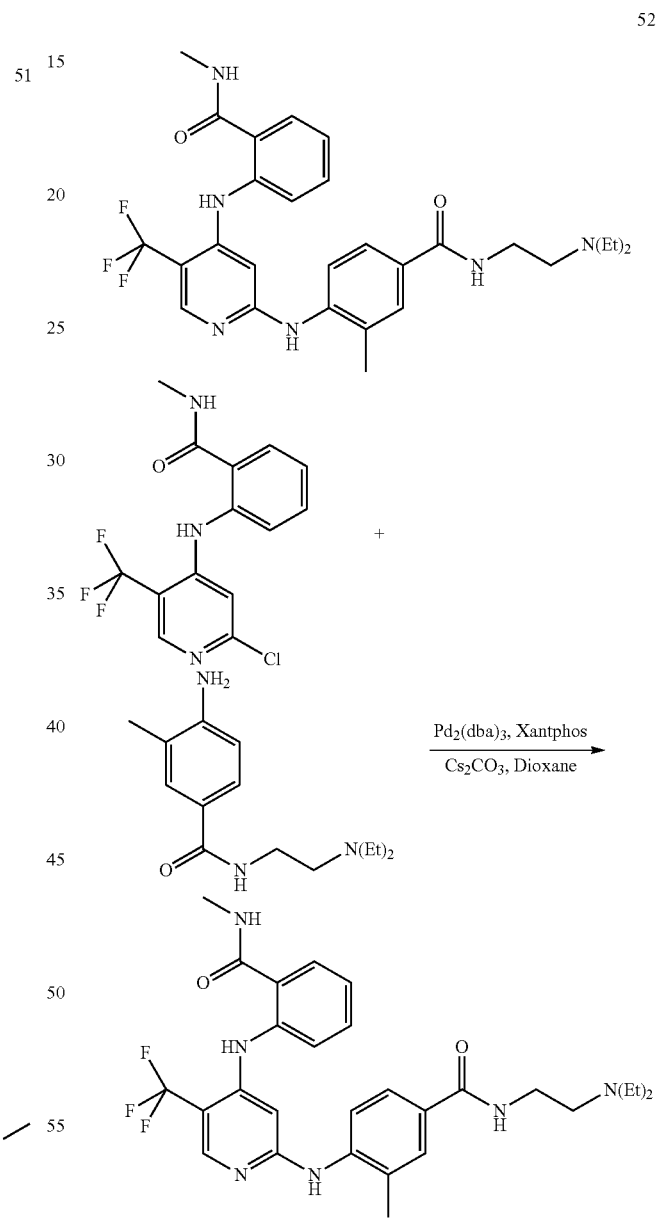

Method D was applied. The bis-TFA salt of the title compound was obtained.

¹H NMR (400 MHz, DMSO-d₆) δ 10.30 (s, 1H), 9.38 (broad s, 1H), 8.87 (s, 1H), 8.71 (q, J=4.8 Hz, 1H), 8.65 (t, J=5.2 Hz, 1H), 8.25 (s, 1H), 7.76-7.71 (m, 3H), 7.66 (dd, J=8.6 Hz, 2.0 Hz, 1H), 7.58 (d, J=7.6 Hz, 1H), 7.50 (td, J=7.6 Hz, 1.2 Hz, 1H), 7.13 (td, J=7.6 Hz, 1.2 Hz, 1H), 6.84 (s, 1H), 3.59 (q, J=6.4 Hz, 2H), 3.26-3.18 (m, 6H), 2.76 (d, J=4.8 Hz, 3H), 2.26 (s, 3H), 1.21 (t, J=7.2 Hz, 6H); ESI-MS (m/z): 543.2 (M+1).

EXAMPLE 44

N-Methyl-2-(2-(2-methyl-4-morpholinophenylamino)-5-(trifluoromethyl)pyridin-4-ylamino)benzamide

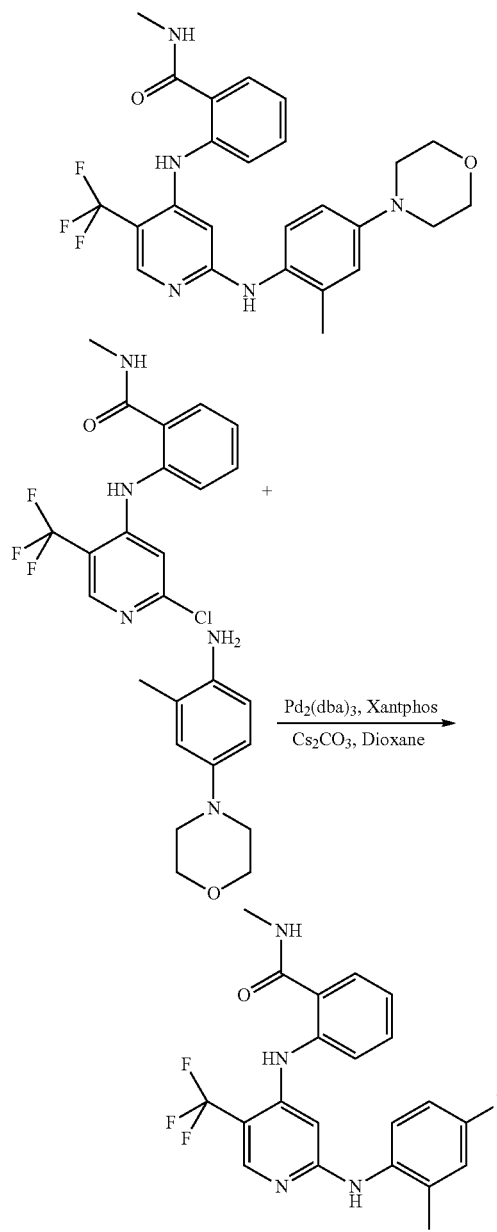

Method D was applied. The TFA salt of the title compound was obtained.

¹H NMR (400 MHz, DMSO-d₆) δ 10.43 (s, 1H), 9.35 (broad s, 1H), 8.71 (q, J=4.0 Hz, 1H), 8.10 (s, 1H), 7.72 (d, J=7.6 Hz, 1H), 7.55-7.49 (m, 2H), 7.21 (t, J=7.6 Hz, 1H), 7.16 (d, J=8.4 Hz, 1H), 6.88 (d, J=2.8 Hz, 1H), 6.83 (dd, J=8.4 Hz, 2.8 Hz, 1H), 6.44 (s, 1H), 3.73 (t, J=4.8 Hz, 4H), 3.10 (t, J=4.8 Hz, 4H), 2.76 (d, J=4.8 Hz, 3H), 2.13 (s, 3H); ESI-MS (m/z): 486.2 (M+1).

EXAMPLE 45

N-Methyl-2-(2-(3-methylpyridin-2-ylamino)-5-(trifluoromethyl)pyridin-4-ylamino)benzamide

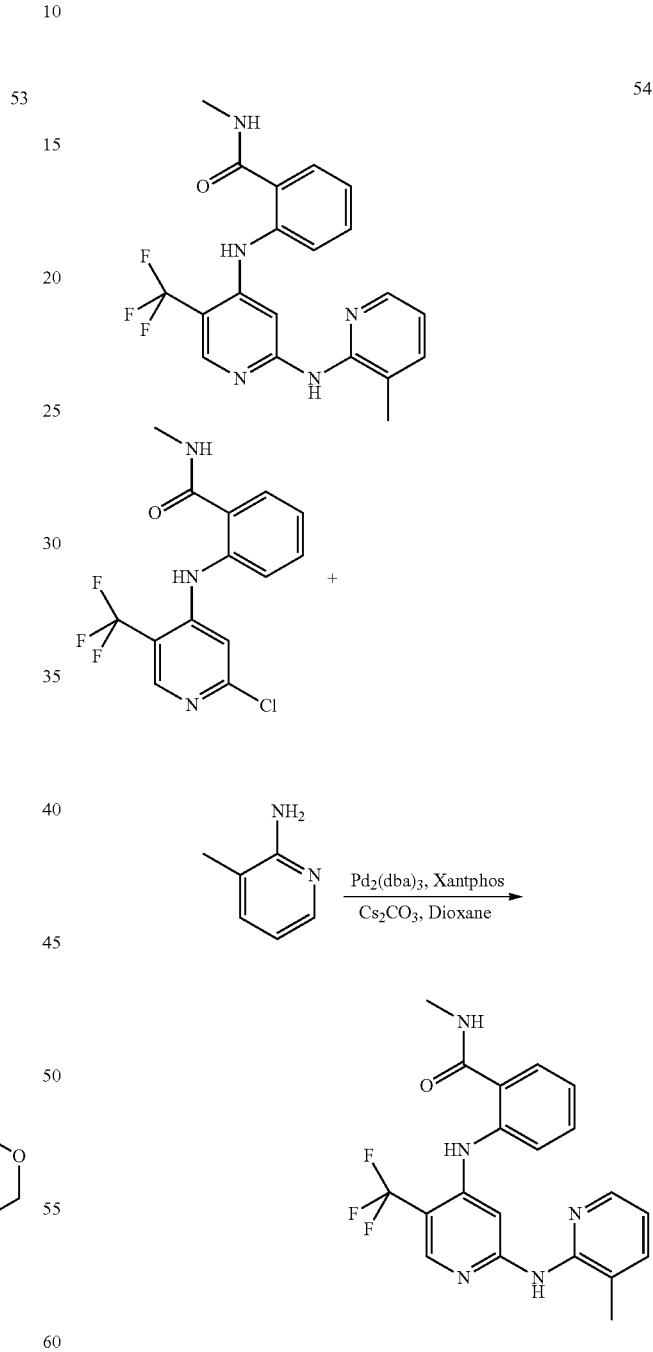

Method D was applied. The TFA salt of the title compound was obtained as a white solid.

¹H-NMR (400 MHz, d₆-DMSO) δ 10.57 (s, 1H), 9.69 (br s, 1H), 8.75 (q, J=4.6 Hz, 1H), 8.44 (s, 1H), 8.21 (d, J=4.5 Hz, 1H), 7.86 (br d, J=6.7 Hz, 1H), 7.77 (dd, J=1.1, 7.9 Hz, 1H), 7.69-7.59 (m, 3H), 7.26 (t, J=7.1 Hz, 1H), 7.17 (t, J=6.4 Hz,

1H), 2.77 (d, J=4.6 Hz, 3H), 2.35 (s, 3H); $^{19}$F-NMR (376 MHz, d$_6$-DMSO) δ −60.6 (br s, 3F), −73.8 (s, 3F); MS (m/z): 402.2 [M+1]$^+$.

EXAMPLE 46

N-methyl-2-(2-(6-methylpyridin-2-ylamino)-5-(trifluoromethyl)pyridin-4-ylamino)benzamide

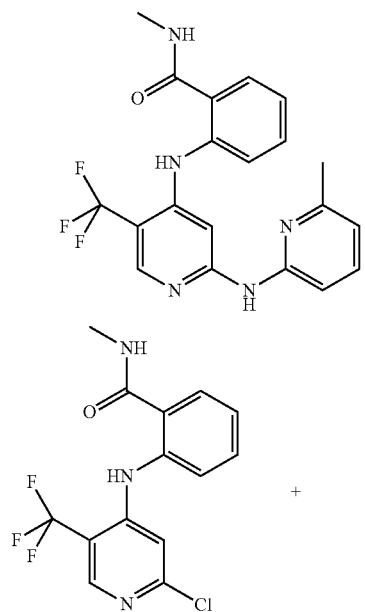

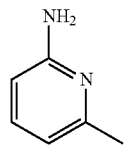

Method D was applied. The TFA salt of the title compound was obtained as a white solid.

$^1$H-NMR (400 MHz, d$_6$-DMSO) δ 10.76 (br s, 1H), 10.53 (s, 1H), 8.74 (q, J=4.4 Hz, 1H), 8.51 (s, 1H), 7.77-7.67 (m, 4H), 7.60-7.56 (m, 1H), 7.25 (t, J=7.5 Hz, 1H), 7.10 (d, J=8.3 Hz, 1H), 6.94 (d, J=7.3 Hz, 1H), 2.77 (d, J=4.5 Hz, 3H), 2.43 (s, 3H); $^{19}$F-NMR (376 MHz, d$_6$-DMSO) δ −60.4 (br s, 3F), −74.3 (s, 3F); MS (m/z): 402.2 [M+1]$^+$.

EXAMPLE 47

N-Methyl-2-(2-(2-oxoindolin-5-ylamino)-5-(trifluoromethyl)pyridin-4-ylamino)benzamide

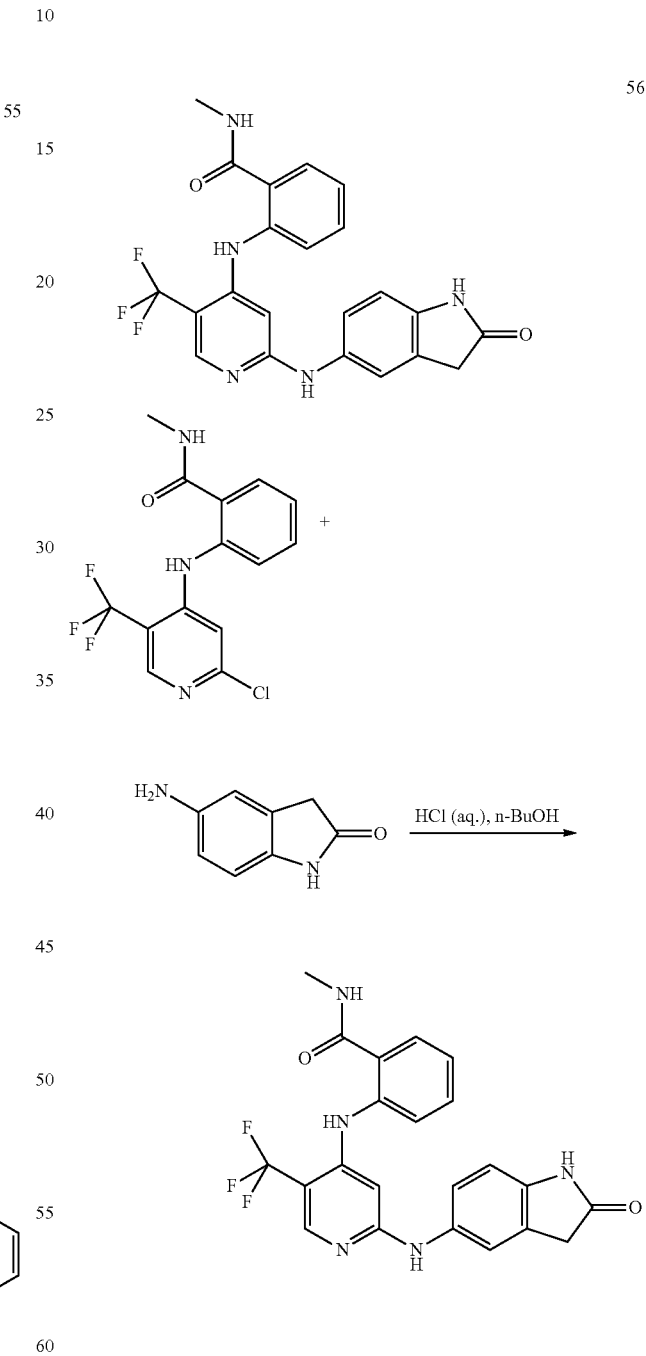

Method F was applied. The TFA salt of the title compound was obtained.

$^1$H NMR (400 MHz, DMSO-d$_6$) δ 10.31 (s, 1H), 10.26 (s, 1H), 9.33 (s, 1H), 8.68 (q, J=4.8 Hz, 1H), 8.21 (s, 1H), 7.71 (dd, J=8.0 Hz, 1.2 Hz, 1H), 7.58 (d, J=7.6 Hz, 1H), 7.52 (td, J=7.8 Hz, 1.2 Hz, 1H), 7.43 (s, 1H), 7.23 (d, J=8.4 Hz, 1H), 7.15 (t, J=6.8 Hz, 1H), 6.76 (d, J=8.4 Hz, 1H), 6.64 (s, 1H), 3.46 (s, 2H), 2.76 (d, J=4.8 Hz, 3H); ESI-MS (m/z): 442.1 (M+1).

EXAMPLE 48

N,N-Dimethyl-4-(4-(2-(methylcarbamoyl)phenylamino)-5-(trifluoromethyl)pyridin-2-ylamino)benzamide

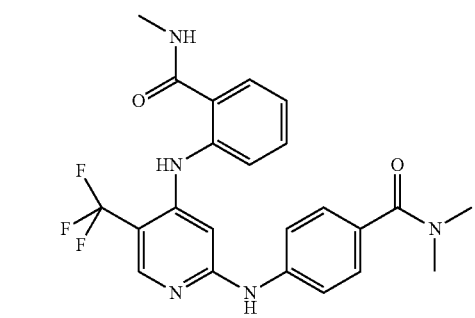

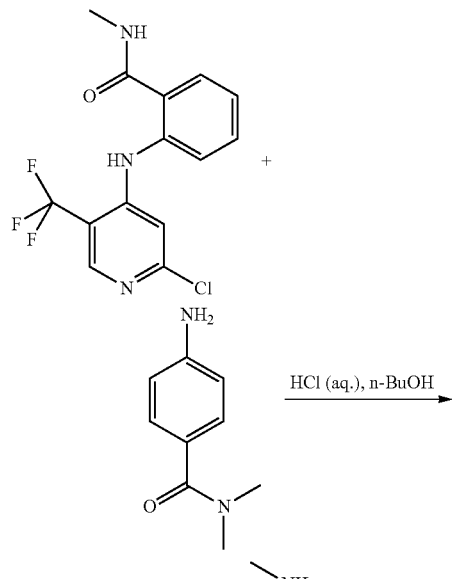

Method F was applied. The TFA salt of the title compound was obtained.

¹H NMR (400 MHz, DMSO-d₆) δ 10.26 (s, 1H), 9.53 (s, 1H), 8.70 (q, J=4.8 Hz, 1H), 8.32 (s, 1H), 7.73 (dd, J=8.0 Hz, 1.2 Hz, 1H), 7.67-7.65 (m, 2H), 7.60 (dd, J=8.0 Hz, 1.2 Hz, 1H), 7.53 (td, J=7.2 Hz, 1.2 Hz, 1H), 7.36-7.34 (m, 2H), 7.15 (td, J=7.2 Hz, 1.2 Hz, 1H), 6.82 (s, 1H), 2.95 (s, 6H), 2.77 (d, J=4.8 Hz, 3H); ESI-MS (m/z): 458.2 (M+1).

EXAMPLE 49

N-Methyl-2-(2-(4-morpholinophenylamino)-5-(trifluoromethyl)pyridin-4-ylamino)benzamide

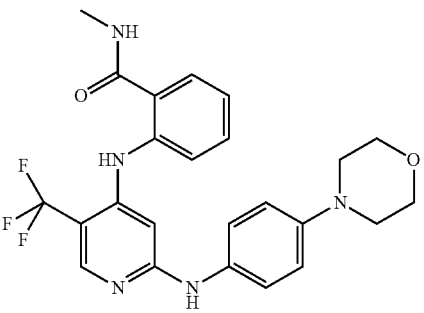

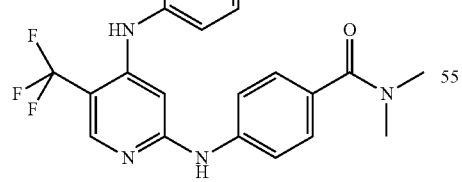

Method F was applied. The TFA salt of the title compound was obtained.

¹H NMR (400 MHz, DMSO-d₆) δ 10.36 (s, 1H), 9.50 (broad s, 1H), 8.70 (q, J=4.8 Hz, 1H), 8.20 (s, 1H), 7.72 (dd, J=8.0 Hz, 1.2 Hz, 1H), 7.58 (dd, J=8.4 Hz, 0.8 Hz, 1H), 7.53 (td, J=8.0 Hz, 1.2 Hz, 1H), 7.35 (d, J=8.8 Hz, 2H), 7.18 (td, J=7.4 Hz, 1.2 Hz, 1H), 6.98 (d, J=9.2 Hz, 2H), 6.62 (s, 1H), 3.75 (t, J=4.4 Hz, 4H), 3.09 (t, J=4.4 Hz, 4H), 2.76 (d, J=4.8 Hz, 3H); ESI-MS (m/z): 472.2 (M+1).

EXAMPLE 50

N-Methyl-2-(2-(5-morpholinopyridin-2-ylamino)-5-(trifluoromethyl)pyridin-4-ylamino)benzamide

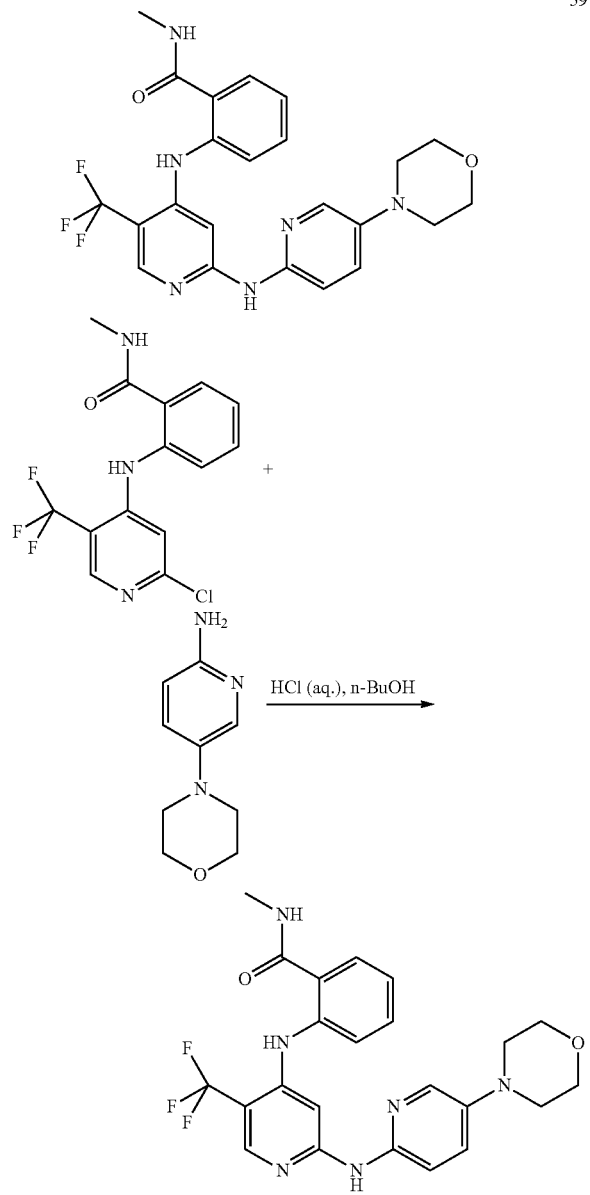

Method F was applied. The TFA salt of the title compound was obtained.

$^1$H NMR (400 MHz, DMSO-d$_6$) δ 10.70 (broad s, 1H), 10.51 (s, 1H), 8.73 (q, J=4.8 Hz, 1H), 8.39 (s, 1H), 7.86 (d, J=3.2 Hz, 1H), 7.76 (dd, J=7.6 Hz, 1.2 Hz, 1H), 7.67-7.64 (m, 2H), 7.59 (td, J=7.8 Hz, 1.2 Hz, 1H), 7.29-7.23 (m, 3H), 3.76 (t, J=4.4 Hz, 4H), 3.11 (t, J=4.4 Hz, 4H), 2.77 (d, J=4.8 Hz, 3H); ESI-MS (m/z): 473.2 (M+1).

EXAMPLE 51

2-(2-(2-Fluoro-4-morpholinophenylamino)-5-(trifluoromethyl)pyridin-4-ylamino)-N-methylbenzamide

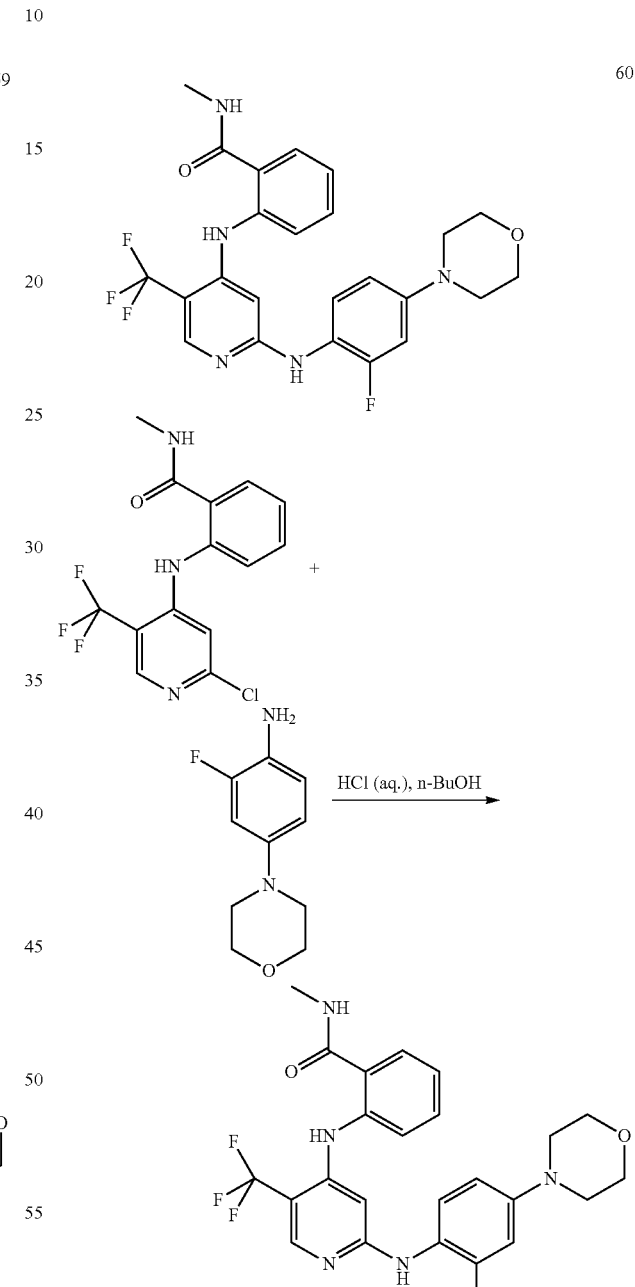

Method F was applied. The title compound was obtained.
$^1$H NMR (400 MHz, DMSO-d$_6$) δ 10.27 (s, 1H), 8.96 (broad s, 1H), 8.68 (q, J=4.8 Hz, 1H), 8.17 (s, 1H), 7.71 (dd, J=8.0 Hz, 1.2 Hz, 1H), 7.55-7.45 (m, 3H), 7.13 (t, J=7.4 Hz, 1H), 6.85 (dd, J=14.2 Hz, 2.4 Hz, 1H), 6.74 (dd, J=9.0 Hz, 2.4 Hz, 1H), 6.62 (s, 1H), 3.72 (t, J=4.8 Hz, 4H), 3.10 (t, J=4.8 Hz, 4H), 2.76 (d, J=4.8 Hz, 3H); ESI-MS (m/z): 490.2 (M+1).

EXAMPLE 52

N-(2-(2-(2-Methoxy-4-morpholinophenylamino)-5-(trifluoromethyl)pyridin-4-ylamino)phenyl)acetamide (61)

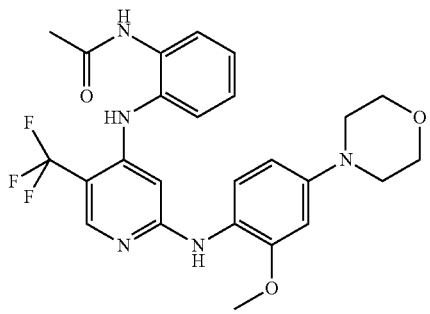

N-(2-(2-chloro-5-(trifluoromethyl)pyridin-4-ylamino)phenyl)acetamide

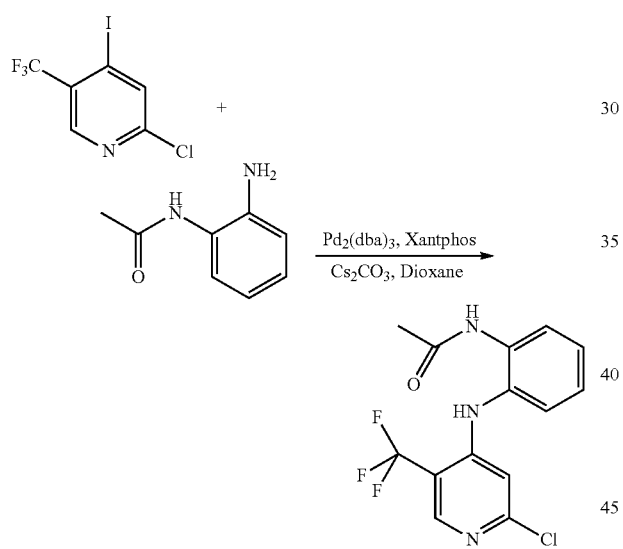

Method B was applied.

N-(2-(2-(2-methoxy-4-morpholinophenylamino)-5-(trifluoromethyl)pyridin-4-ylamino)phenyl)acetamide

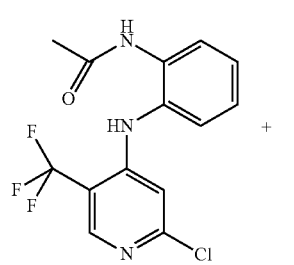

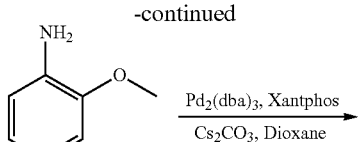

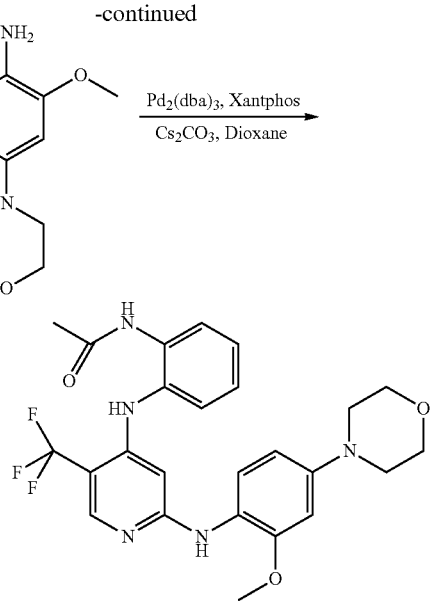

Method C was applied. The title compound was obtained as the TFA salt.

$^1$H NMR (400 MHz, CD$_3$CN-d$_3$) δ 9.94 (broad s, 1H), 8.54 (s, 1H), 8.11 (s, 1H), 7.99 (s, 1H), 7.36-7.25 (m, 4H), 7.00 (d, J=8.8 Hz, 1H), 6.57 (d, J=2.4 Hz, 1H), 6.49 (dd, J=8.8 Hz, 2.4 Hz, 1H), 5.67 (s, 1H), 3.79 (t, J=4.8 Hz, 4H), 3.77 (s, 3H), 3.15 (t, J=4.8 Hz, 4H), 2.07 (s, 3H); ESI-MS (m/z): 502.2 (M+1).

EXAMPLE 53

N$^2$-(2-Methoxy-4-morpholinophenyl)-N$^4$-(2-(pyrimidin-2-yl)phenyl)-5-(trifluoromethyl)pyridine-2,4-diamine (62)

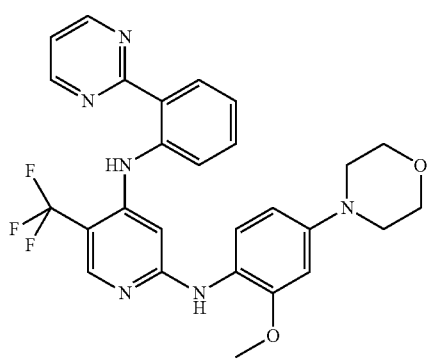

2-Chloro-N-(2-(pyrimidin-2-yl)phenyl)-5-(trifluoromethyl)pyridin-4-amine

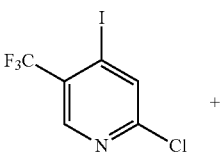

-continued

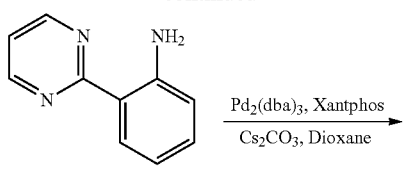

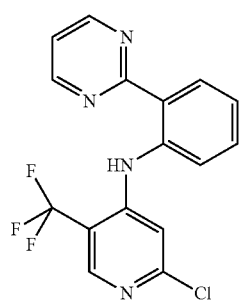

The mixture of 2-chloro-4-iodo-5-(trifluoromethyl)pyridine (142 mg, 0.46 mmol), 2-(pyrimidin-2-yl)aniline (78 mg, 0.46 mmol), Pd$_2$(dba)$_3$ (23 mg, 0.025 mmol), xantphos (23 mg, 0.040 mmol) and cesium carbonate (325 mg, 1.0 mmol) in dioxane (4.5 ml) was microwave heated in a Biotage Initiator microwave synthesizer at 130° C. for 30'. The solvent was removed and the residue was purified by preparative HPLC (0.1% TFA in water/acetonitrile gradient) to yield the title compound.

N$^2$-(2-Methoxy-4-morpholinophenyl)-N$^4$-(2-(pyrimidin-2-yl)phenyl)-5-(trifluoromethyl)pyridine-2,4-diamine

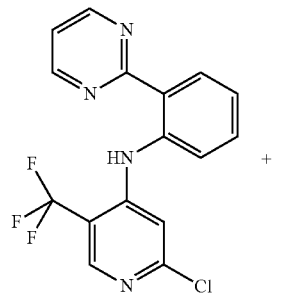

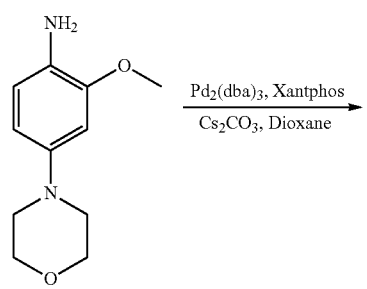

-continued

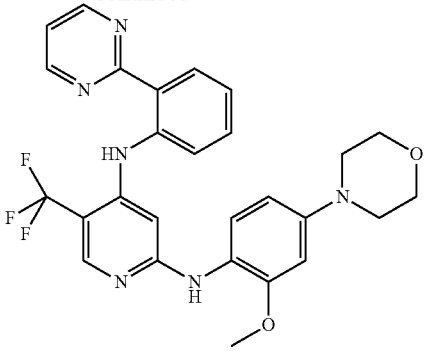

Method C was applied to the mixture of 2-chloro-N-(2-(pyrimidin-2-yl)phenyl)-5-(trifluoromethyl)pyridin-4-amine (22 mg, 0.063 mmol), 2-methoxy-4-morpholinoaniline (20 mg, 0.096 mmol), Pd$_2$(dba)$_3$ (10 mg, 0.011 mmol), xantphos (15 mg, 0.026 mmol) and cesium carbonate (61 mg, 0.19 mmol) in dioxane (2.8 ml). The TFA salt of the title compound was obtained as a yellow solid.

$^1$H-NMR (400 MHz, d$_6$-DMSO) δ 11.36 (s, 1H), 9.22 (br s, 1H), 8.93 (d, J=4.9 Hz, 2H), 8.41 (dd, J=1.4, 8.0 Hz, 1H), 8.12 (s, 1H), 7.64 (d, J=8.2 Hz, 1H), 7.57 (t, J=7.6 Hz, 1H), 7.52 (t, J=4.9 Hz, 1H), 7.31 (t, J=7.5 Hz, 1H), 7.25 (d, J=8.5 Hz, 1H), 6.66 (d, J=2.1 Hz, 1H), 6.61 (s, 1H), 6.52 (dd, J=2.1, 8.6 Hz, 1H), 3.79 (s, 3H), 3.74 (t, J=4.6 Hz, 4H), 3.14 (t, J=4.5 Hz, 4H); MS (m/z): 523.25 [M+1]$^+$.

EXAMPLE 54

N$^2$-(2-Methoxy-4-(4-methylpiperazin-1-yl)phenyl)-N$^4$-(2-(pyrimidin-2-yl)phenyl)-5-(trifluoromethyl)pyridine-2,4-diamine

63

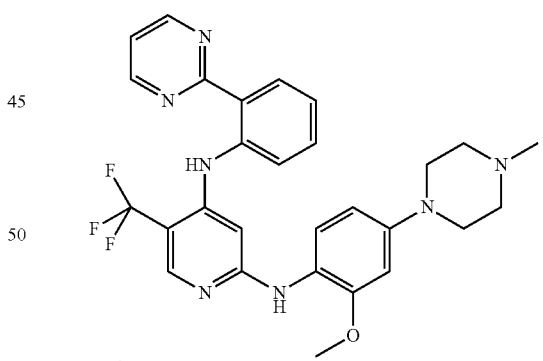

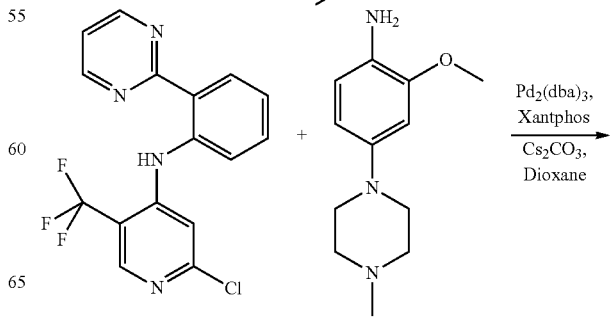

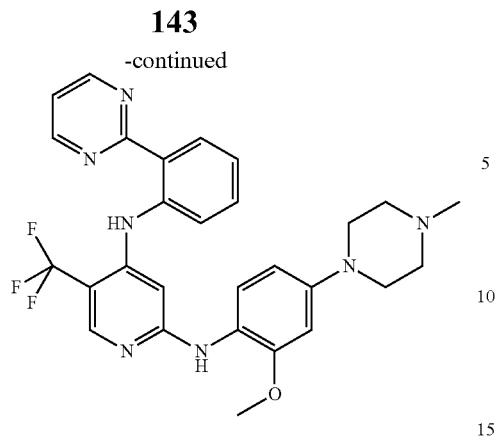

Method C was applied to the mixture of 2-chloro-N-(2-(pyrimidin-2-yl)phenyl)-5-(trifluoromethyl)pyridin-4-amine (30 mg, 0.086 mmol), 2-methoxy-4-(4-methylpiperazin-1-yl)aniline (31 mg, 0.14 mmol), $Pd_2(dba)_3$ (11 mg, 0.012 mmol), xantphos (11 mg, 0.019 mmol) and cesium carbonate (590 mg, 0.18 mmol) in dioxane (3 ml). The bis-TFA salt of the title compound was obtained as a yellow solid.

$^1$H-NMR (400 MHz, $d_6$-DMSO) δ 11.31 (s, 1H), 9.82 (br s, 1H), 8.93 (d, J=4.9 Hz, 3H), 8.42 (dd, J=1.5, 8.0 Hz, 1H), 8.17 (s, 1H), 7.62 (d, J=7.6 Hz, 1H), 7.57-7.51 (m, 2H), 7.39 (d, J=8.5 Hz, 1H), 7.26 (t, J=7.5 Hz, 1H), 6.70 (d, J=2.5 Hz, 1H), 6.63 (s, 1H), 6.55 (dd, J=2.5, 8.7 Hz, 1H), 3.86 (d, J=13.3 Hz, 2H), 3.80 (s, 3H), 3.53 (J=11.5 Hz, 2H), 3.20-3.10 (m, 2H), 2.94 (t, J=12.1 Hz, 2H), 2.87 (s, 3H); $^{19}$F-NMR (376 MHz, $d_6$-DMSO) δ −59.6 (s, 3F), −74.1 (s, 6F); MS (m/z): 536.2 $[M+1]^+$.

EXAMPLE 55

$N^2$-(2-Methoxy-4-morpholinophenyl)-$N^4$-(2-(oxazol-2-yl)phenyl)-5-(trifluoromethyl)pyridine-2,4-diamine

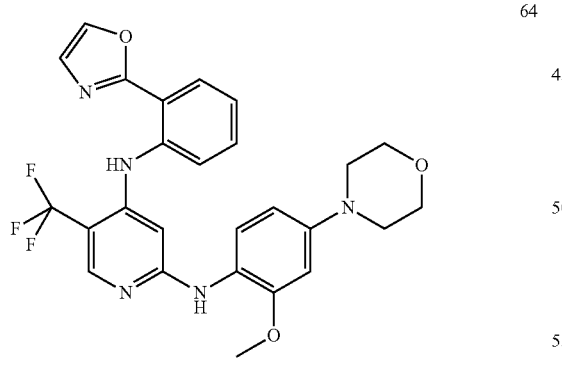

2-Chloro-N-(2-(oxazol-2-yl)phenyl)-5-(trifluoromethyl)pyridin-4-amine

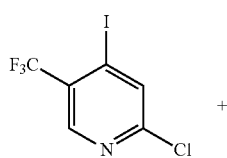

+

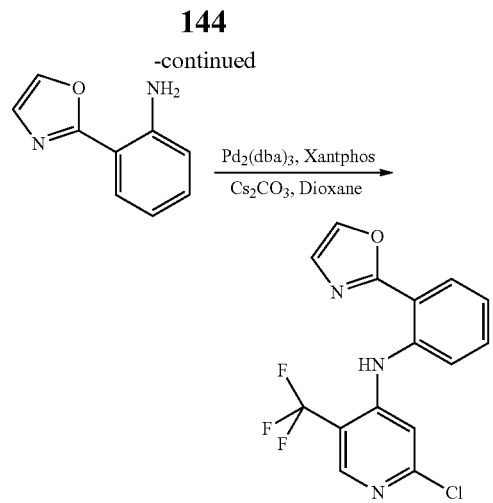

Method B was applied.

$N^2$-(2-methoxyl-4-morpholinophenyl)-$N^4$-(2-(oxazol-2-yl)phenyl)-5-(trifluoromethyl)pyridine-2,4-diamine

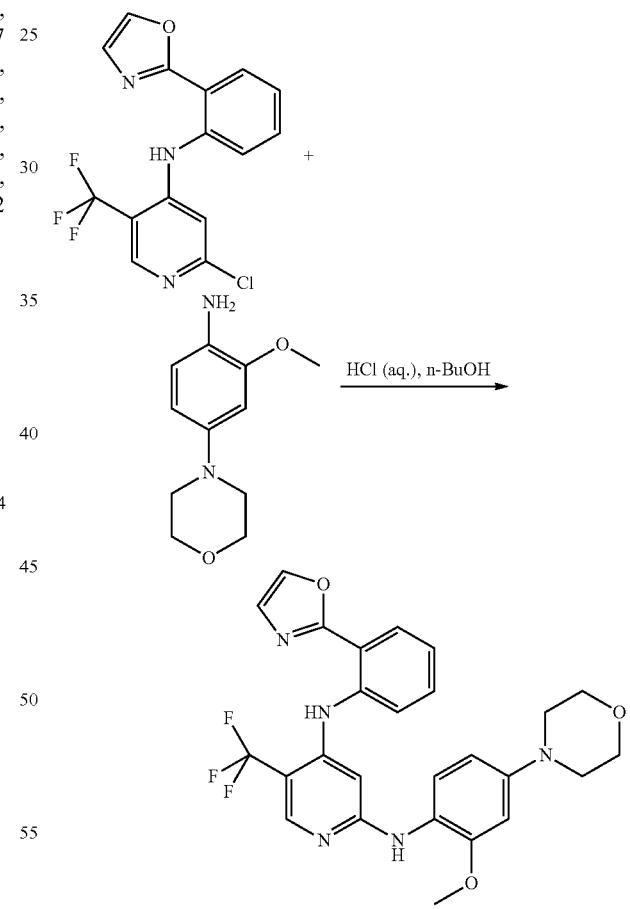

Method F was applied. The TFA salt of the title compound was obtained as a pale yellow solid.

$^1$H-NMR (400 MHz, $d_6$-DMSO) δ 10.08 (s, 1H), 9.00 (vbr s, 1H), 8.29 (d, J=0.8 Hz, 1H), 8.16 (br s, 1H), 8.04 (dd, J=1.2, 7.9 Hz, 1H), 7.61-7.52 (m, 2H), 7.47 (d, J=0.8 Hz, 1H), 7.33-7.25 (m, 2H), 6.64 (2.4 Hz, 1H), 6.54-6.48 (m, 2H), 3.78 (s, 1H), 3.74 (t, J=4.8 Hz, 4H), 3.12 (t, J=4.7 Hz, 4H); $^{19}$F-NMR (376 MHz, $d_6$-DMSO) δ −59.0 (br s, 3F), −74.2 (s, 3F); MS (m/z): 512.2 $[M+1]^+$.

EXAMPLE 56

N⁴-(2-(1H-Pyrazol-1-yl)phenyl)-N²-(2-methoxy-4-morpholinophenyl)-5-(trifluoromethyl)pyridine-2,4-diamine

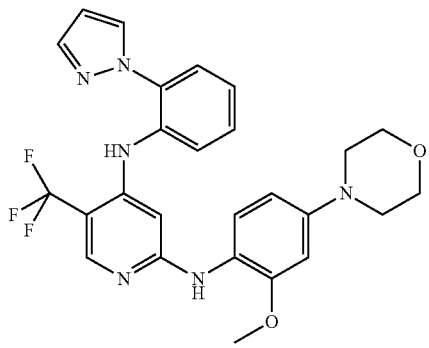

N-(2-(1H-Pyrazol-1-yl)phenyl)-2-chloro-5-(trifluoromethyl)pyridin-4-amine

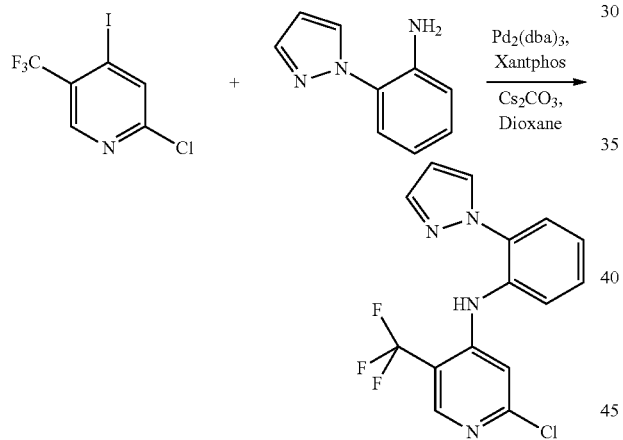

Method B was applied.

N⁴-(2-(1H-Pyrazol-1-yl)phenyl)-N²-(2-methoxy-4-morpholinophenyl)-5-(trifluoromethyl)pyridine-2,4-diamine

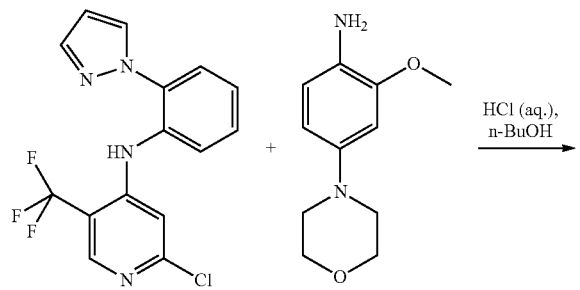

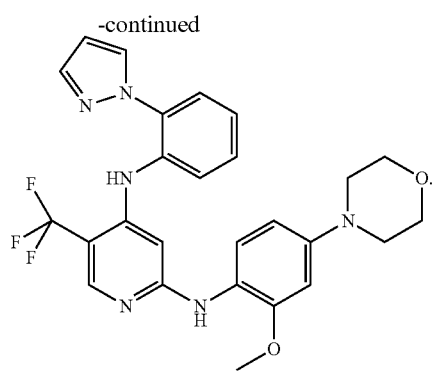

Method F was applied. The TFA salt of the title compound was obtained as a pale yellow solid.

$^{1}$H-NMR (400 MHz, d$_6$-DMSO) δ 9.33 (br s, 1H), 9.25 (vbr s, 1H), 8.21 (d, J=2.2 Hz, 1H), 7.98 (br s, 1H), 7.78 (d, J=1.6 Hz, 1H), 7.70 (dd, J=1.4, 7.8 Hz, 1H), 7.59 (dd, J=1.3, 8.0 Hz, 1H), 7.52-7.42 (m, 2H), 7.16 (d, J=8.8 Hz, 1H), 6.63 (d, J=2.4 Hz, 1H), 6.54-6.52 (m, 1H), 6.49 (dd, J=2.5, 8.7 Hz, 1H), 6.06 (br s, 1H), 3.76 (s, 1H), 3.74 (t, J=5.1 Hz, 4H), 3.13 (t, J=4.7 Hz, 4H); MS (m/z): 511.25 [M+1]⁺.

EXAMPLE 57

N-Methyl-N-(3-((2-(2-oxoindolin-5-ylamino)-5-(trifluoromethyl)pyridin-4-ylamino)methyl)pyridin-2-yl)methanesulfonamide

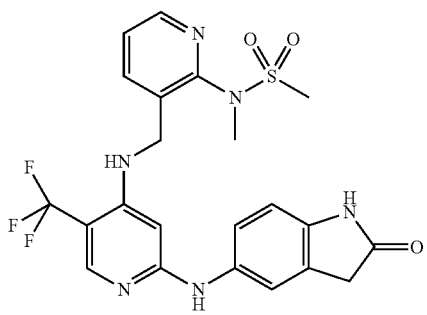

N-(3-Cyanopyridin-2-yl)-N-methylmethanesulfonamide

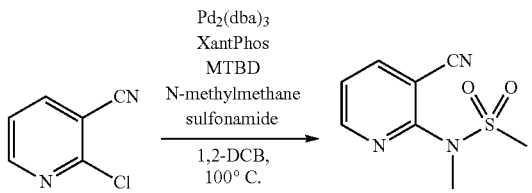

To a 50 mL round bottom flask charged with 2-chloronicotinonitrile (1 g, 7.2 mmol), Pd$_2$(dba)$_3$ (662 mg, 0.72 mmol), XantPhos (418 mg, 0.72 mmol) were added 1,2-dichlorobenzene (10 mL) and MTBD (3.11 mL, 21.7 mmol). The resulting mixture was purged with argon, followed by heating to 100° C. for 1 h. The reaction mixture was poured into 40 mL of buffer (pH 4) and the layers were separated. The organic layer was washed one additional time with the same volume of buffer. The volatiles were dried over Na$_2$SO$_4$ and concentrated. The crude was further purified by flash column chromatography [SiO$_2$, CHCl$_3$/MeOH (95:5)] to afford 1.1 g (5.2 mmol, 72%) of N-(3-cyanopyridin-2-yl)-N-methylmethanesulfonamide.

$^1$H NMR (400 MHz, CDCl$_3$) δ 8.66 (dd, J=1.9, 4.9 Hz, 1H), 8.06 (dd, J=1.9, 7.8 Hz, 1H), 7.39 (dd, J=4.9, 7.8 Hz, 1H)), 3.41 (s, 1H), 3.20 (s, 1H).

tert-Butyl (2-(N-methylmethylsulfonamido)pyridin-3-yl)methylcarbamate

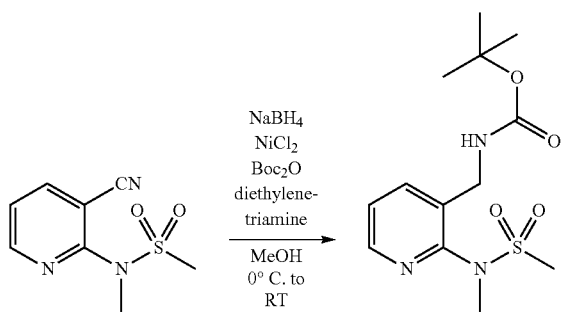 [SMILES: CN(c1ncccc1C#N)S(C)(=O)=O ; CN(c1ncccc1CNC(=O)OC(C)(C)C)S(C)(=O)=O]

To a solution of N-(3-cyanopyridin-2-yl)-N-methylmethanesulfonamide (299 mg, 1.4 mmol) in MeOH (10 mL) under an argon atmosphere at 0° C., were added Boc$_2$O (650 μL, 2.8 mmol) and NiCl$_2$.6H$_2$O (34 mg, 0.14 mmol). NaBH$_4$ (375 mg, 9.9 mmol) was then added portionwise. The reaction is exothermic. The resulting reaction mixture was stirred for 1 h at 0° C., then was added diethylenetriamine (154 μL, 1.4 mmol). The reaction mixture was allowed to warm to room temperature and left to stir for a further 30 min. The volatiles were concentrated. To the remaining residue was added EtOAc (30 mL) and sat. aq. NaHCO$_3$ (20 mL). The layers were separated and the organic layer was washed with an additional portion of sat. aq. NaHCO$_3$ (20 mL). The organic layer was dried over Na$_2$SO$_4$ and evaporated. Flash chromatography [SiO$_2$, CHCl$_3$/MeOH (9:1)] afforded 358 mg (1.1 mmol, 80%) of tert-butyl (2-(N-methylmethylsulfonamido)pyridin-3-yl)methylcarbamate.

$^1$H NMR (400 MHz, CDCl$_3$) δ 8.35 (dd, J=1.9, 4.7 Hz, 1H), 7.91 (m, 1H), 7.31 (dd, J=4.7, 7.7 Hz, 1H)), 5.34 (bs, 1H), 4.48 (d, J=6.4 Hz, 1H), 3.27 (s, 1H), 3.04 (s, 1H), 1.44 (s, 9H).

N-(3-(Aminomethyl)pyridin-2-yl)-N-methylmethanesulfonamide

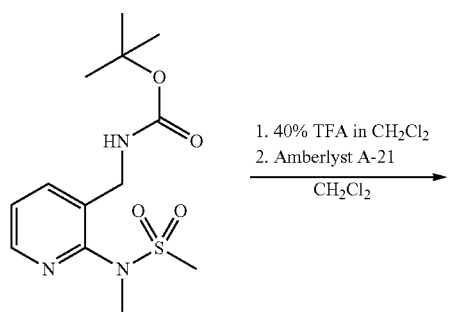

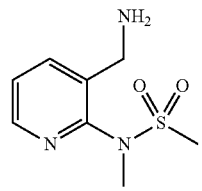

To a 25 mL round bottom flask charged with tert-butyl (2-(N-methylmethylsulfonamido)pyridin-3-yl)methylcarbamate (118 mg, 0.26 mmol) was added a 40% solution of TFA in CH$_2$Cl$_2$ (4 mL). The resulting mixture was stirred for 20 min, then the volatiles were evaporated. Toluene (4 mL) was added to the crude followed by evaporation. This procedure was repeated once. A solution of the crude residue in CH$_2$Cl$_2$ (4 mL) was treated with Amberlyst A-21 (1.8 g) and stirred for 30 min. The Amberlyst A-21 resin was filtered off and washed with CH$_2$Cl$_2$ (20 mL). The volatiles were evaporated to yield N-(3-(aminomethyl)pyridin-2-yl)-N-methylmethanesulfonamide (50 mg, 0.23 mmol, 88%).

$^1$H NMR (400 MHz, CDCl$_3$) δ 8.38 (app d, J=2.5 Hz, 1H), 7.92 (app d, J=7.0 Hz, 1H), 7.33 (app t, J=4.8 Hz, 1H)), 4.03 (s, 1H), 3.26 (s, 1H), 3.08 (s, 1H).

N-(3-((2-Chloro-5-(trifluoromethyl)pyridin-4-ylamino)methyl)pyridin-2-yl)-N-methylmethanesulfonamide

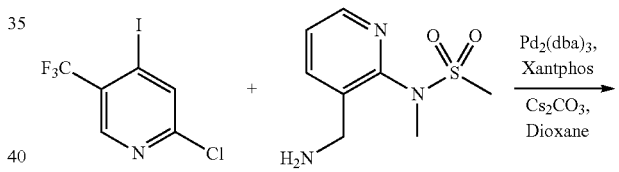

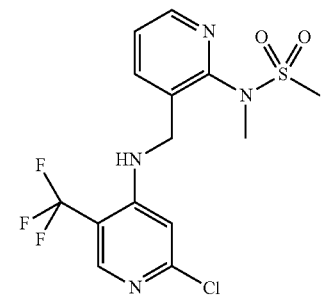

The mixture of 2-chloro-4-iodo-5-(trifluoromethyl)pyridine (1 eq.), N-(3-(aminomethyl)pyridin-2-yl)-N-methylmethanesulfonamide (1 eq.), Pd$_2$(dba)$_3$, xantphos and cesium carbonate in dioxane were heated at 80° C. for 12 h. The solvent was removed and the residue was purified by prep. HPLC (0.1% TFA in water/acetonitrile gradient) to yield the title compound.

149

N-Methyl-N-(3-((2-(2-oxoindolin-5-ylamino)-5-(trifluoromethyl)pyridin-4-ylamino)methyl)pyridin-2-yl)methanesulfonamide

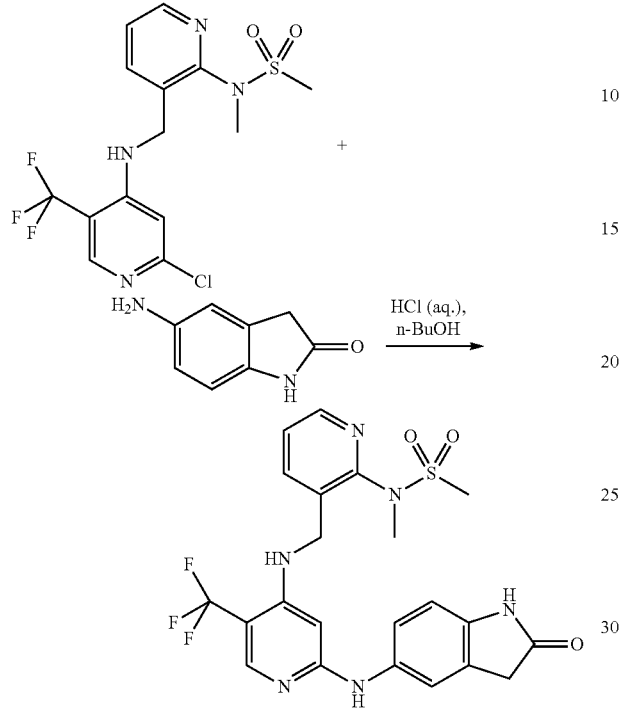

Method F was applied. The TFA salt of the title compound was obtained.

$^1$H NMR (400 MHz, DMSO-$d_6$) δ 10.38 (s, 1H), 9.35 (broad s, 1H), 8.49 (dd, J=4.6 Hz, 2.0 Hz, 1H), 8.07 (s, 1H), 7.66 (dd, J=7.6 Hz, 1.6 Hz, 1H), 7.49-7.46 (m, 1H). 7.07 (s, 1H), 6.92 (dd, J=8.4 Hz, 2.0 Hz, 1H), 6.69 (d, J=8.0 Hz, 1H), 5.49 (s, 1H), 4.54 (d, J=5.6 Hz, 2H), 3.40 (s, 2H), 3.07 (s, 3H), 3.01 (s, 3H); ESI-MS (m/z): 507.15 (M+1).

EXAMPLE 58

2-(5-Cyano-2-(2-methoxy-4-morpholinophenylamino)pyridin-4-ylamino)-N-methylbenzamide

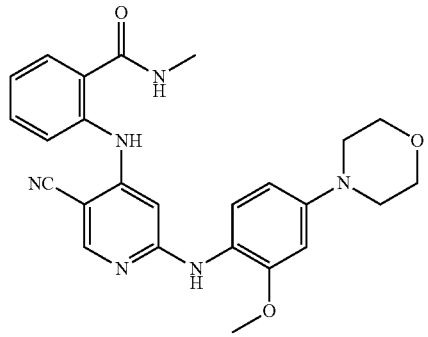

150

2-(2-Bromo-5-cyanopyridin-4-ylamino)-N-methylbenzamide

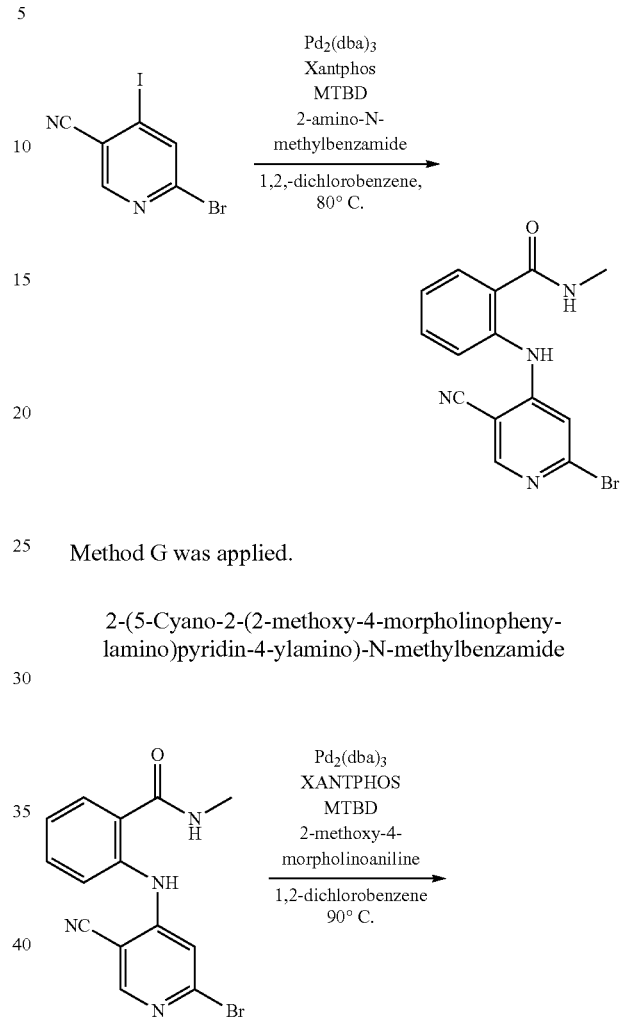

Method G was applied.

2-(5-Cyano-2-(2-methoxy-4-morpholinophenylamino)pyridin-4-ylamino)-N-methylbenzamide

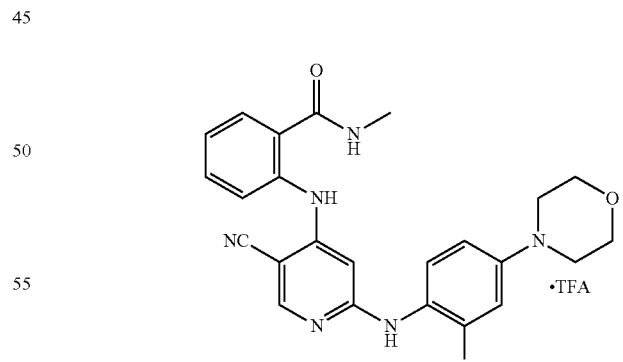

Method H was applied. The TFA salt of the title compound was obtained.

$^1$H NMR (400 MHz, THF-$d_8$) δ 10.77 (s, 1H), 9.94 (br s, 1H), 8.25 (s, 1H), 7.77-7.76 (m, 1H), 7.50 (d, J=7.8 Hz, 1H), 7.39 (d, J=8.0 Hz, 1H), 7.30-7.27 (m, 1H), 7.21-7.19 (m, 1H), 7.00-6.96 (m, 1H), 6.51 (s, 1H), 6.41-6.39 (m, 1H), 6.21 (s,

1H), 3.73 (s, 3H), 3.66-3.63 (m, 4H), 3.01-2.99 (m, 4H), 2.76 (d, 4.6 Hz, 3H); MS (m/z): 459.2 [M+1]⁺.

EXAMPLE 59

2-(5-Cyano-2-(4-(3-(dimethylamino)pyrrolidin-1-yl)-2-methoxyphenylamino)pyridin-4-ylamino)-N-methylbenzamide

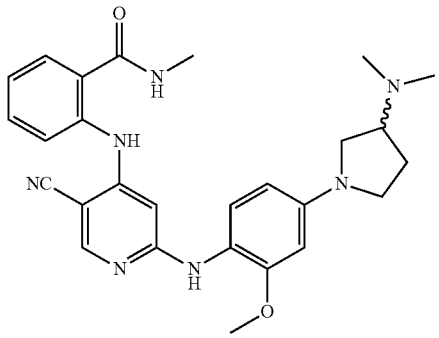

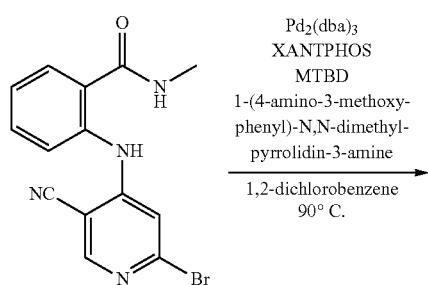

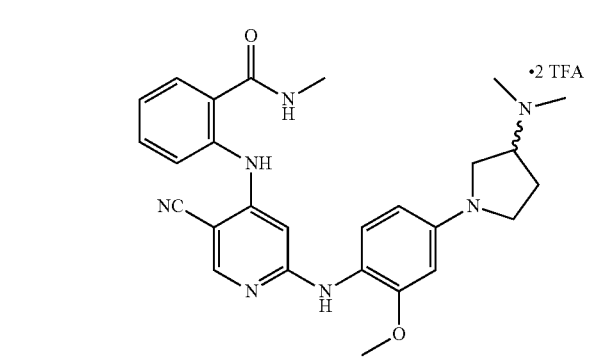

Method H was applied. The bis-TFA salt of the title compound was obtained.

¹H-NMR (400 MHz, CD₃CN) δ 11.69 (br s, 1H), 10.67 (s, 1H), 10.30 (br s, 1H), 8.19 (s, 1H), 7.62 (dd, J=0.8, 7.9 Hz, 1H), 7.48-7.41 (m, 2H), 7.22-7.18 (m, 2H), 7.09 (d, J=8.6 Hz, 1H), 6.26 (d, J=2.4 Hz, 1H), 6.20 (dd, J=2.5, 8.6 Hz, 1H), 6.15 (s, 1H), 3.91-3.84 (m, 4H), 3.66 (m, 1H), 3.60-3.52 (m, 2H), 3.32 (app d, J=8.2 Hz, 1H), 2.86-2.84 (m, 9H), 2.47 (m, 1H), 2.35 (m, 1H); MS (m/z): 486.2 [M+1]⁺,

EXAMPLE 60

2-(5-Cyano-2-(2-methoxy-4-(1,4-dioxa-8-azaspiro[4,5]decan-8-yl)phenylamino)pyridin-4-ylamino)-N-methylbenzamide

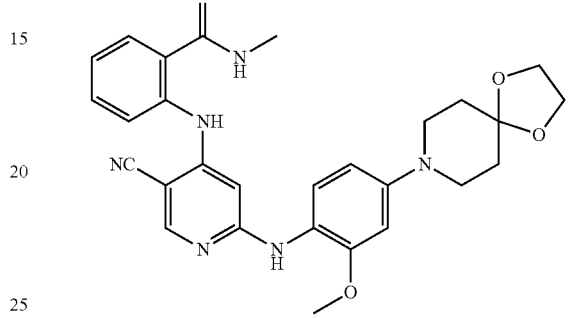

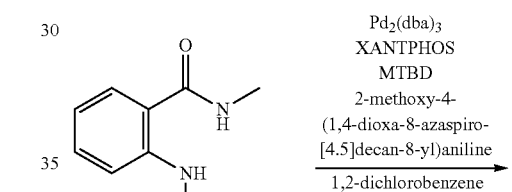

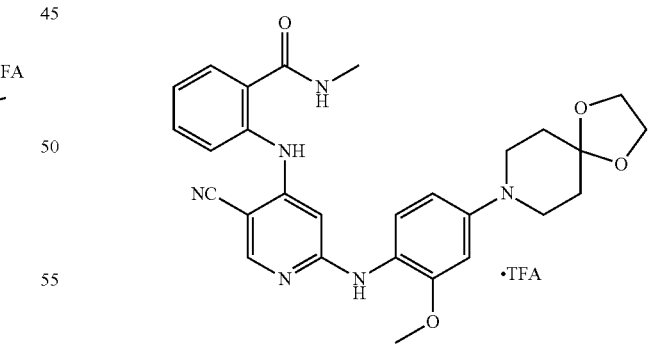

Method H was applied. The TFA salt of the title compound was obtained.

¹H-NMR (400 MHz, THF-d₈) δ 10.65 (s, 1H), 9.56 (br s, 1H), 8.21 (s, 1H), 7.72 (d, J=4.3 Hz, 1H), 7.50 (dd, J=1.1, 7.8 Hz, 1H), 7.39 (d, J=8.2 Hz, 1H), 7.30-7.25 (m, 2H), 6.96 (m, 1H), 6.56 (s, 1H), 6.44 (m, 1H), 6.24 (s, 1H), 3.82-3.81 (m, 4H), 3.72 (s, 3H), 3.27-3.17 (m, 4H), 2.76 (d, J=4.6 Hz, 3H), 1.67 (t, J=5.6 Hz, 4H); MS (m/z): 515.2 [M+1]⁺.

EXAMPLE 61

2-(5-Cyano-2-(2-methoxy-4-thiomorpholinophenylamino)pyridin-4-ylamino)-N-methylbenzamide

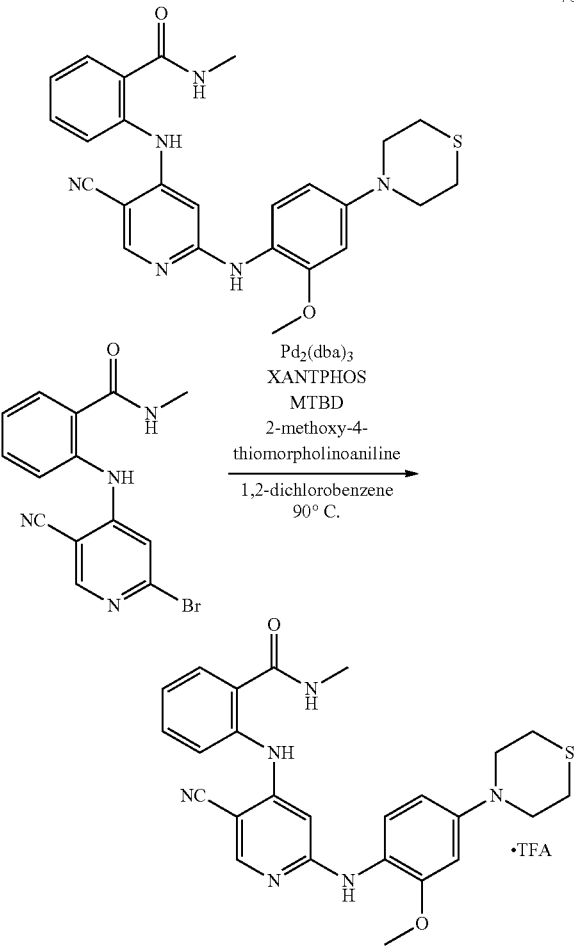

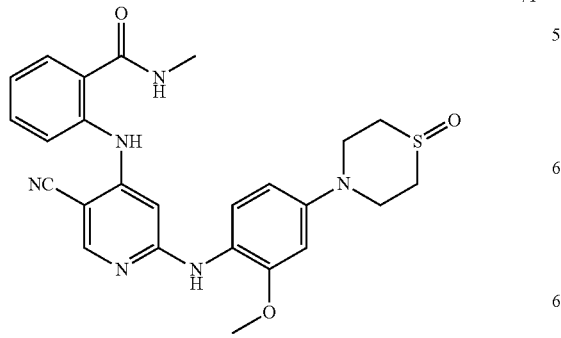

Method H was applied. The TFA salt of the title compound was obtained.

$^1$H-NMR (400 MHz, THF-d$_8$) δ 10.54 (s, 1H), 8.88 (br s, 1H), 8.17 (s, 1H), 7.70 (d, J=4.2 Hz, 1H), 7.50 (dd, J=1.2, 7.8 Hz, 1H), 7.42-7.36 (m, 2H), 7.28 (m, 1H), 6.94 (m, 1H), 6.47 (s, 1H), 6.37 (m, 1H), 6.30 (s, 1H), 3.71 (s, 3H), 3.42-3.32 (m, 4H), 2.76 (d, J=4.6 Hz, 3H), 2.58 (t, J=5.2 Hz, 4H); MS (m/z): 475.2 [M+1]$^+$.

EXAMPLE 62

2-{5-Cyano-2-[2-methoxy-4-(1-oxo-1λ$^4$-thiomorpholin-4-yl)-phenylamino]-Pyridin-4-ylamino}-N-methyl-benzamide

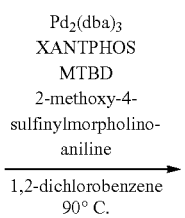

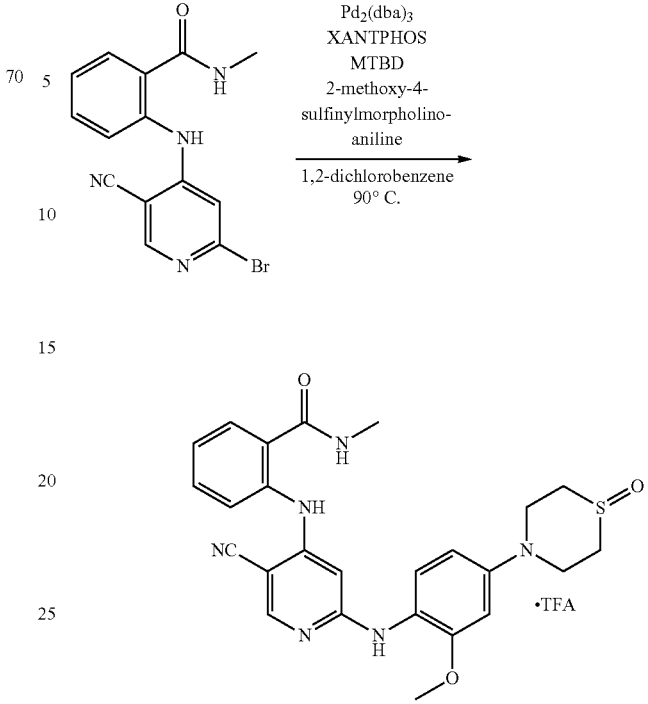

Method H was applied. The TFA salt of the title compound was obtained.

$^1$H-NMR (400 MHz, THF-d$_8$) δ 10.52 (s, 1H), 8.78 (br s, 1H), 8.16 (s, 1H), 7.70 (d, J=4.2 Hz, 1H), 7.50 (dd, J=1.2, 7.8 Hz, 1H), 7.42-7.36 (m, 2H), 7.28 (m, 1H), 6.94 (m, 1H), 6.47 (s, 1H), 6.37 (m, 1H), 6.30 (s, 1H), 3.71 (s, 3H), 3.42-3.32 (m, 4H), 2.76 (d, J=4.6 Hz, 3H), 2.58 (t, J=5.2 Hz, 4H); MS (m/z): 491.5 [M+1]$^+$.

EXAMPLE 63

2-{5-Cyano-2-[4-(1,1-dioxo-1λ$^6$-thiomorpholin-4-yl)-2-methoxy-phenylamino]-pyridin-4-ylamino}-N-methyl-benzamide

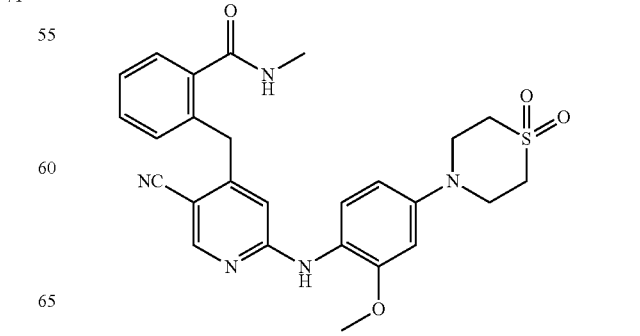

155

-continued

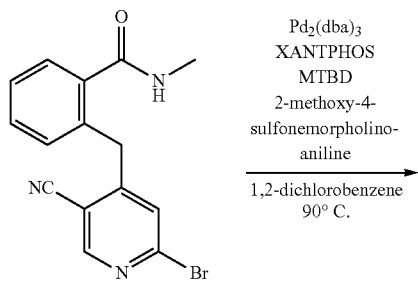

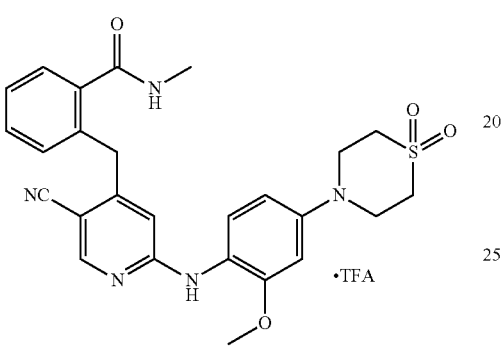

Method H was applied. The TFA salt of the title compound was obtained.

¹H-NMR (400 MHz, CD₃CN) δ 10.56 (s, 1H), 10.08 (br s, 1H), 8.12 (s, 1H), 7.53 (dd, J=1.1, 7.9 Hz, 1H), 7.39-7.32 (m, 2H), 7.13-7.09 (m, 3H), 6.53 (d, J=2.5 Hz, 1H), 6.47 (dd, J=2.4, 8.6 Hz, 1H), 6.11 (s, 1H), 3.77-3.74 (m, 7H), 2.95 (t, J=5.2 Hz, 4H), 2.76 (d, J=4.8 Hz, 3H); MS (m/z): 507.2 [M+1]⁺.

EXAMPLE 64

2-(5-Chloro-2-(2-methoxy-4-morpholinopheny-lamino)pyridin-4-ylamino)-N-methylbenzamide

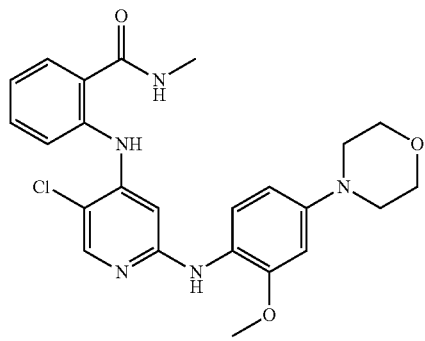

156

2-(2-bromo-5-chloropyridin-4-ylamino)-N-methyl-benzamide

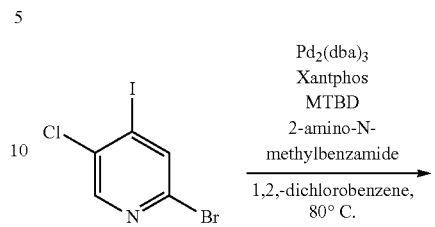

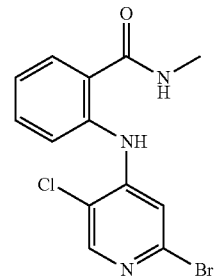

Method G was applied 2-(5-Chloro-2-(2-methoxy-4-morpholinopheny-lamino)pyridin-4-ylamino)-N-methylbenzamide

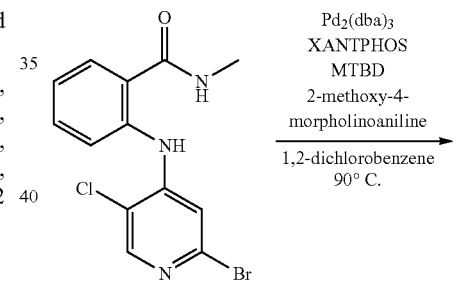

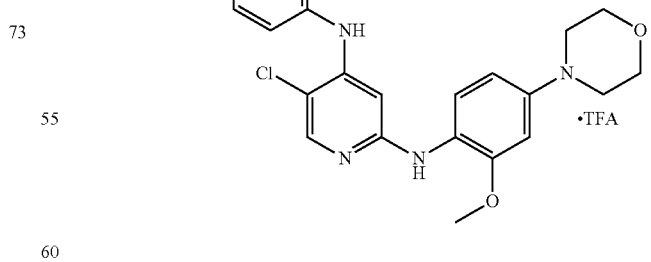

Method H was applied. The TFA salt of the title compound was obtained.

¹H NMR (400 MHz, THF-d₈) δ 10.76 (s, 1H), 10.41 (br s, 1H), 7.94 (s, 1H), 7.79 (m, 1H), 7.50 (dd J=7.8, 1.2 Hz, 1H), 7.40 (d, J=8.2 Hz, 1H), 7.30-7.26 (m, 1H), 7.11, (d, J=8.6 Hz, 1H), 6.99-6.95 (m, 1H), 6.51 (bs, 1H), 6.41-6.38 (m, 1H), 6.26 (s, 1H), 3.74 (s, 3H), 3.65-3.64 (m, 4H), 3.01-2.99 (m, 4H), 2.75 (d, J=4.6 Hz, 3H); MS (m/z): 468.2 [M+1]⁺.

EXAMPLE 65

2-(5-Bromo-2-(2-methoxy-4-morpholinophenylamino)pyridin-4-ylamino)-N-methylbenzamide

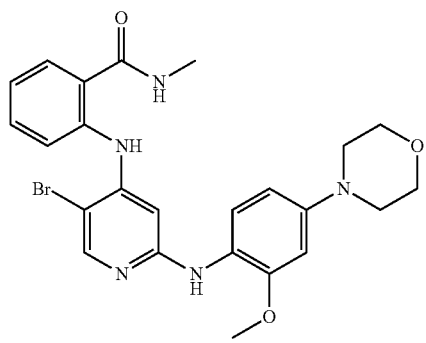

2-(2,5-Dibromopyridin-4-ylamino)-N-methylbenzamide

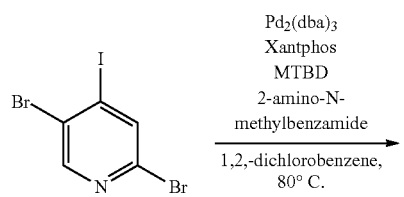

Method G was applied.

2-(5-Bromo-2-(2-methoxy-4-morpholinophenylamino)pyridin-4-ylamino)-N-methylbenzamide

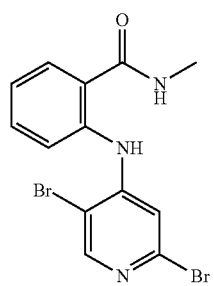
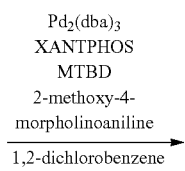

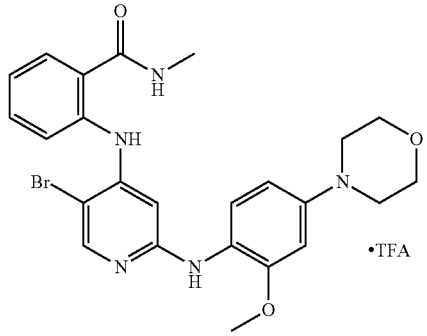

Method H was applied. The TFA salt of the title compound was obtained.

¹H-NMR (400 MHz, THF-d₈) δ 10.80 (br s, 1H), 10.70 (s, 1H), 8.03 (s, 1H), 7.78 (br t, 1H), 7.50 (dd, J=1.2, 7.8 Hz, 1H), 7.39 (d, J=8.2 Hz, 1H), 7.28 (dt, 1H), 7.04-6.97 (m, 2H), 6.52 (d, J=2.4 Hz, 1H), 6.40 (dd, J=2.5, 8.6 Hz, 1H), 6.19 (s, 1H), 3.74 (s, 3H), 3.65 (t, J=4.8 Hz, 4H), 3.00 (t, J=4.8 Hz, 4H), 2.75 (d, J=4.6 Hz, 3H); MS (m/z): 512.1 [M+1]⁺.

EXAMPLE 66

2-(5-Fluoro-2-(2-methoxy-4-morpholinophenylamino)pyridin-4-ylamino)-N-methylbenzamide

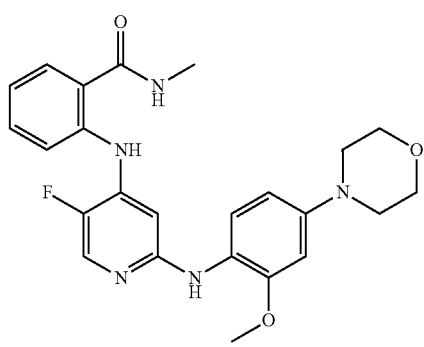

2-(2-Bromo-5-chloropyridin-4-ylamino)-N-methylbenzamide

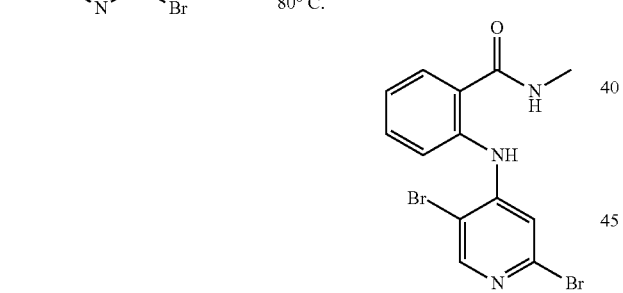

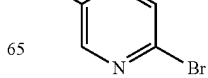
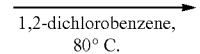

-continued

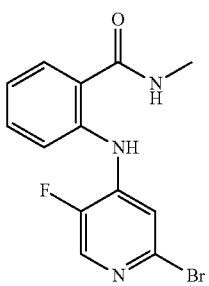

Method G was applied.

2-(5-Fluoro-2-(2-methoxy-4-morpholinophenylamino)pyridin-4-ylamino)-N-methylbenzamide

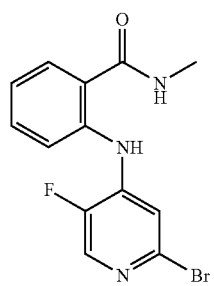

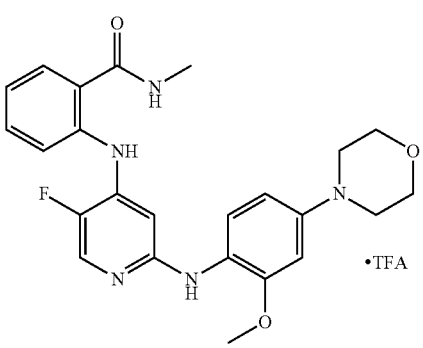

Method H was applied. The TFA salt of the title compound was obtained.

¹H-NMR (400 MHz, CD₃CN) δ 10.47 (br s, 1H), 9.31 (s, 1H), 7.60 (d, J=5.4 Hz, 1H), 7.55 (dd, J=1.2, 8.8 Hz, 1H), 7.43-7.37 (m, 2H), 7.17-7.12 (m, 2H), 6.99 (d, J=8.7 Hz, 1H), 6.56 (d, J=2.6 Hz, 1H), 6.46 (dd, J=2.6, 8.7 Hz, 1H), 6.28 (d, J=7.2 Hz, 1H), 3.72-3.69 (m, 7H), 3.09 (t, J=4.9 Hz, 4H), 2.75 (d, J=4.8 Hz, 3H); MS (m/z): 452.2 [M+1]⁺.

EXAMPLE 67

5-Fluoro-2-(2-(2-methoxy-4-morpholinophenylamino)-5-(trifluoromethyl)pyridin-4-ylamino)-N-methylbenzamide

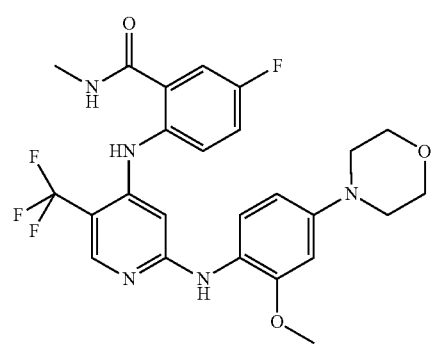

5-Fluoro-N-methyl-2-nitrobenzamide

A mixture of 5-fluoro-2-nitrobenzoic acid (4.775 g, 25.8 mmol), methylamine hydrochloride (2.626 g, 38.9 mmol), EDCI (5.982 g, 31.2 mmol), HOBt (4.227 g, 31.3 mmol) and triethylamine (7.2 mL, 51.65 mmol) in DMF (50 mL) was stirred at room temperature for 24 h. It was diluted with ethyl acetate and washed with saturated sodium bicarbonate, brine and dried over magnesium sulfate. The solvent was removed and the residue was purified by silica gel chromatography (combiflash-companion; ethyl acetate/hexanes gradient) to give the title compound as a yellow solid (yield: 90%).

2-Amino-5-fluoro-N-methylbenzamide

Pd/C (10% wt, 860 mg) was added to 5-Fluoro-N-methyl-2-nitrobenzamide (4.58 g, 23.4 mmol) under argon. Methanol was added (50 mL) and the argon balloon was replaced with a hydrogen balloon. The mixture was stirred for 24 h at room temperature. It was filtered through a celite pad and the solvent was removed to yield the title compound as a pale yellow solid in quantitative yield.

2-(2-chloro-5-(trifluoromethyl)pyridin-4-ylamino)-5-fluoro-N-methylbenzamide

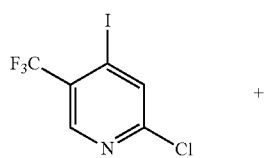

+

-continued

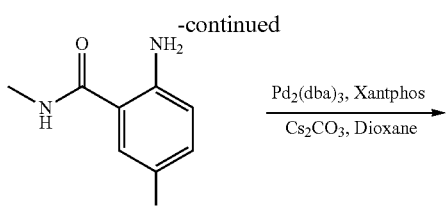

Method B was applied.

5-Fluoro-2-(2-(2-methoxy-4-morpholinopheny-lamino)-5-(trifluoromethyl)pyridin-4-ylamino)-N-methylbenzamide

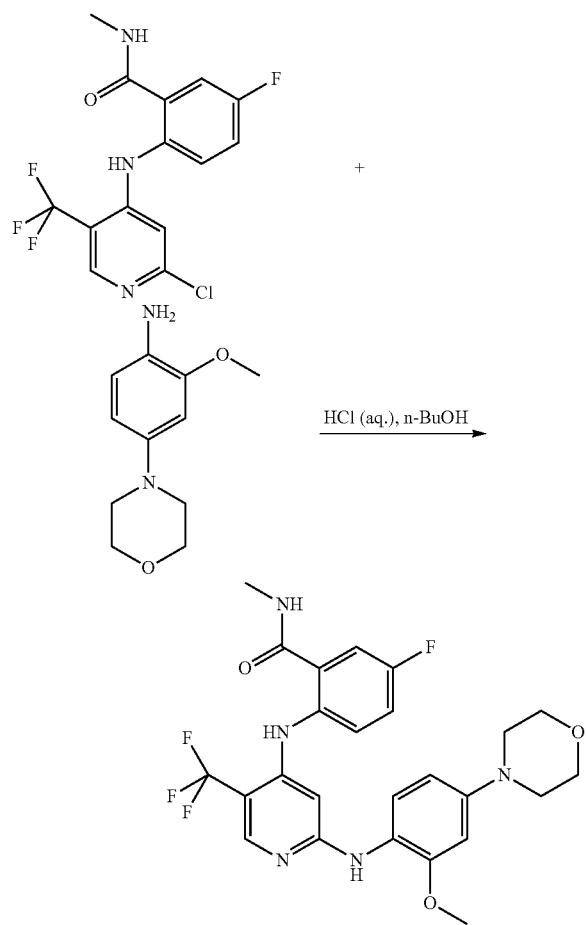

Method F was applied. The HCl salt of the title compound was obtained as a yellow solid.

$^{1}$H-NMR (400 MHz, d$_{6}$-DMSO, HCl-salt) δ 10.09 (s, 1H), 9.83 (br s, 1H), 8.81 (q, J=4.5 Hz, 1H), 8.10 (s, 1H), 7.63-7.56 (m, 2H), 7.49-7.44 (m, 1H), 7.17 (d, J=8.2 Hz, 1H), 6.70 (s, 1H), 6.58 (d, J=8.1 Hz, 1H), 6.34 (s, 1H), 3.79 (s, 3H), 3.86 (t, J=4.7 Hz, 4H), 3.18 (q, J=4.5 Hz, 4H), 2.74 (d, J=4.6 Hz, 3H); $^{19}$F-NMR (376 MHz, d$_{6}$-DMSO) δ −60.5 (s, 3F), −116.1 (br s, 1F); MS (m/z): 520.2 [M+1]$^{+}$.

4-(3-Methoxy-4-nitrophenyl)morpholine

To a solution of 4-fluoro-2-methoxy-1-nitrobenzene (24.4 g, 0.14 mol) in 200 mL DMF was added morpholine (25.7 mL, 0.28 mol), followed by the addition of K$_{2}$CO$_{3}$ (23.6 g, 0.17 mol). The mixture was stirred at room temperature for 48 h. The mixture was poured into 0.7 L H$_{2}$O and the precipitate was collected by filtration. The precipitate was further rinsed with 0.5 L H$_{2}$O. The resulting solid was air dried by purging with a flow of air for 24 h, thus affording 29.3 g of 4-(3-methoxy-4-nitrophenyl)morpholine (0.12 mol, 86%).

2-Methoxy-4-morpholinoaniline

A 1 L round bottom flask charged with 4-(3-methoxy-4-nitrophenyl)morpholine (15.7 g, 66 mmol) in 300 mL MeOH, was evacuated and then backfilled with argon. This sequence was repeated two additional times. The reaction vessel was kept under a stream of argon and Pd(C) (10%, 1.57 g) was added. After the addition of Pd (C) was complete the reaction vessel was evacuated and backfilled with hydrogen gas. This evacuation/backfill sequence was repeated twice. After 18 h the hydrogen gas was evacuated by introducing argon into the round bottom flask. The reaction mixture was filtered through a pad of Celite. The Celite was washed with 200 mL EtOAc. The volatiles were evaporated to yield 13.4 g of 2-methoxy-4-morpholinoaniline (64 mmol, 97%).

EXAMPLE 68

5-Fluoro-N-methyl-2-(2-(2-oxoindolin-5-ylamino)-5-(trifluoromethyl)pyridin-4-ylamino)benzamide

77

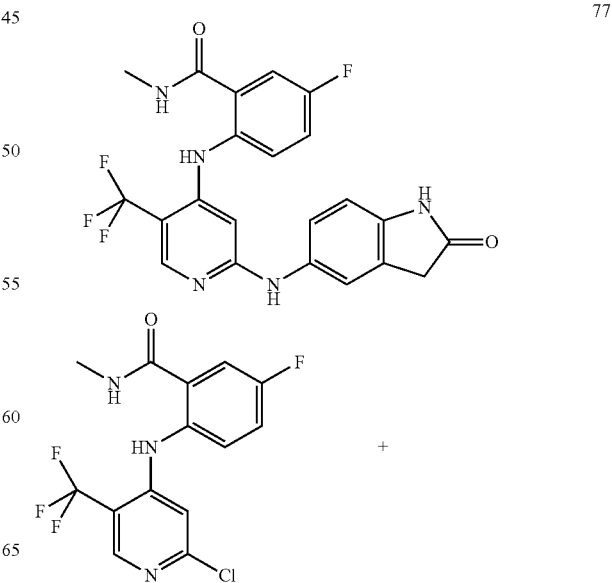

-continued

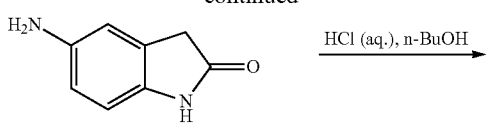

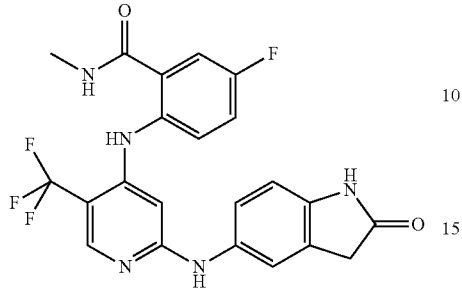

Method F was applied. The TFA salt of the title compound was obtained as a pale yellow solid.

¹H-NMR (400 MHz, d₆-DMSO) δ 10.31 (s, 1H), 9.88 (s, 1H), 9.34 (br s, 1H), 8.70 (q, J=4.4 Hz, 1H), 8.19 (s, 1H), 7.62-7.55 (m, 2H), 7.45-7.41 (m, 2H), 7.21 (dd, J=2.0, 8.3 Hz, 1H), 6.77 (d, J=8.3 Hz, 1H), 6.47 (s, 1H), 3.46 (s, 2H), 2.75 (d, J=4.6 Hz, 3H); ¹⁹F-NMR (376 MHz, d₆-DMSO) δ −59.5 (s, 3F), −74.6 (s, 3F), −118.5 (br s, 1F); MS (m/z): 460.1 [M+1]⁺.

EXAMPLE 69

2-(2-(1H-Indazol-5-ylamino)-5-(trifluoromethyl)pyridin-4-ylamino)-5-fluoro-N-methylbenzamide

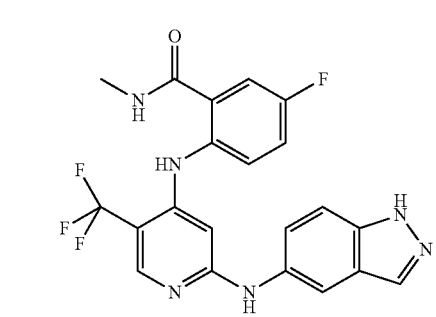

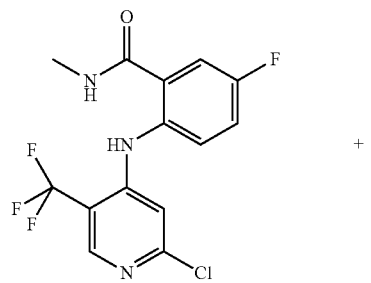

-continued

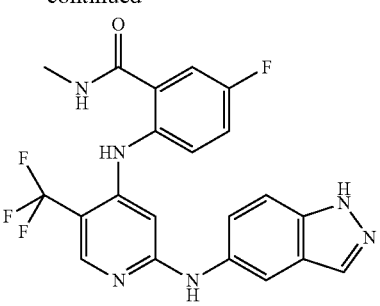

Method F was applied. The HCl salt of the title compound was obtained as a pale yellow solid.

¹H-NMR (400 MHz, d₆-DMSO, HCl-salt) δ 13.10 (vbr s, 1H), 10.06 (s, 2H), 8.76 (q, J=4.4 Hz, 1H), 8.21 (s, 1H), 8.08 (d, J=0.9 Hz, 1H), 7.87 (s, 1H), 7.65 (dd, J=4.9, 9.0 Hz, 1H), 7.60-7.56 (m, 2H), 7.44 (dt, J=3.0, 8.5 Hz, 1H), 7.30 (dd, J=2.0, 8.8 Hz, 1H), 6.51 (s, 1H), 2.74 (d, J=4.6 Hz, 3H); ¹⁹F-NMR (376 MHz, d₆-DMSO) δ 60.1 (s, 3F), −117.1 (br s, 1F); MS (m/z): 445.1 [M+1]⁺.

EXAMPLE 70

5-Fluoro-N-methyl-2-(2-(2-oxo-1,2,3,4-tetrahydroc-quinolin-6-ylamino)-5-(trifluoromethyl)pyridin-4-ylamino)benzamide

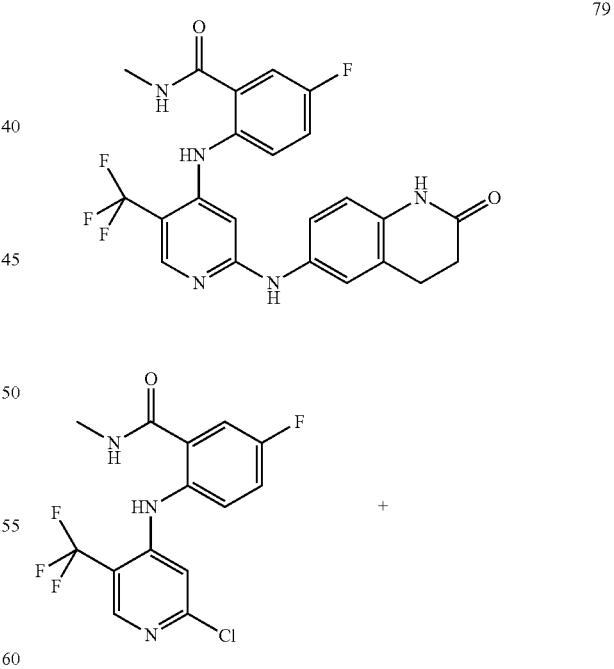

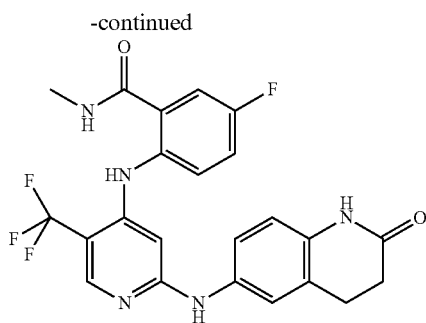

Method F was applied. The HCl salt of the title compound was obtained as a pale yellow solid.

$^1$H-NMR (400 MHz, d$_6$-DMSO, HCl-salt) δ 10.10 (s, 1H), 10.03 (s, 1H), 9.92 (br s, 1H), 8.76 (q, J=4.4 Hz, 1H), 8.21 (s, 1H), 7.65-7.58 (m, 2H), 7.42 (dt, J=3.0, 8.5 Hz, 1H), 7.25 (s, 1H), 7.14 (dd, J=2.3, 8.4 Hz, 1H), 6.84 (d, J=8.4 Hz, 1H), 6.45 (s, 1H), 2.86 (t, J=7.5 Hz, 2H), 2.74 (d, J=4.6 Hz, 3H), 2.24-2.41 (m, 2H); $^{19}$F-NMR (376 MHz, d$_6$-DMSO) δ −60.1 (s, 3F), −117.1 (br s, 1F); MS (m/z): 474.15 [M+1]$^+$.

EXAMPLE 71

5-Fluoro-N-methyl-2-(2-(4-(2-oxopyrrolidin-1-yl)phenylamino)-5-(trifluoromethyl)pyridin-4-ylamino)benzamide

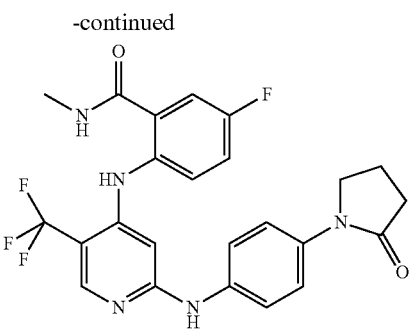

Method F was applied. The TFA salt of the title compound was obtained as a pale yellow solid.

$^1$H-NMR (400 MHz, d$_6$-DMSO) δ 9.90 (s, 1H), 9.44 (br s, 1H), 8.72 (q, J=4.5 Hz, 1H), 8.24 (s, 1H), 7.63-7.50 (m, 6H), 7.42 (dt, J=3.0, 8.5 Hz, 1H), 6.57 (s, 1H), 3.80 (t, J=7.0 Hz, 2H), 2.76 (d, J=4.6 Hz, 3H), 2.46 (t, J=3.3 Hz, 2H), 2.09-2.01 (m, 2H); $^{19}$F-NMR (376 MHz, d$_6$-DMSO) δ −59.45 (s, 3F), −74.8 (s, 3F), −118.75 (br s, 1F); MS (m/z): 488.2 [M+1]$^+$.

EXAMPLE 72

2-(2-(4-Acetamidophenylamino)-5-(trifluoromethyl)pyridin-4-ylamino)-5-fluoro-N-methylbenzamide

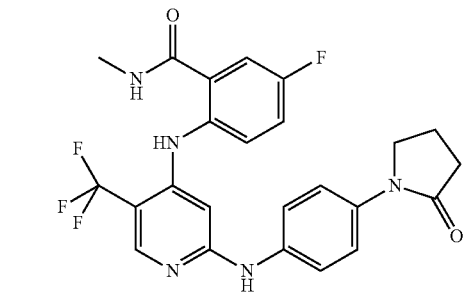

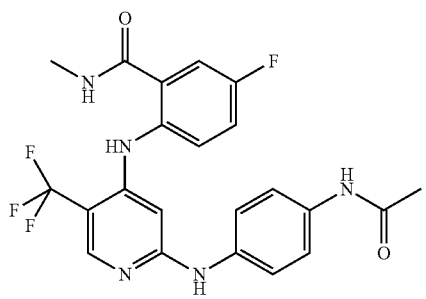

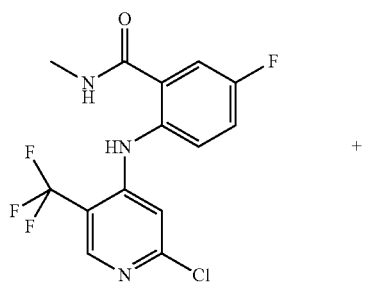

+

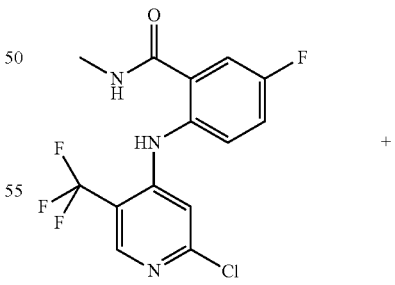

+

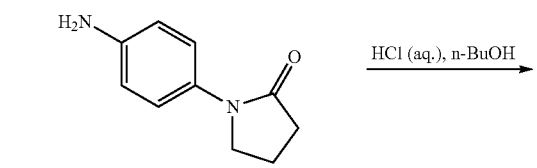

HCl (aq.), n-BuOH →

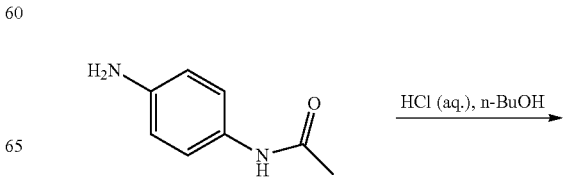

HCl (aq.), n-BuOH →

-continued

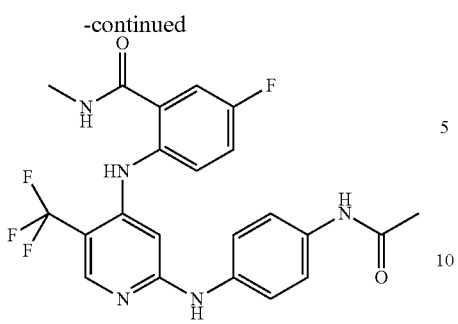

A procedure similar to Method F was applied. The TFA salt of the title compound was obtained as a pale yellow solid.

$^1$H-NMR (400 MHz, d$_6$-DMSO) δ 9.85 (s, 1H), 9.84 (s, 1H), 9.29 (br s, 1H), 8.71 (q, J=4.5 Hz, 1H), 8.22 (s, 1H), 7.62-7.55 (m, 2H), 7.49-7.37 (m, 5H), 6.55 (s, 1H), 2.75 (d, J=4.6 Hz, 3H), 2.01 (s, 3H); $^{19}$F-NMR (376 MHz, d$_6$-DMSO) δ −59.3 (s, 3F), −74.5 (s, 3F), −119.1 (br s, 1F); MS (m/z): 462.1 [M+1]$^+$.

EXAMPLE 73

5-Fluoro-N-methyl-2-(2-(2-oxoindolin-6-ylamino)-5-(trifluoromethyl)pyridin-4-ylamino)benzamide

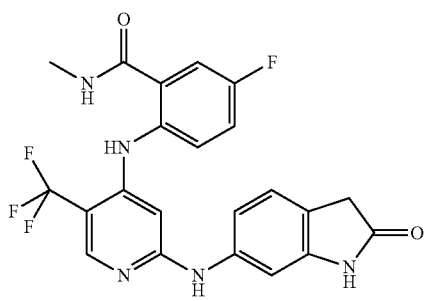

6-Aminooxindole

Methanol (15 mL) and 1.25 M HCl in EtOH (10 ml) was added to 2,4-dinitrophenylacetic acid (837 mg, 3.7 mmol) and Pd/C (10%; 205 mg) under Argon. The argon balloon was replaced with a hydrogen balloon and it was stirred at RT for 12 h and at 50° C. for 24 h. It was cooled to RT and filtered through celite. The solvent was removed and the residue was purified by silica gel chromatography (DCM/methanol gradient) to give the title compound as a red solid.

5-Fluoro-N-methyl-2-(2-(2-oxoindolin-6-ylamino)-5-(trifluoromethyl)pyridin-4-ylamino)benzamide

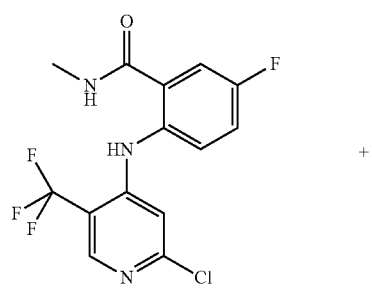

+

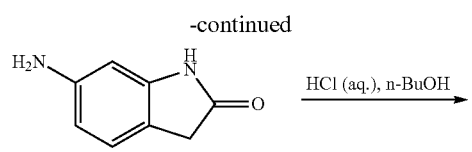

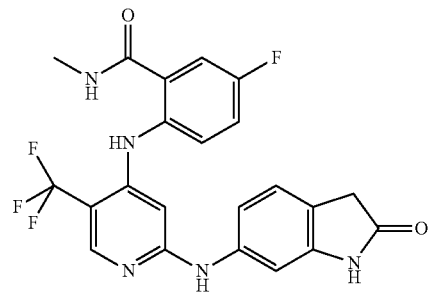

Method F was applied. The TFA salt of the title compound was obtained as a pale yellow solid.

$^1$H-NMR (400 MHz, d$_6$-DMSO) δ 10.34 (s, 1H), 9.86 (s, 1H), 9.29 (s, 1H), 8.72 (q, J=4.5 Hz, 1H), 8.24 (s, 1H), 7.62-7.56 (m, 2H), 7.43 (dt, J=3.0, 8.5 Hz, 1H), 7.25 (d, J=1.5 Hz, 1H), 7.08 (d, J=8.0 Hz, 1H), 7.01 (dd, J=1.9, 8.1 Hz, 1H), 6.62 (s, 1H), 3.38 (s, 2H), 2.76 (d, J=4.5 Hz, 3H); $^{19}$F-NMR (376 MHz, d$_6$-DMSO) δ −59.3 (s, 3F), −74.5 (s, 3F), −119.3 (br s, 1F); MS (m/z): 460.2 [M+1]$^+$.

EXAMPLE 74

5-Fluoro-N-methyl-2-(2-(2-methyl-4,5'-bipyrimidin-6-ylamino)-5-(trifluoromethyl)pyridin-4-ylamino)benzamide

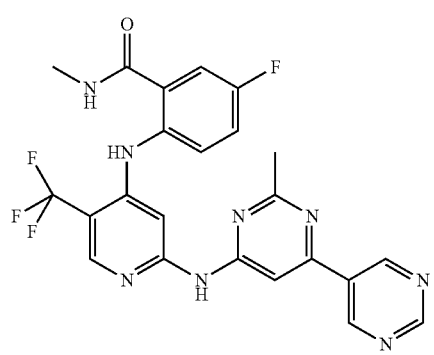

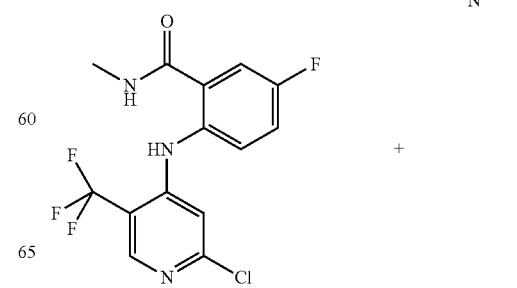

+

-continued

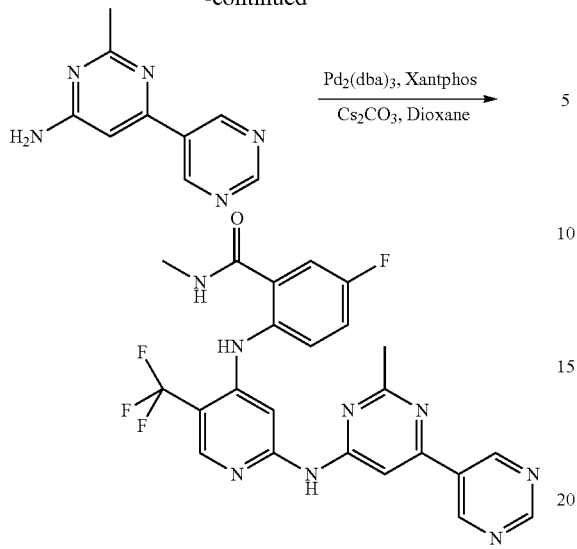

Method B was applied. The TFA salt of the title compound was obtained as a pale yellow solid.

$^1$H-NMR (400 MHz, d$_6$-DMSO) δ 10.55 (s, 1H), 10.09 (s, 1H), 9.32 (s, 1H), 9.32 (s, 2H), 8.76 (q, J=4.5 Hz, 1H), 8.45 (s, 1H), 8.08 (s, 1H), 7.93 (s, 1H), 7.70 (dd, J=4.9, 9.0 Hz, 1H), 7.61 (dd, J=3.0, 9.4 Hz, 1H), 7.47 (dt, J=3.0, 8.5 Hz, 1H), 2.77 (d, J=4.5 Hz, 3H), 2.49 (s, 3H); $^{19}$F-NMR (376 MHz, d$_6$-DMSO) δ −60.0 (s, 3F), −74.8 (s, 3F), −118.8 (br s, 1F); MS (m/z): 499.2 [M+1]$^+$.

2-Methyl-4,5'-bipyrimidin-6-amine

To a microwave vial were added 6-chloro-2-methylpyrimidin-4-amine (700 mg, 4.88 mmol), pyrimidin-5-ylboronic acid (725 mg, 5.86 mmol), PdCl$_2$(PPh$_3$)$_2$ (684 mg, 0.97 mmol), dioxane (10 mL) and Na$_2$CO$_3$ (2 M, 7 mL, 14 mmol) under Argon. The vial was microwave heated for 1 h at 160° C. Water was added, and extracted with 10% MeOH/CHCl$_3$ (3*50 mL). The organic layers were combined and concentrated under reduced pressure and the crude was purified by silica gel chromatography to yield the title compound as a white solid; MS (m/z): [M+H]$^+$188.2.

EXAMPLE 75

2-(2-(5-Acetamidopyridin-2-ylamino)-5-(trifluoromethyl)pyridin-4-ylamino)-5-fluoro-N-methylbenzamide

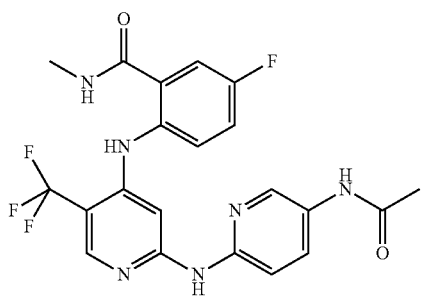

84

-continued

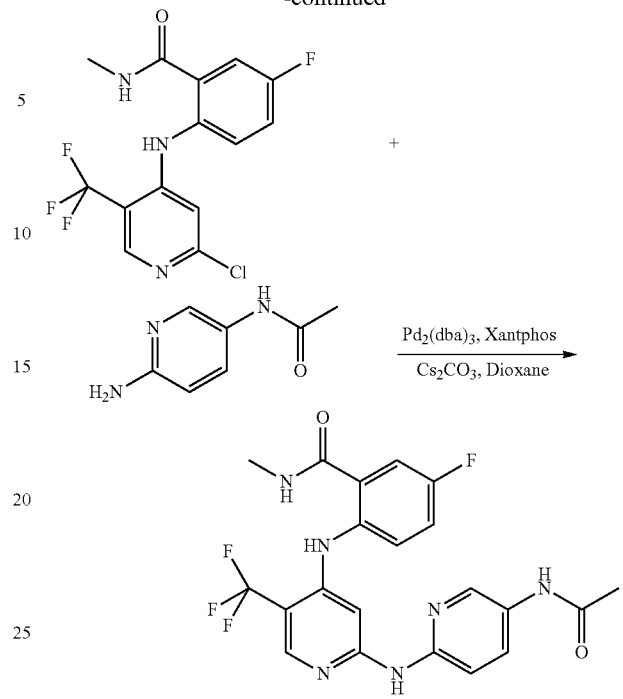

Method B was applied. The TFA salt of the title compound was obtained as a pale yellow solid.

$^1$H-NMR (400 MHz, d$_6$-DMSO) δ 10.68 (vbr s, 1H), 10.14 (br s, 1H), 10.08 (s, 1H), 8.73 (q, J=4.5 Hz, 1H), 8.56 (br s, 1H), 8.37 (s, 1H), 7.96 (dd, J=2.5, 9.0 Hz, 1H), 7.67 (dd, J=4.9, 9.0 Hz, 1H), 7.61 (dd, J=3.0, 9.4 Hz, 1H), 7.47 (dt, J=2.9, 8.5 Hz, 1H), 7.31 (d, J=8.7 Hz, 1H), 7.25 (br s, 1H), 2.76 (d, J=4.6 Hz, 3H), 2.06 (s, 3H); $^{19}$F-NMR (376 MHz, d$_6$-DMSO) δ −60.35 (br s, 3F), −74.1 (s, 3F), −117.7 (br s, 1F); MS (m/z): 463.2 [M+1]$^+$.

N-(6-Nitropyridin-3-yl)acetamide

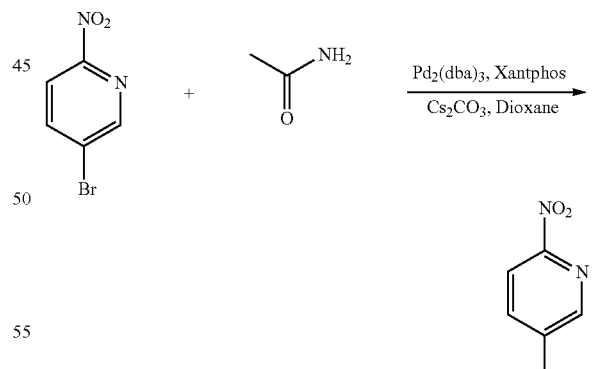

A procedure similar to Method A was used, but it was heated for 48 h.

N-(6-nitropyridin-3-yl)acetamide

To N-(6-Nitropyridin-3-yl)acetamide in methanol (150 mL) was added Pd/C (10% Pd in carbon) under argon. Hydrogen balloon was used as the hydrogen source. The reaction was stirred at room temperature overnight. The mixture was filtered through celite and the celite pad was washed several times. The solvent was removed to obtain the desired product (quantitative yield).

EXAMPLE 76

5-Fluoro-2-(2-(3-methoxyphenylamino)-5-(trifluoromethyl)pyridin-4-ylamino)-N-methylbenzamide

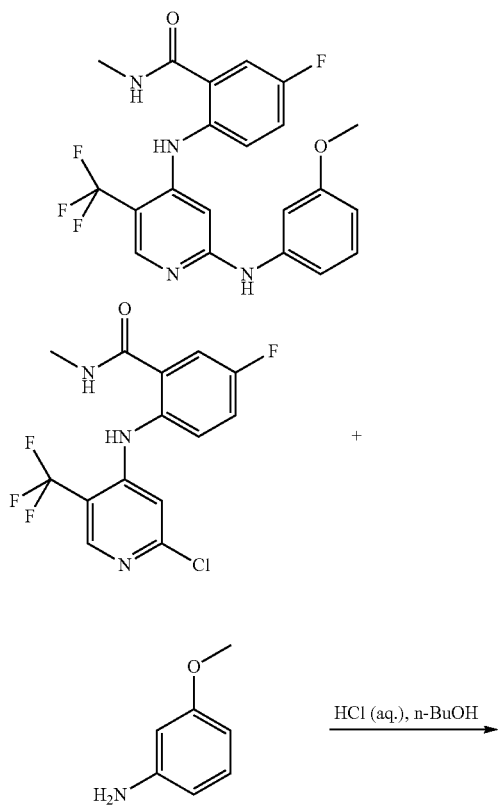

Method F was applied. The TFA salt of the title compound was obtained as a pale yellow solid.

$^1$H-NMR (400 MHz, d$_6$-DMSO) δ 9.88 (s, 1H), 9.41 (s, 1H), 8.71 (q, J=4.6 Hz, 1H), 8.27 (s, 1H), 7.63-7.56 (m, 2H), 7.43-7.38 (m, 1H), 7.23 (t, J=2.1 Hz, 1H), 7.19 (t, J=8.1 Hz, 1H), 7.08-7.06 (m, 1H), 6.60 (s, 1H), 6.59-6.56 (m, 1H), 3.73 (s, 3H), 2.76 (d, J=4.6 Hz, 3H); $^{19}$F-NMR (376 MHz, d$_6$-DMSO) δ −59.5 (s, 3F), −74.8 (s, 3F), −118.8 (br s, 1F); MS (m/z): 435.1 [M+1]$^+$.

EXAMPLE 77

N-Methyl-3-(2-(2-oxoindolin-5-ylamino)-5-(trifluoromethyl)pyridin-4-ylamino)picolinamide

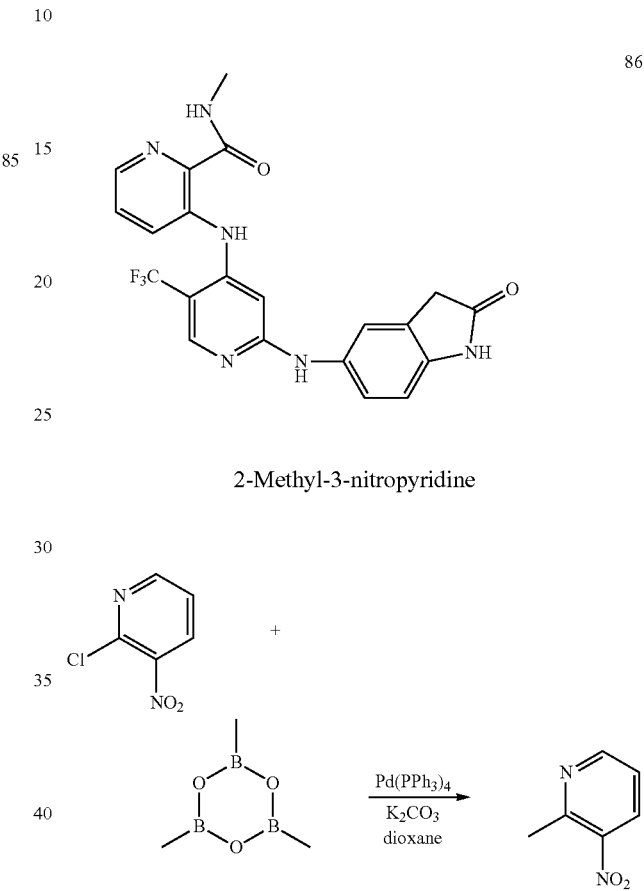

2-Methyl-3-nitropyridine

Reference: Gray, M.; Andrews, I. P.; Hook, D. F.; Kitteringham, J.; Voyle, M.; *Tetrahedron Lett.;* 2000, 41, 6237-6240.

The mixture of 2-chloro-3-nitropyridine (50 g, 0.315 mol, 1.0 eq), TMB (50 mL, 1.1 eq), (PPh$_3$)$_4$Pd (O) (36.4 g, 0.1 eq), K$_2$CO$_3$ (130.6 g, 3.0 eq) and dioxane (1500 mL) was refluxed under argon for 2 days. The mixture was cooled to room temperature and filtered through a celite pad to remove K$_2$CO$_3$ and catalyst. The celite pad was washed with EtOAc. The organic solutions were combined and concentrated to get the crude which was purified by silica gel chromatography (0%~40% EtOAc/Hex) to obtain the desired product 2-methyl-3-nitropyridine (30.5 g, isolated yield 70%) (Note: isolated yield 42% was obtained when the reaction was refluxed for 24 h).

3-Nitropicolinic acid

Reference: Journal of the American Chemical Society (1954), 76, 3167-8.

The nitropicoline (0.92 g 6.66 mmol) in water (66 mL) was heated to 90° C. and treated with potassium permanganate (1.97 g, 13.32 mmol) over a period of 30 min while stirring.

The reaction mixture was cooled to 50° C. and filtered. The manganese dioxide was washed first with water and then EtOAc to remove un-reacted starting material and then the filtrate was extracted three times with EtOAc. The aqueous layer was evaporated to small volume and treated with somewhat more than the calculated amount of hydrogen chloride to acidify the solution to pH 5-6. The water was removed under reduced pressure. The crude acid was dissolved in methanol and the mixture was filtered and washed with methanol. The combined methanol solutions were concentrated to obtain the acid with no further purification (42% conversion, 58% recovered nitropicoline could be reused to make the acid).

N-Methyl-3-nitropicolinamide

To a mixture of 3-nitropicolinic acid (8.7 g, 51.8 mmol, 1.0 eq), methylamine hydrogen chloride (4.2 g, 1.2 eq), EDC (14.9 g, 1.5 eq), HOBt (8.4 g, 1.2 eq) in DMF (30 mL) was added DIEA (54 mL, 6.0 eq). The mixture was stirred at room temperature overnight. The crude was concentrated and dissolved in EtOAc. It was washed with saturated NaHCO₃ solution. The solvent was removed and the crude was purified by silica gel chromatography (20%~80% EtOAc/Hex) to obtain the desired product N-methyl-3-nitropicolinamide (3.0 g, isolated yield 32%).

3-Amino-N-methylpicolinamide

To N-methyl-3-nitropicolinamide (3.0 g, 16.6 mmol) in methanol (150 mL) was added Pd/C (10% Pd in carbon, 0.45 g, 15 wt %) under argon. Hydrogen balloon was used as the hydrogen source. The reaction was stirred at room temperature overnight. The mixture was filtered through celite and the celite pad was washed several times. The solvent was removed to obtain the desired product (quantitative yield).

3-(2-Chloro-5-(trifluoromethyl)pyridin-4-ylamino)-N-methylpicolinamide

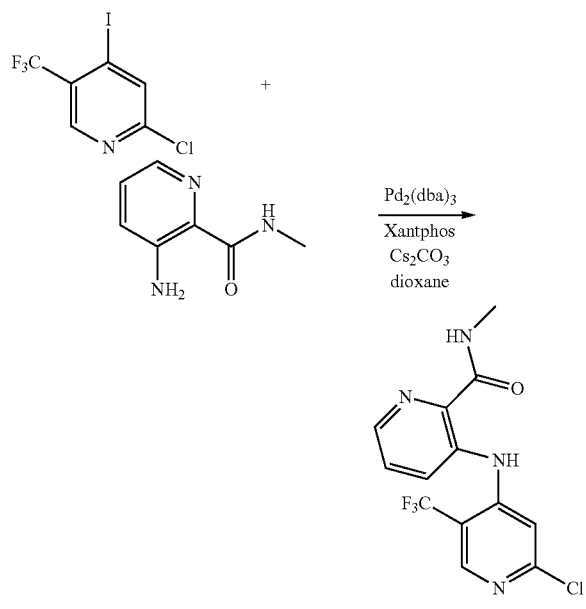

The mixture of 2-chloro-4-iodo-5-(trifluoromethyl)pyridine (0.615 g, 2.0 mmol, 1.0 eq), 3-amino-N-methylpicolinamide (0.303 g, 1.2 eq), Pd2(dba)3 (0.183 g, 0.1 eq), Xantphos (0.347 g, 0.3 eq), Cs₂CO₃ (1.3 g, 2.0 eq) in dioxane (15 mL) was stirred at 90° C. in an oil bath overnight. The mixture was cooled to room temperature and filtered through a celite pad. The celite pad was washed with methanol. The solvent was removed to obtain the crude which was purified by silica gel chromatography (20%~80% EtOAc/Hex) to obtain the desired product (0.146 g, isolated yield 22%).

N-Methyl-3-(2-(2-oxoindolin-5-ylamino)-5-(trifluoromethyl)pyridin-4-ylamino)picolinamide

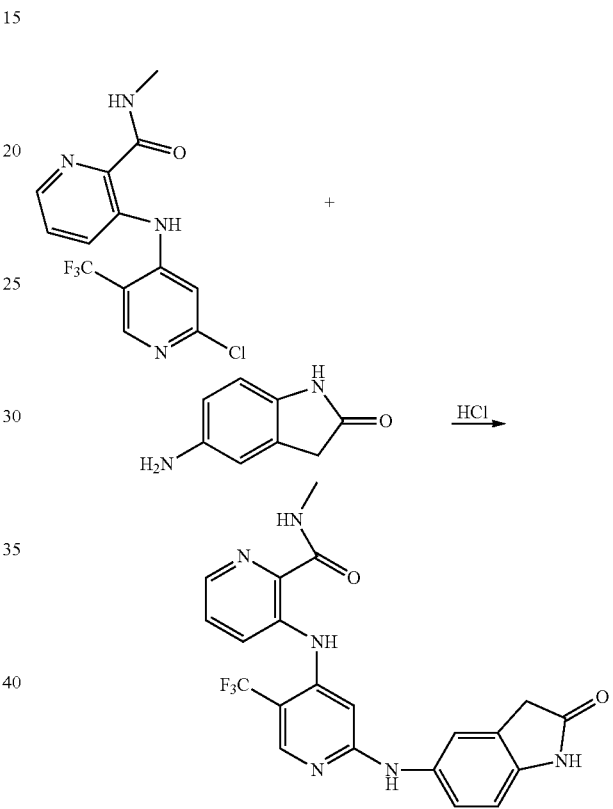

To a high pressure vial was added 3-(2-chloro-5-(trifluoromethyl)pyridin-4-ylamino)-N-methylpicolinamide (0.205 g, 0.62 mmol) and 5-aminoindolin-2-one (0.138 g, 1.2 eq) and n-BuOH (5 mL). HCl (~1.25M HCl in ethanol, 0.5 mL, 1.0 eq) was added to the above mixture. The vial was sealed and heated at 160° C. with stirring overnight in an oil bath. The mixture was cooled to room temperature and concentrated under reduced pressure to obtain the crude. The crude was dissolved in EtOAc and washed with saturated NaHCO₃ solution. The organic layers were concentrated and the crude was purified by silica gel chromatography (20%~100% EtOAc/Hex). The product was precipitated from EtOAc and filtered to obtain the desired product as the free base (isolated yield 56%). The product was converted to the HCl salt.

$^1$H NMR (400 MHz, DMSO-$d_6$, HCl-salt) δ 11.25 (s, 1H), 10.37 (s, 1H), 9.77 (br s, 1H), 9.09 (q, J=4.7 Hz, 1H), 8.30 (dd, J=1.2, 4.4 Hz, 1H), 8.28 (s, 1H), 8.11 (dd, J=1.2, 8.5 Hz, 1H), 7.60 (dd, J=4.4, 8.5 Hz, 1H), 7.43 (s, 1H), 7.24 (dd, J=2.1, 8.3 Hz, 1H), 6.80 (d, J=8.3 Hz, 1H), 6.77 (s, 1H), 3.49 (s, 2H), 2.81 (d, J=4.9 Hz, 3H);

$^{19}$F-NMR (376 MHz, $d_6$-DMSO) δ −59.45 (s, 3F).

EXAMPLE 78

3-(2-(2-Methoxy-4-morpholinophenylamino)-5-(trifluoromethyl)pyridin-4-ylamino)-N-methylpicolinamide

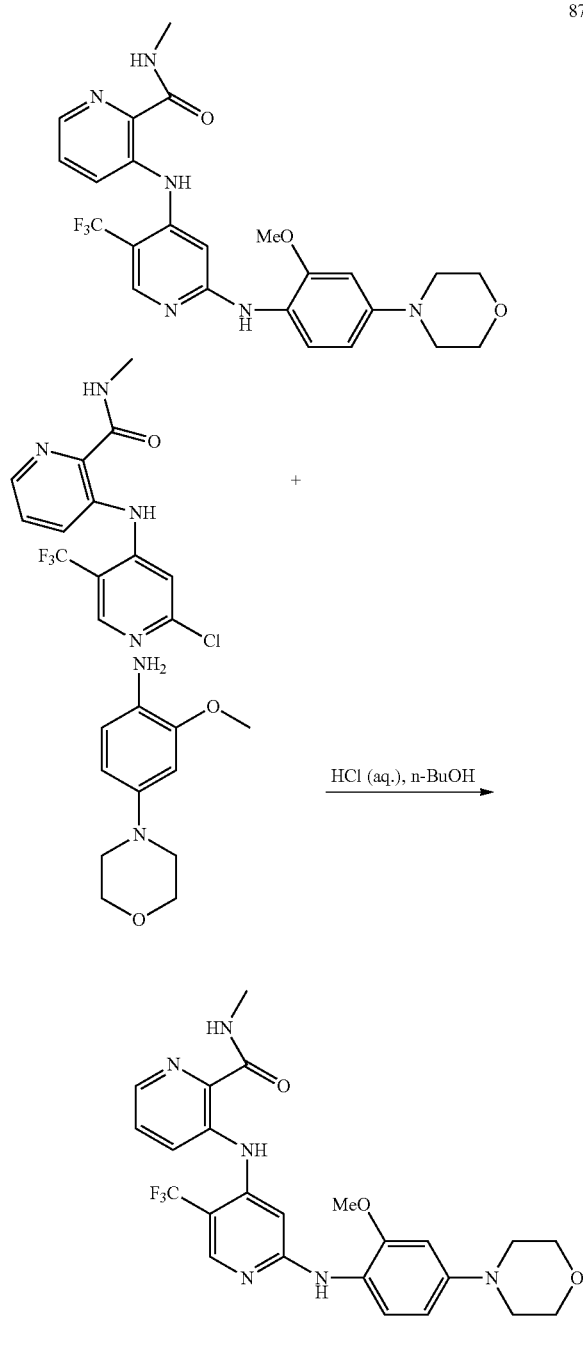

Method F was applied. The TFA salt of the title compound was obtained as a solid.

$^1$H NMR (400 MHz, DMSO-d$_6$) δ 11.28 (s, 1H), 9.27 (broad s, 1H), 9.09 (q, J=4.8 Hz, 1H), 8.31 (dd, J=4.6 Hz, 0.8 Hz, 1H), 8.19 (s, 1H), 8.04 (dd, J=8.2 Hz, 0.8 Hz, 1H), 7.62-7.58 (m, 1H), 7.38 (d, J=8.4 Hz, 1H), 7.10-6.69 (m, 2H), 6.55 (dd, J=8.8, 2.4 Hz, 1H), 3.81 (s, 3H), 3.75 (t, J=4.4 Hz, 4H), 3.15 (t, J=4.4 Hz, 4H), 2.81 (d, J=4.8 Hz, 3H).

EXAMPLE 79

3-(2-(5-(Dimethylcarbamoyl)pyridin-2-ylamino)-5-(trifluoromethyl)pyridin-4-ylamino)-N-methylpicolinamide

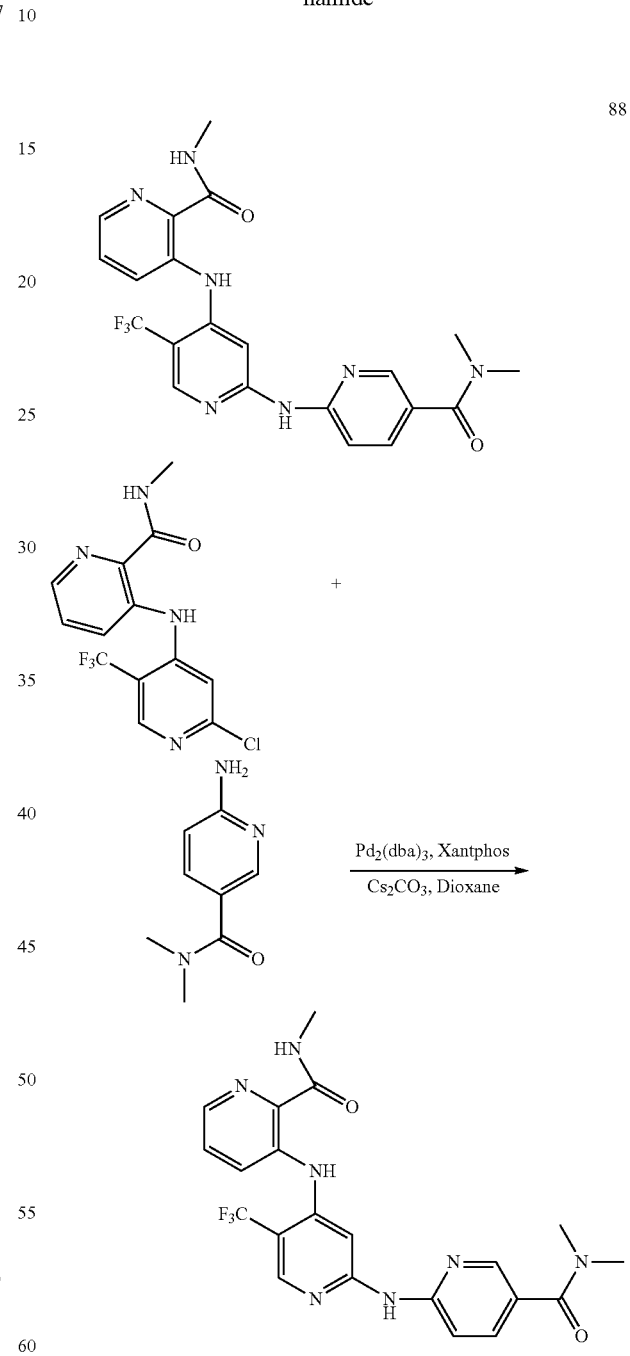

Method D was applied. The TFA salt of the title compound was obtained as a pale yellow solid.

$^1$H NMR (400 MHz, DMSO-d$_6$) δ 11.36 (s, 1H), 10.54 (broad s, 1H), 9.10 (q, J=4.8 Hz, 1H), 8.46 (s, 1H), 8.32-8.30 (m, 2H), 8.19 (dd, J=8.4 Hz, 1.2 Hz, 1H), 7.97 (s, 1H), 7.83

(dd, J=8.4, 2.4 Hz, 1H), 7.68-7.65 (m, 1H), 7.58 (d, J=8.8 Hz, 1H), 2.98 (s, 6H), 2.82 (d, J=4.8 Hz, 3H); ESI-MS (m/z): 460.2 (M+1).

EXAMPLE 80

3-(2-(1H-Indazol-5-ylamino)-5-(trifluoromethyl)pyridin-4-ylamino)-N-methylpicolinamide

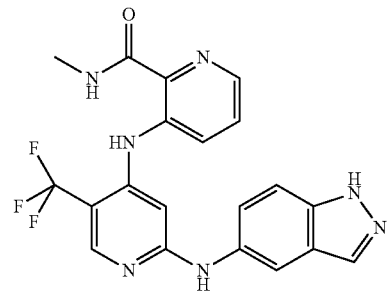

+

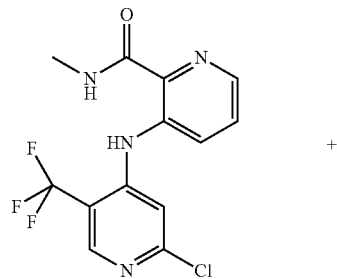

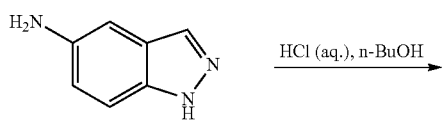

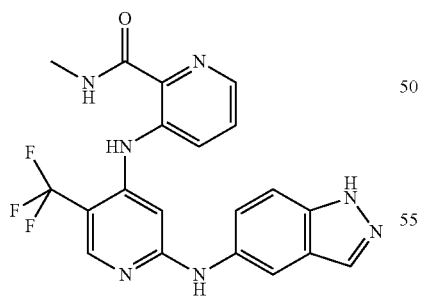

Method F was applied. The HCl salt of the title compound was obtained as a pale yellow solid.

$^1$H-NMR (400 MHz, d$_6$-DMSO, HCl-salt) δ 13.0 (vbr s, 1H), 11.29 (s, 1H), 9.97 (br s, 1H), 9.08 (q, J=4.7 Hz, 1H), 8.31 (s, 1H), 8.29 (dd, J=1.2, 3.2 Hz, 1H), 8.14 (dd, J=1.2, 8.5 Hz, 1H), 8.07 (d, J=0.9 Hz, 1H), 7.99 (d, J=0.9 Hz, 1H), 7.60 (dd, J=4.4, 8.5 Hz, 1H), 7.56 (d, J=8.8 Hz, 1H), 7.36 (dd, J=2.0, 8.9 Hz, 1H), 6.84 (s, 1H), 2.81 (d, J=4.9 Hz, 3H); $^{19}$F-NMR (376 MHz, d$_6$-DMSO) δ−59.5 (s, 3F); MS (m/z): 428.15 [M+1]$^+$.

EXAMPLE 81

N-Methyl-3-(2-(2-oxo-1,2,3,4-tetrahydroquinolin-6-ylamino)-5-(trifluoromethyl)pyridin-4-ylamino)picolinamide

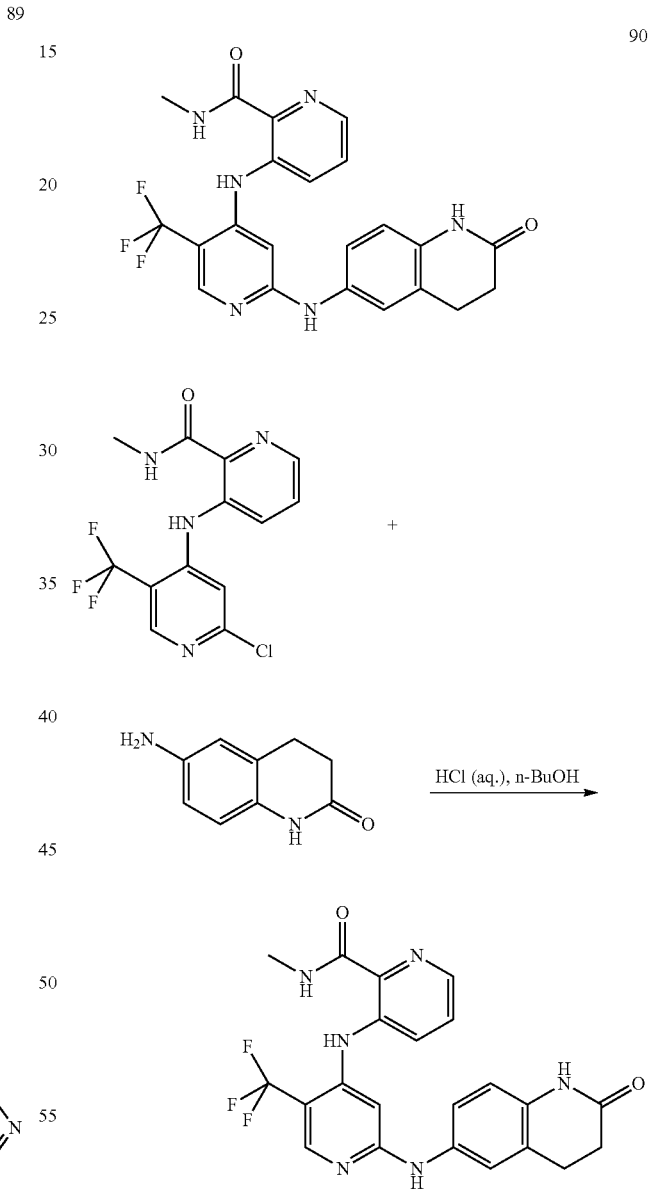

Method F was applied. The HCl salt of the title compound was obtained as a pale yellow solid.

$^1$H-NMR (400 MHz, d$_6$-DMSO, HCl-salt) δ 11.18 (s, 1H), 10.03 (s, 1H), 9.56 (br s, 1H), 9.07 (q, J=4.7 Hz, 1H), 8.30 (s, 1H), 8.28 (dd, J=1.2, 4.4 Hz, 1H), 8.10 (dd, J=1.2, 8.5 Hz, 1H), 7.57 (dd, J=4.4, 8.5 Hz, 1H), 7.38 (d, J=1.9 Hz, 1H), 7.24 (dd, J=2.3, 8.5 Hz, 1H), 6.82 (d, J=8.5 Hz, 1H), 6.78 (s, 1H), 2.86 (t, J=7.5 Hz, 2H), 2.81 (d, J=4.9 Hz, 3H), 2.45-2.41 (m, 2H); ¹⁹F-NMR (376 MHz, d₆-DMSO) δ −59.2 (s, 3F); MS (m/z): 457.2 [M+1]⁺.

EXAMPLE 82

N-Methyl-3-(2-(2-oxoindolin-6-ylamino)-5-(trifluoromethyl)pyridin-4-ylamino)picolinamide

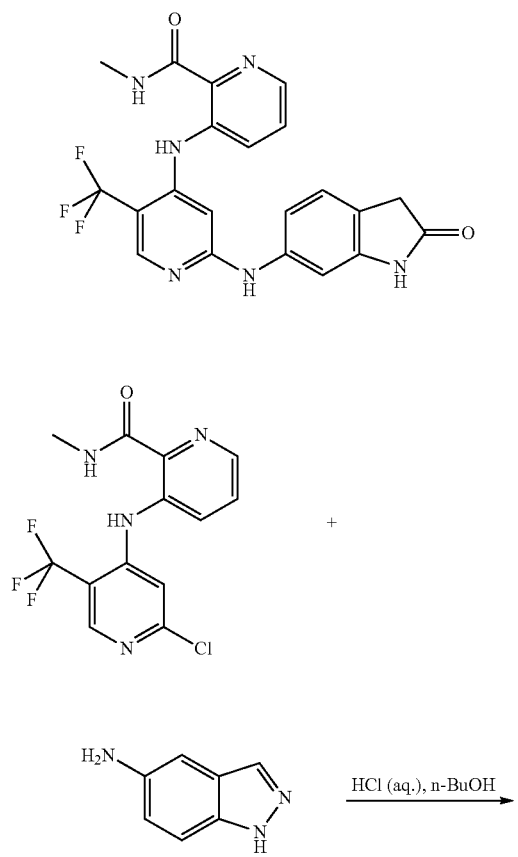

Method F was applied. The TFA salt of the title compound was obtained as a pale yellow solid.

¹H-NMR (400 MHz, d₆-DMSO) δ 11.08 (s, 1H), 10.35 (s, 1H), 9.38 (s, 1H), 9.05 (q, J=4.8 Hz, 1H), 8.33 (s, 1H), 8.26 (dd, J=1.3, 4.4 Hz, 1H), 8.08 (dd, J=1.3, 8.5 Hz, 1H), 7.59 (dd, J=4.4, 8.5 Hz, 1H), 7.31 (d, J=1.6 Hz, 1H), 7.11-7.04 (m, 2H), 6.85 (s, 1H), 3.39 (s, 2H), 2.81 (d, J=4.9 Hz, 3H); ¹⁹F-NMR (376 MHz, d₆-DMSO) δ −59.0 (s, 3F), −74.7 (s, 3F); MS (m/z): 443.15 [M+1]⁺.

EXAMPLE 83

3-(2-(4-(Dimethylcarbamoyl)-2-methoxyphenylamino)-5-(trifluoromethyl)pyridin-4-ylamino)-N-methylpicolinamide

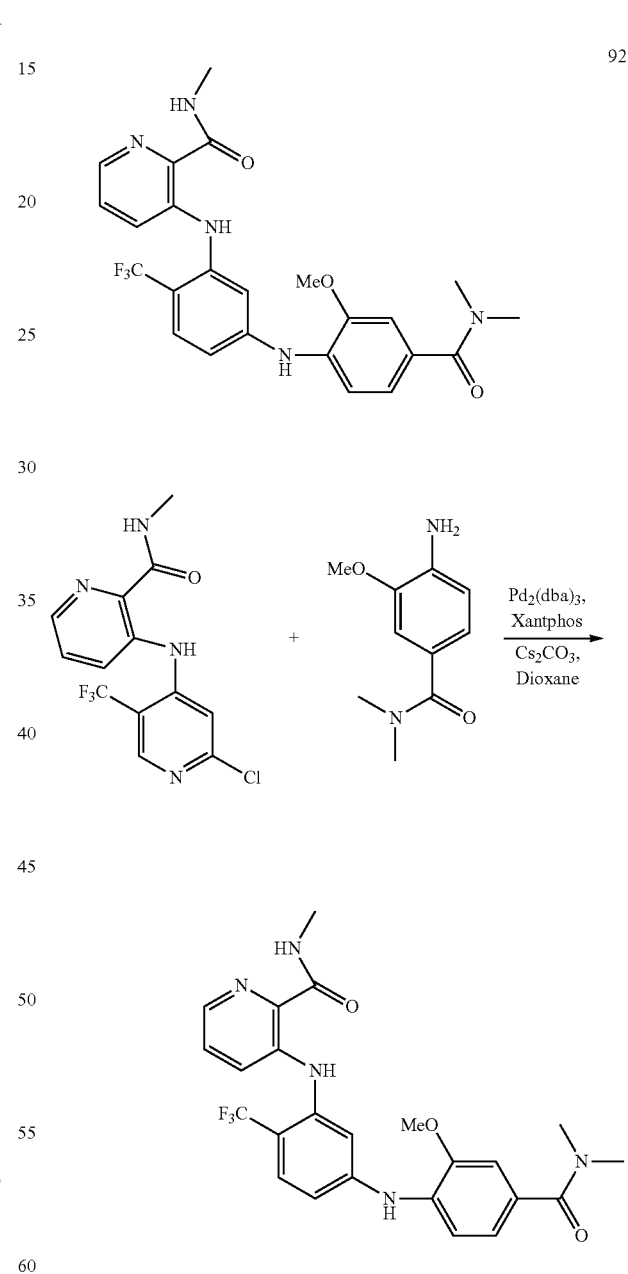

Method D was applied. The TFA salt of the title compound was obtained as a pale yellow solid.

ESI-MS (m/z): 489.2 (M+1).

EXAMPLE 84

N,N-Dimethyl-3-(2-(2-oxoindolin-5-ylamino)-5-(trifluoromethyl)pyridin-4-ylamino)picolinamide

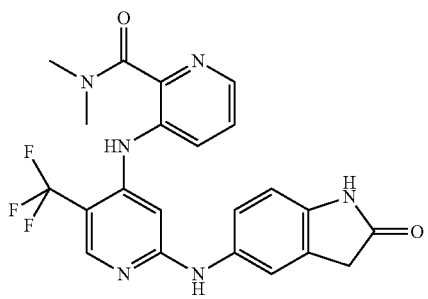

3-Amino-N,N-dimethylpicolinamide

To the mixture of 3-aminopicolinic acid (0.32 g, 2.32 mmol), dimethylamine hydrogen chloride (0.227 g, 1.2 eq), EDC (0.667 g, 1.5 eq), HOBt (0.376 g, 1.2 eq) in DMF (10 mL) was added DIEA (2.0 mL, 5.0 eq). The mixture was stirred at room temperature overnight. The crude was concentrated and dissolved in EtOAc. It was washed with saturated NaHCO$_3$. The solvent was removed and the crude was purified by silica gel chromatography (0%~20% MeOH/DCM) to obtain the desired product 3-amino-N,N-dimethylpicolinamide (0.375 g, isolated yield ~98%).

3-(2-Chloro-5-(trifluoromethyl)pyridin-4-ylamino)-N,N-dimethylpicolinamide

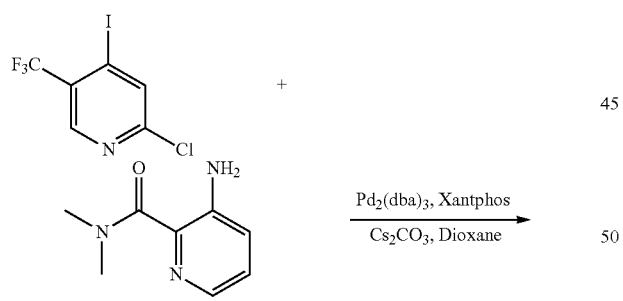

Method C was applied.

N,N-Dimethyl-3-(2-(2-oxoindolin-5-ylamino)-5-(trifluoromethyl)pyridin-4-ylamino)picolinamide

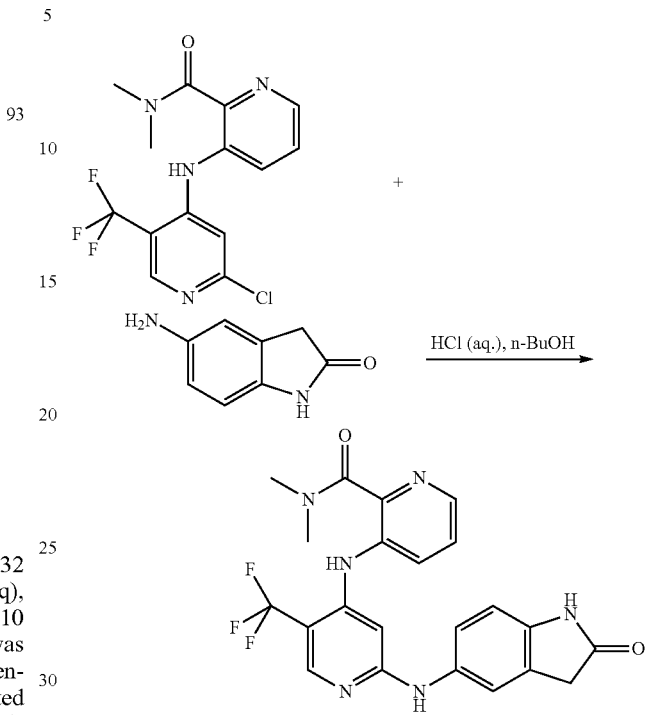

Method F was applied. The TFA salt of the title compound was obtained as a solid.

$^1$H NMR (400 MHz, DMSO-d$_6$) δ 10.32 (s, 1H), 9.43 (broad s, 1H), 8.66 (broad s, 1H), 8.43 (dd, J=4.6 Hz, 1.6 Hz, 1H), 8.18 (s, 1H), 8.01 (dd, J=8.2 Hz, 1.2 Hz, 1H), 7.58-7.54 (m, 1H), 7.40 (s, 1H), 7.20 (dd, J=8.2 Hz, 2.4 Hz, 1H), 6.75 (d, J=8.4 Hz, 1H), 6.20 (s, 1H), 3.45 (s, 2H), 2.97 (s, 3H), 2.96 (s, 3H); ESI-MS (m/z): 457.15 (M+1).

EXAMPLE 85

4,5-Difluoro-2-(2-(2-methoxy-4-morpholinophenylamino)-5-(trifluoromethyl)pyridin-4-ylamino)-N-methylbenzamide

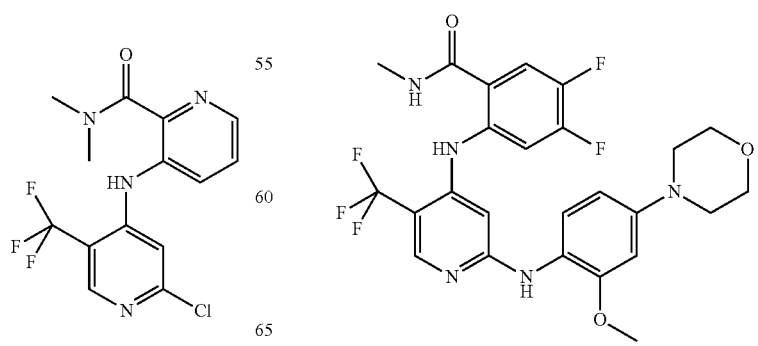

4,5-Difluoro-N-methyl-2-nitrobenzamide

To a mixture of 4,5-difluoro-2-nitrobenzoic acid (1.872 g, 9.22 mmol), methylamine hydrogen chloride (0.75 g, 1.2 eq), EDC (2.12 g, 1.2 eq), HOBt (1.5 g, 1.2 eq) in DMF (20 mL) was added DIEA (5.0 mL, 3.0 eq). The mixture was stirred at room temperature for 15 min. It was concentrated and the crude was dissolved in EtOAc. It was washed with a saturated NaHCO$_3$. The solvent was removed and the crude was purified by silica gel chromatography (20%~80% EtOAc/Hex) to obtain the desired product 4,5-difluoro-N-methyl-2-nitrobenzamide (1.33 g, isolated yield 67%).

2-Amino-4,5-difluoro-N-methylbenzamide

To 4,5-difluoro-N-methyl-2-nitrobenzamide (1.33 g, 6.15 mmol) in methanol (50 mL) was added Pd/C (10% Pd in carbon, 200 mg, 15 wt %) under argon. A hydrogen balloon was used as hydrogen source. The reaction was stirred at room temperature overnight. The mixture was filtered through celite and the celite pad was washed several times. The solvent was removed the crude was purified by silica gel chromatography to obtain the desired product (quantitative yield).

2-(2-Chloro-5-(trifluoromethyl)pyridin-4-ylamino)-4,5-difluoro-N-methylbenzamide

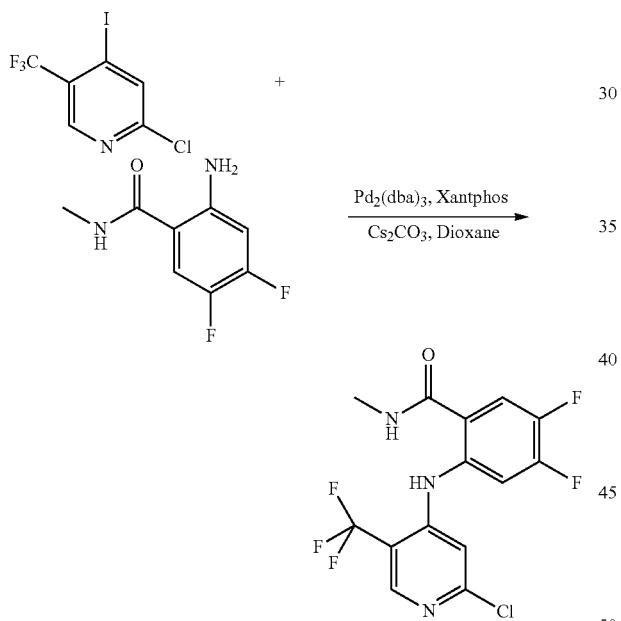

Method C was applied.

4,5-Difluoro-2-(2-(2-methoxy-4-morpholinophenylamino)-5-(trifluoromethyl)pyridin-4-ylamino)-N-methylbenzamide

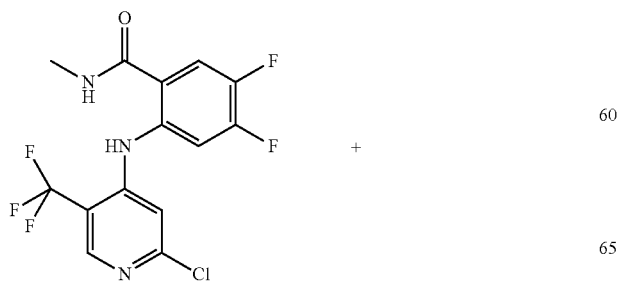

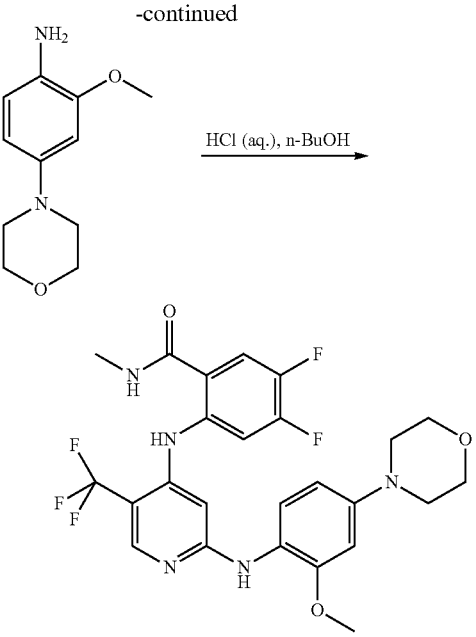

Method F was applied. The HCl salt of the title compound was obtained as a solid.

$^1$H NMR (400 MHz, DMSO-d$_6$) δ 10.60 (s, 1H), 10.06 (broad s, 1H), 8.97-8.91 (m, 1H), 8.16 (s, 1H), 7.97-7.92 (m, 1H), 7.75-7.69 (m, 1H), 7.27 (d, J=6.4 Hz, 1H), 6.80 (s, 1H), 6.66-6.60 (m, 2H), 3.81 (s, 3H), 3.80-3.76 (m, 4H), 3.25-3.20 (m, 4H), 2.75 (d, J=4.8 Hz, 3H); ESI-MS (m/z): 538.2 (M+1).

EXAMPLE 86

4,5-Difluoro-N-methyl-2-(2-(2-oxoindolin-5-ylamino)-5-(trifluoromethyl)pyridin-4-ylamino)benzamide

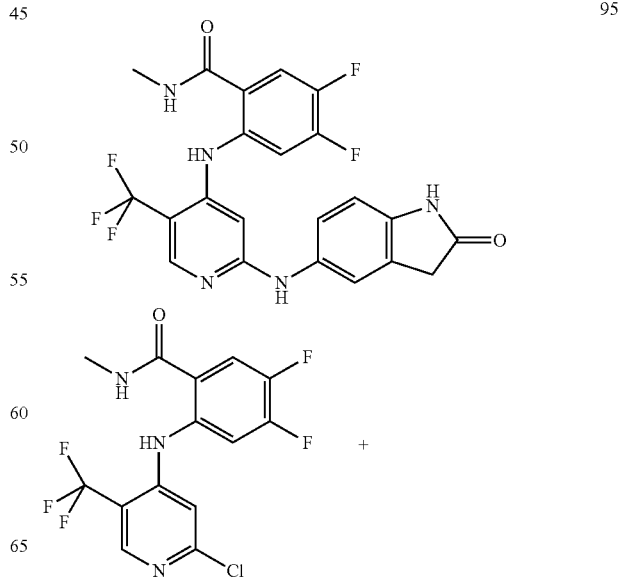

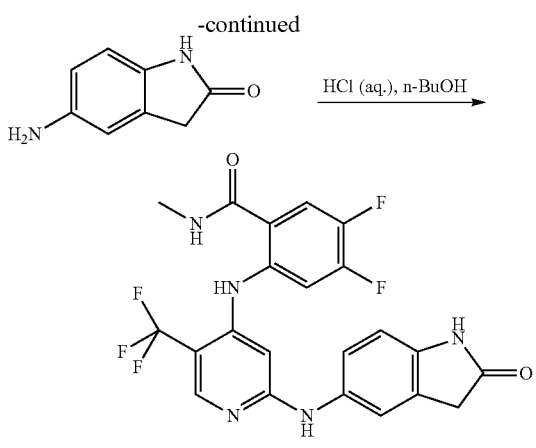

Method F was applied. The HCl salt of the title compound was obtained as a solid.

¹H NMR (400 MHz, DMSO-d₆) δ 10.60 (s, 1H), 10.45 (s, 1H), 10.21 (broad s, 1H), 8.95-8.90 (m, 1H), 8.26 (s, 1H), 7.95-7.92 (m, 1H), 7.79-7.73 (m, 1H), 7.36 (s, 1H), 7.22 (dd, J=8.2 Hz, 2.0 Hz, 1H), 6.82 (d, J=8.4 Hz, 1H), 6.65 (s, 1H), 3.47 (s, 2H), 2.74 (d, J=4.8 Hz, 3H); ESI-MS (m/z): 478.1 (M+1).

EXAMPLE 87

N-Methyl-3-(2-(2-oxoindolin-5-ylamino)-5-(trifluoromethyl)pyridin-4-ylamino)isonicotinamide

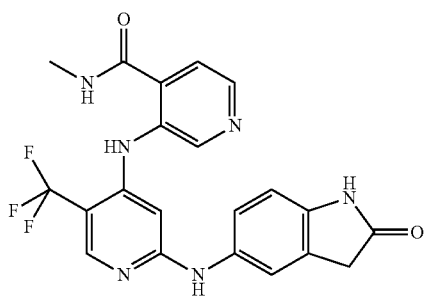

N-Methyl-3-nitroisonicotinamide

To the mixture of 3-nitroisonicotinic acid (4.78 g, 28.4 mmol), methylamine hydrogen chloride (2.88 g, 1.5 eq), EDC (6.53 g, 1.2 eq), HOBt (4.59 g, 1.2 eq) in DMF (50 mL) was added DIEA (25 mL, 5.0 eq). The mixture was stirred at room temperature overnight. It was concentrated and the crude was dissolved in EtOAc. It was washed with saturated NaHCO₃ solution. The solvent was removed and the crude was purified by silica gel chromatography (0%~20% MeOH/DCM) to obtain the desired product N-methyl-3-nitroisonicotinamide (878 mg, isolated yield 17%).

3-Amino-N-methylisonicotinamide

To N-methyl-3-nitroisonicotinamide (0.878 g) in methanol (50 mL) was added Pd/C (10% Pd in carbon, 100 mg, 11 wt %) under argon. A hydrogen balloon was used as the hydrogen source. The reaction was stirred at room temperature overnight. The mixture was filtered through celite and the celite pad was washed several times. The methanol phase was combined, concentrated and the crude was purified by silica gel chromatography to obtain the desired product (quantitative yield).

3-(2-Chloro-5-(trifluoromethyl)pyridin-4-ylamino)-N-methylisonicotinamide

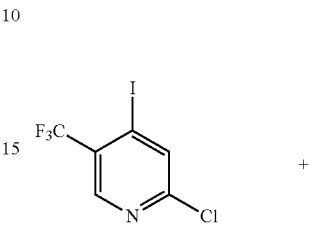

+

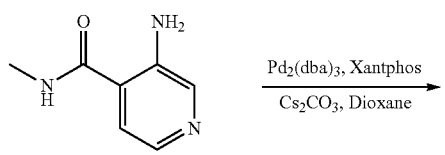

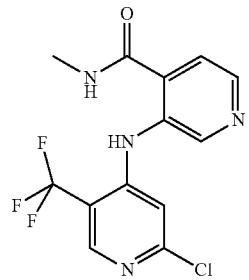

Method C was applied.

N-Methyl-3-(2-(2-oxoindolin-5-ylamino)-5-(trifluoromethyl)pyridin-4-ylamino)isonicotinamide

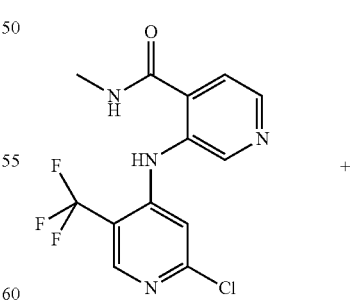

+

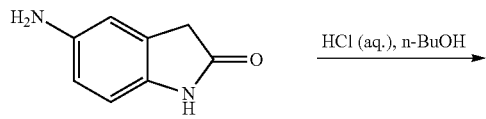

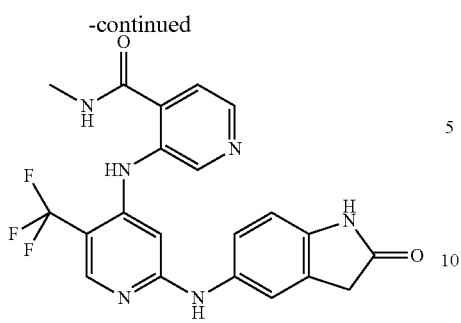

Method F was applied. The HCl salt of the title compound was obtained.

¹H NMR (400 MHz, DMSO-d₆) δ 10.44 (s, 1H), 10.13 (broad s, 1H), 10.04 (s, 1H), 9.12 (q, J=4.8 Hz, 1H), 8.91 (s, 1H), 8.51 (d, J=4.8 Hz, 1H), 8.25 (s, 1H), 7.77 (d, J=5.2 Hz, 1H), 7.34 (s, 1H), 7.19 (dd, J=2.0, 8.4 Hz, 1H), 6.81 (d, J=8.4 Hz, 1H), 6.56 (s, 1H), 3.49 (s, 2H), 2.77 (d, J=4.8 Hz, 3H); ESI-MS (m/z): 443.2 (M+1).

EXAMPLE 88

N-Methyl-4-(2-(2-oxoindolin-5-ylamino)-5-(trifluoromethyl)pyridin-4-ylamino)nicotinamide

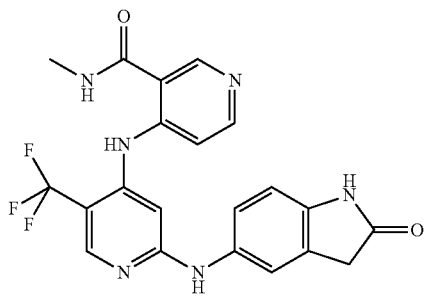

4-Amino-N-methylnicotinamide

To the mixture of 4-aminonicotinic acid (691 mg, 5.0 mmol), methylamine hydrogen chloride (410 mg, 1.2 eq), EDC (1.15 g, 1.2 eq), HOBt (810 mg, 1.2 eq) in DMF (20 mL) was added DIEA (3.0 mL, 3.0 eq). The mixture was stirred at room temperature overnight. It was concentrated and dissolved in EtOAc. It was washed with saturated NaHCO₃ solution. It was concentrated and purified by silica gel with chromatography (0%~20% MeOH/DCM) to obtain the desired product 4-amino-N-methylnicotinamide.

4-(2-Chloro-5-(trifluoromethyl)pyridin-4-ylamino)-N-methylnicotinamide

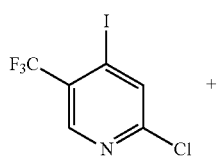

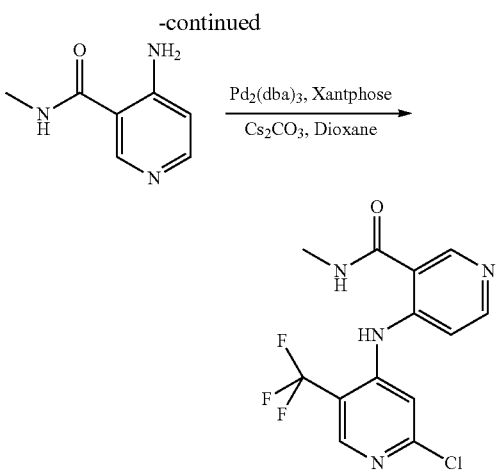

Method C was applied.

N-Methyl-4-(2-(2-oxoindolin-5-ylamino)-5-(trifluoromethyl)pyridin-4-ylamino)nicotinamide

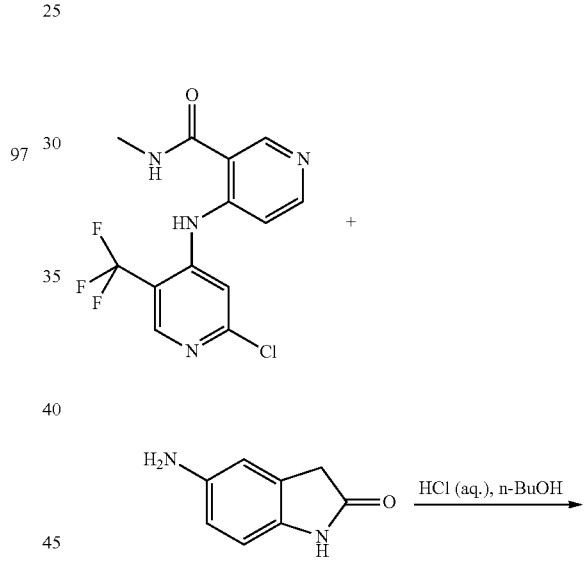

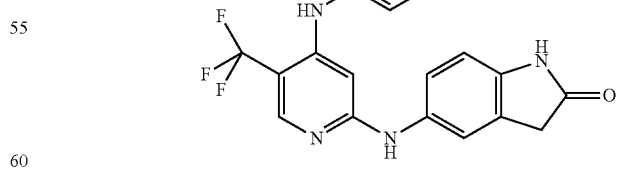

Method F was applied. The HCl salt of the title compound was obtained.

¹H NMR (400 MHz, DMSO-d₆) δ 11.43 (s, 1H), 10.29 (s, 1H), 9.47 (s, 1H), 9.08 (br d, J=3.6 Hz, 1H), 8.87 (s, 1H), 8.49-8.41 (m, 2H), 7.56 (s, 1H), 7.50 (d, J=6.4 Hz, 1H), 7.32

(dd, J=8.4, 1.6 Hz, 1H), 6.85 (s, 1H), 6.78 (d, J=8.4 Hz, 1H), 3.48 (s, 2H), 2.82 (d, J=4.8 Hz, 3H); ESI-MS (m/z): 443.2 (M+1).

EXAMPLE 89

N-Methyl-2-(2-(2-oxoindolin-5-ylamino)-5-(trifluoromethyl)pyridin-4-ylamino)nicotinamide

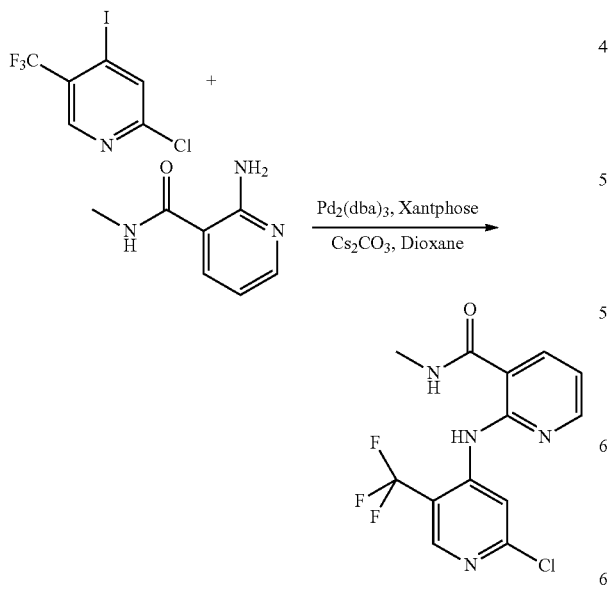

2-Amino-N-methylnicotinamide

To the mixture of 2-aminonicotinic acid (2.0 g, 14.5 mmol), methylamine hydrogen chloride (1.47 g, 1.5 eq), EDC (4.49 g, 1.5 eq), HOBt (2.35 g, 1.2 eq) in DMF (20 mL) was added DIEA (7.6 mL, 3.0 eq). The mixture was stirred at room temperature overnight. The crude was concentrated and dissolved in EtOAc. It was washed with saturated NaHCO$_3$. The solvent was removed and the crude was purified by silica gel chromatography (0%~20% MeOH/DCM) to obtain the desired product 2-amino-N-methylnicotinamide (2.16 g, isolated yield ~98%).

2-(2-Chloro-5-(trifluoromethyl)pyridin-4-ylamino)-N-methylnicotinamide

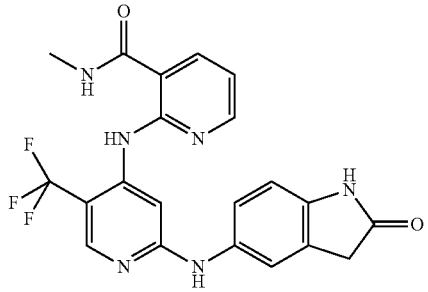

Method C was applied.

N-Methyl-2-(2-(2-oxoindolin-5-ylamino)-5-(trifluoromethyl)pyridin-4-ylamino)nicotinamide

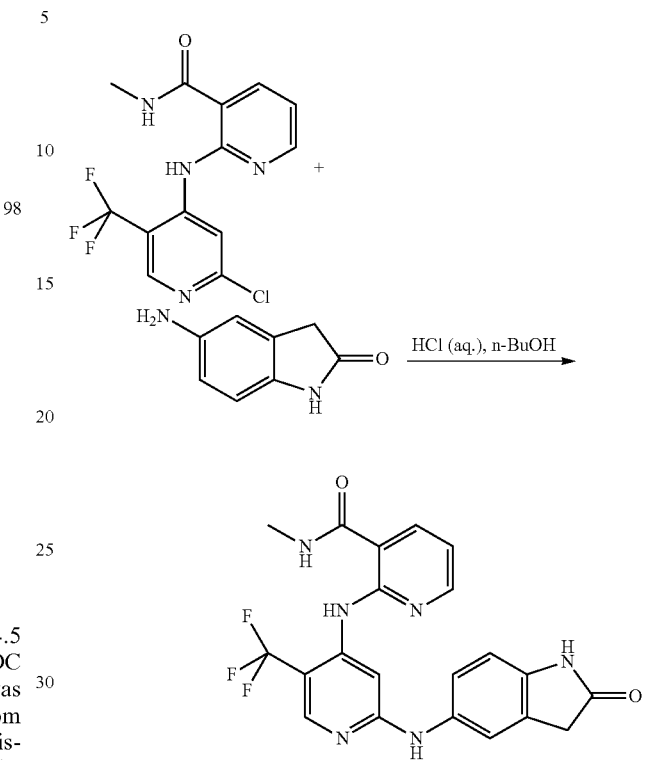

Method F was applied. The title compound was obtained as a solid.

$^1$H NMR (400 MHz, DMSO-d$_6$) δ 11.57 (s, 1H), 10.29 (s, 1H), 9.40 (broad s, 1H), 8.90-8.85 (m, 1H), 8.42 (dd, J=4.8 Hz, 1.6 Hz, 1H), 8.25 (s, 1H), 8.20 (dd, J=8.0 Hz, 2.0 Hz, 1H), 8.16 (s, 1H), 7.52 (s, 1H), 7.32 (dd, J=8.4 Hz, 2.0 Hz, 1H), 7.13-7.09 (m, 1H), 6.78 (d, J=8.4 Hz, 1H), 3.49 (s, 2H), 2.81 (d, J=4.8 Hz, 3H); ESI-MS (m/z): 443.1 (M+1).

EXAMPLE 90

N-Methyl-4-(2-(2-oxoindolin-5-ylamino)-5-(trifluoromethyl)pyridin-4-ylamino)pyrimidine-5-carboxamide

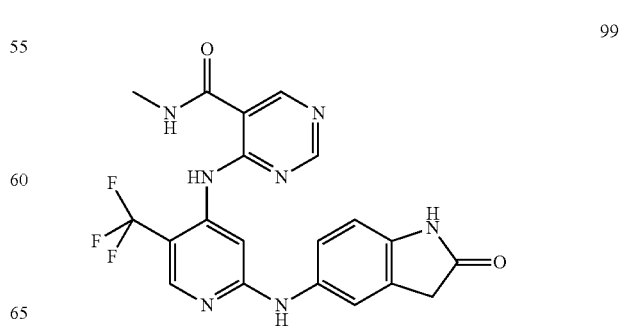

4-Amino-N-methylpyrimidine-5-carboxamide

To the mixture of 4-aminopyrimidine-5-carboxylic acid (0.75 g, 5.39 mmol), methylamine hydrogen chloride (0.44 g, 1.2 eq), EDC (1.67 g, 1.5 eq), HOBt (0.87 g, 1.2 eq) in DMF (20 mL) was added DIEA (3.8 mL, 4.0 eq). The mixture was stirred at room temperature overnight. The crude was concentrated and dissolved in EtOAc. It was washed with saturated NaHCO₃ solution. The solvent was removed and the crude was purified by silica gel chromatography (0%~20% MeOH/DCM) to obtain the desired product 4-amino-N-methylpyrimidine-5-carboxamide (0.701 g, isolated yield 85%).

4-(2-Chloro-5-(trifluoromethyl)pyridin-4-ylamino)-N-methylpyrimidine-5-carboxamide

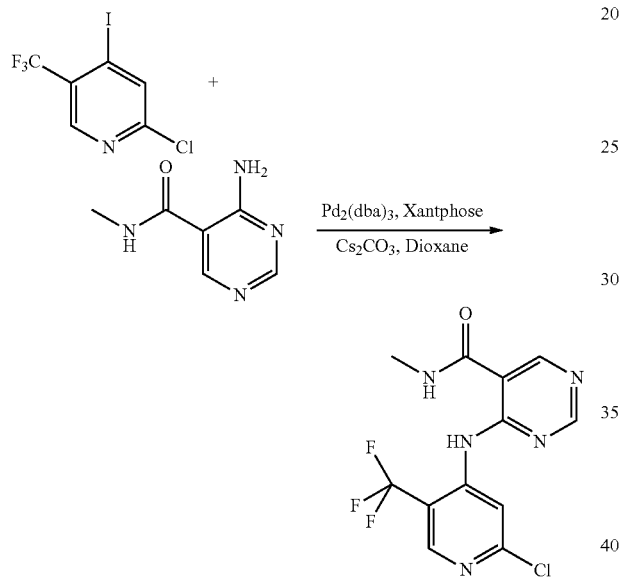

Method C was applied.

N-Methyl-4-(2-(2-oxoindolin-5-ylamino)-5-(trifluoromethyl)pyridin-4-ylamino)pyrimidine-5-carboxamide

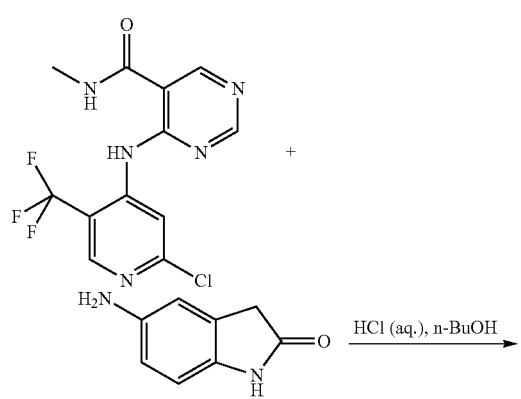

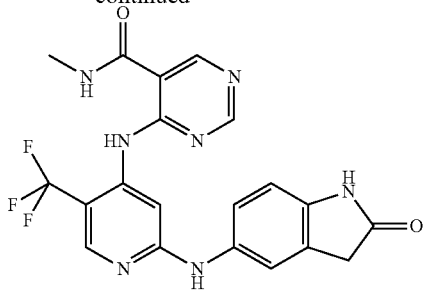

Method F was applied. The TFA salt of the title compound was obtained.

$^1$H NMR (400 MHz, DMSO-d$_6$) δ 11.76 (s, 1H), 10.28 (s, 1H), 9.48 (s, 1H), 9.05-9.01 (m, 1H), 8.98 (s, 1H), 8.86 (s, 1H), 8.33 (s, 1H), 7.99 (s, 1H), 7.56 (s, 1H), 7.35 (dd, J=8.4, 1.6 Hz, 1H), 6.78 (d, J=8.4 Hz, 1H), 3.49 (s, 2H), 2.83 (d, J=4.8 Hz, 3H); ESI-MS (m/z): 444.15 (M+1).

EXAMPLE 91

N-Methyl-3-(2-(2-oxoindolin-5-ylamino)-5-(trifluoromethyl)pyridin-4-ylamino)pyrazine-2-carboxamide

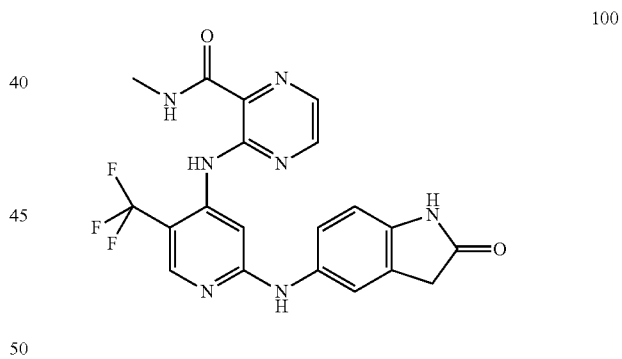

100

3-Amino-N-methylpyrazine-2-carboxamide

A mixture of 3-aminopyrazine-2-carboxylic acid (965 mg, 6.94 mmol), methylamine hydrochloride (697 mg, 10.3 mmol), EDCI (1.61 g, 8.4 mmol), HOBt (1.136 g, 8.4 mmol) and DIEA (2.42 mL, 13.9 mmol) in DMF (24 mL) was stirred at room temperature for 48 h. It was diluted with ethyl acetate and washed with saturated sodium bicarbonate, brine and dried over magnesium sulfate. The solvent was removed and the residue was purified by silica gel chromatography (combiflash-companion; DCM/MeOH gradient) to give the title compound.

3-(2-Chloro-5-(trifluoromethyl)pyridin-4-ylamino)-N-methylpyrazine-2-carboxamide

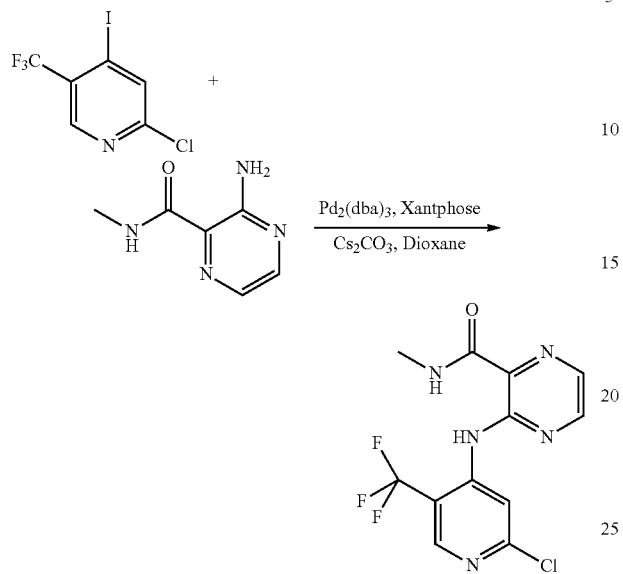

Method B was applied.

N-Methyl-3-(2-(2-oxoindolin-5-ylamino)-5-(trifluoromethyl)pyridin-4-ylamino)pyrazine-2-carboxamide

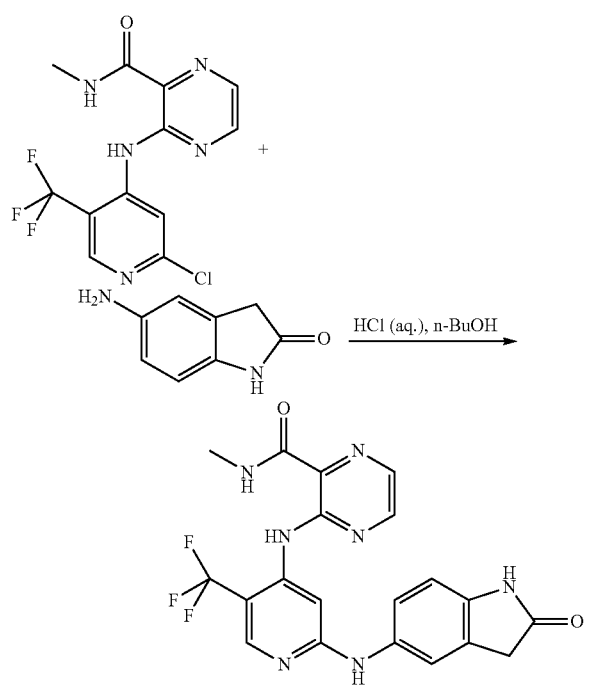

Method F was applied. The TFA salt of the title compound was obtained as a brownish solid.

$^1$H-NMR (400 MHz, $d_6$-DMSO) δ 11.98 (s, 1H), 10.30 (s, 1H), 9.47 (s, 1H), 9.18 (q, J=4.7 Hz, 1H), 8.52 (d, J=2.4 Hz, 1H), 8.30 (s, 1H), 8.26 (d, J=2.4 Hz, 1H), 8.10 (s, 1H), 7.54 (s, 1H), 7.33 (dd, J=2.1, 8.4 Hz, 1H), 6.79 (d, J=8.3 Hz, 1H), 3.49 (s, 2H), 2.94 (d, J=4.8 Hz, 3H); $^{19}$F-NMR (376 MHz, $d_6$-DMSO) δ −58.8 (s, 3F), −74.6 (s, 3F); MS (m/z): 444.2 [M+1]$^+$.

EXAMPLE 92

N-(2-(2-(2-Oxoindolin-5-ylamino)-5-(trifluoromethyl)pyridin-4-ylamino)phenyl) acetamide

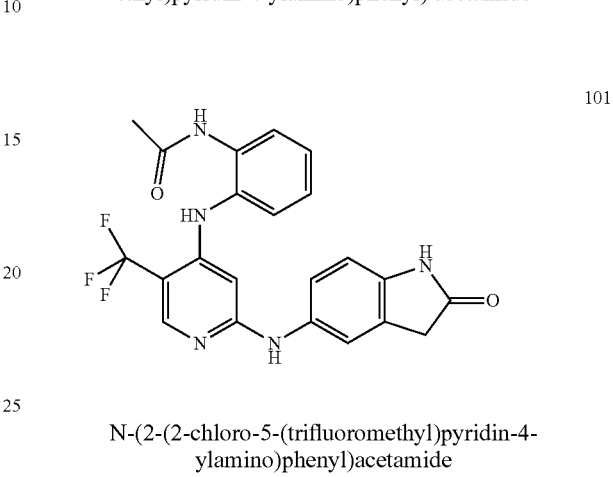

N-(2-(2-chloro-5-(trifluoromethyl)pyridin-4-ylamino)phenyl)acetamide

Method C was applied.

N-(2-(2-(2-Oxoindolin-5-ylamino)-5-(trifluoromethyl)pyridin-4-ylamino)phenyl)acetamide

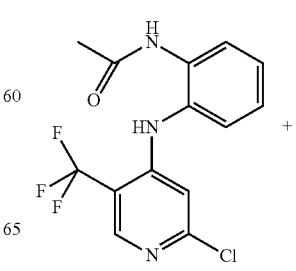

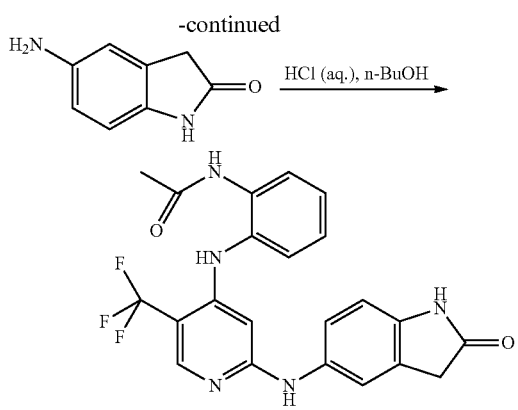

A procedure similar to Method F was applied. The TFA salt of the title compound was obtained.

$^1$H NMR (400 MHz, DMSO-$d_6$) δ 10.33 (s, 1H), 10.14 (s, 1H), 9.43 (broad s, 1H), 8.12 (s, 1H), 7.90 (broad s, 1H), 7.50-7.46 (m, 1H), 7.37-7.27 (m, 4H), 7.15-7.10 (m, 1H), 6.75 (d, J=8.4 Hz, 1H), 6.04 (s, 1H), 3.44 (s, 2H), 2.05 (s, 3H); ESI-MS (m/z): 442.2 (M+1).

EXAMPLE 93

5-(4-(2-(Pyrimidin-2-yl)phenylamino)-5-(trifluoromethyl)pyridin-2-ylamino)indolin-2-one

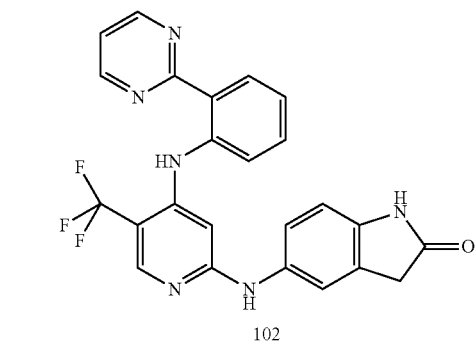

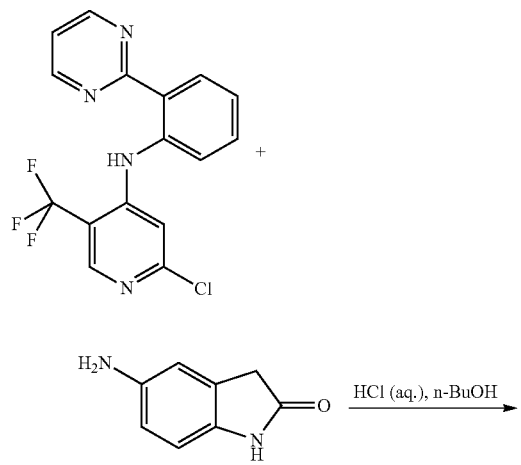

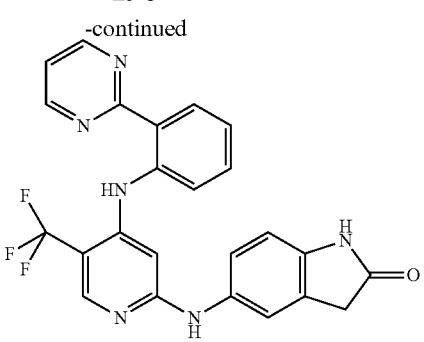

Method F was applied. The TFA salt of the title compound was obtained as a yellow solid.

$^1$H-NMR (400 MHz, $d_6$-DMSO) δ 11.26 (s, 1H), 10.30 (s, 1H), 9.36 (br s, 1H), 8.93 (d, J=4.9 Hz, 2H), 8.42 (dd, J=1.6, 8.0 Hz, 1H), 8.23 (s, 1H), 7.68 (dd, J=0.8, 8.2 Hz, 1H), 7.59-7.55 (m, 1H), 7.51 (t, J=4.9 Hz, 1H), 7.42 (s, 1H), 7.29-7.25 (m, 1H), 7.22 (dd, J=2.1, 8.3 Hz, 1H), 6.76 (d, J=8.3 Hz, 1H), 6.71 (s, 1H), 3.46 (s, 1H); $^{19}$F-NMR (376 MHz, $d_6$-DMSO) δ −59.6 (s, 3F), −74.6 (s, 3F); MS (m/z): 463.2 [M+1]$^+$.

EXAMPLE 94

5-(4-(Pyridin-2-ylamino)-5-(trifluoromethyl)pyridin-2-ylamino)indolin-2-one

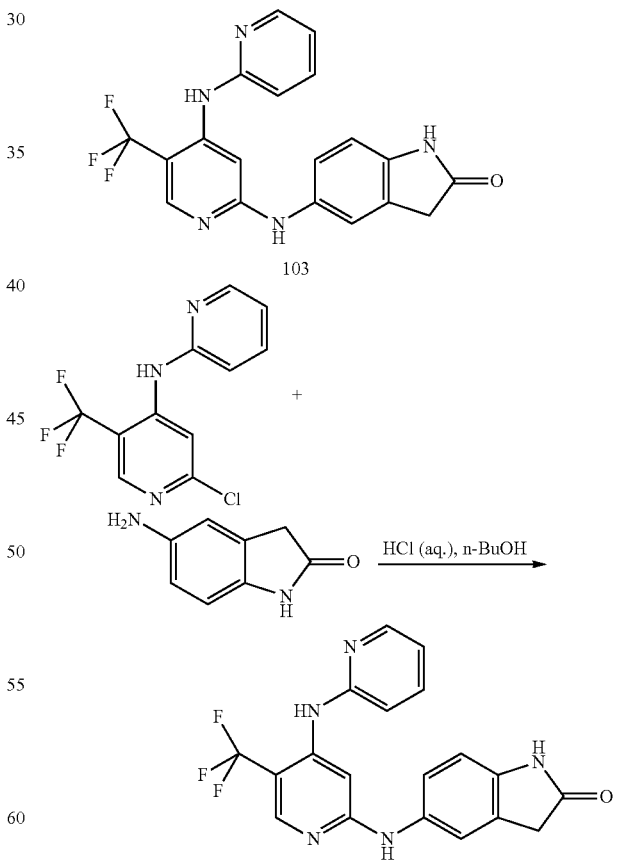

Method F was applied. The TFA salt of the title compound was obtained as a pale yellow solid.

$^1$H-NMR (400 MHz, $d_6$-DMSO) δ 10.33 (s, 1H), 9.53 (s, 1H), 8.45 (br s, 1H), 8.29 (dd, J=1.2, 5.0 Hz, 1H), 8.25 (s, 1H), 7.81-7.76 (m, 1H), 7.53 (s, 1H), 7.44 (s, 1H), 7.33 (d, J=8.3

Hz, 1H), 7.26 (dd, J=2.1, 8.3 Hz, 1H), 7.08-7.05 (m, 1H), 6.79 (d, J=8.3 Hz, 1H), 3.48 (s, 2H); $^{19}$F-NMR (376 MHz, d$_6$-DMSO) δ −58.2 (s, 3F), −74.6 (s, 3F); MS (m/z): 386.2 [M+1]$^+$.

EXAMPLE 95

N$^4$-(Pyridin-2-yl)-N$^2$-(3-(1,2,3,6-tetrahydropyridin-4-yl)-1H-indol-5-yl)-5-(trifluoromethyl)pyridine-2,4-diamine

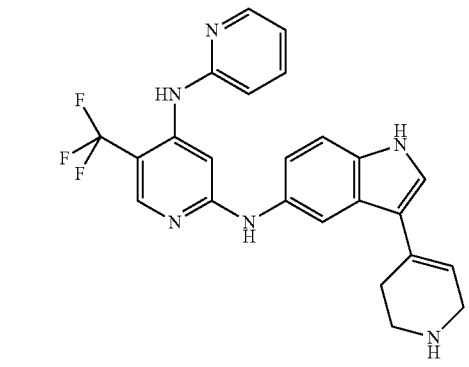

104

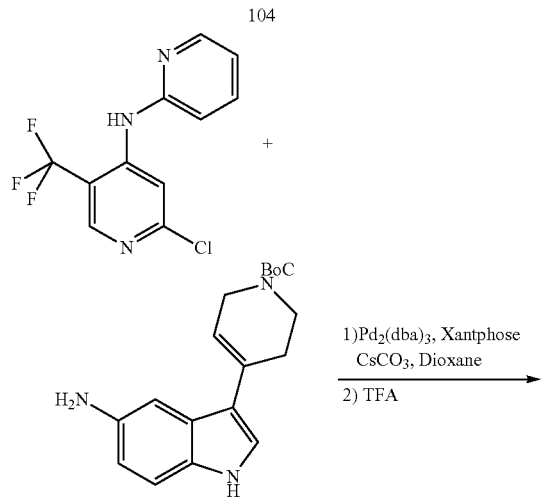

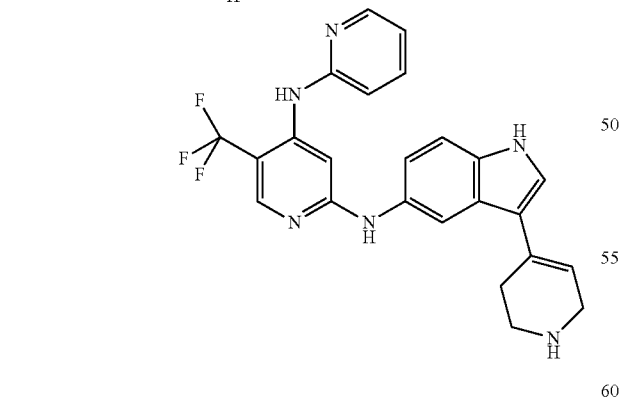

Method D followed by TFA treatment was applied. It was purified by preparative HPLC. The bis-TFA salt of the title compound was obtained as a solid.
$^1$H NMR (400 MHz, DMSO-d$_6$) δ 9.70 (vbr s, 1H), 9.08 (broad s, 2H), 8.86 (broad s, 1H), 8.71 (s, 1H), 8.52 (s, 1H), 8.41 (d, J=8.8 Hz, 1H), 8.40-8.36 (m, 1H), 8.17 (s, 1H), 7.91 (d, J=1.6 Hz, 1H), 7.83-7.79 (m, 1H), 7.43 (d, J=8.4 Hz, 1H), 7.32 (dd, J=9.0 Hz, 2.0 Hz, 1H), 7.12-7.08 (m, 1H), 6.23 (s, 1H), 3.89-3.82 (m, 2H), 3.43-3.34 (m, 2H), 2.82-2.75 (m, 2H); ESI-MS (m/z): 451.0 (M+1).

tert-Butyl 4-(5-nitro-1H-indol-3-yl)-5,6-dihydropyridine-1(2H)-carboxylate

The mixture of tert-butyl 3-bromo-5-nitro-1H-indole-1-carboxylate (341.2 mg, 1.0 mmol, 1.0 eq), tert-butyl 4-(4,4,5,5-tetramethyl-1,3,2-dioxaborolan-2-yl)-5,6-dihydropyridine-1(2H)-carboxylate (309.2 mg, 1.0 eq), (PPh$_3$)$_4$Pd (O) (231.1 mg, 0.2 eq), Na$_2$CO$_3$ (2M, 1.5 mL, 3.0 eq) and dioxane (10 mL) was degassed and heated at 120° C. in a microwave-oven synthesizer for 2 h. The mixture was cooled to room temperature and filtered through a celite pad to remove Na$_2$CO$_3$ and catalyst. EtOAc was used to wash the celite pad. The solvent was removed and the crude was purified by silica gel with chromatography (0%~20% MeOH/DCM) to obtain the desired product tert-butyl 4-(5-nitro-1H-indol-3-yl)-5,6-dihydropyridine-1(2H)-carboxylate (184.1 mg, isolated yield 54%).

tert-Butyl 4-(5-amino-1H-indol-3-yl)-5,6-dihydropyridine-1(2H)-carboxylate

To a solution of 7.4 mL dioxane, 5.5 mL ethanol and 3.7 mL distilled water was added tert-butyl 4-(5-nitro-1H-indol-3-yl)-5,6-dihydropyridine-1(2H)-carboxylate (184 mg, 0.54 mmol). To the mixture was added powdered iron (0) (0.15 g, 5.0 eq) and ammonium chloride (0.885 g, 4.0 eq). The reaction was heated to 70° C. under argon for 3 h. The reaction was cooled and filtered and washed with MeOH. The solvent was removed to obtain the crude which was purified by silica gel chromatography to afford the desired compound tert-butyl 4-(5-amino-1H-indol-3-yl)-5,6-dihydropyridine-1(2H)-carboxylate.

EXAMPLE 96

N,N-Dimethyl-2-oxo-2-(5-(4-(pyridin-2-ylamino)-5-(trifluoromethyl)pyridin-2-ylamino)-1H-indol-3-yl)acetamide

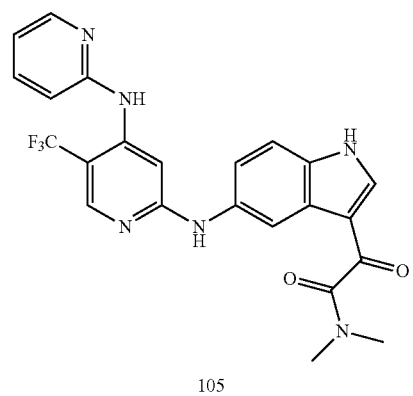

105

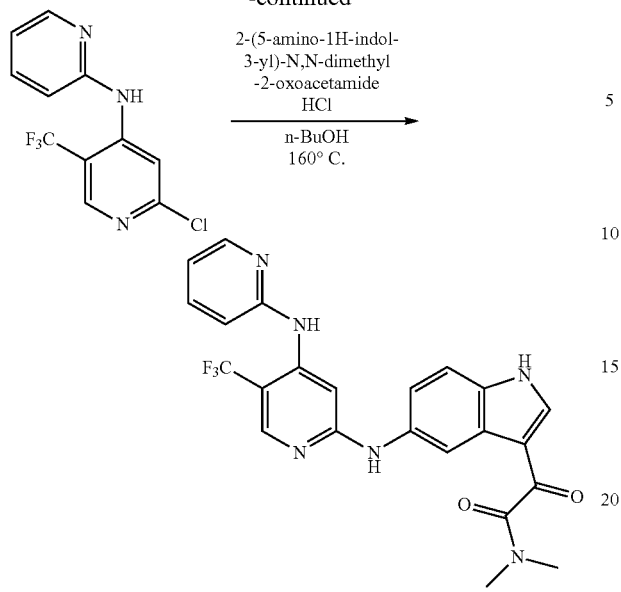

Method F was applied. The TFA salt of the title compound was obtained as a solid.

$^1$H-NMR (400 MHz, DMSO-$d_6$) δ 12.26 (d, J=2.7 Hz, 1H), 9.67 (br s, 1H), 8.41 (br s, 1H), 8.22-8.16 (m, 3H), 8.02 (d, J=3.2 Hz, 1H), 7.71 (m, 1H), 7.54 (s, 1H), 7.46-7.39 (m, 2H), 7.27 (d, J=8.3 Hz, 1H), 6.97 (m, 1H), 2.92 (s, 3H), 2.86 (s, 3H); MS (m/z): 469.2 [M+1]$^+$.

N,N-Dimethyl-2-(5-nitro-1H-indol-3-yl)-2-oxoacetamide

Reference: Macor, J. E.; Post, R.; Ryan, K. *Synth. Commun.* 1993, 23, 65-72.

To a stirred mixture of 5-nitroindole (5.00 g, 30.8 mmol) and phtalimide (2.00 g, 40% by weight) in anhydrous ether (125 mL) was added oxalyl chloride (8.09 mL, 95.6 mmol). The resulting mixture was stirred at room temperature for 24 h. The solids were filtered off, rinsed with several portions of ether and air-dried for 15 min. This intermediate was suspended in 100 mL anhydrous ether and cooled to 0° C. To this mixture was 2M dimethylamine in THF (154 mL, 0.308 mol) added in small increments. After the addition was complete the reaction was stirred for an additional 1 h at room temperature. The volatiles were evaporated and the crude re-crystallized in refluxing MeOH afforded N,N-dimethyl-2-(5-nitro-1H-indol-3-yl)-2-oxoacetamide (5.2 g, 20.02 mmol, 65%).

$^1$H NMR (400 MHz, DMSO-$d_6$) δ 12.77 (bs, 1H), 8.97 (d, J=2.3 Hz, 1H), 8.42 (s, 1H), 8.16 (dd, J=2.3, 8.9 Hz, 1H), 7.73 (d, J=9.0 Hz, 1H), 3.02 (s, 3H), 2.96 (s, 3H).

N,N-Dimethyl-2-(5-nitro-1H-indol-3-yl)-2-oxoacetamide

A mixture of N,N-dimethyl-2-(5-nitro-1H-indol-3-yl)-2-oxoacetamide (500 mg, 1.91 mmol) and 10% palladium on carbon in MeOH (30 mL) was stirred under a hydrogen atmosphere for 12 h. The reaction mixture was filtered through celite and the celite pad was washed with MeOH (100 mL). The volatiles were concentrated to yield N,N-dimethyl-2-(5-nitro-1H-indol-3-yl)-2-oxoacetamide (0.375 mg, 1.62 mmol, 85%).

$^1$H NMR (400 MHz, DMSO-$d_6$) δ 11.93 (bs, 1H), 7.86 (s, 1H), 7.37 (bs, 1H), 7.24 (d, J=8.6 Hz, 1H), 6.66 (dd, J=2.2, 8.6 Hz, 1H), 4.95 (bs, 2H), 3.03 (s, 3H), 2.95 (s, 3H).

EXAMPLE 97

N-Methyl-2-(2-(2-methyl-4,5'-bipyrimidin-6-ylamino)-5-(trifluoromethyl)pyridin-4-ylamino)benzenesulfonamide

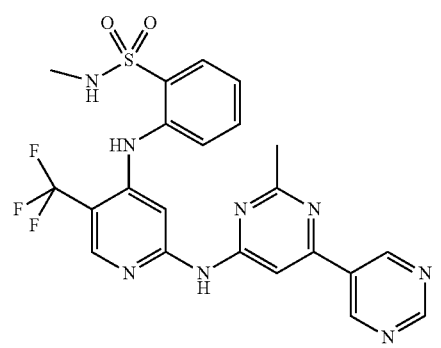

106

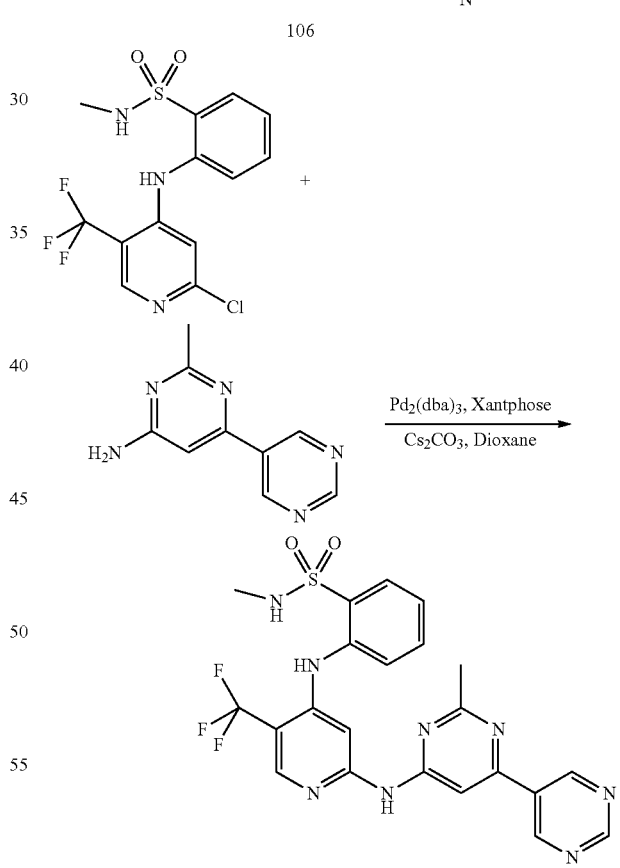

Method D was applied. The title compound was obtained as a white solid.

$^1$H-NMR (400 MHz, $d_6$-DMSO) δ 10.54 (s, 1H), 9.32 (s, 3H), 8.51 (s, 1H), 8.34 (s, 1H), 8.12 (s, 1H), 7.95 (s, 1H), 7.87 (dd, J=1.2, 7.9 Hz, 1H), 7.77-7.73 (m, 3H), 7.40-7.36 (m,

1H), 2.45 (d, J=5.0 Hz, 3H), 2.43 (s, 3H); $^{19}$F-NMR (376 MHz, d$_6$-DMSO) δ −59.3 (s, 3F); MS (m/z): 517.15 [M+1]$^+$.

EXAMPLE 98

N-Isopropyl-2-(2-(2-methoxy-4-morpholinophenylamino)-5-(trifluoromethyl)pyridin-4-ylamino)benzenesulfonamide

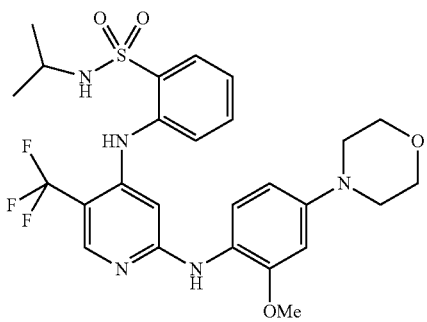

N-Isopropyl-2-nitrobenzenesulfonamide

To the solution of 2-nitrobenzene-1-sulfonyl chloride (1.11 g, 5.0 mmol) in MeOH (30 mL) was added isopropylamine (0.85 mL, 2.0 eq) and Et$_3$N (1.4 mL, 2.0 eq). The mixture was stirred overnight at room temperature. The solvent was removed and the crude was purified by silica gel chromatography to obtain the desired product N-isopropyl-2-nitrobenzenesulfonamide (0.774 g, isolated yield 63%).

2-Amino-N-isopropylbenzenesulfonamide

To N-isopropyl-2-nitrobenzenesulfonamide (774 mg) in methanol (50 mL) was added Pd/C (10% Pd in carbon, 150 mg, 19 wt %) under argon protection. A hydrogen balloon was used as the hydrogen source. The reaction was stirred at room temperature overnight. The mixture was filtered through celite and the celite pad was washed several times. The solvent was removed and the crude was purified by silica gel chromatography to obtain the desired product 2-amino-N-isopropylbenzenesulfonamide (quantitative yield).

2-(2-Chloro-5-(trifluoromethyl)pyridin-4-ylamino)-N-isopropylbenzenesulfonamide

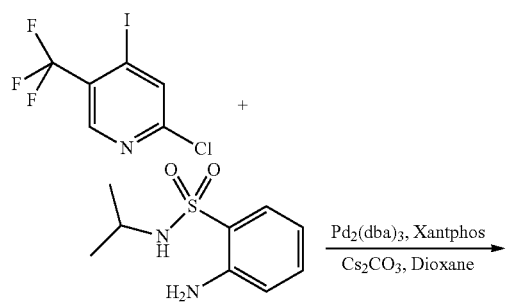

Method C was applied.

N-Isopropyl-2-(2-(2-methoxy-4-morpholinophenylamino)-5-(trifluoromethyl)pyridin-4-ylamino)benzenesulfonamide

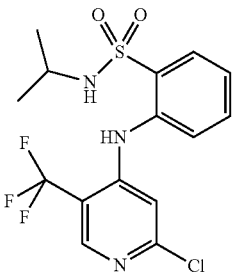

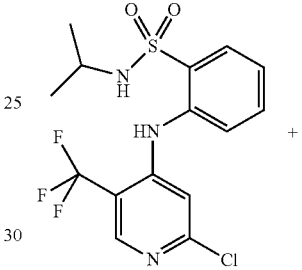

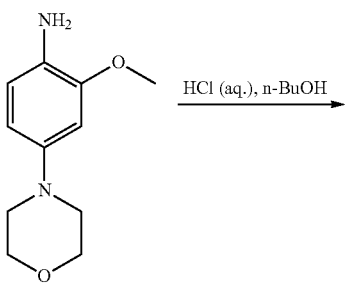

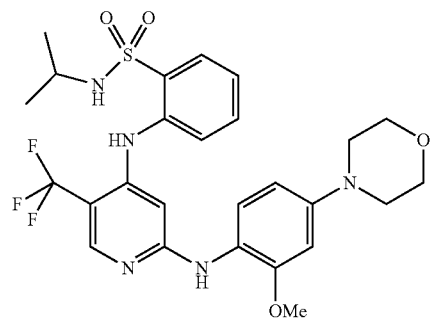

Method F was applied. The TFA salt of the title compound was obtained as a solid.

$^1$H NMR (400 MHz, DMSO-d$_6$) δ 9.01 (broad s, 1H), 8.26 (broad s, 1H), 8.17 (s, 1H), 7.86 (dd, J=8.0 Hz, 1.2 Hz, 1H), 7.80 (d, J=8.0 Hz, 1H), 7.68-7.62 (m, 1H), 7.56 (d, J=8.0 Hz, 1H), 7.34-7.30 (m, 2H), 6.63 (d, J=2.4 Hz, 1H), 6.49 (dd, J=8.8 Hz, 2.4 Hz, 1H), 6.39 (s, 1H), 3.78 (s, 3H), 3.74 (t, J=4.4 Hz, 4H), 3.30-3.24 (m, 1H), 3.11 (t, J=4.4 Hz, 4H), 0.94 (s, 3H), 0.92 (s, 3H).

EXAMPLE 99

N-Isopropyl-2-(2-(2-methyl-4,5'-bipyrimidin-6-ylamino)-5-(trifluoromethyl)pyridin-4-ylamino)benzenesulfonamide

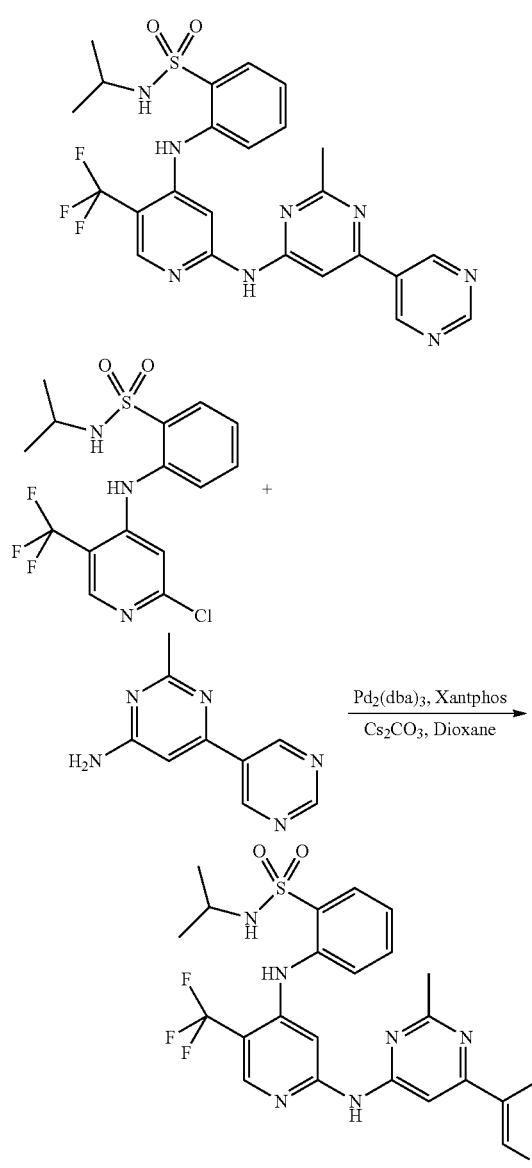

Method D was applied. The TFA salt of the title compound was obtained as a solid.

$^1$H NMR (400 MHz, DMSO-$d_6$) δ 10.62 (broad s, 1H), 9.33 (s, 1H), 9.31 (s, 2H), 8.53 (s, 1H), 8.27 (broad s, 1H), 8.25 (broad s, 1H), 7.92-7.85 (m, 3H), 7.73-7.66 (m, 2H), 7.36-7.32 (m, 1H), 3.32-3.26 (m, 1H), 2.39 (s, 3H), 0.93 (s, 3H), 0.91 (s, 3H); ESI-MS (m/z): 545.2 (M+1).

EXAMPLE 100

N-Methyl-5-morpholino-2-(2-(2-oxoindolin-5-ylamino)-5-(trifluoromethyl)pyridin-4-ylamino)benzamide

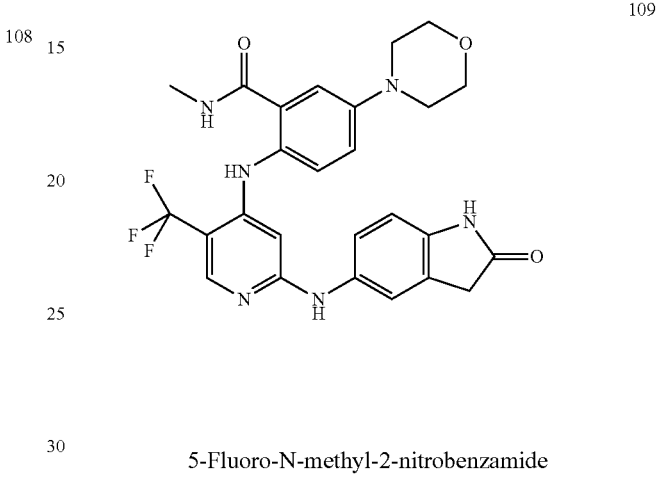

5-Fluoro-N-methyl-2-nitrobenzamide

To the mixture of 5-fluoro-2-nitrobenzoic acid (371 mg, 2.0 mmol), methylamine hydrogen chloride (162 mg, 1.2 eq), EDC (575 mg, 1.5 eq), HOBt (324 mg, 1.2 eq) in DMF (10 mL) was added DIEA (1.8 mL, 5.0 eq). The mixture was stirred at room temperature overnight. The crude was concentrated and dissolved in EtOAc. It was washed with saturated NaHCO$_3$ solution. The solvent was removed and the crude was purified by silica gel chromatography (0%~20% MeOH/DCM) to obtain the desired product 5-fluoro-N-methyl-2-nitrobenzamide (356 mg, isolated yield 90%).

N-Methyl-5-morpholino-2-nitrobenzamide

To the solution of 5-fluoro-N-methyl-2-nitrobenzamide (178 mg, 0.9 mmol) and morpholine (94 mg, 1.2 eq) in anhydrous DMF (3.0 mL) was added Cs$_2$CO$_3$ (350 mg, 1.2 eq). The mixture was stirred at 100° C. in an oil bath overnight. The mixture was cooled and the solvent was removed to obtain the crude which was purified by silica gel chromatography to obtain the desired compound N-methyl-5-morpholino-2-nitrobenzamide (206 mg, isolated yield 86%).

2-Amino-N-methyl-5-morpholinobenzamide

To N-methyl-5-morpholino-2-nitrobenzamide (256 mg) in ethanol (20 mL) was added Pd/C (10% Pd in carbon, 50 mg, 20 wt %) under argon. A hydrogen balloon was used as the hydrogen source. The reaction was stirred at room temperature overnight. The mixture was filtered through celite and the celite pad was washed several times. The solvent was removed and the crude was purified by silica gel chromatography to obtain the desired product 2-amino-N-methyl-5-morpholinobenzamide (quantitative yield).

2-(2-Chloro-5-(trifluoromethyl)pyridin-4-ylamino)-N-methyl-5-morpholinobenzamide

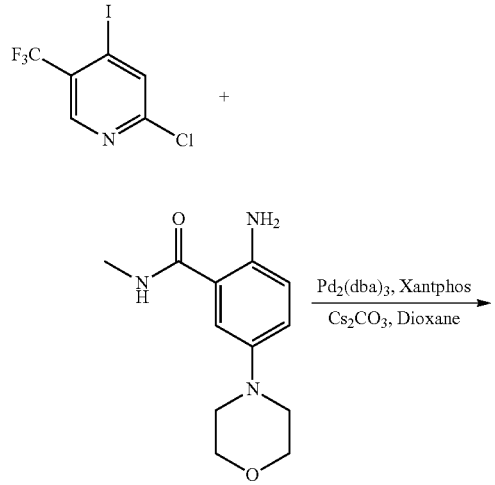

Method C was applied.

N-Methyl-5-morpholino-2-(2-(2-oxoindolin-5-ylamino)-5-(trifluoromethyl)pyridin-4-ylamino)benzamide

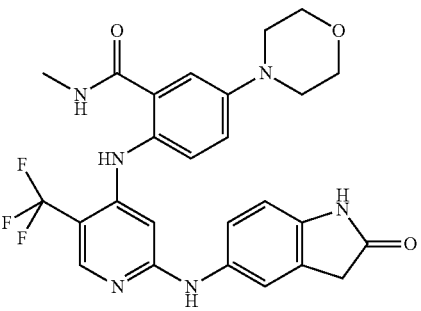

Method F was applied. The TFA salt of the title compound was obtained as a solid.

$^1$H NMR (400 MHz, DMSO-d$_6$) δ 11.37 (s, 1H), 9.67 (s, 1H), 9.56 (broad s, 1H), 8.57 (q, J=4.8 Hz, 1H), 8.13 (s, 1H), 7.40 (d, J=8.8 Hz, 1H), 7.31 (s, 1H), 7.20-7.12 (m, 3H), 6.79 (d, J=8.4 Hz, 1H), 6.33 (s, 1H), 3.76 (t, J=4.4 Hz, 4H), 3.47 (s, 2H), 3.16 (t, J=4.4 Hz, 4H), 2.74 (d, J=4.8 Hz, 3H); ESI-MS (m/z): 527.2 (M+1).

EXAMPLE 101

N-Methyl-2-(2-(5-(morpholine-4-carbonyl)pyridin-2-ylamino)-5-(trifluoromethyl)pyridin-4-ylamino)benzamide

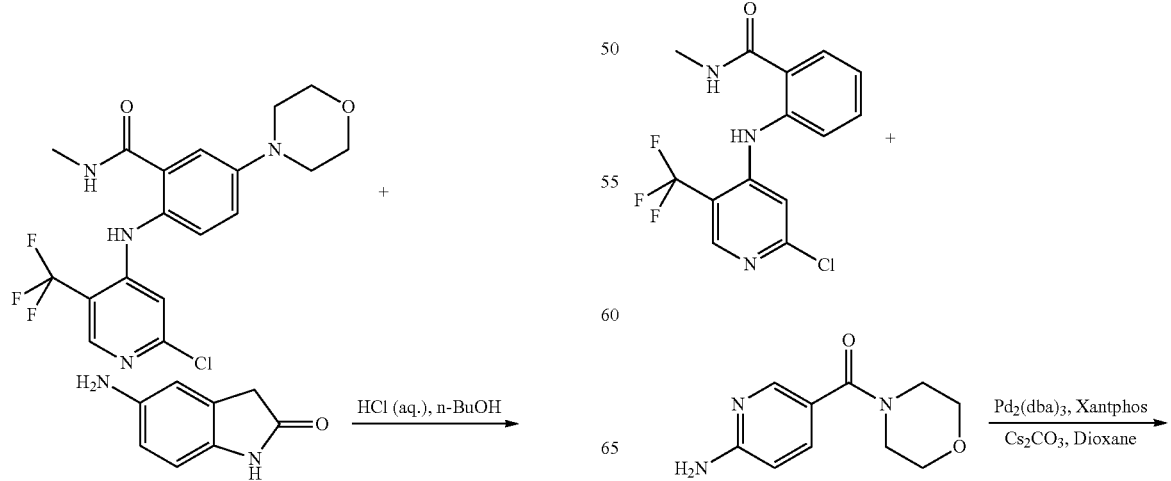

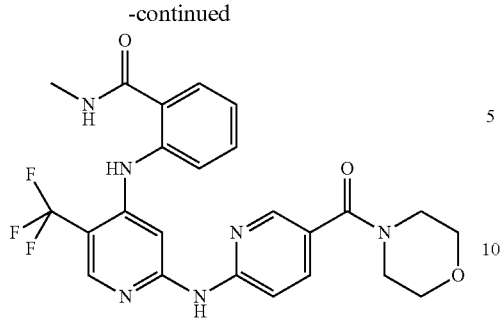

Method D was applied. The TFA salt of the title compound was obtained as a white solid.

$^1$H-NMR (400 MHz, d$_6$-DMSO) δ 10.55 (br s, 1H), 10.50 (s, 1H), 8.71 (q, J=4.4 Hz, 1H), 8.40 (s, 1H), 8.27 (d, J=2.0 Hz, 1H), 7.81 (dd, J=2.3, 8.6 Hz, 2H), 7.75 (dd, J=1.4, 7.9 Hz, 1H), 7.68 (dd, J=0.7, 8.2 Hz, 1H), 7.60-7.56 (m, 1H), 7.53 (d, J=8.6 Hz, 1H), 7.23-7.19 (m, 1H), 3.61 (br s, 4H), 3.51 (br s, 4H), 2.77 (d, J=4.6 Hz, 3H); $^{19}$F-NMR (376 MHz, d$_6$-DMSO) δ −60.1 (s, 3F), −74.45 (s, 3F); MS (m/z): 501.2 [M+1]$^+$.

Method D was applied. The title compound was obtained as a white solid.

$^1$H-NMR (400 MHz, d$_6$-DMSO) δ 10.47 (br s, 1H), 10.37 (br s, 1H), 8.71 (q, J=4.4 Hz, 1H), 8.62 (d, J=2.1 Hz, 1H), 8.39 (q, s, 2H), 8.08 (dd, J=2.4, 8.8 Hz, 1H), 8.03 (br s, 1H), 7.74 (dd, J=1.4, 7.9 Hz, 1H), 7.68 (dd, J=0.7, 8.2 Hz, 1H), 7.59-7.55 (m, 2H), 7.20-7.16 (m, 1H), 2.78 (d, J=4.6 Hz, 6H); $^{19}$F-NMR (376 MHz, d$_6$-DMSO) δ−59.8 (s, 3F); MS (m/z): 445.1 [M+1]$^+$.

EXAMPLE 102

N-Methyl-6-(4-(2-(methylcarbamoyl)phenylamino)-5-(trifluoromethyl)pyridin-2-ylamino)nicotinamide

EXAMPLE 103

N-Methyl-2-(4-(2-(methylcarbamoyl)phenylamino)-5-(trifluoromethyl)pyridin-2-ylamino)isonicotinamide

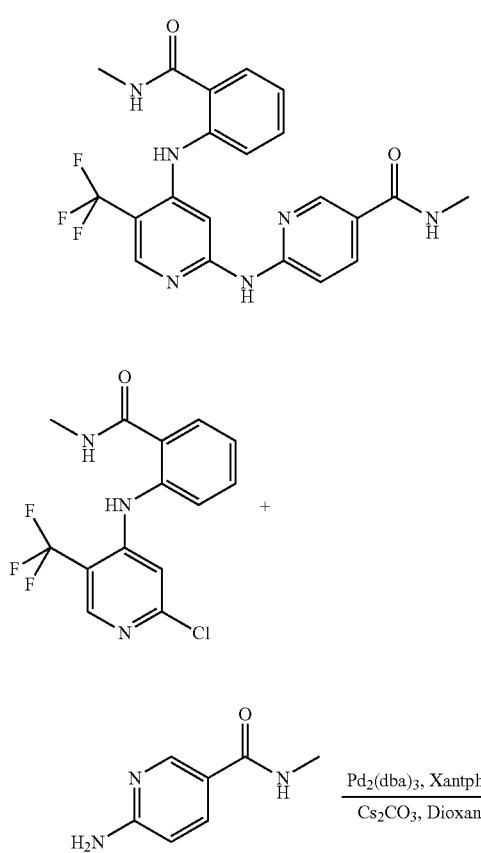

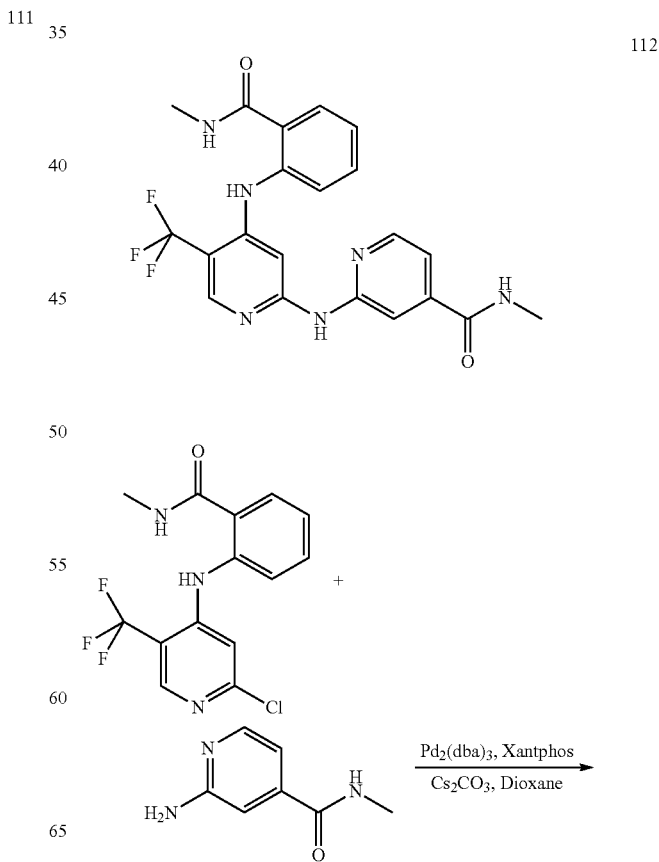

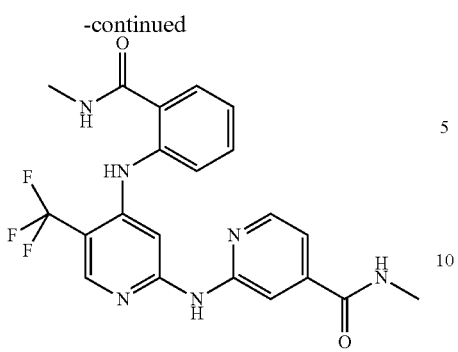

Method D was applied. The TFA salt of the title compound was obtained as a white solid.

$^1$H-NMR (400 MHz, d$_6$-DMSO) δ 10.63 (br s, 1H), 10.51 (s, 1H), 8.73-8.66 (m, 2H), 8.41 (s, 1H), 8.33 (d, J=5.3 Hz, 1H), 7.77-7.74 (m, 2H), 7.69-7.66 (m, 2H), 7.61-7.56 (m, 1H), 7.32 (dd, J=1.1, 5.3 Hz, 1H), 7.24-7.20 (m, 1H), 2.79 (d, J=4.6 Hz, 3H), 2.77 (d, J=4.6 Hz, 3H); $^{19}$F-NMR (376 MHz, d$_6$-DMSO) δ −60.2 (s, 3F), −74.4 (s, 3F); MS (m/z): 445.1 [M+1]$^+$.

EXAMPLE 104

2-(2-(Benzo[d][1,3]dioxol-5-ylamino)-5-(trifluoromethyl)pyridin-4-ylamino)-N-methylbenzamide

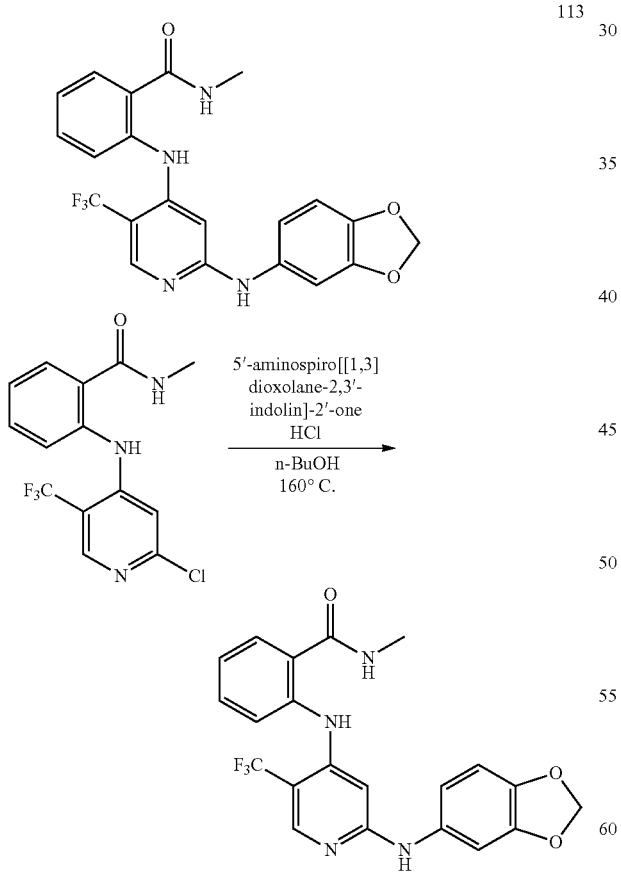

Method F was applied. The TFA salt of the title compound was obtained as a solid.

$^1$H-NMR (400 MHz, DMSO-d$_6$) δ 10.28 (s, 1H), 9.37 (s, 1H), 8.68 (d, J=4.6 Hz, 1H), 8.23 (s, 1H), 7.72 (dd, J=1.4, 7.9 Hz, 1H), 7.58 (dd, J=1.0, 8.2 Hz, 1H), 7.53-7.48 (m, 1H), 7.24 (br s, 1H), 7.18-7.13 (m, 1H), 6.87-6.86 (m, 2H), 6.65 (s, 1H), 5.98 (s, 2H), 2.76 (d, J=4.6 Hz, 3H); MS (m/z): 431.1 [M+1]$^+$.

EXAMPLE 105

N-Methyl-2-(2-(1-methyl-2-oxoindolin-5-ylamino)-5-(trifluoromethyl)pyridin-4-ylamino)benzamide

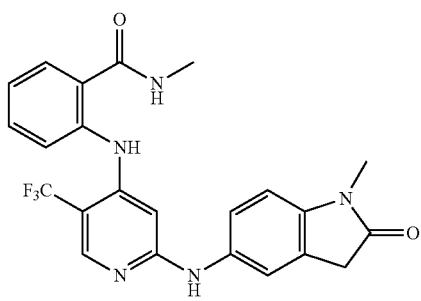

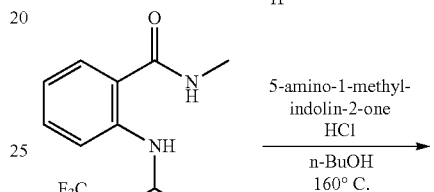

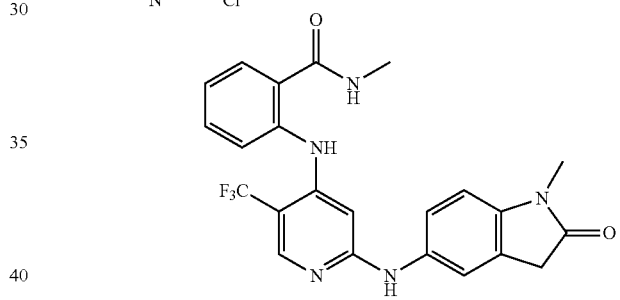

Method F was applied. The TFA salt of the title compound was obtained as a solid.

$^1$H-NMR (400 MHz, DMSO-d$_6$) δ 10.29 (s, 1H), 9.42 (br s, 1H), 8.68 (d, J=4.6 Hz, 1H), 8.23 (s, 1H), 7.72 (dd, J=1.3, 7.9 Hz, 1H), 7.60-7.49 (m, 3H), 7.33 (dd, J=2.1, 8.4 Hz, 1H), 7.16 (m, 1H), 6.93 (d, J=8.4 Hz, 1H), 6.65 (s, 1H), 3.54 (s, 2H), 3.10 (s, 3H), 2.76 (d, J=4.6 Hz, 3H); MS (m/z): 456.1 [M+1]$^+$.

2-Chloro-N-methyl-N-(4-nitrophenyl)acetamide

Reference: Hennessy, E. J.; Buchwald, S. L. *J. Am. Chem. Soc.* 2003, 125, 12084-12085.

Chloroacetyl chloride (1.05 mL, 13.1 mmol) is added in one portion to a biphasic mixture of N-methyl-4-nitroaniline (1.0 g, 6.57 mmol), KOH (1.11 g, 19.7 mmol) in 12 mL EtOAc and 12 mL H$_2$O, cooled to 0° C. The resulting mixture is stirred at this temperature for 5 min, then the ice bath was removed and it was allowed to warm to RT. The reaction was stirred for an additional one hour at RT.

1-Methyl-5-nitroindolin-2-one

Reference: Hennessy, E. J.; Buchwald, S. L. *J. Am. Chem. Soc.* 2003, 125, 12084-12085

The mixture of 2-Chloro-N-methyl-N-(4-nitrophenyl)acetamide (100 mg, 0.44 mmol), Pd$_2$(dba)$_3$ (20 mg, 0.022 mmol), 2-(di-tert-butylphosphino)biphenyl (13 mg, 0.044 mmol) and triethylamine (91 μl, 0.66 mmol) in toluene was heated at 80° C. for 3 h. The reaction was 78% complete by NMR.

5-Amino-1-methylindolin-2-one

To a suspension of 1-methyl-5-nitroindolin-2-one (92 mg, 0.48 mmol) in 20 mL MeOH, was Pd(C) (9.2 mg, 10 weight %) added. The round bottom flask was capped with a rubber septum and put under a hydrogen atmosphere. After 18 h the hydrogen gas was evacuated by introducing argon to the round bottom flask. The reaction mixture was filtered through celite. The celite was washed with EtOAc (2×30 ml). The volatiles were evaporated to afford the title compound in quantitative yield.

EXAMPLE 106

N-Methyl-2-(2-(3-(1,2,3,6-tetrahydropyridin-4-yl)-1H-indol-5-ylamino)-5-(trifluoromethyl)pyridin-4-ylamino)benzamide

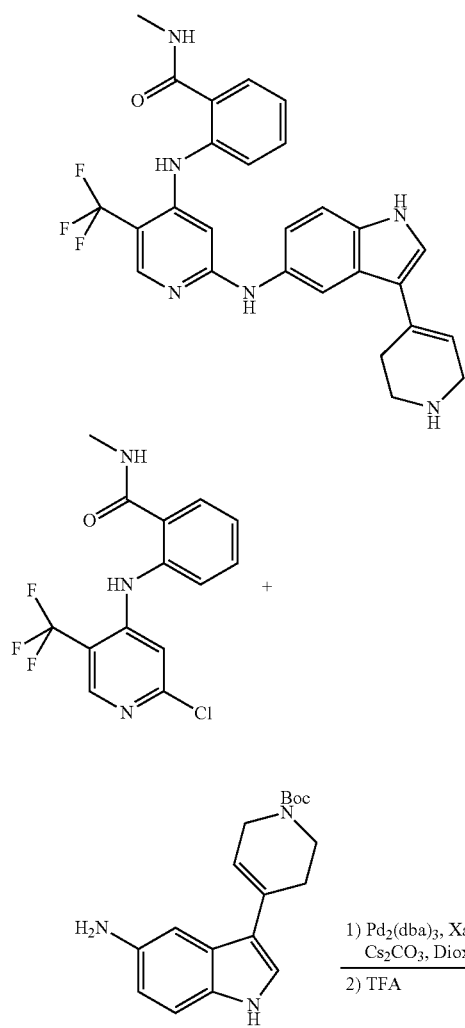

Method D followed by TFA treatment was applied. It was purified by preparative HPLC. The bis-TFA salt of the title compound was obtained as a solid.

$^1$H NMR (400 MHz, DMSO-d$_6$) δ 10.75 (s, 1H), 9.05 (broad s, 2H), 8.77-8.72 (m, 1H), 8.68 (s, 1H), 8.29 (d, J=8.8 Hz, 1H), 8.10 (s, 1H), 7.79-7.77 (m, 2H), 7.74 (s, 1H), 7.55-7.51 (m, 2H), 7.21-7.13 (m, 2H), 6.19 (s, 1H), 3.87-3.80 (m, 2H), 3.40-3.33 (m, 2H), 2.79 (d, J=4.8 Hz, 3H), 2.77-2.72 (m, 2H); ESI-MS (m/z): 506.98 (M+1).

EXAMPLE 107

N-Methyl-2-(2-(3-(1,2,3,6-tetrahydropyridin-4-yl)-1H-indazol-5-ylamino)-5-(trifluoromethyl)pyridin-4-ylamino)benzamide

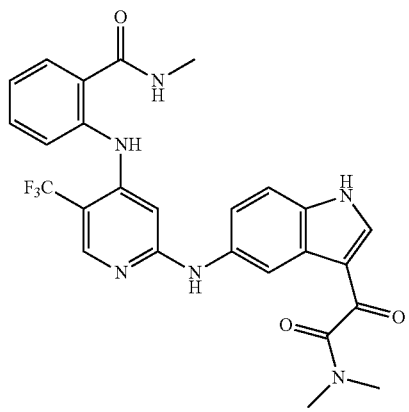

Method D followed by TFA treatment was applied. It was purified by preparative HPLC. The bis-TFA salt of the title compound was obtained as a solid.

$^1$H NMR (400 MHz, DMSO-d$_6$) δ 10.64 (s, 1H), 9.11 (broad s, 1H), 8.77 (q, J=4.8 Hz, 1H), 8.67-8.64 (m, 2H), 7.91 (s, 1H), 7.80 (dd, J=8.0 Hz, 1.2 Hz, 1H), 7.69 (d, J=7.6 Hz, 1H), 7.58-7.53 (m, 1H), 7.47 (s, 1H), 7.24-7.19 (m, 2H), 6.58 (s, 1H), 3.92-3.86 (m, 2H), 3.41-3.33 (m, 2H), 2.80-2.75 (m, 5H).

tert-Butyl 4-(5-nitro-1H-indazol-3-yl)-5,6-dihydro-pyridine-1(2H)-carboxylate The mixture of 3-bromo-5-nitro-1H-indazole (484.1 mg, 2.0 mmol, 1.0 eq), tert-butyl 4-(4,4,5,5-tetramethyl-1,3,2-dioxaborolan-2-yl)-5,6-dihydropyridine-1(2H)-carboxylate (927.7 mg, 1.0 eq), (PPh$_3$)$_4$Pd (0) (462 mg, 0.2 eq), Na$_2$CO$_3$ (2M, 3.0 mL, 3.0 eq) in dioxane (12 mL) was degassed and heated at 120° C. in a microwave-oven synthesizer for 2 h. The mixture was cooled to room temperature and filtered through a celite pad to remove Na$_2$CO$_3$ and catalyst. The celite pad was washed with EtOAc. The solvent was removed and the crude was purified by silica gel chromatography (0%~20% MeOH/DCM) to obtain the desired product tert-butyl 4-(5-nitro-1H-indazol-3-yl)-5,6-dihydropyridine-1(2H)-carboxylate (618 mg, isolated yield 90%).

tert-Butyl 4-(5-amino-1H-indazol-3-yl)-5,6-dihydro-pyridine-1(2H)-carboxylate To a solution of 25 mL dioxane, 19 mL ethanol and 12 mL distilled water was added tert-butyl 4-(5-nitro-1H-indazol-3-yl)-5,6-dihydropyridine-1(2H)-carboxylate (618 mg, 1.79 mmol). To the mixture was added powdered iron (0) (502 mg, 5.0 eq) and ammonium chloride (385 mg, 4.0 eq). The reaction was heated to 70° C. under argon for 3 h. The reaction was cooled, filtered and washed with MeOH. The solvent was removed to obtain the crude which was purified by silica gel chromatography to afford the desired compound tert-butyl 4-(5-amino-1H-indazol-3-yl)-5,6-dihydropyridine-1(2H)-carboxylate.

EXAMPLE 108

N,N-Dimethyl-2-oxo-2-(5-(4-(pyridin-2-ylamino)-5-(trifluoromethyl)pyridin-2-ylamino)-1H-indol-3-yl)acetamide

117

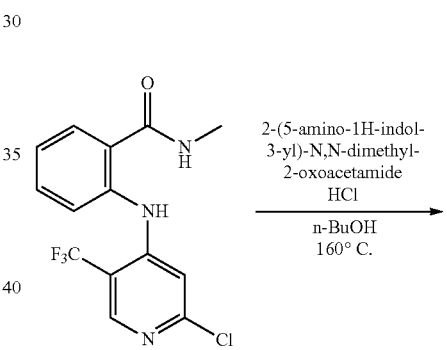

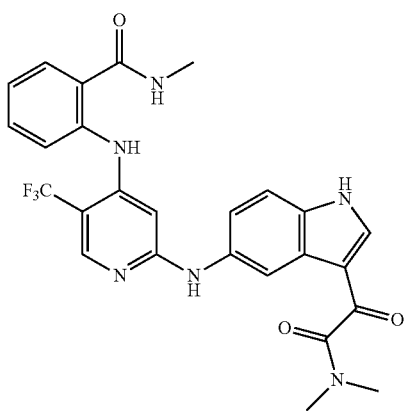

Method F was applied. The TFA salt of the title compound was obtained.

$^1$H-NMR (400 MHz, DMSO-d$_6$) δ 12.19 (d, J=2.8 Hz, 1H), 10.26 (s, 1H), 9.45 (br s, 1H), 8.60 (m, 1H) 8.18 (s, 1H), 8.12 (s, 1H), 8.00 (d, J=3.3 Hz, 1H), 7.63 dd, (J=1.4, 7.9 Hz, 1H), 7.53 (d, J=7.6 Hz, 1H), 7.44-7.37 (m, 3H), 7.05 (m, 1H), 6.68 (s, 1H), 2.92 (s, 3H), 2.86 (s, 3H), 2.69 (d, J=4.6 Hz, 3H); MS (m/z): 525.1 [M+1]⁺.

EXAMPLE 109

2-(2-(4-acetamidophenylamino)-5-(trifluoromethyl)pyridin-4-ylamino)-N-methylbenzamide

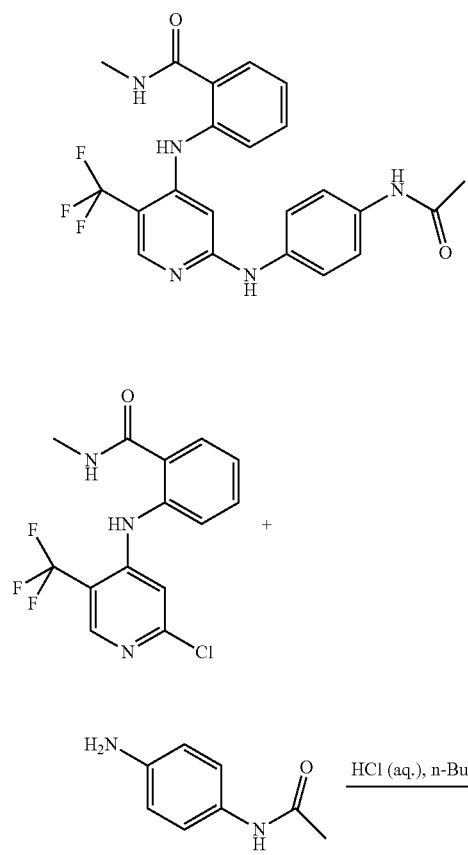

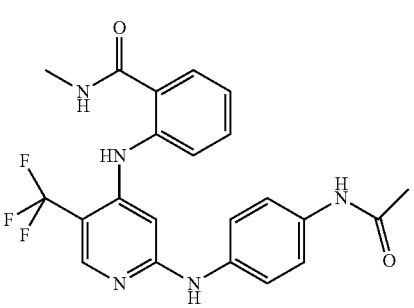

A procedure similar to Method F was applied. The TFA salt of the title compound was obtained as a pale yellow solid.

¹H-NMR (400 MHz, d₆-DMSO) δ 10.24 (s, 1H), 9.84 (s, 1H), 9.33 (br s, 1H), 8.67 (q, J=4.4 Hz, 1H), 8.24 (s, 1H), 7.71 (dd, J=1.4, 7.9 Hz, 1H), 7.58 (dd, J=0.8, 7.9 Hz, 1H), 7.52-7.43 (m, 5H), 7.16-7.12 (m, 1H), 6.70 (s, 1H), 2.76 (d, J=4.5 Hz, 3H), 2.01 (s, 3H); ¹⁹F-NMR (376 MHz, d₆-DMSO) δ −59.3 (s, 3F), −74.45 (s, 3F); MS (m/z): 444.2 [M+1]⁺.

EXAMPLE 110

N-Methyl-N-(3-((2-(2-oxo-2,3-dihydrobenzo[d]oxazol-6-ylamino)-5-(trifluoromethyl)pyridin-4-ylamino)-methyl)pyridin-2-yl)methanesulfonamide

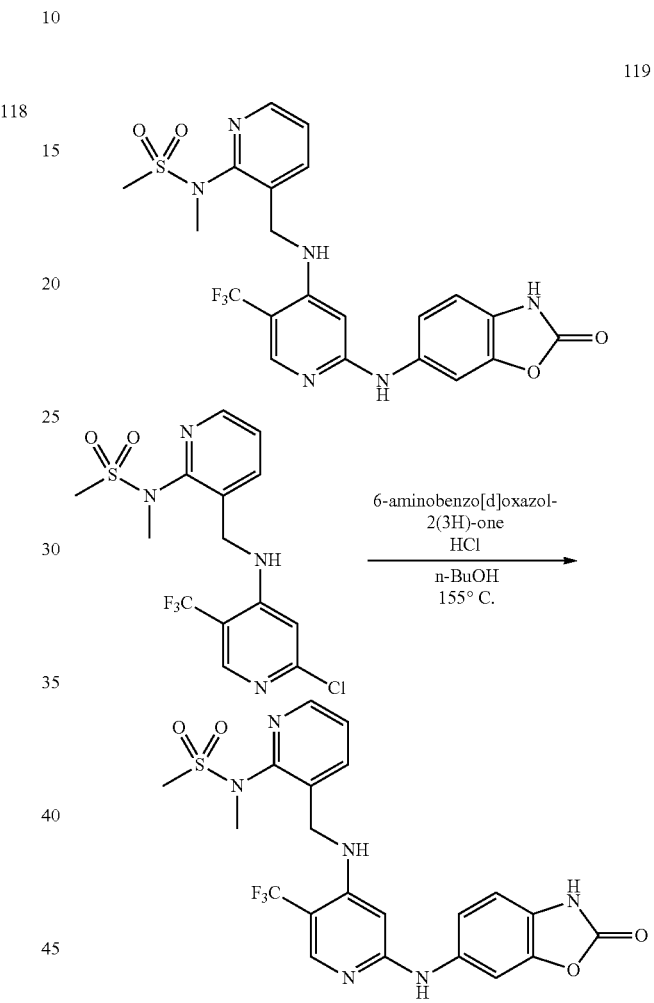

Method F was applied. The TFA salt of the title compound was obtained.

¹H-NMR (400 MHz, DMSO-d₆) δ 11.54 (s, 1H), 9.18 (s, 1H), 8.44 (s, 1H), 8.06 (s, 1H), 7.60 (d, J=7.0 Hz, 1H), 7.42 (m, 1H), 7.35 (broad s, 1H), 7.21 (m, 1H), 6.92-6.86 (m, 2H), 5.56 (s, 1H), 4.51 (broad s, 2H), 3.06 (s, 3H), 2.97 (s, 3H); MS (m/z): 509.1 [M+1]⁺.

EXAMPLE 111

FAK Biochemical Assay

All experiments were performed in Greiner FIA black 384-well low volume plates.

A 5 µl mixture of a 200 nM Ulight-poly GT substrate (Perkin Elmer) and 10 µM ATP in Kinase buffer (50 mM Hepes pH 7.3, 10 mM MgCl₂, 1 mM EGTA, 0.01% Tween-20, 2 mM dithriothreitol) was dispensed into the wells. 20 µl of 90% DMSO/10% water containing the compounds to be tested was added to the wells. Kinase reaction was started by addition of 5 μl of 1 nM FAK (411-686, activated by Src and repurified) in Kinase buffer. After 50 min at RT the reaction was stopped with 5 μl of 40 mM EDTA in detection buffer (Perkin Elmer, Lance detection buffer) followed by a 5 μl addition of 8 nM LANCE E1-W1024 anti-phosphotyrosine (PY20) antibody in detection buffer. After 1 h incubation at RT the plate was read on the Viewlux in HTRF mode.

EXAMPLE 112

FAK Cellular Assay

FAK pY397 ELISA assay: MDA MB231 cells are plated in 6-well dish in 10% FBS-DMEM. After allowing for attachment overnight, cells are treated with compounds for 1 h followed by a PBS wash. Cells are lysed and amount of phosphorylated FAK in the lysate is quantified using the FAK ELISA kit from Biosource/Invitrogen (Carlsbad, Calif.).

Most of the compounds 1-123 as shown in Table 1 were tested in this assay, and of the compounds that were tested, all showed 50% inhibitory concentrations ($IC_{50}$) of less than 10 μM against focal adhesion kinase in the above cell-free assay, except for compounds 3 and 5 shown above in Table 1 which possess $IC_{50}$ values of greater than 10 μM; or showed greater than about 50% inhibition of FAK in the cellular assay at concentrations of 1 μM; or both. Certain of the compounds have not yet been evaluated for biological activity.

All publications, patents, and patent documents cited in the specification are incorporated by reference herein, as though individually incorporated by reference. In the case of any inconsistencies, the present disclosure, including any definitions therein, will prevail. The invention has been described with reference to various non-limiting examples and embodiments. However, it should be understood that many variations and modifications can be made while remaining within the spirit and scope of the present invention.

What is claimed is:
1. A compound selected from the following group:

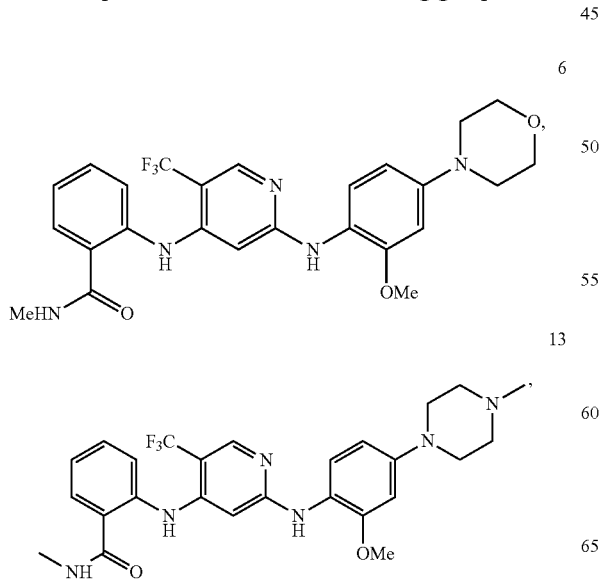

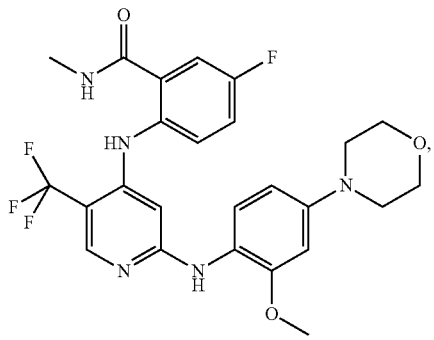
76
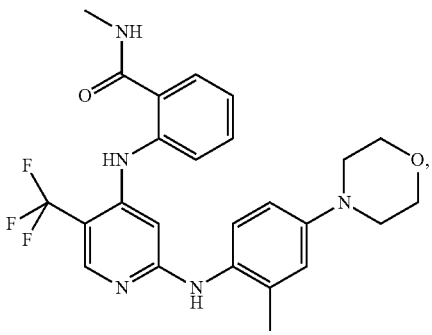
53
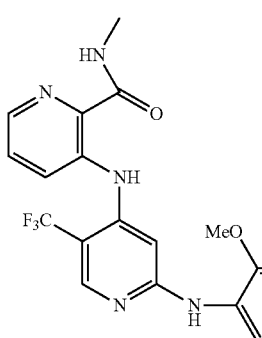
87
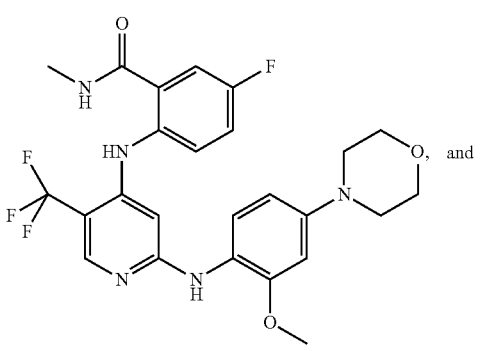
76, and
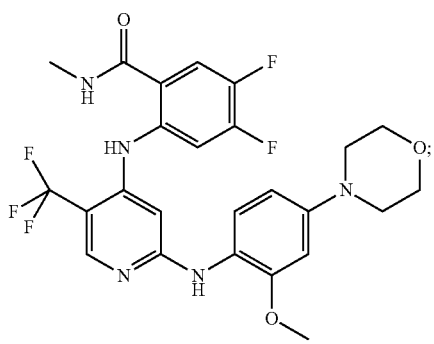
94
or a salt thereof.
2. The compound of claim 1 selected from the following group:
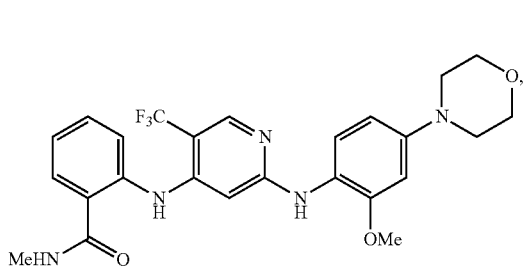
6
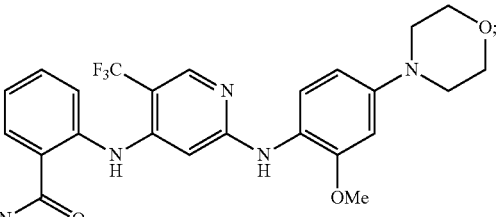
87
or a salt thereof.
3. The compound of claim 1
6
or a salt thereof.

4. The compound of claim 1
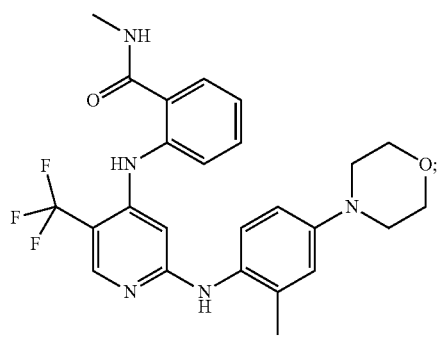
53
or a salt thereof.
5. The compound of claim 1
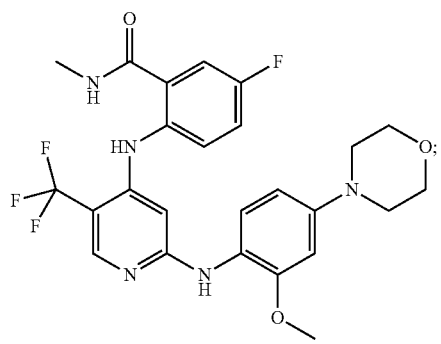
76
or a salt thereof.
6. The compound of claim 1
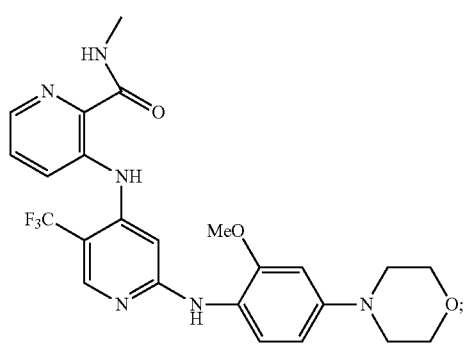
87
or a salt thereof.
7. A pharmaceutical composition comprising a compound selected from the group of claim 1:
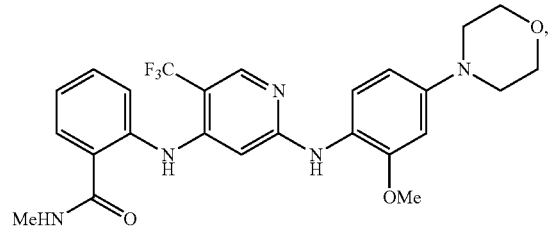
6
-continued
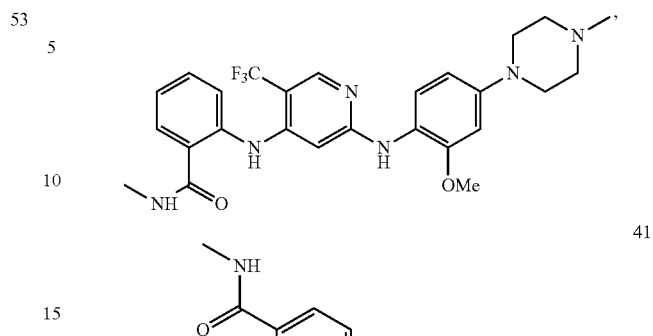
13
41
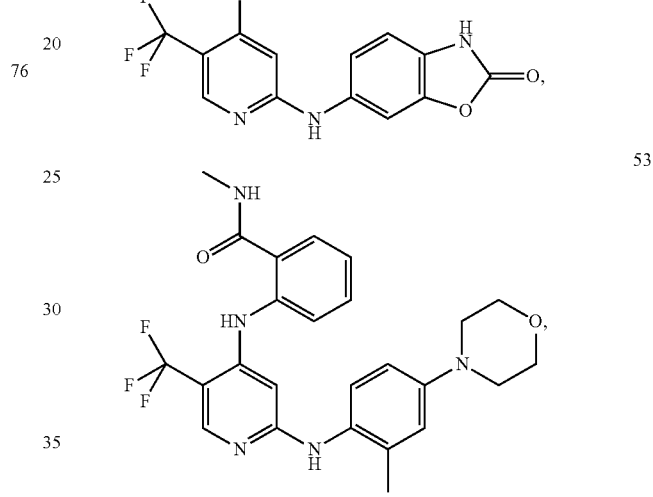
53
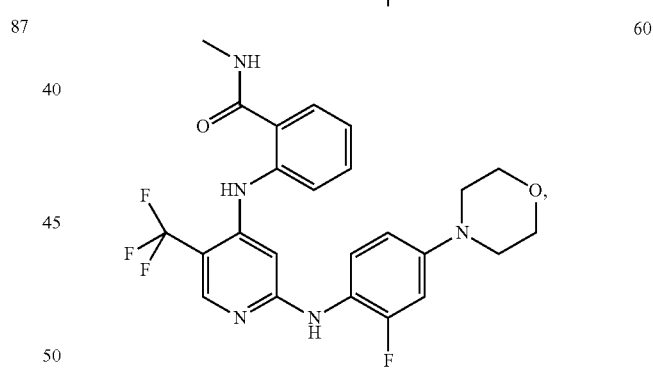
60
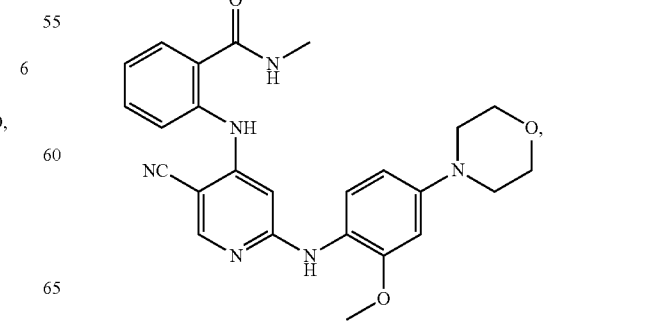
67

-continued
73
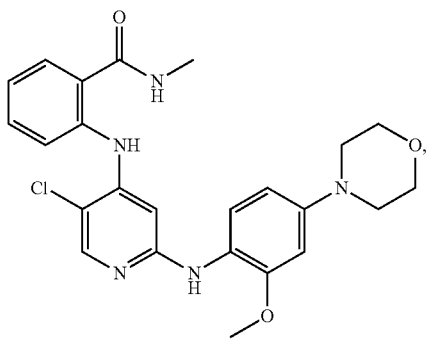
76
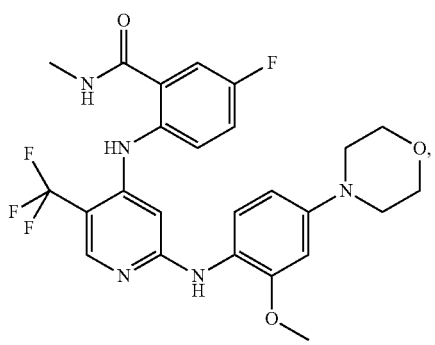
87
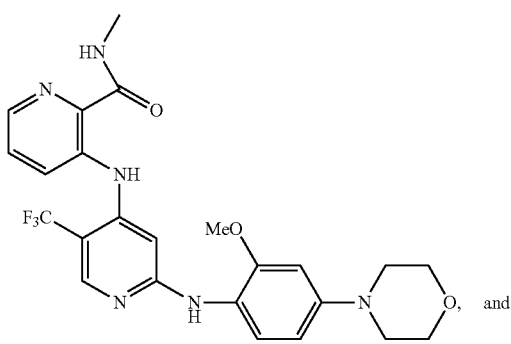
94
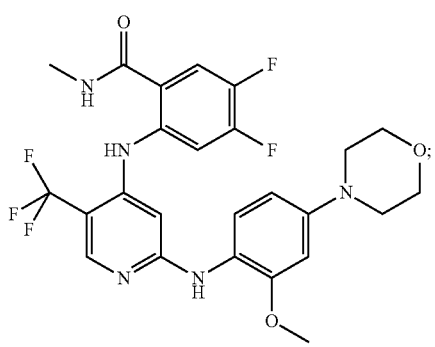
or a salt thereof;
and a pharmaceutically acceptable diluent, excipient or carrier.
8. The pharmaceutical composition of claim 7 comprising a compound selected from the following group:
5
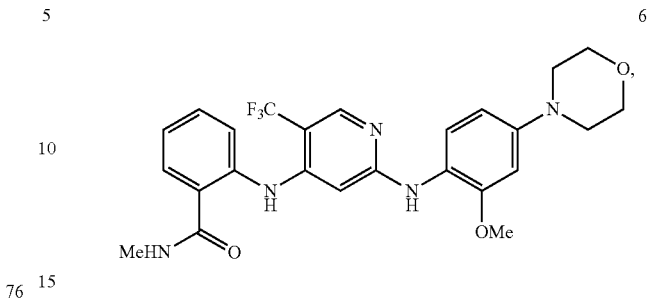
53
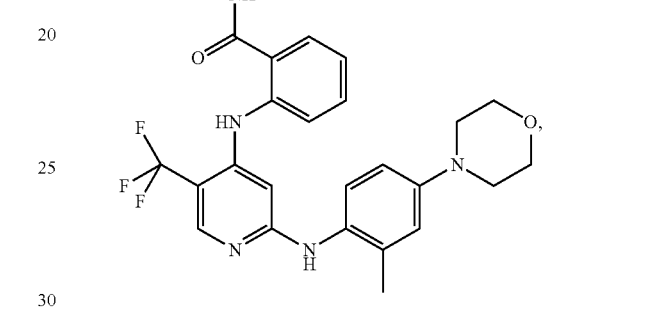
76
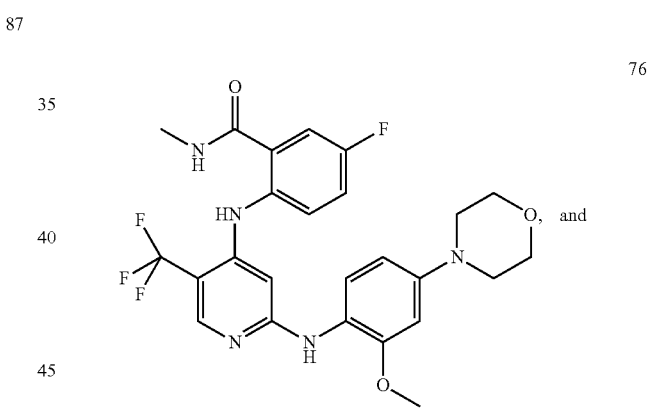
87
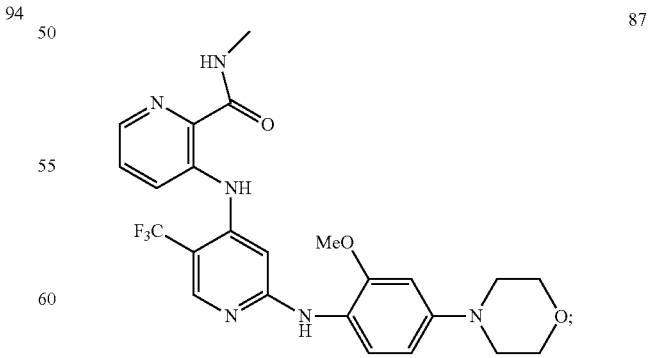
or a salt thereof;
and a pharmaceutically acceptable diluent, excipient or carrier.

9. The pharmaceutical composition of claim 7 comprising:

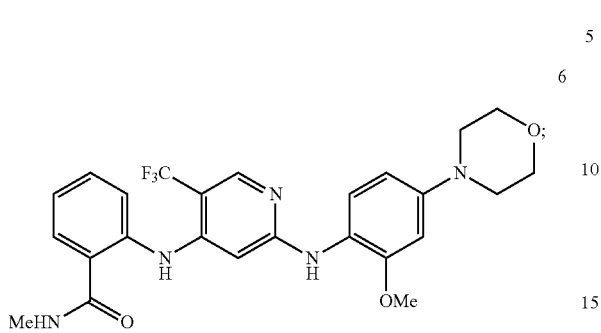

or a salt thereof;
and a pharmaceutically acceptable diluent, excipient or carrier.

10. The pharmaceutical composition of claim 7 comprising:

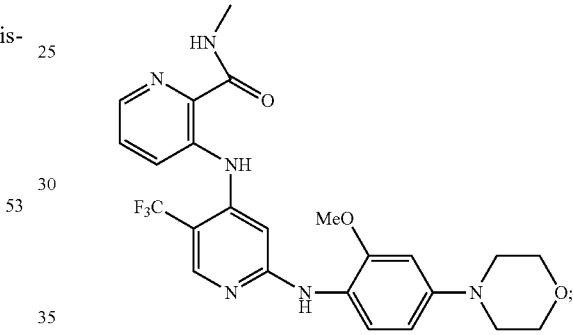

or a salt thereof;
and a pharmaceutically acceptable diluent, excipient or carrier.

11. The pharmaceutical composition of claim 7 comprising:

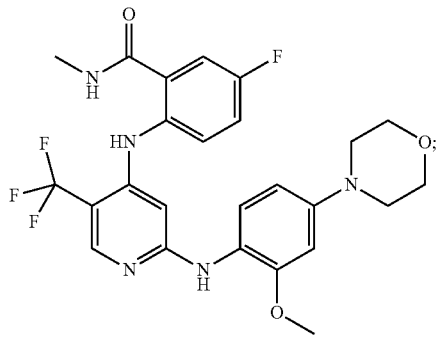

or a salt thereof;
and a pharmaceutically acceptable diluent, excipient or carrier.

12. The pharmaceutical composition of claim 7 comprising:

or a salt thereof;
and a pharmaceutically acceptable diluent, excipient or carrier.

13. A method of inhibiting a focal adhesion kinase (FAK), in vitro or in vivo, comprising contacting a compound selected from claim 1 at an effective concentration with the focal adhesion kinase.

14. A pharmaceutical composition comprising a compound of claim 1 and a suitable excipient.

15. A pharmaceutical combination comprising a compound of claim 1 and an effective amount of a second medicament.

16. A pharmaceutical composition comprising the combination of claim 15 and a suitable excipient.

* * * * *

UNITED STATES PATENT AND TRADEMARK OFFICE
CERTIFICATE OF CORRECTION

PATENT NO. : 8,501,763 B2  
APPLICATION NO. : 12/531010  
DATED : August 6, 2013  
INVENTOR(S) : Liang et al.

Page 1 of 3

It is certified that error appears in the above-identified patent and that said Letters Patent is hereby corrected as shown below:

On Title page, in column 2, under "Other Publications", line 1, delete "al." and insert --al.,--, therefor On Title page, in column 2, under "Other Publications", line 2, delete "solids"" and insert --solids",--, therefor In the Specification In column 1, line 7, delete "§371" and insert --§ 371--, therefor In column 1, line 28, delete "J L" and insert --J. L.--, therefor In column 1, line 36, delete "H" and insert --H.--, therefor In column 3, line 43-44, delete "comprises" and insert --comprise--, therefor In column 6, line 32, delete "CH(CH3)," and insert --CH(CH$_3$),--, therefor In column 6, line 32, delete "CH(CH3)2," and insert --CH(CH$_3$)$_2$,--, therefor In column 6, line 32, delete "C(CH3)=CH2," and insert --C(CH$_3$)=CH$_2$,--, therefor In column 6, line 33, delete "C(CH3)=CH(CH3)," and insert --C(CH$_3$)=CH(CH$_3$),--, therefor In column 6, line 33, delete "C(CH2CH3)=CH2," and insert --C(CH$_2$CH$_3$)=CH$_2$,--, therefor In column 9, line 28, delete "Spiro" and insert --spiro--, therefor In column 9, line 66, delete "amino" and insert --amido--, therefor In column 11, line 10, after "heterocyclyl,", delete "wherein each", therefor In column 11, line 14, after "attached", insert --to--, therefor Signed and Sealed this  
Twenty-eighth Day of October, 2014

Michelle K. Lee  
*Deputy Director of the United States Patent and Trademark Office*

CERTIFICATE OF CORRECTION (continued)
U.S. Pat. No. 8,501,763 B2

In column 11, line 67, delete "1,2" and insert --1, 2--, therefor

In column 12, line 32, after "of", delete "any of", therefor

In column 14, line 1, delete "agent" and insert --agent.--, therefor

In column 73, line 64, delete "78" and insert --78°--, therefor

In column 74, line 9, delete "78" and insert --78°--, therefor

In column 74, line 23, delete "78" and insert --78°--, therefor

In column 74, line 50, delete "78" and insert --78°--, therefor

In column 74, line 64, delete "78" and insert --78°--, therefor

In column 122, line 1-11 (approx.), delete "  therefor

In column 144, line 21, delete "methoxyl" and insert --methoxy--, therefor

In column 146, line 48, delete "XantPhos" and insert --Xantphos--, therefor

In column 146, line 57, delete "XantPhos" and insert --Xantphos--, therefor

In column 147, line 30, delete "NiCl₂.6H₂O" and insert --NiCl₂ 6H₂O--, therefor

In column 147, line 46, delete "1H))," and insert --1H),--, therefor

In column 152, line 37 (approx.), delete "c." and insert --C.--, therefor

In column 154, line 54-67 (approx.), delete "  " and insert -- 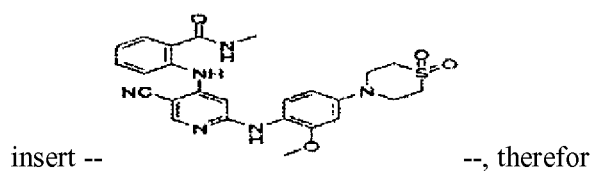 --, therefor

CERTIFICATE OF CORRECTION (continued)
U.S. Pat. No. 8,501,763 B2

In column 155, line 1-11 (approx.), delete " 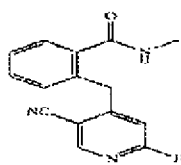 " and insert -- 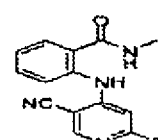 --, therefor In column 155, line 16-29 (approx.), delete " 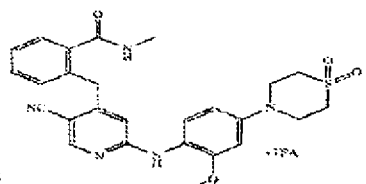 " and insert --  --, therefor In column 179, line 41-45 (approx.), delete " 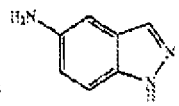 " and insert -- 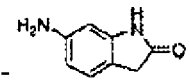 --, therefor In column 180, line 15-28 (approx.), delete " 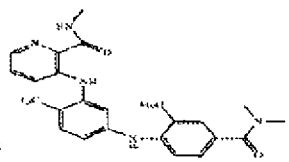 " and insert -- 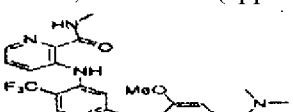 --, therefor In column 180, line 46-59 (approx.), delete " 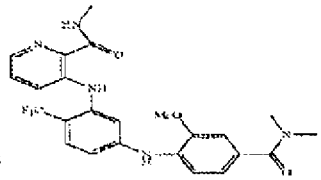 " and insert -- 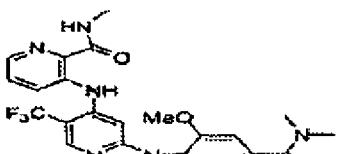 --, therefor